US009096571B2

(12) United States Patent
Ryu et al.

(10) Patent No.: US 9,096,571 B2
(45) Date of Patent: Aug. 4, 2015

(54) PICOLINAMIDE AND PYRIMIDINE-4-CARBOXAMIDE COMPOUNDS, PROCESS FOR PREPARING AND PHARMACEUTICAL COMPOSITION COMPRISING THE SAME

(75) Inventors: Je Ho Ryu, Seoul (KR); Shin Ae Kim, Suwon-si (KR); Keun Ho Ryu, Seoul (KR); Jae Sun Kim, Suwon-si (KR); Nam Ho Kim, Yongin-si (KR); Hye Young Han, Seoul (KR); Yong Hyuk Kim, Suwon-si (KR); Won-No Youn, Seoul (KR); Yoon-Jung Lee, Yongin-si (KR); Hyun Joo Son, Seoul (KR); Bong-Yong Lee, Seoul (KR); Sung Hoon Park, Seoul (KR); Ju Young Lee, Suwon-si (KR); Hyun Jung Lee, Seoul (KR); Hoe Chul Jung, Seoul (KR); Young Ah Shin, Yongin-si (KR); Jung A Lee, Uiwang-si (KR); Bo Ram Lee, Seoul (KR); Joon Ho Sa, Seoul (KR)

(73) Assignee: SK CHEMICALS CO., LTD., Suwon (KR)

( * ) Notice: Subject to any disclaimer, the term of this patent is extended or adjusted under 35 U.S.C. 154(b) by 162 days.

(21) Appl. No.: 13/696,400

(22) PCT Filed: May 4, 2011

(86) PCT No.: PCT/KR2011/003362
§ 371 (c)(1),
(2), (4) Date: Jan. 15, 2013

(87) PCT Pub. No.: WO2011/139107
PCT Pub. Date: Nov. 10, 2011

(65) Prior Publication Data
US 2013/0210811 A1    Aug. 15, 2013

(30) Foreign Application Priority Data

May 7, 2010   (KR) .................. 10-2010-0043168
Apr. 22, 2011  (KR) .................. 10-2011-0037758

(51) Int. Cl.
| | | |
|---|---|---|
| A61K 31/47 | (2006.01) |
| A61K 31/55 | (2006.01) |
| A61K 31/445 | (2006.01) |
| A61K 31/497 | (2006.01) |
| C07D 401/04 | (2006.01) |
| C07D 401/14 | (2006.01) |
| C07D 403/04 | (2006.01) |
| C07D 403/14 | (2006.01) |
| C07D 405/14 | (2006.01) |
| C07D 213/81 | (2006.01) |
| C07D 401/06 | (2006.01) |
| C07D 401/12 | (2006.01) |
| C07D 405/12 | (2006.01) |
| C07D 239/557 | (2006.01) |

(52) U.S. Cl.
CPC ............ *C07D 401/04* (2013.01); *C07D 213/81* (2013.01); *C07D 239/557* (2013.01); *C07D 401/06* (2013.01); *C07D 401/12* (2013.01); *C07D 401/14* (2013.01); *C07D 403/04* (2013.01); *C07D 403/14* (2013.01); *C07D 405/12* (2013.01); *C07D 405/14* (2013.01)

(58) Field of Classification Search
CPC .. C07D 401/04; C07D 401/14; C07D 403/04; C07D 403/14; C07D 405/14; A61K 31/47; A61K 31/55; A61K 31/445; A61K 31/497
USPC ............... 514/218, 318, 253.13, 253.09, 316, 514/235.5, 314, 252.14, 252.18, 252.19; 540/575; 544/130, 295, 365, 364; 546/167, 187, 194
See application file for complete search history.

(56) References Cited

U.S. PATENT DOCUMENTS

| 2008/0032967 A1 | 2/2008 | Ashwell et al. |
| 2009/0197859 A1 | 8/2009 | Collantes |
| 2010/0022546 A1 | 1/2010 | Jimenenz |

FOREIGN PATENT DOCUMENTS

| WO | 2009/152356 | 12/2009 |
| WO | 2009152356 | * 12/2009 |

OTHER PUBLICATIONS

Extended European Search Report of corresponding European application No. 11777588.2 mailed Jul. 1, 2014.
Ge, et al., "11 beta-hydroxysteroid dehydrogenase type 1 inhibitors as promising therapeutic drugs for diabetes: status and development," Current Medicinal Chemistry, vol. 17, No. 5, Jan. 1, 2010, pp. 412-422, XP055122277.
Office Action for corresponding Taiwanese application No. 100115922 dated Dec. 9, 2014.
International Search Report of corresponding application No. PCT/KR2011/003362 mailed Jan. 13, 2012.

* cited by examiner

*Primary Examiner* — James O Wilson
*Assistant Examiner* — Ebenezer O Sackey
(74) *Attorney, Agent, or Firm* — Lowe Hauptman & Ham, LLP

(57) ABSTRACT

Provided are picolinamide and pyrimidine-4-carboxamide compounds, a method for preparing the same, a pharmaceutical composition containing the same, and a medical use using the compound as an agent for preventing, regulating, and treating diseases related to regulation of glucocorticoids by using selective inhibitory activity of the compound for an 11β-HSD1 enzyme. The picolinamide and pyrimidine-4-carboxamide compounds of the present invention are selective inhibitors of human-derived 11β-HSD1 enzymes, and are useful in an agent for preventing, regulating, and treating diseases related to glucocorticoid regulation in which human-derived 11β-HSD1 enzymes are involved, for example, metabolic syndromes such as, type 1 and type 2 diabetes, diabetes later complications, latent autoimmune diabetes adult (LADA), insulin tolerance syndromes, obesity, impaired glucose tolerance (IGT), impaired fasting glucose (IFG), damaged glucose tolerance, dyslipidemia, atherosclerosis, hypertension, etc.

8 Claims, No Drawings

PICOLINAMIDE AND PYRIMIDINE-4-CARBOXAMIDE COMPOUNDS, PROCESS FOR PREPARING AND PHARMACEUTICAL COMPOSITION COMPRISING THE SAME

TECHNICAL FIELD

The present invention relates to a novel amide compound, i.e., picolinamide and pyrimidine-4-carboxamide compounds, a method for preparing the same, a pharmaceutical composition comprising the same, and a medical use using the compound as an agent for preventing, regulating, and treating diseases related to regulation of glucocorticoids by using selective inhibitory activity of the compound for an 11β-HSD1 enzyme.

BACKGROUND ART

Glucocorticoids (cortisol for human) act as an important role in the maintenance of glucose homeostasis and metabolism of lipid and protein in the body. Particularly, excessive glucocorticoids in the liver and adipose tissues cause metabolic syndromes, such as, insulin resistances, visceral obesity, hypertension, and dyslipidemia.

It has been known that 11β-hydroxysteroid dehydrogenase (11β-HSD) has two kinds of isozymes, type 1 and type 2. First, 11β-HSD1 is an NADPH-dependent reductase, and an important enzyme for converting inactive glucocorticoid, cortisone, into active glucocorticoid, cortisol, in the liver, adiopose, and brain tissues. 11β-HSD2 performs an action contrary to 11β-HSD1 in an NAD-dependent manner, and is expressed mainly in the kidney.

It was reported that 11β-HSD1-overexpressed transgenic mice had a normal cortisol level in the blood, but had an increased cortisol level in the adiopose, which caused insulin resistances, visceral obesity, hyperlipidemia, and hypertension, and that they showed a larger increase in body weight and a larger increase rate in body weight than a non-transgenic mouse group [Masuzaki H. Science 2001, 294, 2166-2170; Masuzaki H. J. Clin. Invest. 2003, 112, 83-90]. In addition, it was reported that 11β-HSD1 knowout mice showed an improvement in glucose tolerance, a deterioration in blood triglycerides, and an increase in HDL-cholesterol [Morton N. M. J. Biol. Chem. 2001, 276, 41293-41300].

Carbenoxolone (CBX), which is a nonselective inhibitor of 11β-HSD1, improves insulin sensitivity of healthy candidates and type 2 diabetic patients, but not the obese [Andrew, R. C. J. Clin. Endocrionl. Metab. 2003, 88, 285-291]. However, the CBX was reported to cause hypopotassemia and hypertension due to nonselective inhibition for 11β-HSD1 and 11β-HSD2, and thus the development thereof is limited to therapeutic agents [Kotelevtsev, Y. J. Clin. Invest. 1999, 103, 683-689].

Therefore, the effective and selective inhibitors of 11β-HSD1 enzymes inhibit the conversion of glucocorticoids into the active type to suppress the action of glucocorticoids in the tissue, and as a result, they can be used as therapeutic agents for metabolic syndromes caused by glucocorticoids, such as non-insulin dependent type 2 diabetes, obesity, hyperlipidemia, hypertension, glucose tolerance, and the like.

For this reason, the present inventors searched compounds having effective and selective inhibitory activity for 11β-HSD1 enzymes for the purpose of regulating or treating metabolic syndromes such as obesity, diabetes, etc. As a result, they could synthesize novel picolinamide and pyrimidine-4-carboxamide compounds, and verify that these novel compounds exhibited effective and selective inhibitory activity for 11β-HSD1 enzymes.

DISCLOSURE

Technical Problem

An object of the present invention is to provide a novel amide compound, i.e., picolinamide and pyrimidine-4-carboxamide compounds, or a pharmaceutically acceptable salt, solvate, hydrate, prodrug, racemate, or stereoisomer thereof.

Another object of the present invention is to provide a pharmaceutical composition for inhibiting human-derived 11β-HSD1 enzymes, comprising the novel amide compound, or the pharmaceutically acceptable salt, solvate, hydrate, prodrug, racemate, or stereoisomer thereof as an active ingredient.

Still another object of the present invention is to provide an agent for preventing, regulating, and treating diseases related to glucocorticoid regulation in which human-derived 11β-HSD1 enzymes are involved, for example, metabolic syndromes such as, type 1 and type 2 diabetes, diabetes later complications, latent autoimmune diabetes adult (LADA), insulin tolerance syndromes, obesity, impaired glucose tolerance (IGT), impaired fasting glucose (IFG), damaged glucose tolerance, dyslipidemia, atherosclerosis, hypertension, etc.

Technical Solution

In one general aspect, the present invention provides a novel amide compound represented by the formula 1 below, i.e., picolinamide and pyrimidine-4-carboxamide compounds, or a pharmaceutically acceptable salt, solvate, hydrate, prodrug, racemate, or stereoisomer thereof.

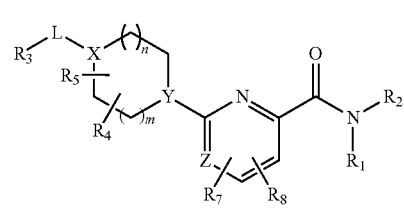

[Formula 1]

[In the formula 1,

X represents N or CR, and Y represents N or CH, provided that X and Y are not carbon at the same time;

Z represents N or CH;

$R_1$ and $R_2$ independently represent hydrogen, (C1-C10)alkyl, (C3-C10)cycloalkyl, norbornyl, adamantyl, noradamantyl, (C6-C20)aryl, (C6-C20)ar(C1-C10)alkyl, or (C3-C20)heteroaryl, or $R_1$ and $R_2$ may be linked to each other, together with nitrogen atoms to which they are bound, to form (C1-C10) saturated or unsaturated heterocycle, biheterocycle or fused heterocycle, provided that both $R_1$ and $R_2$ are not hydrogen at the same time;

L represents a single bond, —O—, —$NR_{11}$—, —CO—, —$SO_2$—, —$(CR_{21}R_{22})$—$(CH_2)_c$— (c represents an integer of 0 to 5), —$CO(CR_{21}R_{22})_d$— (d represents an integer of 1 to 6), (C3-C10)cycloalkylene, (C6-C20)arylene or (C3-C20)heteroarylene;

R$_{21}$ and R$_{22}$ independently represent hydrogen or (C1-C10)alkyl, or R$_{21}$ and R$_{22}$ may be linked via alkylene or alkenylene to form a cycloaliphatic ring or an aromatic ring;

R and R$_3$ independently represent hydrogen, (C1-C10)alkyl, (C3-C10)cycloalkyl, (C1-C10)alkoxy, halogen, hydroxy, cyano, —NR$_{31}$R$_{32}$, nitro, —CONH$_2$, —CO$_2$R$_{33}$, —SO$_3$H, —SO$_2$NR$_{34}$R$_{35}$, —SO$_2$R$_{36}$, —O(CH$_2$)$_a$CO$_2$H (a represents an integer of 1 to 3), —O(CH$_2$)$_b$CONH$_2$ (b represents an integer of 1 to 3), —NH(CO)R$_{37}$, —NH(SO$_2$)R$_{38}$, 5- to 7-membered heterocycle, (C6-C20)aryl or (C3-C20)heteroaryl;

R$_4$ and R$_5$ independently represent hydrogen, (C1-C10)alkyl, (C3-C10)cycloalkyl, (C1-C10)alkoxy, halogen, hydroxy, cyano, amino, nitro, —CONH$_2$ or —CO$_2$R$_{12}$, and include all of isomers and racemic compounds thereof all, or R$_4$ and R$_5$ may be substituted with adjacent carbon atoms to form (C1-C10) saturated or unsaturated carbocycle, heterocycle, bicarbocycle, biheterocycle, fused carbocycle, or fused heterocycle, or may be linked to R$_3$ to form saturated or unsaturated carbocycle;

R$_6$ and R$_7$ independently represent hydrogen, (C1-C10)alkyl, (C3-C10)cycloalkyl, (C1-C10)alkoxy, halogen, hydroxy, cyano, amino, nitro, —CONH$_2$ or —CO$_2$R$_{12}$;

the cycloalkylene, arylene or heteroarylene of L; the alkyl, cycloalkyl, norbornyl, adamantyl, noradamantyl, aryl, aralkyl or heteroaryl of R$_1$ and R$_2$; the saturated or unsaturated heterocycle, biheterocycle or fused heterocycle formed by the linkage of R$_1$ and R$_2$; the alkyl, cycloalkyl, alkoxy, heterocycle, aryl or heteroaryl of R and R$_3$; the alkyl, cycloalkyl or alkoxy of R$_4$ and R$_5$; the saturated or unsaturated carbocycle, heterocycle, bicarbocycle, biheterocycle, fused carbocycle or fused heterocycle formed by the substitution of R$_4$ and R$_5$ with adjacent carbon atoms; and the alkyl, cycloalkyl or alkoxy of R$_6$ and R$_7$ may be further substituted with one or more substituent(s) selected from the group consisting of (C1-C10)alkyl, (C3-C10)cycloalkyl, (C1-C10)alkoxy, halo(C1-C10)alkyl, halo(C1-C10)alkoxy, halogen, hydroxy, cyano, —NR$_{41}$R$_{42}$, nitro, —CO$_2$R$_{43}$, —CONH$_2$, —SO$_3$H, —SO$_2$NR$_{44}$R$_{45}$, —SO$_2$(CH$_2$)$_c$NR$_{44}$R$_{45}$ (c represents an integer of 1 to 3), —SO$_2$R$_{46}$, —O(CH$_2$)$_c$CO$_2$H (c represents an integer of 1 to 3), —O(CH$_2$)$_d$CONH$_2$ (d represents an integer of 1 to 3), —NH(CO)R$_{47}$, —NH(SO$_2$)R$_{48}$, (C6-C20)aryl and (C3-C20)heteroaryl;

R$_{11}$, R$_{12}$, R$_{31}$, R$_{32}$, R$_{33}$, R$_{34}$, R$_{35}$, R$_{36}$, R$_{37}$, R$_{38}$, R$_{41}$, R$_{42}$, R$_{43}$, R$_{44}$, R$_{45}$, R$_{46}$, R$_{47}$ and R$_{48}$ independently represent hydrogen, (C1-C10)alkyl, (C3-C10)cycloalkyl or (C6-C20)aryl; and m and n independently represent an integer of 0 to 3, provided that m+n represents an integer of 2 or more.]

Here, R$_1$ and R$_2$ independently represent hydrogen, (C3-C10)cycloalkyl, norbornyl, adamantyl, noradamantyl or (C6-C20)ar(C1-C10)alkyl, or R$_1$ and R$_2$ may be linked to each other to form heterocycle selected from the following:

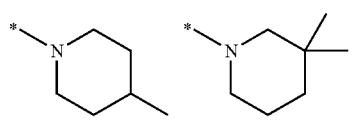

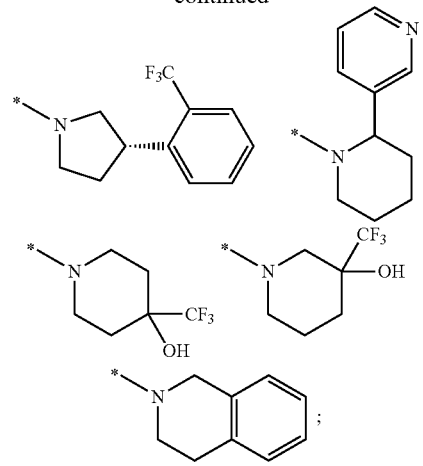

L represents a single bond, —CO—, —SO$_2$—, —(CR$_{21}$R$_{22}$)—(CH$_2$)$_c$— (c represents an integer of 0 to 5),

—CO(CR$_{21}$R$_{22}$)$_d$— (d represents an integer of 1 to 6), (C3-C10)cycloalkylene, (C6-C20)arylene or (C3-C20)heteroarylene;

R$_{21}$ and R$_{22}$ independently represent hydrogen or (C1-C10)alkyl;

R$_3$ represents hydrogen, (C1-C10)alkyl, (C3-C10)cycloalkyl, (C1-C10)alkoxy, halogen, hydroxy, cyano, —NR$_{31}$R$_{32}$, nitro, —CONH$_2$, —CO$_2$R$_{33}$, —SO$_2$NR$_{34}$R$_{35}$, —SO$_2$R$_{36}$, —O(CH$_2$)$_a$CO$_2$H (a represents an integer of 1 to 3), —O(CH$_2$)$_b$CONH$_2$ (b represents an integer of 1 to 3), —NH(CO)R$_{37}$, —NH(SO$_2$)R$_{38}$, 5- to 7-membered heterocycle, (C6-C20)aryl or (C3-C20)heteroaryl;

R$_6$ and R$_7$ independently represent hydrogen, (C1-C10)alkyl or halogen;

the cycloalkylene, arylene or heteroarylene of the L; the cycloalkyl, norbornyl, adamantyl, noradamantyl or aralkyl of R$_1$ and R$_2$; the alkyl, cycloalkyl, alkoxy, heterocycle, aryl or heteroaryl of R$_3$; and the alkyl of R$_6$ and R$_7$ may be further substituted with one or more substituent(s) selected from the group consisting of (C1-C10)alkyl, (C3-C10)cycloalkyl, (C1-C10)alkoxy, halo(C1-C10)alkyl, halo(C1-C10)alkoxy, halogen, hydroxy, cyano, —NR$_{41}$R$_{42}$, nitro, —CO$_2$R$_{43}$, —CONH$_2$, —SO$_3$H, —SO$_2$NR$_{44}$R$_{45}$, —SO$_2$(CH$_2$)$_c$NR$_{44}$R$_{45}$ (c represents an integer of 1 to 3), —SO$_2$R$_{46}$, —O(CH$_2$)$_c$CO$_2$H (c represents an integer of 1 to 3), —O(CH$_2$)$_d$CONH$_2$ (d represents an integer of 1 to 3), —NH(CO)R$_{47}$, —NH(SO$_2$)R$_{48}$, (C6-C20)aryl and (C3-C20) heteroaryl; and R$_{11}$, R$_{12}$, R$_{31}$, R$_{32}$, R$_{33}$, R$_{34}$, R$_{35}$, R$_{36}$, R$_{37}$, R$_{38}$, R$_{41}$, R$_{42}$, R$_{43}$, R$_{44}$, R$_{45}$, R$_{46}$, R$_{47}$ and R$_{48}$ independently represent hydrogen, (C1-C10)alkyl, (C3-C10)cycloalkyl or (C6-C20)aryl.

The compound of the present invention may be prepared by using a known organic synthesis method including methods described in detail in the examples.

A picolinamide compound of the present invention may be obtained according to the Scheme 1 below.

Scheme 1

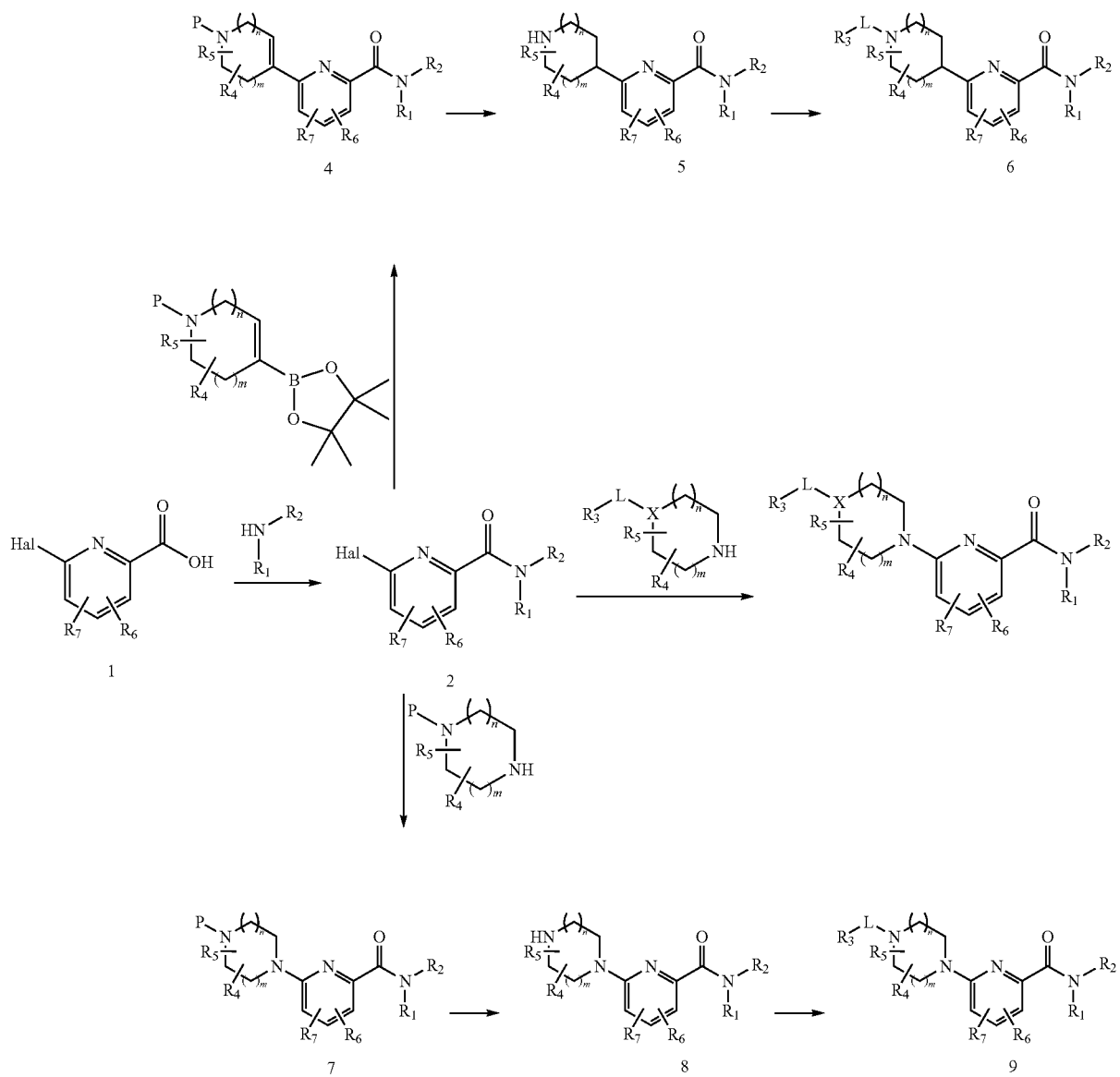

(In the Scheme 1, P is a protection group.)

A picolinic acid (1) substituted in the 6-position with halogen or triflate was reacted with appropriate amine and coupling reagents at room temperature to obtain an intermediate 2. An appropriately substituted heterocycle containing an N atom was input thereto, followed by microwave reaction, high-temperature reaction, or metal catalyzed reaction, or the like, to obtain a final compound 3.

In addition, the intermediate 2 was reacted with a heterocycle including one N atom protected by an appropriate protecting group and another N atom, by microwave reaction, high-temperature reaction, or metal catalyzed reaction, followed by deprotection, to obtain an intermediate 8. Various substituents (-L-$R_3$) were introduced thereinto through a method of alkylation, carbonylation, sulfonylation, reductive amination, coupling using metal catalysts, or the like, to allow efficient synthesis of various derivatives.

On the other hand, in order to obtain a compound 6 in which a heterocycle is linked to the 6-position of picolinamide by a C—C bond, the intermediate 2 was reacted with a heterocycle including 4,4,5,5-tetramethyl-2-vinyl-1,3,2-dioxaborolane with an N atom protected by an appropriate protecting group, through metal catalyzed reaction, followed by hydrogenation and deprotection reaction, to obtain an intermediate 5. Various substituents (-L-$R_3$) may be introduced thereinto through a method of alkylation, carbonylation, sulfonylation, reductive amination, coupling using metal catalysts, or the like.

In a case where each of the final compounds 3, 6, and 9 has a functional group of $NO_2$, CN, $CO_2R$, $CO_2H$, $NH_2$, OH, or the like, a further final compound can be obtained through reaction of reduction, hydrolysis, amination, alkylation, carbonylation, sulfonylation, or the like.

Meanwhile, a pyrimidine-4-carboxamide compound of the present invention can be obtained according to the Scheme 2 below.

[Scheme 2]
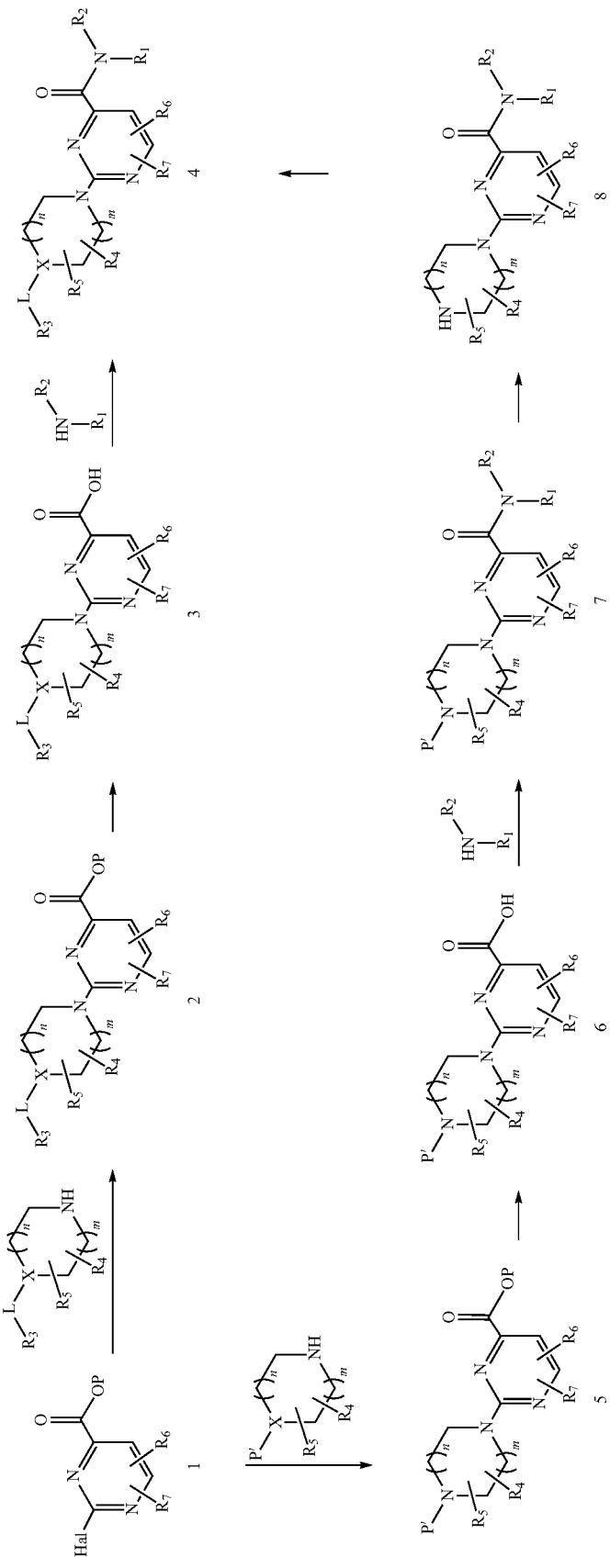

(In the Scheme 2, P and P' are protection groups.)

A pyrimidine-4-carboxylic acid substituted in the 2-position with halogen or triflate was protected by an appropriate protection group (1), and then reacted with an appropriately substituted heterocycle including an N atom by microwave reaction or high-temperature reaction, followed by deprotection, to allow synthesis of an intermediate 3. This was reacted with appropriate amine and coupling reagents at room temperature to obtain a final compound 4.

In addition, the compound 1 was reacted with a heterocycle including one N atom protected by an appropriate protecting group and another N atom by microwave reaction or high-temperature reaction, followed by deprotection of a carboxylic acid-protecting group, to obtain an intermediate 6. This was reacted with appropriate amine and coupling reagents at room temperature, followed by deprotection of amine-protecting group, to allow synthesis of an intermediate 8. Various substituents (-L-$R_3$) were introduced thereinto by a method of alkylation, carbonylation, sulfonylation, reductive amination, coupling using metal catalysts, or the like, to allow efficient synthesis of various derivatives.

In a case where the final compounds 4 has a functional group such as $NO_2$, CN, $CO_2R$, $CO_2H$, $NH_2$, OH, or the like, a further final compound can be obtained through the reaction of reduction, hydrolysis, amination, alkylation, carbonylation, sulfonylation, or the like.

In another general aspect, the present invention provides a pharmaceutical composition comprising the amide compound of the formula 1, or the pharmaceutically acceptable salt, solvate, hydrate, prodrug, racemate, or stereoisomer thereof, and a pharmaceutical acceptable carrier.

In still another general aspect, the present invention provides an 11β-HSD1 inhibitor comprising the amide compound of the formula 1, or the pharmaceutically acceptable salt, solvate, hydrate, prodrug, racemate, or stereoisomer thereof. Moreover, the present invention provides a pharmaceutical composition for treating and/or preventing diseases caused, mediated, and/or spread by the high cortisol level, the pharmaceutical composition comprising the amide compound of the formula 1, or the pharmaceutically acceptable salt, solvate, hydrate, prodrug, racemate, or stereoisomer thereof, and a pharmaceutically acceptable carrier.

In still another general aspect, the present invention provides a pharmaceutical composition for treating and/or preventing metabolic syndromes, diabetes, especially non-insulin dependent diabetes, prediabetes, insulin tolerance, low glucose tolerance, hyperglycemia, obesity and weight-related disorders, dyslipidemia, hyperlipidemia, hypertriglyceridemia, hypercholesterolemia, lipid disorders such as low HDL levels or high LDL levels, glaucoma, osteoporosis, cognitive disorders, glucocorticoid-mediated effects on neuron functions, such as anxiety or depression, neurodegenerative diseases, immune disorders such as tuberculosis, leprosy or psoriasis, hypertension, atherosclerosis and complications thereof, vessel restenosis, cardiovascular disease, pancreatitis, retinitis, neuropathy, or nephropathy, the pharmaceutical composition comprising the amide compound of the formula 1, or the pharmaceutically acceptable salt, solvate, hydrate, prodrug, racemate, or stereoisomer thereof, and a pharmaceutically acceptable carrier.

The amide compound of the present invention may be generally used as a free acid or a free base. Unlike this, the amide compound of the present invention may be used as an acid or base addition salt. An acid addition salt of a free amino compound of the present invention may be prepared by the method well known to the art, and formed from an organic acid and an inorganic acid. Suitable examples of the organic acid includes maleic acid, fumaric acid, benzoic acid, ascorbic acid, succinic acid, methanesulfonic acid, acetic acid, trifluoroacetic acid, oxalic acid, propionic acid, tartaric acid, salicylic acid, citric acid, gluconic acid, lactic acid, mandelic acid, cinnamic acid, aspartic acid, stearic acid, palmitic acid, glycolic acid, glutamic acid, and benzenesulfonic acid. Suitable examples of the inorganic acid include hydrochloric acid, hydrobromide acid, sulfuric acid, phosphoric acid and nitric acid. Examples of the base addition salt include salts formed together with carboxylate anions, and include salts formed together with organic and inorganic cations, for example, cations selected from alkaline and alkaline earth metals (e.g., lithium, sodium, potassium, magnesium, barium and calcium), and ammonium ions and substituted derivatives thereof (e.g., dibenzylammonium, benzylammonium, 2-hydroxyethylammonium, or the like). Therefore, the term, "pharmaceutically acceptable salt" in the formula 1 means to include any acceptable salt types.

Further, a prodrug may be included in the scope of the present invention. The prodrug, when administered to the patient, is a covalently bound carrier in which the compound of the formula 1 was released in vivo. The prodrug is generally prepared by modifying a functional group, and this modification is cut by conventional operations or in the body, to generate a parent compound. The prodrug, when administered to the patient, is cut to form a hydroxy, amine, or sulfuhydryl group, and thus the prodrug includes the compound of the present invention bound to a group forming the hydroxy, amine, or sulfuhydryl group. Therefore, representative examples of the prodrug include, but are not limited to, acetate, formate and benzoate derivatives of alcohol and amine functional groups of the compounds of the formula 1. Furthermore, esters such as methyl ester, ethyl ester, or the like may be used for the carboxylic acid group (—COOH).

As for a stereoisomer, the compound of the formula 1 may have a chiral center, and may exist as a racemate, a racemic mixture, and an individual enantiomer or diastereomer. These isomers may be separated or degraded by a conventional method, and any certain isomer may be obtained by a conventional synthetic method or a stereospecific or asymmetric synthetic method. These all isomer types and mixtures thereof are included in the scope of the present invention.

Some of crystalline forms of the compound of the formula 1 may exist in a polymorphic form, and this is included in the present invention. Moreover, several of compounds of the formula 1 may form hydrates or solvates together with water or other organic solvents. These hydrates or solvates are also included in the scope of the present invention.

A pharmaceutical composition of the present invention may comprise, as an active ingredient, an amide compound represented by the formula 1, a pharmaceutically acceptable salt, a solvate, a hydrate, a prodrug, a racemate, or a stereoisomer thereof, and usual nontoxic pharmaceutically acceptable carriers, adjuvants, vehicles, or the like may be added thereto, to be formulated to a usual formulation in the pharmaceutical field, for example, an oral administration formulation such as a tablet, a capsule, a troche, a liquid, suspension, or the like, or a parenteral formulation.

The vehicles usable in the pharmaceutical composition of the present invention may include sweetener, binder, solvent, dissolution aid, wetting agent, emulsifier, appearance agent, adsorbent, disintegrant, antioxidant, preservatives, glidant, filler, fragrance, and the like. For example, lactose, dextrose, sucrose, mannitol, sorbitol, cellulose, glycine, silica, talc, stearic acid, sterin, magnesium stearate, magnesium aluminum silicate, starch, gelatin, tragacanth gum, alginic acid, sodium alginate, methyl cellulose, sodium carboxyl methyl cellulose, agar, water, ethanol, polyethylene glycol, polyvinyl pyrrolidone, sodium chloride, calcium chloride, orange essence, strawberry essence, vanilla fragrance, and the like, may be included.

Advantageous Effects

Novel picolinamide and pyrimidine-4-carboxamide compounds of the present invention, a pharmaceutically acceptable salt, a solvate, a hydrate, a prodrug, a racemate, or a stereoisomer thereof has selective inhibitory activity for human-derived 11β-HSD1 enzymes. Therefore, the compounds of the present invention has useful effects as agents for preventing, regulating, and treating diseases related to glucocorticoid regulation which are caused from activity of 11β-HSD1 enzymes, for example, metabolic syndromes such as, type 1 and type 2 diabetes, diabetes later complications, latent autoimmune diabetes adult (LADA), insulin tolerance syndromes, obesity, impaired glucose tolerance (IGT), impaired fasting glucose (IFG), damaged glucose tolerance, dyslipidemia, atherosclerosis, hypertension, etc.

MODE FOR INVENTION

The present invention as described above will be described in detail on the bases of the examples, experimental examples, and preparation examples below. However, these examples, experimental examples, and preparation examples are illustrated by was of example only and do not intend to limit the scope of the present invention.

EXAMPLES

Example 1

Synthesis of N-cyclohexyl-6-(piperidin-1-yl)picolinamide

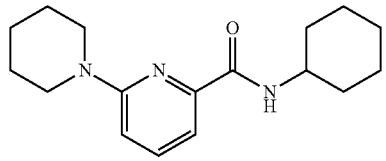 [SMILES: O=C(NC1CCCCC1)c1cccc(N2CCCCC2)n1]

Step 1: Synthesis of 6-bromo-N-cyclohexylpicolinamide (Intermediate 1)

After 6-bromopicolinic acid (500 mg, 2.48 mmol) was suspended in acetonitrile (25 ml), cyclohexylamine (0.34 ml, 2.97 mmol), N,N-diisopropylethylamine (0.65 ml, 3.72 mmol), and HBTU (1.13 g, 2.97 mmol) were sequentially added thereto, and then the resulting mixture was stirred at room temperature under nitrogen stream for 3 hours. The resulting reaction liquid was concentrated under reduced pressure, and then the residue thus obtained was subjected to MPLC (30% EtOAc/Hexanes), to obtain 624 mg of colorless oil (94%).

Step 2: Synthesis of N-cyclohexyl-6-(piperidin-1-yl)picolinamide 6-bromo-N-cyclohexylpicolinamide (55 mg, 0.194 mmol), piperidine (18 mg, 0.213 mmol), $Pd_2(dba)_3$ (3.5 mg, 0.00388 mmol), xantphos (6.7 mg, 0.0116 mmol), and sodium-tert-butoxide (27.4 mg, 0.285 mmol) were suspended in toluene (3 ml), and then stirred at 100° C. under nitrogen stream for 3 hours. The resulting reaction liquid was concentrated under reduced pressure, and then the residue thus obtained was subjected to MPLC (30% EtOAc/Hexanes), to obtain 51 mg of pale yellow oil (83%). MS (ESI): 288 $[M+H]^+$ The following examples were synthesized in the same method as the above example 1, by using the intermediate 1 and an appropriate amine start material.

| Examples | Structures | MS (ESI) |
|---|---|---|
| 2 | 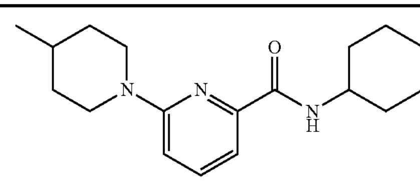 | 302 $[M + H]^+$ |
| 3 | 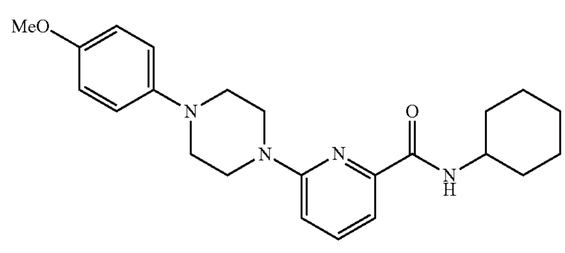 [SMILES: COc1ccc(N2CCN(c3cccc(C(=O)NC4CCCCC4)n3)CC2)cc1] | 395 $[M + H]^+$ |

| Examples | Structures | MS (ESI) |
|---|---|---|
| 4 | 4-Cl-C6H4-piperazine-pyridine-C(O)NH-cyclohexyl | 399 [M + H]⁺ |
| 5 | 4-F-C6H4-piperazine-pyridine-C(O)NH-cyclohexyl | 383 [M + H]⁺ |

Example 6

Synthesis of (4-methylpiperidin-1-yl) (6-(piperidin-1-yl)pyridin-2-yl)methanone

Step 1: Synthesis of (6-bromopyridin-2-yl)(4-methylpiperidin-1-yl)methanone (Intermediate 2)

After 6-bromopicolinic acid (500 mg, 2.48 mmol) was suspended in acetonitrile (25 ml), 4-methylpiperidine (0.44 ml, 3.72 mmol), N,N-diisopropylethylamine (0.65 ml, 3.72 mmol), and HBTU (1.13 g, 2.97 mmol) were sequentially added thereto, and then the resulting mixture was stirred at room temperature under nitrogen stream for 4 hours. The resulting reaction liquid was concentrated under reduced pressure, and then the residue thus obtained was subjected to MPLC (30% EtOAc/Hexanes), to obtain 677 mg of white solid (97%).

Step 2: Synthesis of (4-methylpiperidin-1-yl)(6-(piperidin-1-yl)pyridin-2-yl)methanone (6-bromopyridin-2-yl)(4-methylpiperidin-1-yl)methanone (40 mg, 0.142 mmol), piperidine (13 mg, 0.156 mmol), Pd$_2$(dba)$_3$ (2.6 mg, 0.00284 mmol), xantphos (5.0 mg, 0.00864 mmol), and sodium-tert-butoxide (20.0 mg, 0.208 mmol) were suspended in toluene (2 ml), and then stirred at 100° C. under nitrogen stream for 3 hours. The resulting reaction liquid was concentrated under reduced pressure, and then the residue thus obtained was subjected to MPLC (30% EtOAc/Hexanes), to obtain 31 mg of pale yellow oil (80%). MS (ESI): 288 [M+H]⁺

The following examples were synthesized in the same method as the above example 6, by using the intermediate 2 and an appropriate amine start material.

| Examples | Structures | MS (ESI) |
|---|---|---|
| 7 | 4-methylpiperidine-pyridine-C(O)-4-methylpiperidine | 302 [M + H]⁺ |
| 8 | 4-MeO-C6H4-piperazine-pyridine-C(O)-4-methylpiperidine | 395 [M + H]⁺ |

| Examples | Structures | MS (ESI) |
|---|---|---|
| 9 | 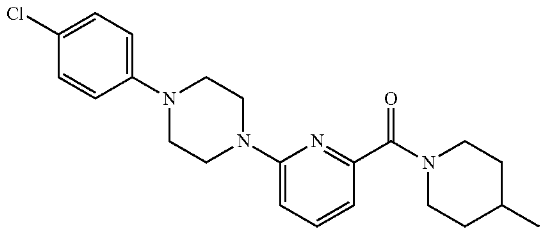 [SMILES: CC1CCN(C(=O)c2cccc(N3CCN(c4ccc(Cl)cc4)CC3)n2)CC1] | 399 [M + H]⁺ |
| 10 | 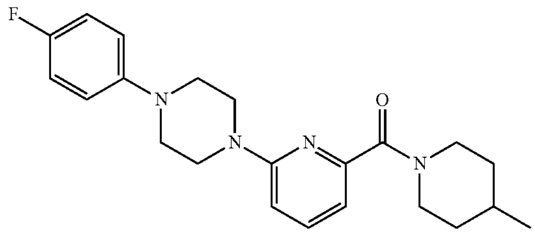 [SMILES: CC1CCN(C(=O)c2cccc(N3CCN(c4ccc(F)cc4)CC3)n2)CC1] | 383 [M + H]⁺ |

Example 11

Synthesis of (3,3-dimethylpiperidin-1-yl)(6-(4-(4-methoxyphenyl)piperazin-1-yl)pyridin-2-yl) methanone

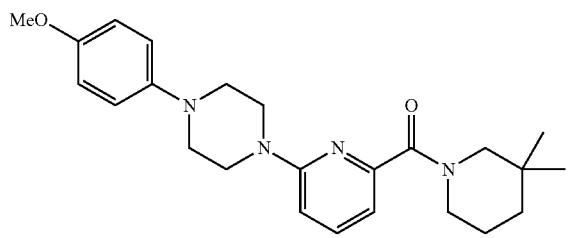 [SMILES: COc1ccc(N2CCN(c3cccc(C(=O)N4CCCC(C)(C)C4)n3)CC2)cc1]

Step 1: Synthesis of (6-bromopyridin-2-yl)(3,3-dimethylpiperidin-1-yl)methanone (Intermediate 3)

After 6-bromopicolinic acid (200 mg, 0.99 mmol) was suspended in acetonitrile (8 ml), 3,3-dimethylpiperidine (0.17 ml, 1.19 mmol), N,N-diisopropylethylamine (0.26 ml, 1.49 mmol), and HBTU (0.45 g, 1.19 mmol) were sequentially added thereto, and then the resulting mixture was stirred at room temperature under nitrogen stream for 3 hours.

Distilled water (15 ml) was added to the resulting reaction liquid, followed by extraction with MC (50 ml×2). The organic layer was dried over anhydrous magnesium sulfate, followed by filtration and concentration, and then the residue thus obtained was subjected to MPLC (20% EtOAc/Hexanes), to obtain 292 mg of colorless oil (99%).

Step 2: Synthesis of (3,3-dimethylpiperidin-1-yl)(6-(4-(4-methoxyphenyl)piperazin-1-yl)pyridin-2-yl) methanone (6-bromopyridin-2-yl)(3,3-dimethylpiperidin-1-yl) methanone (40 mg, 0.135 mmol), 1-(4-methoxyphenyl)piperazine (29 mg, 0.149 mmol), Pd₂(dba)₃ (2.5 mg, 0.00273 mmol), xantphos (4.7 mg, 0.00812 mmol), and sodium-tert-butoxide (19.0 mg, 0.198 mmol) were suspended in toluene (2 ml), and then stirred at 100° C. under nitrogen stream for 2 hours. The resulting reaction liquid was concentrated under reduced pressure, and then the residue thus obtained was subjected to MPLC (50% EtOAc/Hexanes), to obtain 47 mg of pale yellow solid (85%). MS (ESI): 409 [M+H]⁺

The following examples were synthesized in the same method as the above example 11, by using the intermediate 3 and an appropriate amine start material.

| Examples | Structures | MS (ESI) |
|---|---|---|
| 12 | 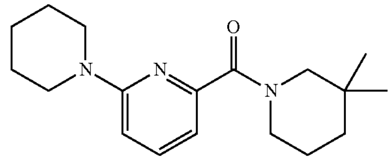 [SMILES: CC1(C)CCCN(C(=O)c2cccc(N3CCCCC3)n2)C1] | 302 [M + H]⁺ |
| 13 | 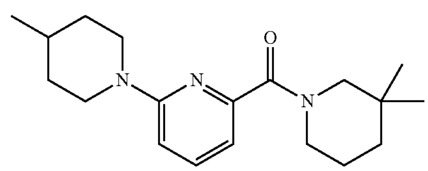 | 316 [M + H]⁺ |

| Examples | Structures | MS (ESI) |
|---|---|---|
| 14 | 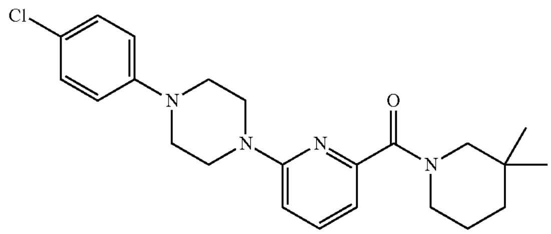 [SMILES: CC1(C)CCCN(C(=O)c2cccc(N3CCN(c4ccc(Cl)cc4)CC3)n2)C1] | 413 [M + H]⁺ |
| 15 | 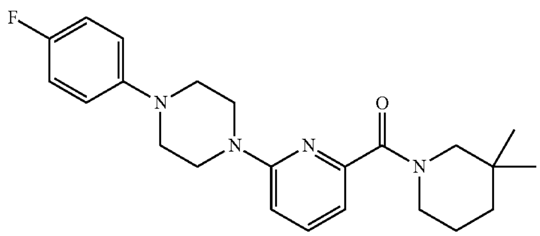 [SMILES: CC1(C)CCCN(C(=O)c2cccc(N3CCN(c4ccc(F)cc4)CC3)n2)C1] | 397 [M + H]⁺ |

Example 16

Synthesis of N-(adamantan-2-yl)-6-(4-(4-methoxyphenyl)piperazin-1-yl)picolinamide

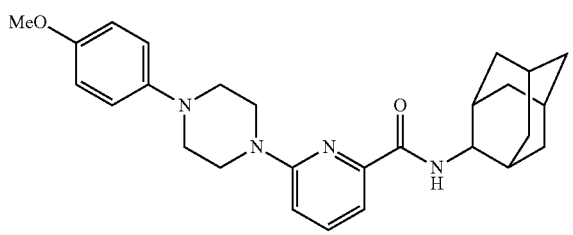 [SMILES: COc1ccc(N2CCN(c3cccc(C(=O)NC4C5CC6CC(C5)CC4C6)n3)CC2)cc1]

Step 1: Synthesis of N-(adamantan-2-yl)-6-bromopicolinamide (Intermediate, 4)

After 6-bromopicolinic acid (500 mg, 2.48 mmol) was suspended in acetonitrile (25 ml), 2-adamantylamine hydrochloride (558 mg, 2.97 mmol), N,N-diisopropylethylamine (1.30 ml, 7.44 mmol), and HBTU (1.13 g, 2.97 mmol) were sequentially added thereto, and then the resulting mixture was stirred at room temperature under nitrogen stream for 3 hours. The resulting reaction liquid was concentrated under reduced pressure, and then the residue thus obtained was subjected to MPLC (30% EtOAc/Hexanes), to obtain 602 mg of white solid (73%).

Step 2: Synthesis of N-(Adamantan-2-yl)-6-(4-(4-methoxyphenyl)piperazin-1-yl)picolinamide N-(adamantan-2-yl)-6-bromopicolinamide (55 mg, 0.194 mmol), 1-(4-methoxyphenyl)piperazine (41 mg, 0.213 mmol), Pd₂(dba)₃ (3.5 mg, 0.00388 mmol), xantphos (6.7 mg, 0.0116 mmol), and sodium-tert-butoxide (27.4 mg, 0.285 mmol) were suspended in toluene (3 ml), and then stirred at 100° C. under nitrogen stream for 3 hours. The resulting reaction liquid was concentrated under reduced pressure, and then the residue thus obtained was subjected to MPLC (30% EtOAc/Hexanes), to obtain 64 mg of pale yellow solid (84%). MS (ESI): 447 [M+H]⁺

The following examples were synthesized in the same method as the above example 16, by using the intermediate 4 and an appropriate amine start material.

| Examples | Structures | MS (ESI) |
|---|---|---|
| 17 | 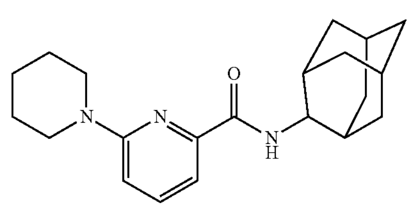 [SMILES: O=C(NC1C2CC3CC(C2)CC1C3)c1cccc(N2CCCCC2)n1] | 340 [M + H]⁺ |

| Examples | Structures | MS (ESI) |
|---|---|---|
| 18 | 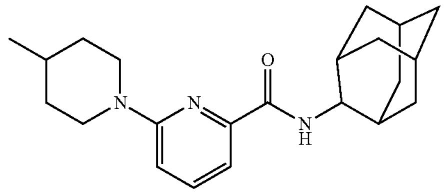 [SMILES: CC1CCN(c2cccc(C(=O)NC3C4CC5CC(C4)CC3C5)n2)CC1] | 354 [M + H]⁺ |
| 19 | 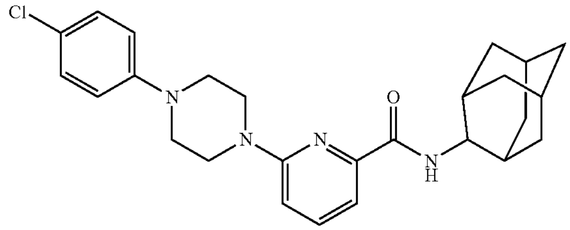 [SMILES: O=C(NC1C2CC3CC(C2)CC1C3)c1cccc(N2CCN(c3ccc(Cl)cc3)CC2)n1] | 451 [M + H]⁺ |
| 20 | 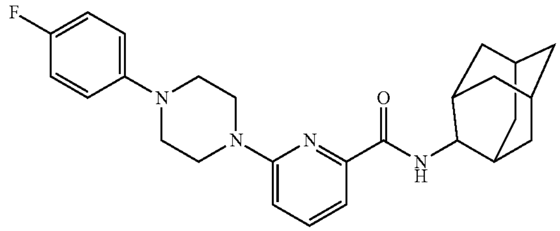 [SMILES: O=C(NC1C2CC3CC(C2)CC1C3)c1cccc(N2CCN(c3ccc(F)cc3)CC2)n1] | 435 [M + H]⁺ |
| 21 | 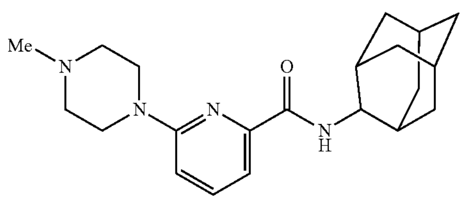 [SMILES: CN1CCN(c2cccc(C(=O)NC3C4CC5CC(C4)CC3C5)n2)CC1] | 355 [M + H]⁺ |
| 22 | 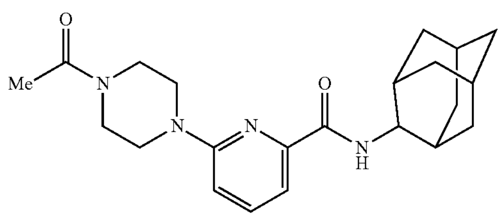 [SMILES: CC(=O)N1CCN(c2cccc(C(=O)NC3C4CC5CC(C4)CC3C5)n2)CC1] | 383 [M + H]⁺ |

Example 23

Synthesis of N-(adamantan-2-yl)-6-(piperazin-1-yl)picolinamide

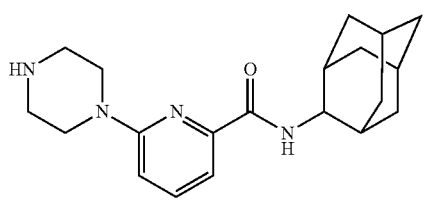 [SMILES: O=C(NC1C2CC3CC(C2)CC1C3)c1cccc(N2CCNCC2)n1]

Step 1: Synthesis of tert-butyl 4-(6-(adamantan-2-ylcarbamoyl)pyridin-2-yl)piperazine-1-carboxylate N-(adamantan-2-yl)-6-bromopicolinamide (80 mg, 0.239 mmol), tert-butyl piperazine-1-carboxylate (49 mg, 0.263 mmol), Pd$_2$(dba)$_3$ (4.4 mg, 0.005 mmol), xantphos (8.3 mg, 0.014 mmol), and sodium-tert-butoxide (34 mg, 0.359 mmol) were suspended in toluene (3 ml), and then stirred at 100° C. under nitrogen stream for 3 hours. The resulting reaction liquid was concentrated under reduced pressure, and then the residue thus obtained was subjected to MPLC (40% EtOAc/Hexanes), to obtain 86.8 mg of pale yellow oil (83%).

Step 2: Synthesis of N-(adamantan-2-yl)-6-(piperazin-1-yl)picolinamide

After tert-butyl 4-(6-(adamantan-2-ylcarbamoyl)pyridin-2-yl)piperazine-1-carboxylate (86 mg, 0.195 mmol) was dissolved in MC (2 ml), trifluoroacetic acid (2 ml) was added thereto, and then the resulting mixture was stirred at room temperature under nitrogen stream for 4 hours. The resulting reaction liquid was concentrated under reduced pressure, followed by addition of a saturated aqueous NaHCO$_3$ solution (10 ml), and then extracted with MC (15 ml×2). The organic layer was dried over anhydrous magnesium sulfate, followed by filtration and concentration, and then the residue thus obtained was subjected to MPLC (10% MeOH/MC), to obtain 65 mg of colorless oil (98%). MS (ESI): 341 [M+H]$^+$ Example 24

Synthesis of N-(adamantan-2-yl)-6-(4-(2-hydroxyethyl)piperazin-1-yl)picolinamide

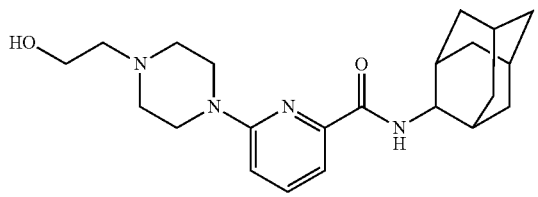 [SMILES: O=C(NC1C2CC3CC(C2)CC1C3)c1cccc(N2CCN(CCO)CC2)n1]

After N-(adamantan-2-yl)-6-(piperazin-1-yl)picolinamide (34 mg, 0.100 mmol) was dissolved in DMF (2 ml), 2-bromoethanol (19 mg, 0.150 mmol) and potassium carbonate (41 mg, 0.300 mmol) were added thereto, and then the resulting mixture was stirred at 100° C. under nitrogen stream for 18 hours. The resulting reaction liquid was concentrated under reduced pressure, and then the residue thus obtained was subjected to MPLC (10% MeOH/MC), to obtain 37 mg of colorless oil (96%). MS (ESI): 385 [M+H]$^+$ Example 25

Synthesis of methyl 3-(4-(6-(adamantan-2-ylcarbamoyl)pyridin-2-yl)piperazin-1-yl)propanoate

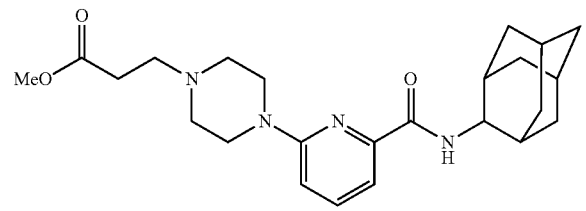 [SMILES: COC(=O)CCN1CCN(c2cccc(C(=O)NC3C4CC5CC(C4)CC3C5)n2)CC1]

After N-(adamantan-2-yl)-6-(piperazin-1-yl)picolinamide (34 mg, 0.100 mmol) was dissolved in DMF (2 ml), 3-bromopropanoic acid methyl ester (25 mg, 0.150 mmol) and potassium carbonate (41 mg, 0.300 mmol) were added thereto, and then the resulting mixture was stirred at 100° C. under nitrogen stream for 24 hours. The resulting reaction liquid was filtered and concentrated under reduced pressure, and then the residue thus obtained was subjected to MPLC (60% EtOAc/Hexanes), to obtain 41 mg of white solid (96%). MS (ESI): 427 [M+H]$^+$ Example 26

Synthesis of (3-(4-(6-(adamantan-2-ylcarbamoyl)pyridin-2-yl)piperazin-1-yl)propanoic acid

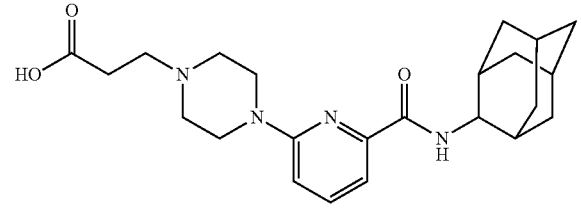 [SMILES: O=C(O)CCN1CCN(c2cccc(C(=O)NC3C4CC5CC(C4)CC3C5)n2)CC1]

Methyl 3-(4-(6-(adamantan-2-ylcarbamoyl)pyridin-2-yl)piperazin-1-yl)propanoate (43 mg, 0.101 mmol) was added into 4N aqueous HCl solution (2 ml), and heated at reflux for 2 hours. The resulting reaction liquid was concentrated under reduced pressure, and then neutralized by slow addition of a saturated aqueous NaHCO$_3$ solution, followed by extraction with a mixture solution (10 ml×2) of THF:MC=4:1. The organic layer was dried over anhydrous magnesium sulfate, followed by filtration and concentration, and then the residue thus obtained was subjected to MPLC (10% MeOH/MC), to obtain 27 mg of pale yellow oil (65%). MS (ESI): 413 [M+H]$^+$ Example 27

Synthesis of N-(adamantan-2-yl)-6-(4-(3-amino-3-oxopropyl)piperazin-1-yl)picolinamide

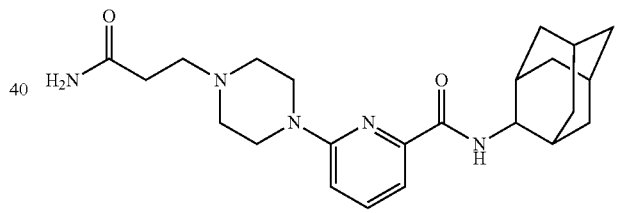

7N ammonia in methanol (2 ml) was added into methyl 3-(4-(6-(adamantan-2-ylcarbamoyl)pyridin-2-yl)piperazin-1-yl)propanoate (94 mg, 0.22 mmol), and then the resulting mixture was stirred at room temperature for 48 hours. The resulting reaction liquid was concentrated under reduced pressure, and then the residue thus obtained was subjected to MPLC (10% MeOH/MC), to obtain 54 mg of colorless oil (60%). MS (ESI): 412 [M+H]

Example 28

Synthesis of (S)-(6-(piperidin-1-yl)pyridin-2-yl)(3-(2-(trifluoromethyl)phenyl)pyrrolidin-1-yl)methanone

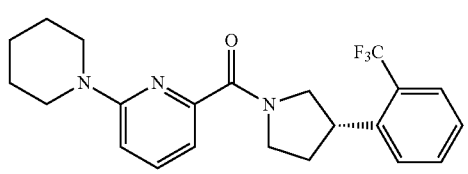 [SMILES: O=C(c1cccc(N2CCCCC2)n1)N1CC[C@@H](c2ccccc2C(F)(F)F)C1]

Step 1: Synthesis of (S)-(6-bromopyridin-2-yl)(3-(2-(trifluoromethyl)phenyl)pyrrolidin-1-yl)methanone (Intermediate 5)

After 6-bromopicolinic acid (430 mg, 2.13 mmol) was suspended in acetonitrile (25 ml), (S)-3-(2-(trifluoromethyl)phenyl)pyrrolidine (503 mg, 2.34 mmol), N,N-diisopropylethylamine (0.56 ml, 3.20 mmol), and HBTU (969 mg, 2.56 mmol) were sequentially added thereto, and then the resulting mixture was stirred at room temperature under nitrogen stream for 3 hours. The resulting reaction liquid was concentrated under reduced pressure, and then the residue thus obtained was subjected to MPLC (40% EtOAc/Hexanes), to obtain 765 mg of white solid (90%).

Step 2: Synthesis of (S)-(6-(piperidin-1-yl)pyridin-2-yl)(3-(2-(trifluoromethyl)phenyl)pyrrolidin-1-yl)methanone (S)-(6-Bromopyridin-2-yl)(3-(2-(trifluoromethyl)phenyl)pyrrolidin-1-yl)methanone (60 mg, 0.150 mmol), piperidine (15 mg, 0.180 mmol), $Pd_2(dba)_3$ (3 mg, 0.003 mmol), xantphos (5 mg, 0.009 mmol), and sodium-tert-butoxide (22 mg, 0.225 mmol) were suspended in toluene (3 ml), and then stirred at 100° C. under nitrogen stream for 3 hours. A saturated aqueous ammonium chloride solution (15 ml) was added to the resulting reaction liquid, followed by extraction with MC (15 ml×2). The organic layer was dried over anhydrous magnesium sulfate, followed by filtration and concentration, and then the residue thus obtained was subjected to MPLC (50% EtOAc/Hexanes), to obtain 39 mg of pale yellow oil (64%). MS (ESI): 404 $[M+H]^+$

Example 29

Synthesis of (6-(piperidin-1-yl)pyridin-2-yl)(2-(pyridin-3-yl)piperidin-1-yl)methanone

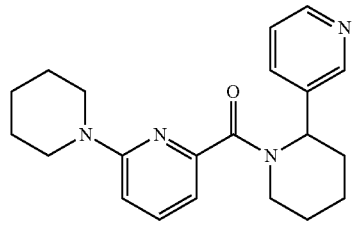 [SMILES: O=C(c1cccc(N2CCCCC2)n1)N1CCCCC1c1cccnc1]

Step 1: Synthesis of (6-bromopyridin-2-yl)(2-(pyridin-3-yl)piperidin-1-yl)methanone (Intermediate 6)

After 6-bromopicolinic acid (565 mg, 2.80 mmol) was suspended in acetonitrile (25 ml), anabasine (499 mg, 3.07 mmol), N,N-diisopropylethylamine (0.73 ml, 4.20 mmol), and HBTU (1.27 g, 3.36 mmol) were sequentially added thereto, and then the resulting mixture was stirred at room temperature under nitrogen stream for 3 hours. The resulting reaction liquid was concentrated under reduced pressure, and then the residue thus obtained was subjected to MPLC (40% EtOAc/Hexanes), to obtain 255 mg of white solid (26%).

Step 2: Synthesis of (6-(piperidin-1-yl)pyridin-2-yl)(2-(pyridin-3-yl)piperidin-1-yl)methanone (6-bromopyridin-2-yl)(2-(pyridin-3-yl)piperidin-1-yl)methanone (60 mg, 0.173 mmol), piperidine (18 mg, 0.208 mmol), $Pd_2(dba)_3$ (3 mg, 0.003 mmol), xantphos (6 mg, 0.010 mmol), and sodium-tert-butoxide (25 mg, 0.260 mmol) were suspended in toluene (3 ml), and then stirred at 100° C. under nitrogen stream for 3 hours. A saturated aqueous ammonium chloride solution of (15 ml) was added to the resulting reaction liquid, followed by extraction with MC (15 ml×2). The organic layer was dried over anhydrous magnesium sulfate, followed by filtration and concentration, and then the residue thus obtained was subjected to MPLC (90% EtOAc/Hexanes), to obtain 39 mg of pale yellow oil (64%). MS (ESI): 351 $[M+H]^+$

Example 30

Synthesis of (4-hydroxy-4-(trifluoromethyl)piperidin-1-yl)(6-(piperidin-1-yl)pyridin-2-yl)methanone

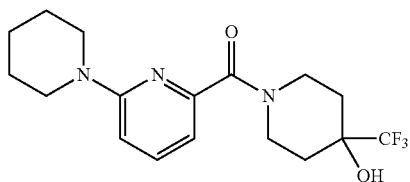 [SMILES: O=C(c1cccc(N2CCCCC2)n1)N1CCC(O)(C(F)(F)F)CC1]

Step 1: Synthesis of 1-(6-bromopicolinoyl)piperidin-4-one

After 6-bromopicolinic acid (600 mg, 2.97 mmol) was suspended in acetonitrile (25 ml), 4-piperidone monohydrate hydrochloride (500 mg, 3.27 mmol), N,N-diisopropylethylamine (1 ml, 7.43 mmol), and HBTU (1.1 g, 3.56 mmol) were sequentially added thereto, and then the resulting mixture was stirred at room temperature under nitrogen stream for 13 hours. The resulting reaction liquid was concentrated under reduced pressure, followed by addition of MC (50 ml), and then washed with distilled water. The organic layer was dried over anhydrous magnesium sulfate, followed by filtration and concentration, and then the residue thus obtained was subjected to MPLC (3% MeOH/MC), to obtain 752 mg of yellow solid (89%).

Step 2: Synthesis of (6-bromopyridin-2-yl)(4-hydroxy-4-(trifluoromethyl)piperidin-1-yl)methanone (Intermediate 7)

After 1-(6-bromopicolinoyl)piperidin-4-one (100 mg, 0.353 mmol) was dissolved in THF (1.5 ml), trimethyl(trifluoromethyl)silane (0.5M solution in THF, 1.4 ml, 0.706 mmol) and tetrabutylammonium fluoride (1.0M solution in THF, 0.74 ml, 0.741 mmol) were sequentially added thereto at 0° C., and then the resulting mixture was stirred at room temperature for 13 hours. A saturated aqueous ammonium chloride solution (0.6 ml) was added to the resulting reaction liquid, and then the resulting mixture was stirred for 10 minutes, followed by extraction with MC (10 ml×2). The organic layer was dried over anhydrous magnesium sulfate, followed by filtration and concentration, and then the residue thus obtained was subjected to MPLC (3% MeOH/MC), to obtain 120 mg of white solid (97%).

Step 3: Synthesis of (4-hydroxy-4-(trifluoromethyl)piperidin-1-yl)(6-(piperidin-1-yl)pyridin-2-yl)methanone (6-Bromopyridin-2-yl)(4-hydroxy-4-(trifluoromethyl)piperidin-1-yl)methanone (61 mg, 0.172 mmol), piperidine (0.02 ml, 0.189 mmol), Pd$_2$(dba)$_3$ (3 mg, 0.003 mmol), xantphos (6 mg, 0.010 mmol), and sodium-tert-butoxide (25 mg, 0.258 mmol) were suspended in toluene (1.5 ml), and then stirred at 100° C. under nitrogen stream for 2 hours. Distilled water (5 ml) was added to the resulting reaction liquid, followed by extraction with 5% MeOH/MC (10 ml×2). The organic layer was dried over anhydrous magnesium sulfate, followed by filtration and concentration, and then the residue thus obtained was subjected to MPLC (50% EtOAc/Hexanes), to obtain 37 mg of yellow solid (61%). MS (ESI): 358 [M+H]$^+$ Example 31

Synthesis of (3-hydroxy-3-(trifluoromethyl)piperidin-1-yl)(6-(piperidin-1-yl)pyridin-2-yl)methanone

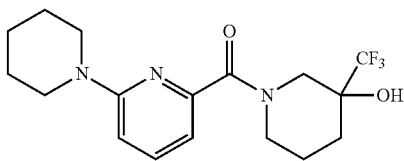 [SMILES: O=C(c1cccc(N2CCCCC2)n1)N1CCCC(O)(C(F)(F)F)C1]

Step 1: Synthesis of tert-butyl 3-(trifluoromethyl)-3-hydroxypiperidine-1-carboxylate After tert-butyl 3-oxopiperidine-1-carboxylate (1 g, 5.02 mmol) was dissolved in THF (20 ml), and then trimethyl (trifluoromethyl)silane (0.5M solution in THF, 20 ml, 10.0 mmol) and tetrabutylammonium fluoride (1.0M solution in THF, 10.5 ml, 10.5 mmol) were sequentially added thereto at 0° C., followed by stirring at room temperature for 2 hours. A saturated aqueous ammonium chloride solution (5 ml) was added to the resulting reaction liquid, followed by stirring for 20 minutes. The resulting reaction liquid was concentrated under reduced pressure, and then MC (100 ml) was added to the residue thus obtained, followed by washing with distilled water (20 ml). The organic layer was dried over anhydrous magnesium sulfate, followed by filtration and concentration, and then the residue thus obtained was subjected to MPLC (20% EtOAc/Hexanes), to obtain 709 mg of white solid (53%).

Step 2: Synthesis of (6-bromopyridin-2-yl)(3-hydroxy-3-(trifluoromethyl)piperidin-1-yl)methanone (Intermediate 8)

After tert-butyl 3-(trifluoromethyl)-3-hydroxypiperidine-1-carboxylate (709 mg, 2.63 mmol) was dissolved in THF (10 ml), followed by addition of HCl (2.0M solution in diethyl ether, 30 ml), and then the resulting mixture was stirred at room temperature for 2 hours. The resulting reaction liquid was concentrated under reduced pressure and dried under vacuum, and then the residue thus obtained was dissolved in acetonitrile (30 ml). 6-Bromopicolinic acid (638 mg, 3.16 mmol) was added thereto, and cooled to 0° C. N,N-Diisopropylethylamine (1.1 ml, 6.58 mmol) and HBTU (1.2 g, 3.16 mmol) were sequentially added thereto, and then the resulting mixture was stirred at room temperature under nitrogen stream for 20 hours. The resulting reaction liquid was concentrated under reduced pressure, followed by addition of MC (50 ml), and then washed with distilled water. The organic layer was dried over anhydrous magnesium sulfate, followed by filtration and concentration, and then the residue thus obtained was subjected to MPLC (3% MeOH/MC), to obtain 800 mg of white solid (86%).

Step 3: Synthesis of (3-hydroxy-3-(trifluoromethyl) piperidin-1-yl)(6-(piperidin-1-yl)pyridin-2-yl)methanone After (6-bromopyridin-2-yl)(3-hydroxy-3-(trifluoromethyl)piperidin-1-yl)methanone (60 mg, 0.170 mmol) was suspended in acetonitrile (2 ml), piperidine (0.13 ml, 1.36 mmol) and triethylamine (0.05 ml, 0.340 mmol) were added thereto, and then the resulting mixture was stirred at 100° C. for 14 hours. The resulting reaction liquid was concentrated under reduced pressure, and then the residue thus obtained was subjected to MPLC (50% EtOAc/Hexanes), to obtain 53 mg of white solid (87%). MS (ESI): 358 [M+H]$^+$ The following examples were synthesized in the same method as the above examples 28, 29, 30, or 31, by using the intermediates 5, 6, 7, or 8 and 1-(4-chlorophenyl)piperazine.

| Examples | Structures | MS (ESI) |
|---|---|---|
| 32 | ![structure] | 515 [M + H]$^+$ |
| 33 | ![structure] | 462 [M + H]$^+$ |

| Examples | Structures | MS (ESI) |
|---|---|---|
| 34 | 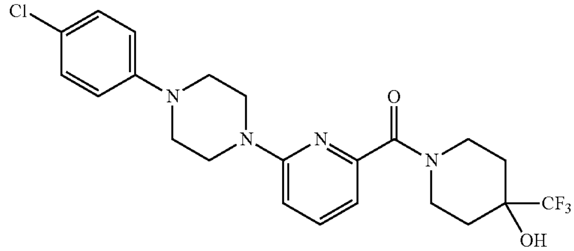 [SMILES: O=C(c1cccc(N2CCN(c3ccc(Cl)cc3)CC2)n1)N1CCC(O)(C(F)(F)F)CC1] | 469 [M + H]⁺ |
| 35 | 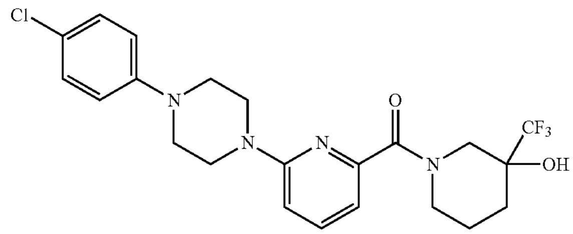 [SMILES: O=C(c1cccc(N2CCN(c3ccc(Cl)cc3)CC2)n1)N1CCCC(O)(C(F)(F)F)C1] | 469 [M + H]⁺ |

Example 36

Synthesis of (N-((E)-5-hydroxyadamantan-2-yl)-6-(piperidin-1-yl)picolinamide)

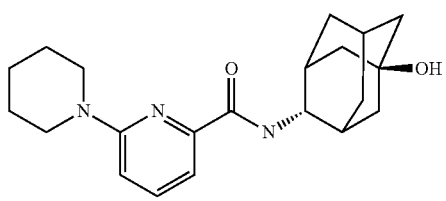 [SMILES: O=C(N[C@H]1C2CC3CC1C[C@](O)(C3)C2)c1cccc(N2CCCCC2)n1]

Step 1: Synthesis of 6-bromo-N-((E)-5-hydroxyadamantan-2-yl)picolinamide (Intermediate 9)

After 6-bromopicolinic acid (17.5 g, 87 mmol) was suspended in acetonitrile (500 ml), 5-hydroxy-2-adamantanemine (2:1 E/Z mixture, 17.4 g, 104 mmol), N,N-diisopropylethylamine (18.1 ml, 104 mmol), and HBTU (39.4 g, 104 mmol) were sequentially added thereto, and then the resulting mixture was stirred at room temperature under nitrogen stream for 15 hours. The resulting reaction liquid was concentrated under reduced pressure, followed by addition of distilled water (200 ml), and then extracted with 10% MeOH/MC (300 ml×2). The organic layer was dried over anhydrous sodium sulfate, followed by filtration and concentration, and then the residue thus obtained was subjected to MPLC (70% EtOAc/Hexanes), to obtain 18.4 g of white solid (60%).

Step 2: Synthesis of N-((E)-5-hydroxyadamantan-2-yl)-6-(piperidin-1-yl)picolinamide Method A: 6-Bromo-N-((E)-5-hydroxyadamantan-2-yl) picolinamide (60 mg, 0.171 mmol), piperidine (17 mg, 0.205 mmol), Pd₂(dba)₃ (3 mg, 0.003 mmol), xantphos (6 mg, 0.010 mmol), and sodium-tert-butoxide (25 mg, 0.257 mmol) were suspended in toluene (3 ml), and then the resulting liquid was stirred at 100° C. under nitrogen stream for 4 hours. A saturated aqueous ammonium chloride solution (15 ml) was added to the resulting reaction liquid, followed by extraction with MC (15 ml×2). The organic layer was dried over anhydrous sodium sulfate, followed by filtration and concentration, and then the residue thus obtained was subjected to MPLC (4% MeOH/MC), to obtain 44 mg of white solid (73%).

Method B: 6-Bromo-N-((E)-5-hydroxyadamantan-2-yl) picolinamide (50 mg, 0.142 mmol) was dissolved in acetonitrile (1 ml), followed by addition of piperidine (48 mg, 0.568 mmol) and triethylamine (0.04 ml, 0.284 mmol), and then the resulting liquid was subjected to microwave irradiation at 150° C. for 2 hours. The resulting reaction liquid was concentrated under reduced pressure, followed by addition of a saturated aqueous ammonium chloride solution (10 ml), and extracted with MC (20 ml×2). The organic layer was dried over anhydrous sodium sulfate, followed by filtration and concentration, and then the residue thus obtained was subjected to MPLC (4% MeOH/MC), to obtain 32 mg of white solid (63%). MS (ESI): 356 [M+H]⁺

The following examples were synthesized in the same method as the above example 36, by using the intermediate 9 and an appropriate amine start material.

| Examples | Structures | MS (ESI) | Methods |
| --- | --- | --- | --- |
| 37 | 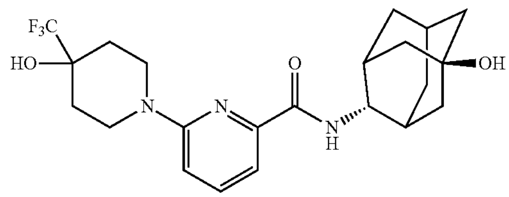 [SMILES: O=C(N[C@H]1C2CC3CC1C[C@](O)(C3)C2)c1cccc(N2CCC(O)(C(F)(F)F)CC2)n1] | 440 [M + H]⁺ | B |
| 38 | 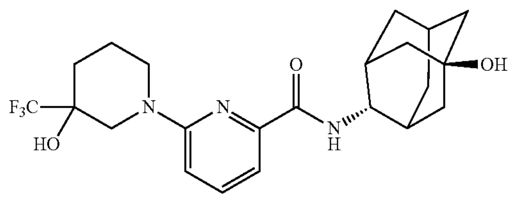 [SMILES: O=C(N[C@H]1C2CC3CC1C[C@](O)(C3)C2)c1cccc(N2CCCC(O)(C(F)(F)F)C2)n1] | 440 [M + H]⁺ | B |
| 39 | 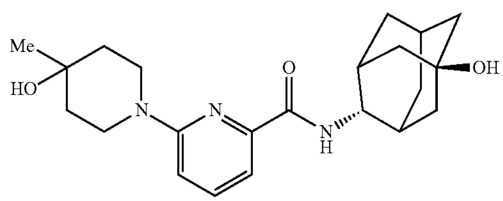 [SMILES: CC1(O)CCN(c2cccc(C(=O)N[C@H]3C4CC5CC3C[C@](O)(C5)C4)n2)CC1] | 793 [2M + Na]⁺ | B |
| 40 | 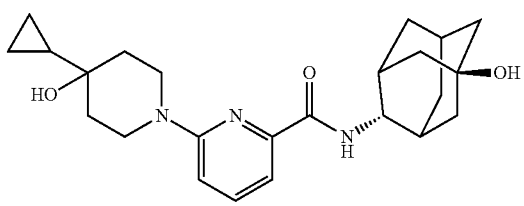 [SMILES: O=C(N[C@H]1C2CC3CC1C[C@](O)(C3)C2)c1cccc(N2CCC(O)(C3CC3)CC2)n1] | 412 [M + H]⁺ | B |
| 41 | 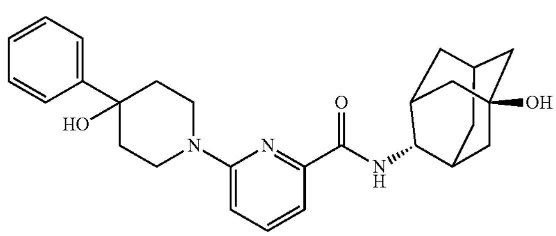 [SMILES: O=C(N[C@H]1C2CC3CC1C[C@](O)(C3)C2)c1cccc(N2CCC(O)(c3ccccc3)CC2)n1] | 448 [M + H]⁺ | B |
| 42 | 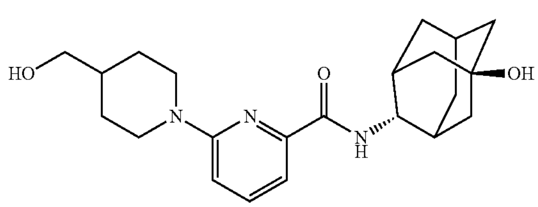 [SMILES: O=C(N[C@H]1C2CC3CC1C[C@](O)(C3)C2)c1cccc(N2CCC(CO)CC2)n1] | 386 [M + H]⁺ | B |
| 43 | 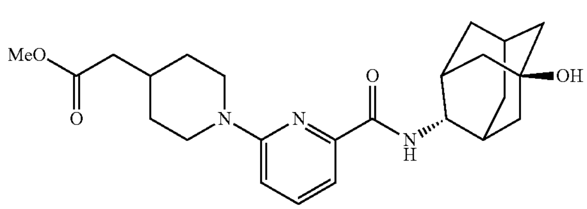 [SMILES: COC(=O)CC1CCN(c2cccc(C(=O)N[C@H]3C4CC5CC3C[C@](O)(C5)C4)n2)CC1] | 428 [M + H]⁺ | B |

-continued
| Examples | Structures | MS (ESI) | Methods |
|---|---|---|---|
| 44 | 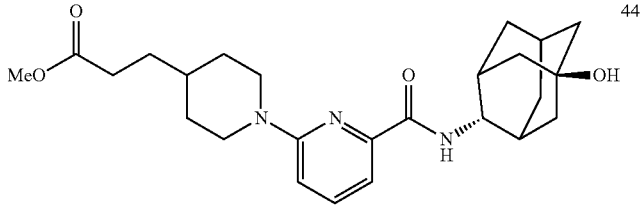 | 442 [M + H]<sup>+</sup> | B |
| 45 | 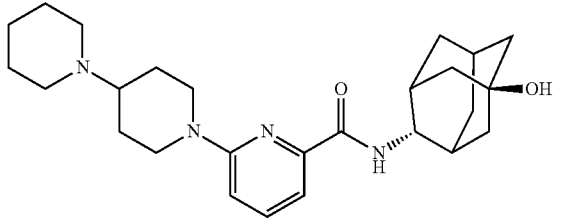 [SMILES: O=C(N[C@H]1C2CC3CC1C[C@](O)(C3)C2)c1cccc(N2CCC(N3CCCCC3)CC2)n1] | 439 [M + H]<sup>+</sup> | A |
| 46 | 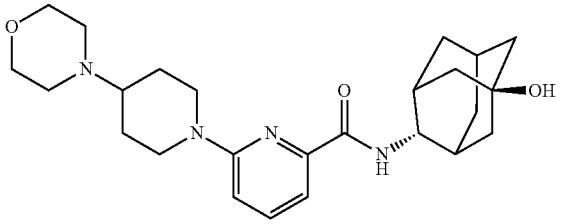 [SMILES: O=C(N[C@H]1C2CC3CC1C[C@](O)(C3)C2)c1cccc(N2CCC(N3CCOCC3)CC2)n1] | 441 [M + H]<sup>+</sup> | A |
| 47 | 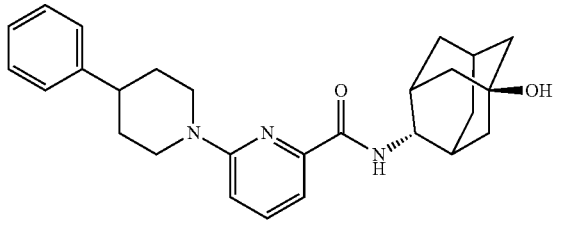 | 432 [M + H]<sup>+</sup> | A |
| 48 | 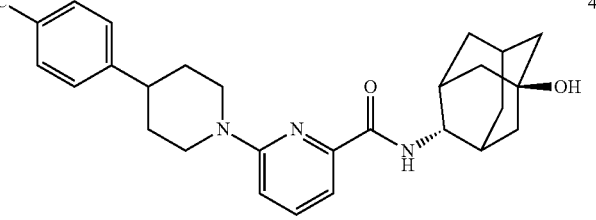 | 457 [M + H]<sup>+</sup> | B |
| 49 | 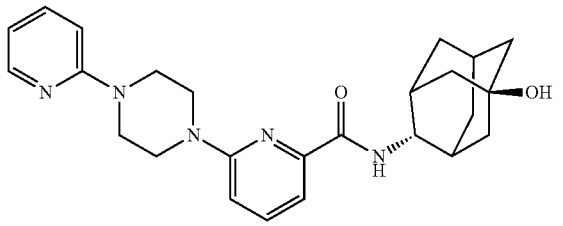 [SMILES: O=C(N[C@H]1C2CC3CC1C[C@](O)(C3)C2)c1cccc(N2CCC(c3ccccc3)CC2)n1] | 434 [M + H]<sup>+</sup> | A |

-continued

| Examples | Structures | MS (ESI) | Methods |
|---|---|---|---|
| 50 | 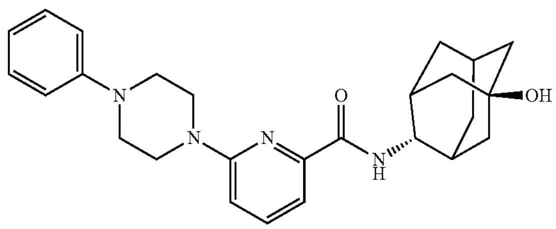 [SMILES: O=C(N[C@H]1C2CC3CC1C[C@](O)(C3)C2)c1cccc(N2CCN(c3ccccc3)CC2)n1] | 433 [M + H]⁺ | A |
| 51 | 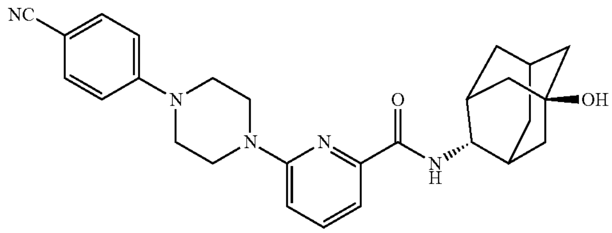 | 458 [M + H]⁺ | A |
| 52 | 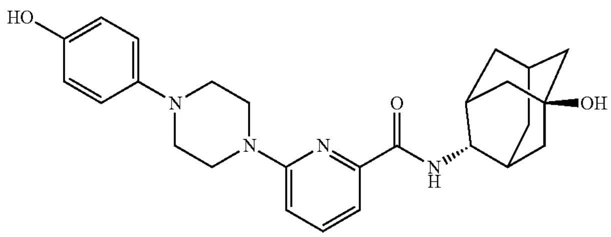 [SMILES: N#Cc1ccc(N2CCN(c3cccc(C(=O)N[C@H]4C5CC6CC4C[C@](O)(C6)C5)n3)CC2)cc1] | 449 [M + H]⁺ | B |
| 53 | 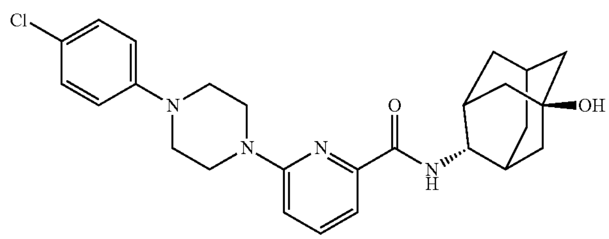 [SMILES: O=C(N[C@H]1C2CC3CC1C[C@](O)(C3)C2)c1cccc(N2CCN(c3ccc(Cl)cc3)CC2)n1] | 467 [M + H]⁺ | A |
| 54 | 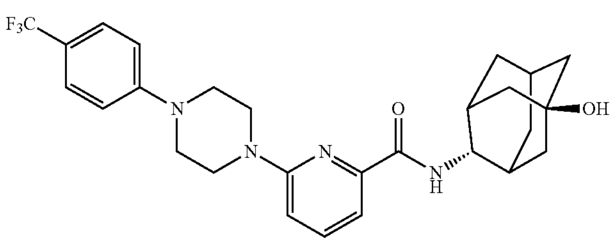 | 501 [M + H]⁺ | A |
| 55 | 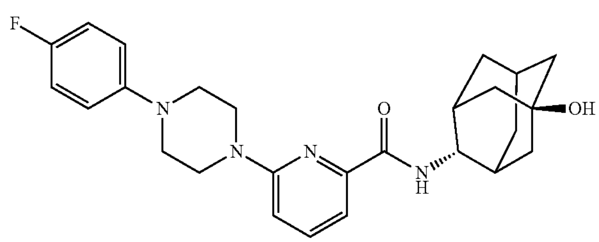 [SMILES: O=C(N[C@H]1C2CC3CC1C[C@](O)(C3)C2)c1cccc(N2CCN(c3ccc(F)cc3)CC2)n1] | 451 [M + H]⁺ | A |

-continued
| Examples | Structures | MS (ESI) | Methods |
|---|---|---|---|
| 56 | 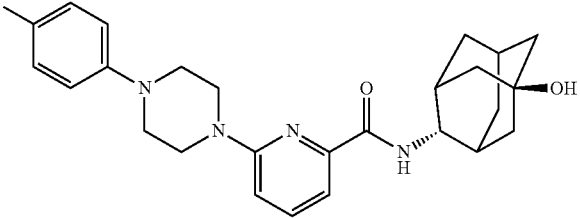 | 447 [M + H]+ | A |
| 57 | 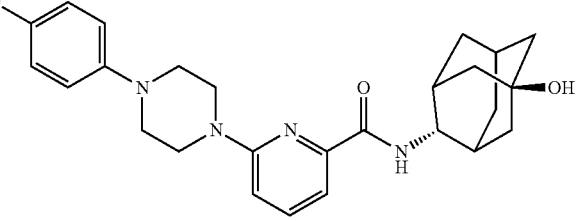 | 463 [M + H]+ | A |
| 58 | 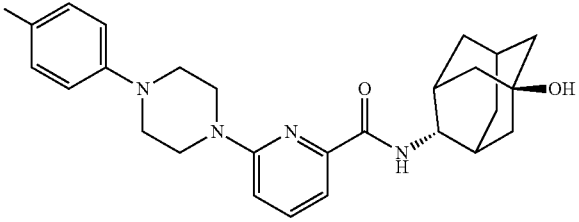 | 478 [M + H]+ | A |
| 59 | 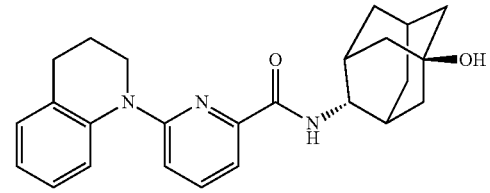 [SMILES: O=C(N[C@H]1C2CC3CC1C[C@](O)(C3)C2)c1cccc(N2CCCc3ccccc32)n1] | 829 [2M + Na]+ | A |
| 60 | 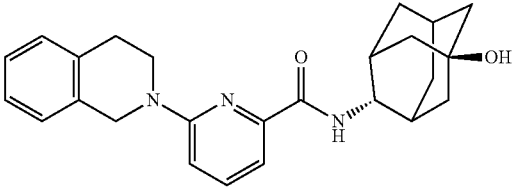 [SMILES: O=C(N[C@H]1C2CC3CC1C[C@](O)(C3)C2)c1cccc(N2CCc3ccccc3C2)n1] | 829 [2M + Na]+ | A |
| 61 | 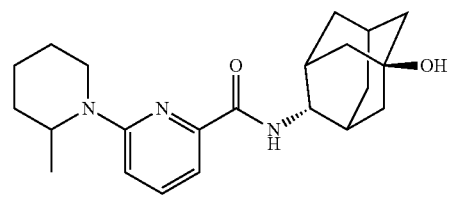 [SMILES: CC1CCCCN1c1cccc(C(=O)N[C@H]2C3CC4CC2C[C@](O)(C4)C3)n1] | 370 [M + H]+ | A |
| 62 | 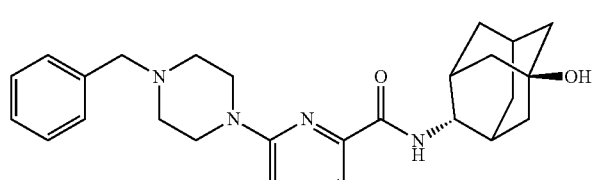 | 447 [M + H]+ | A |

Example 63

Synthesis of N-((E)-5-hydroxyadamantan-2-yl)-6-(piperazin-1-yl)picolinamide

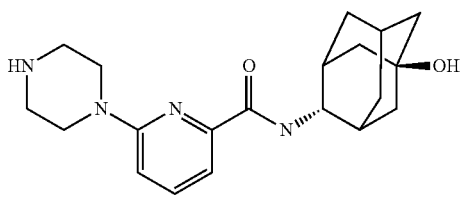 [SMILES: O=C(N[C@H]1C2CC3CC1C[C@](O)(C3)C2)c1cccc(N2CCNCC2)n1]

After 6-(4-benzylpiperazin-1-yl)-N-((E)-5-hydroxyadamantan-2-yl)picolinamide (150 mg, 0.336 mmol) was dissolved in MeOH (5 ml), followed by addition of Pd (10 wt % on activated carbon, 50 mg), and then the resulting mixture was stirred at room temperature under hydrogen stream for 15 hours. The resulting reaction liquid was filtered, and then concentrated under reduced pressure. The residue thus obtained was subjected to recrystallization (MC/Et$_2$O), to obtain 114 mg of white solid (95%). MS (ESI): 357 [M+H]$^+$

Example 64

Synthesis of N-((E)-5-hydroxyadamantan-2-yl)-6-(4-(pyridin-3-ylmethyl)piperazin-1-yl)picolinamide

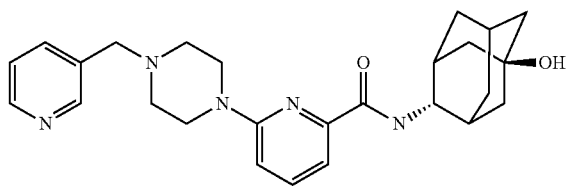 [SMILES: O=C(N[C@H]1C2CC3CC1C[C@](O)(C3)C2)c1cccc(N2CCN(Cc3cccnc3)CC2)n1]

After N-((E)-5-hydroxyadamantan-2-yl)-6-(piperazin-1-yl)picolinamide (40 mg, 0.112 mmol) and 3-(bromomethyl)pyridine hydrobromide (31 mg, 0.123 mmol) were suspended in 1,2-dichloroethane (2 ml), followed by addition of N,N-diisopropylethylamine (0.06 ml, 0.336 mmol), and then the resulting liquid was stirred at 70° C. under nitrogen stream for 2 hours. A saturated aqueous ammonium chloride solution (10 ml) of was added to the resulting reaction liquid, followed by extraction with MC (15 ml×2). The organic layer was dried over anhydrous sodium sulfate, followed by filtration and concentration, and then the residue thus obtained was subjected to MPLC (6% MeOH/MC), to obtain 30 mg of colorless oil (60%). MS (ESI): 448 [M+H]$^+$

Example 65

Synthesis of N-((E)-5-hydroxyadamantan-2-yl)-6-(4-(pyridin-2-ylmethyl)piperazin-1-yl)picolinamide

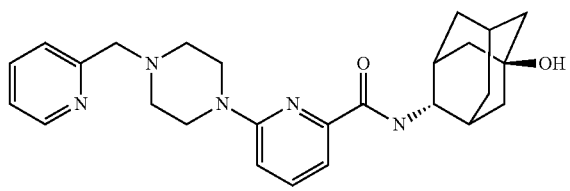 [SMILES: O=C(N[C@H]1C2CC3CC1C[C@](O)(C3)C2)c1cccc(N2CCN(Cc3ccccn3)CC2)n1]

The same method as the example 64, except that 2-(bromomethyl)pyridine hydrobromide was used instead of 3-(bromomethyl)pyridine hydrobromide, was performed to obtain 36 mg of colorless oil (72%). MS (ESI): 448 [M+H]$^+$

Example 66

Synthesis of N-((E)-5-hydroxyadamantan-2-yl)-6-(4-(2-hydroxyethyl)piperazin-1-yl)picolinamide)

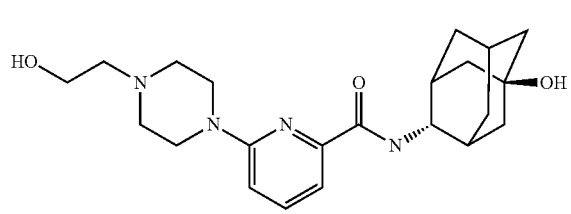 [SMILES: O=C(N[C@H]1C2CC3CC1C[C@](O)(C3)C2)c1cccc(N2CCN(CCO)CC2)n1]

The same method as the example 24, except that N-((E)-5-hydroxyadamantan-2-yl)-6-(piperazin-1-yl)picolinamide (70 mg, 0.196 mmol) was used instead of N-(adamantan-2-yl)-6-(piperazin-1-yl)picolinamide, was performed to obtain 45 mg of white solid (57%). MS (ESI): 401 [M+H]$^+$

Example 67

Synthesis of methyl 3-(4-(6-(((E)-5-hydroxyadamantan-2-yl)carbamoyl)pyridin-2-yl)piperazin-1-yl)propanoate

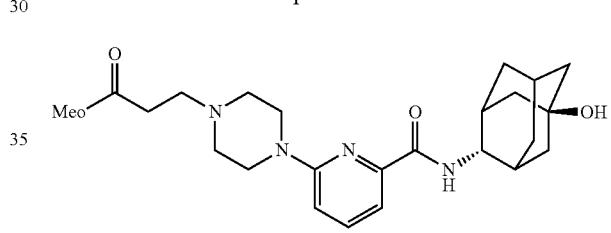

The same method as the example 25, except that N-((E)-5-hydroxyadamantan-2-yl)-6-(piperazin-1-yl)picolinamide (160 mg, 0.449 mmol) was used instead of N-(adamantan-2-yl)-6-(piperazin-1-yl)picolinamide, was performed to obtain 180 mg of white solid (81%). MS (ESI): 443 [M+H]$^+$

Example 68

Synthesis of 3-(4-(6-(((E)-5-hydroxyadamantan-2-yl)carbamoyl)pyridin-2-yl)piperazin-1-yl)propanoic acid

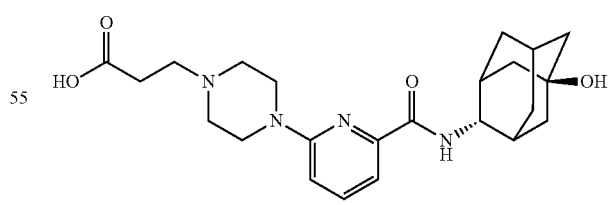

The same method as the example 26, except that methyl 3-(4-(6-(((E)-5-hydroxyadamantan-2-yl)carbamoyl)pyridin-2-yl)piperazin-1-yl)propanoate (70 mg, 0.158 mmol) was used instead of methyl 3-(4-(6-(adamantan-2-ylcarbamoyl)pyridin-2-yl)piperazin-1-yl)propanoate, was performed to obtain 41 mg of pale yellow solid (60%). MS (ESI): 429 [M+H]$^+$

Example 69

Synthesis of (6-(4-(3-amino-3-oxopropyl)piperazin-1-yl)-N-((E)-5-hydroxyadamantan-2-yl)picolinamide

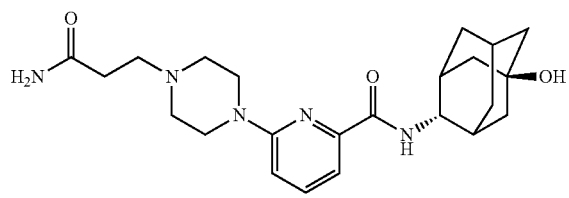 [SMILES: NC(=O)CCN1CCN(c2cccc(C(=O)N[C@H]3C4CC5CC3C[C@](O)(C5)C4)n2)CC1]

The same method as the example 27, except that methyl 3-(4-(6-(((E)-5-hydroxyadamantan-2-yl)carbamoyl)pyridin-2-yl)piperazin-1-yl)propanoate (100 mg, 0.225 mmol) was used instead of methyl 3-(4-(6-(adamantan-2-ylcarbamoyl)pyridin-2-yl)piperazin-1-yl)propanoate, was performed to obtain 10 mg of white solid (10%). MS (ESI): 428 [M+H]+

Example 70

Synthesis of 6-(4-(2-Amino-2-oxoethyl)piperidin-1-yl)-N-((E)-5-hydroxyadamantan-2-yl)picolinamide)

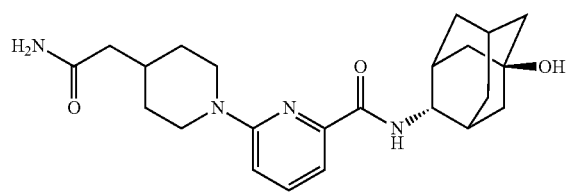 [SMILES: NC(=O)CC1CCN(c2cccc(C(=O)N[C@H]3C4CC5CC3C[C@](O)(C5)C4)n2)CC1]

Methyl 2-(1-(6-(((E)-5-hydroxyadamantan-2-yl)carbamoyl)pyridin-2-yl)piperidin-4-yl)acetate (50 mg, 0.117 mmol) was dissolved in DMF (1 ml), followed by addition of formamide (0.02 ml, 0.526 mmol). NaOMe (25% solution in MeOH, 0.03 ml, 0.129 mmol) was added dropwise thereto, while stirring at 100° C. under nitrogen stream, and then the resulting liquid was stirred for 2 hours. Distilled water (0.1 ml) was added to the resulting reaction liquid, followed by concentration under reduced pressure, and then a saturated aqueous ammonium chloride solution (10 ml) was added thereto, followed by extraction with MC (15 ml×2). The organic layer was dried over anhydrous sodium sulfate, followed by filtration and concentration, and then the residue thus obtained was subjected to MPLC (7% MeOH/MC), to obtain 31 mg of white solid (64%). MS (ESI): 413 [M+H]+

Example 71

Synthesis of 2-(1-(6-(((E)-5-hydroxyadamantan-2-yl)carbamoyl)pyridin-2-yl)piperidin-4-yl)acetic acid

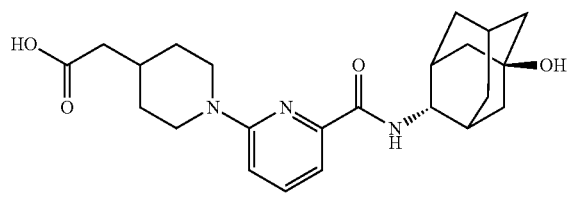 [SMILES: O=C(O)CC1CCN(c2cccc(C(=O)N[C@H]3C4CC5CC3C[C@](O)(C5)C4)n2)CC1]

Methyl 2-(1-(6-(((E)-5-hydroxyadamantan-2-yl)carbamoyl)pyridin-2-yl)piperidin-4-yl)acetate (40 mg, 0.094 mmol) was dissolved in MeOH (2 ml), followed by addition of 10% aqueous NaOH solution (0.17 ml, 0.468 mmol), and then the resulting mixture was stirred at room temperature for 20 hours. The resulting reaction liquid was concentrated under reduced pressure, and dissolved by addition of distilled water (5 ml), and then the resulting liquid was neutralized by addition of 1N aqueous HCl solution, while stirring at 0° C. The precipitated solid was filtered, followed by vacuum drying, to obtain 24 mg of white solid (62%). MS (ESI): 414 [M+H]+

Example 72

Synthesis of 6-(4-(3-amino-3-oxopropyl)piperidin-1-yl)-N-((E)-5-hydroxyadamantan-2-yl)picolinamide

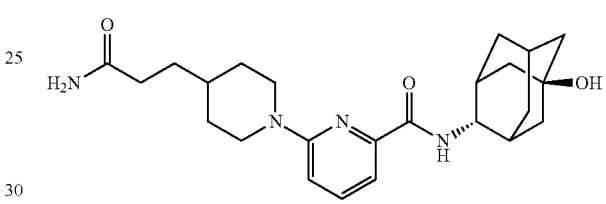

The same method as the example 70, except that methyl 3-(1-(6-(((E)-5-hydroxyadamantan-2-yl)carbamoyl)pyridin-2-yl)piperazin-4-yl)propanoate (50 mg, 0.113 mmol) was used instead of methyl 2-(1-(6-(((E)-5-hydroxyadamantan-2-yl)carbamoyl)pyridin-2-yl)piperidin-4-yl)acetate, was performed to obtain 38 mg of white solid (79%). MS (ESI): 427 [M+H]+

Example 73

Synthesis of 3-(1-(6-(((E)-5-hydroxyadamantan-2-yl)carbamoyl)pyridin-2-yl)piperidin-4-yl)propanoic acid

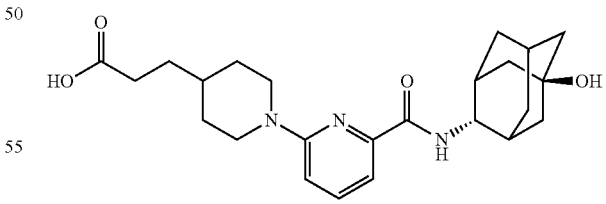

The same method as the example 71, except that methyl 3-(1-(6-(((E)-5-hydroxyadamantan-2-yl)carbamoyl)pyridin-2-yl)piperazin-4-yl)propanoate (40 mg, 0.091 mmol) was used instead of methyl 2-(1-(6-(((E)-5-hydroxyadamantan-2-yl)carbamoyl)pyridin-2-yl)piperidin-4-yl)acetate, was performed to obtain 30 mg of white solid (78%). MS (ESI): 428 [M+H]+

Example 74

Synthesis of 6-(4-(4-carbamoylphenyl)piperazin-1-yl)-N-((E)-5-hydroxyadamantan-2-yl)picolinamide

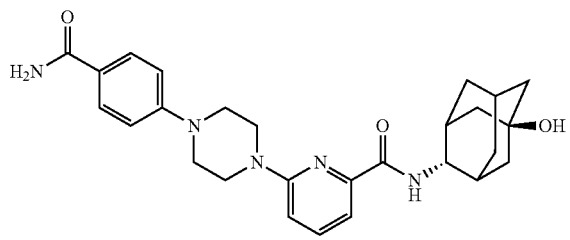 [SMILES: NC(=O)c1ccc(N2CCN(c3cccc(C(=O)N[C@H]4C5CC6CC4C[C@](O)(C6)C5)n3)CC2)cc1]

6-(4-(4-Cyanophenyl)piperazin-1-yl)-N-((E)-5-hydroxyadamantan-2-yl)picolinamide (53 mg, 0.116 mmol) was suspended in ethanol (0.53 ml), followed by addition of 1N aqueous NaOH solution (0.46 ml, 0.463 mmol) and hydrogen peroxide (30% solution in water, 0.024 ml, 0.232 mmol), and then the resulting mixture was stirred at room temperature under hydrogen stream for 2 hours. The resulting reaction liquid was concentrated under reduced pressure, and then neutralized by addition of 1N aqueous HCl solution, followed by extraction with MC (15 ml×2). The organic layer was dried over anhydrous sodium sulfate, followed by filtration and concentration, and then the residue thus obtained was subjected to MPLC (10% MeOH/MC), to obtain 32 mg of white solid (58%). MS (ESI): 973 [2M+Na]$^+$

Example 75

Synthesis of 6-(4-(4-carbamoylphenyl)piperidin-1-yl)-N-((E)-5-hydroxyadamantan-2-yl)picolinamide

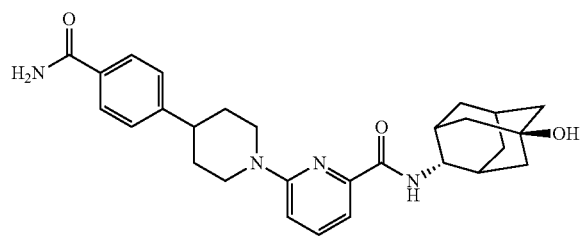 [SMILES: NC(=O)c1ccc(C2CCN(c3cccc(C(=O)N[C@H]4C5CC6CC4C[C@](O)(C6)C5)n3)CC2)cc1]

The same method as the example 74, except that 6-(4-(4-cyanophenyl)piperidin-1-yl)-N-((E)-5-hydroxyadamantan-2-yl)picolinamide (45 mg, 0.098 mmol) was used instead of 6-(4-(4-cyanophenyl)piperazin-1-yl)-N-((E)-5-hydroxyadamantan-2-yl)picolinamide, was performed to obtain 21 mg of colorless oil (45%). MS (ESI): 475 [M+H]$^+$

Example 76

Synthesis of 6-(4-(4-Aminophenyl)piperazin-1-yl)-N-((E)-5-hydroxyadamantan-2-yl)picolinamide

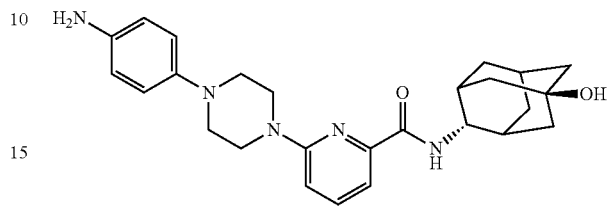

N-((E)-5-Hydroxyadamantan-2-yl)-6-(4-(4-nitrophenyl)piperazin-1-yl)picolinamide (40 mg, 0.084 mmol) was dissolved in 10% MeOH/MC, followed by addition of Pd (10 wt % on activated carbon, 2 mg), and then the resulting liquid was stirred at room temperature under hydrogen stream for 4 hours. The resulting reaction liquid was filtered, and then concentrated under reduced pressure. The residue thus obtained was subjected to MPLC (100% EtOAc), to obtain 30 mg of yellow solid (80%). MS (ESI): 448 [M+H]$^+$

Example 77

Synthesis of N-((E)-5-hydroxyadamantan-2-yl)-6-(4-(4-(methylsulfonyl)phenyl)piperazin-1-yl)picolinamide

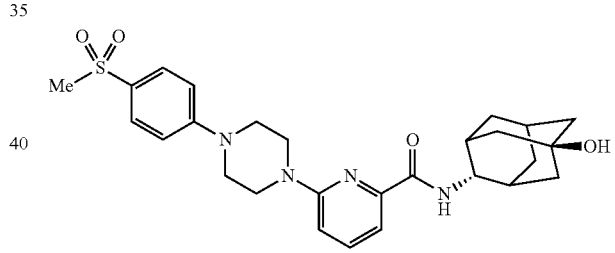

Step 1: Synthesis of 1-(4-(methylsulfonyl)phenyl)piperazin

1-Bromo-4-(methylsulfonyl)benzene (275 mg, 1.169 mmol), piperazine (302 mg, 3.507 mmol), Pd$_2$(dba)$_3$ (21 mg, 0.023 mmol), BINAP (44 mg, 0.070 mmol), and sodium-tert-butoxide (169 mg, 1.754 mmol) were suspended in toluene (5 ml), and then the resulting liquid was stirred at 100° C. under nitrogen stream for 15 hours. Distilled water (15 ml) was added to the resulting reaction liquid, followed by extraction with MC (20 ml×3). The organic layer was dried over anhydrous sodium sulfate, followed by filtration and concentration, and then the residue thus obtained was subjected to MPLC (15% MeOH/MC), to obtain 56 mg of pale yellow solid (20%).

Step 2: Synthesis of N-((E)-5-Hydroxyadamantan-2-yl)-6-(4-(4-(methylsulfonyl)phenyl)piperazin-1-yl)picolinamide 6-Bromo-N-((E)-5-hydroxyadamantan-2-yl)picolinamide (60 mg, 0.171 mmol), 1-(4-(methylsulfonyl)piperazine (49 mg, 0.205 mmol), Pd$_2$(dba)$_3$ (3.1 mg, 0.003 mmol), xantphos (5.9 mg, 0.010 mmol), and sodium-tert-butoxide (25 mg, 0.257 mmol) were suspended in toluene (3 ml), and then the resulting liquid was stirred at 100° C. under nitrogen stream for 4 hours. Distilled water (10 ml) was added to the resulting reaction liquid, followed by extraction with MC (15 ml×2). The organic layer was dried over anhydrous sodium sulfate, followed by filtration and concentration, and then the residue thus obtained was subjected to MPLC (4% MeOH/MC), to obtain 34 mg of pale yellow solid (39%). MS (ESI): 511 [M+H]$^+$ The following examples were synthesized in the same method as the above example 77, by using an appropriate bromobenzene start material.

| Examples | Structures | MS (ESI) |
|---|---|---|
| 78 | 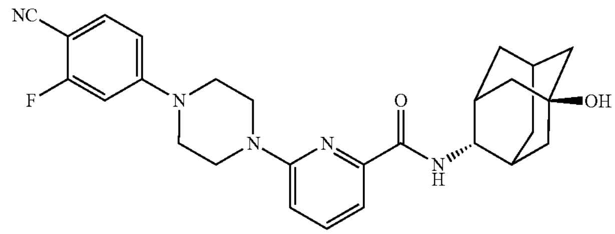 [SMILES: N#Cc1ccc(N2CCN(c3cccc(C(=O)N[C@H]4C5CC6CC4C[C@](O)(C6)C5)n3)CC2)cc1F] | 476 [M + H]$^+$ |
| 79 | 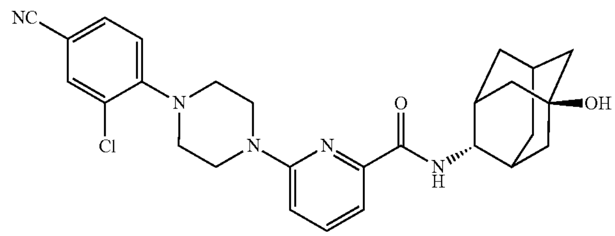 [SMILES: N#Cc1ccc(N2CCN(c3cccc(C(=O)N[C@H]4C5CC6CC4C[C@](O)(C6)C5)n3)CC2)c(Cl)c1] | 492 [M + H]$^+$ |
| 80 | 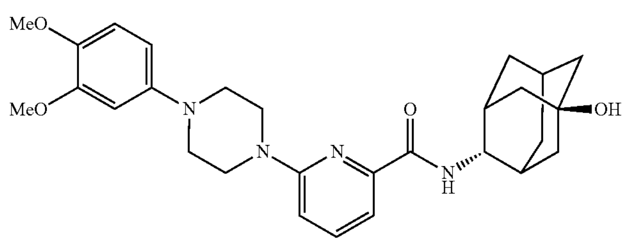 [SMILES: COc1ccc(N2CCN(c3cccc(C(=O)N[C@H]4C5CC6CC4C[C@](O)(C6)C5)n3)CC2)cc1OC] | 493 [M + H]$^+$ |
| 81 | 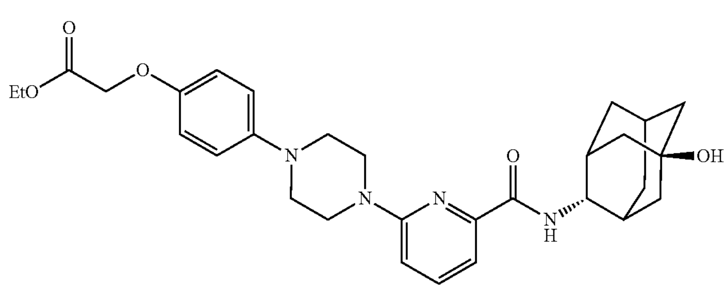 [SMILES: CCOC(=O)COc1ccc(N2CCN(c3cccc(C(=O)N[C@H]4C5CC6CC4C[C@](O)(C6)C5)n3)CC2)cc1] | 535 [M + H]$^+$ |

Example 82

Synthesis of 6-(4-(4-Carbamoyl-3-fluorophenyl)piperazin-1-yl)-N-((E)-5-hydroxyadamantan-2-yl)picolinamide

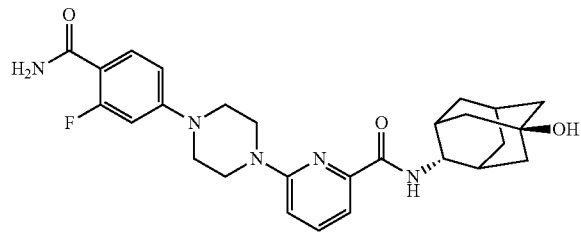 [SMILES: NC(=O)c1ccc(N2CCN(c3cccc(C(=O)N[C@H]4C5CC6CC4C[C@](O)(C6)C5)n3)CC2)cc1F]

The same method as the example 74, except that 6-(4-(4-cyano-3-fluorophenyl)piperazin-1-yl)-N-((E)-5-hydroxyadamantan-2-yl)picolinamide (75 mg, 0.158 mmol) was used instead of 6-(4-(4-cyanophenyl)piperazin-1-yl)-N-((E)-5-hydroxyadamantan-2-yl)picolinamide, was performed to obtain 72 mg of white solid (92%). MS (ESI): 494 [M+H]$^+$

Example 83

Synthesis of 6-(4-(4-Carbamoyl-2-chlorophenyl)piperazin-1-yl)-N-((E)-5-hydroxyadamantan-2-yl)picolinamide

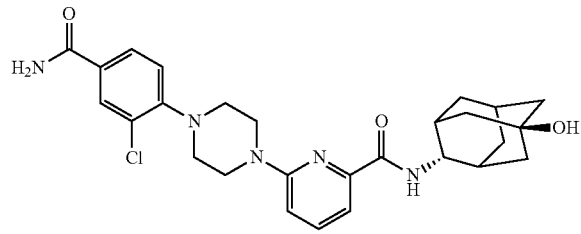 [SMILES: NC(=O)c1ccc(N2CCN(c3cccc(C(=O)N[C@H]4C5CC6CC4C[C@](O)(C6)C5)n3)CC2)c(Cl)c1]

The same method as the example 74, except that 6-(4-(4-cyano-2-chlorophenyl)piperazin-1-yl)-N-((E)-5-hydroxyadamantan-2-yl)picolinamide (154 mg, 0.313 mmol) was used instead of 6-(4-(4-cyanophenyl)piperazin-1-yl)-N-((E)-5-hydroxyadamantan-2-yl)picolinamide, was performed to obtain 96 mg of white solid (60%). MS (ESI): 510 [M+H]$^+$

Example 84

Synthesis of 2-(4-(4-(6-(((E)-5-Hydroxyadamantan-2-yl)carbamoyl)pyridin-2-yl)piperazin-1-yl)phenoxy)acetic acid

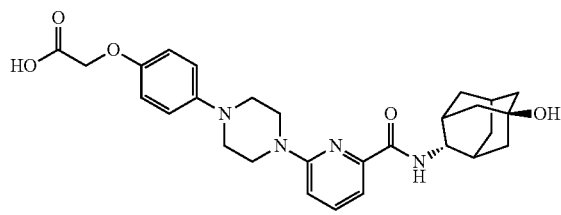 [SMILES: O=C(O)COc1ccc(N2CCN(c3cccc(C(=O)N[C@H]4C5CC6CC4C[C@](O)(C6)C5)n3)CC2)cc1]

Ethyl 2-(4-(4-(6-(((E)-5-hydroxyadamantan-2-yl)carbamoyl)pyridin-2-yl)piperazin-1-yl)phenoxy)acetate (82 mg, 0.153 mmol) was dissolved in EtOH (3 ml), followed by addition of 1N aqueous NaOH solution (0.46 ml, 0.460 mmol), and then the resulting liquid was stirred at 60° C. for 2 hours. The resulting reaction liquid was concentrated under reduced pressure, and dissolved by addition of distilled water (5 ml), and then the resulting liquid was neutralized by addition of 1N aqueous HCl solution, while stirring at 0° C. The precipitated solid was filtered, followed by vacuum drying, to obtain 56 mg of pale yellow solid (72%). MS (ESI): 507 [M+H]$^+$

Example 85

Synthesis of 6-(4-(5-chloropyridin-2-yl)piperazin-1-yl)-N-((E)-5-hydroxyadamantan-2-yl)picolinamide

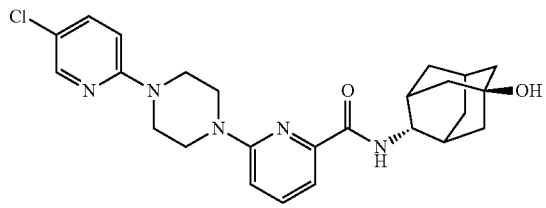 [SMILES: O=C(N[C@H]1C2CC3CC1C[C@](O)(C3)C2)c1cccc(N2CCN(c3ccc(Cl)cn3)CC2)n1]

Step 1: Synthesis of tert-butyl 4-(5-chloropyridin-2-yl)piperazine-1-carboxylate Tert-butyl piperazine-1-carboxylate (300 mg, 1.611 mmol) and 2-bromo-5-chloropyridine (465 mg, 2.416 mmol) were dissolved in acetonitrile (3 ml), followed by addition of triethylamine (0.45 ml, 3.222 mmol), and then the resulting liquid was subjected to microwave irradiation at 150° C. for 2 hours. The resulting reaction liquid was concentrated under reduced pressure, followed by addition of a saturated aqueous ammonium chloride solution (10 ml), and extracted with MC (15 ml×2). The organic layer was dried over anhydrous sodium sulfate, followed by filtration and concentration, and then the residue thus obtained was subjected to MPLC (20% EtOAc/Hexanes), to obtain 177 mg of colorless oil (37%).

Step 2: Synthesis of 1-(5-Chloropyridin-2-yl)piperazine

Tert-butyl 4-(5-chloropyridin-2-yl)piperazine-1-carboxylate (170 mg, 0.571 mmol) was dissolved in MC (3 ml), followed by addition of trifluoroacetic acid (3 ml), and then the resulting mixture was stirred at room temperature for 2 hours. The resulting reaction liquid was concentrated under reduced pressure, followed by addition of a saturated aqueous NaHCO$_3$ solution (15 ml), and extracted with MC (15 ml×3). The organic layer was dried over anhydrous sodium sulfate, followed by filtration, concentration, and vacuum drying, to obtain 112 mg of white solid (99%).

Step 3: Synthesis of 6-(4-(5-Chloropyridin-2-yl)piperazin-1-yl)-N-((E)-5-hydroxyadamantan-2-yl)picolinamide 6-Bromo-N-((E)-5-hydroxyadamantan-2-yl)picolinamide (50 mg, 0.142 mmol), 1-(5-chloropyridin-2-yl)piperazine (34 mg, 0.171 mmol), $Pd_2(dba)_3$ (2.6 mg, 0.003 mmol), xantphos (4.9 mg, 0.009 mmol), and sodium-tert-butoxide (20 mg, 0.213 mmol) were suspended in toluene (3 ml), and then the resulting liquid was stirred at 100° C. under nitrogen stream for 3 hours. A saturated aqueous ammonium chloride solution (15 ml) was added to the resulting reaction liquid, followed by extraction with MC (20 ml×2). The organic layer was dried over anhydrous sodium sulfate, followed by filtration and concentration, and then the residue thus obtained was subjected to MPLC (5% MeOH/MC), to obtain 24 mg of yellow solid (36%). MS (ESI): 468 [M+H]$^+$ The following examples were synthesized in the same method as the above example 85, by using an appropriate 2-bromopyridine start material.

| Examples | Structures | MS (ESI) |
|---|---|---|
| 86 | 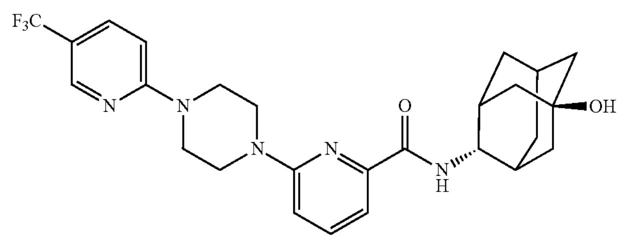 | 502 [M + H]$^+$ |
| 87 | 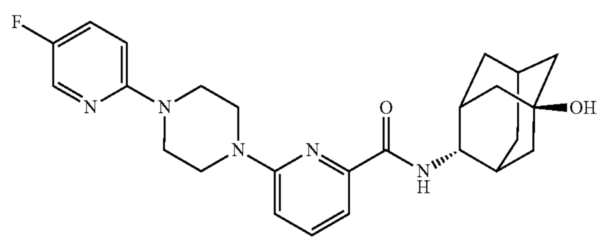 [SMILES: O=C(N[C@H]1C2CC3CC1C[C@](O)(C3)C2)c1cccc(N2CCN(c3ccc(F)cn3)CC2)n1] | 452 [M + H]$^+$ |
| 88 | 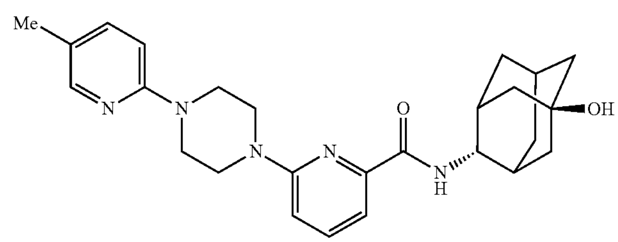 [SMILES: N#Cc1ccc(N2CCN(c3cccc(C(=O)N[C@H]4C5CC6CC4C[C@](O)(C6)C5)n3)CC2)nc1] | 448 [M + H]$^+$ |
| 89 | 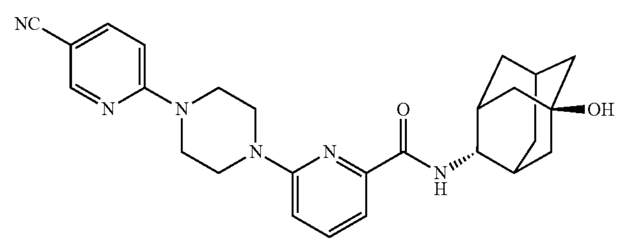 | 459 [M + H]$^+$ |

Example 90

Synthesis of 6-(4-(5-carbamoylpyridin-2-yl)piperazin-1-yl)-N-((E)-5-hydroxyadamantan-2-yl)picolinamide

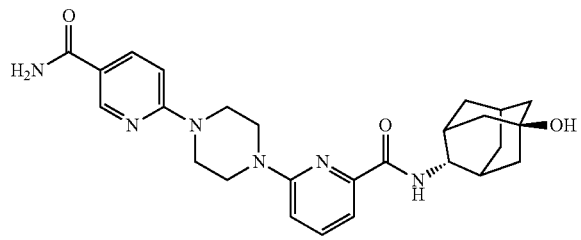 [SMILES: NC(=O)c1ccc(N2CCN(c3cccc(C(=O)N[C@H]4C5CC6CC4C[C@](O)(C6)C5)n3)CC2)nc1]

The same method as the example 74, except that 6-(4-(5-cyanopyridin-2-yl)piperazin-1-yl)-N-((E)-5-hydroxyadamantan-2-yl)picolinamide (67 mg, 0.146 mmol) was used instead of 6-(4-(4-cyanophenyl)piperazin-1-yl)-N-((E)-5-hydroxyadamantan-2-yl)picolinamide, was performed to obtain 58 mg of pale yellow solid (83%). MS (ESI): 477 [M+H]$^+$

Example 91

Synthesis of 6-(4-(4-fluorophenyl)piperidin-1-yl)-N-((E)-5-hydroxyadamantan-2-yl)picolinamide

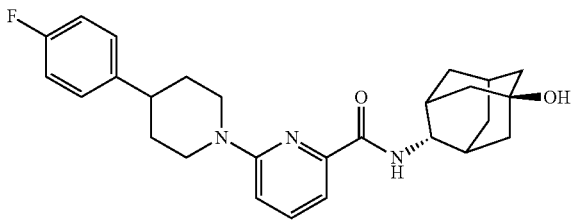 [SMILES: O=C(N[C@H]1C2CC3CC1C[C@](O)(C3)C2)c1cccc(N2CCC(c3ccc(F)cc3)CC2)n1]

Step 1: Synthesis of tert-butyl 4-(((trifluoromethyl)sulfonyl)oxy)-5,6-dihydropyridine-1(2H)-carboxylate Diisopropylamine (4.6 ml, 32.6 mmol) was dissolved in THF (35 ml), and then the resulting liquid was stirred at −78° C. under nitrogen stream, followed by slow addition of n-BuLi (1.6M solution in hexane, 20 ml, 32.6 mmol). Following stirring for 5 minutes, t-butoxycarbonyl-4-piperidone (5 g, 25.1 mmol) was added and dissolved in THF (25 ml), followed by stirring for 10 minutes, and then N-phenyl trifluoromethane sulfone imide (9.8 g, 27.6 mmol) was added and dissolved in THF (25 ml), followed by stirring for 30 minutes. The reaction temperature was raised to room temperature, followed by stirring for two and a half hours, and then the reaction was terminated by adding a saturated aqueous NaHCO$_3$ solution (50 ml) to the resulting liquid. 5% citric acid (50 ml) was added thereto, followed by extraction with diethylether (200 ml). The organic layer was sequentially washed with 1N aqueous NaOH solution (100 ml×2), distilled water (100 ml), and a saturated aqueous sodium chloride solution of (100 ml), and then dried over anhydrous magnesium sulfate, followed by filtration and concentration. The residue thus obtained was subjected to MPLC (10% EtOAc/Hexanes), to obtain 4.64 g of yellow oil (56%).

Step 2: Synthesis of tert-butyl 4-(4,4,5,5-tetramethyl-1,3,2-dioxaborolan-2-yl)-5,6-dihydropyridine-1(2H)-carboxylate Tert-butyl 4-(((trifluoromethyl)sulfonyl)oxy)-5,6-dihydropyridine-1(2H)-carboxylate (4.64 g, 14 mmol) was dissolved in 1,4-dioxane (70 ml), and then bis(pinacholato)diboron (3.91 g, 15.4 mmol), KOAc (4.12 g, 42.0 mmol), PdCl$_2$dppf (343 mg, 0.42 mmol), and dppf (233 mg, 0.42 mmol) are sequentially added thereto. The resulting mixture was stirred at 80° C. under nitrogen stream for 6 hours. Distilled water (50 ml) was added to the resulting reaction liquid, followed by extraction with MC (80 ml×3). The organic layer was dried over anhydrous magnesium sulfate, followed by filtration and concentration, and then the residue thus obtained was subjected to MPLC (10% EtOAc/Hexanes), to obtain 2.45 g of yellow solid (57%).

Step 3: Synthesis of tert-butyl 4-(4-fluorophenyl)-5,6-dihydropyridine-1(2H)-carboxylate Tert-butyl 4-(4,4,5,5-tetramethyl-1,3,2-dioxaborolan-2-yl)-5,6-dihydropyridine-1(2H)-carboxylate (120 mg, 0.388 mmol) was dissolved in toluene/EtOH (3 ml/0.15 ml), and then 1-bromo-4-fluorobenzene (0.05 ml, 0.466 mmol), Pd(PPh$_3$)$_4$ (22 mg, 0.02 mmol), and K$_2$CO$_3$ (107 mg, 0.776 mmol) were sequentially added thereto. The resulting mixture was stirred at 100° C. under nitrogen stream for 2 hours. Distilled water (3 ml) was added to the resulting reaction liquid, followed by extraction with MC (10 ml×3). The organic layer was dried over anhydrous magnesium sulfate, followed by filtration and concentration, and then the residue thus obtained was subjected to MPLC (6% EtOAc/Hexanes), to obtain 48 mg of colorless oil (45%).

Step 4: Synthesis of tert-butyl 4-(4-fluorophenyl)piperidine-1-carboxylate

Tert-butyl 4-(4-fluorophenyl)-5,6-dihydropyridine-1(2H)-carboxylate (48 mg, 0.173 mmol) was dissolved in EtOH (2 ml), followed by addition of Pd (10 wt % on activated carbon, 5 mg), and then the resulting liquid was stirred at room temperature under hydrogen stream for 2 hours. The resulting reaction liquid was filtered, concentrated under reduced pressure, and dried under vacuum, to obtain 46 mg of colorless oil (95%).

Step 5: Synthesis of 4-(4-fluorophenyl)piperidine)

Tert-butyl 4-(4-fluorophenyl)piperidine-1-carboxylate (46 mg, 0.165 mmol) was dissolved in MC (2 ml), followed by addition of trifluoroacetic acid (1 ml), and then the resulting mixture was stirred at room temperature for 4 hours. The resulting reaction liquid was neutralized by slow addition of a saturated aqueous NaHCO$_3$ solution at 0° C., and then extracted with 5% MeOH/MC (10 ml×2). The organic layer was dried over anhydrous magnesium sulfate, followed by filtration, concentration, and vacuum drying, to obtain 22 mg of colorless oil (74%).

Step 6: Synthesis of 6-(4-(4-fluorophenyl)piperidin-1-yl)-N-((E)-5-hydroxyadamantan-2-yl)picolinamide 6-Bromo-N-((E)-5-hydroxyadamantan-2-yl)picolinamide (40 mg, 0.114 mmol), 4-(4-fluorophenyl)piperidine (22 mg, 0.125 mmol), Pd$_2$(dba)$_3$ (2 mg, 2 mol %), xantphos (4 mg, 6 mol %), and sodium-tert-butoxide (16 mg, 0.171 mmol) were suspended in toluene (1.5 ml), and then the resulting liquid was stirred at 100° C. under nitrogen stream for 2 hours. Distilled water (3 ml) was added to the resulting reaction liquid, followed by extraction with MC (10 ml×3). The organic layer was dried over anhydrous sodium sulfate, followed by filtration and concentration, and then the residue thus obtained was subjected to MPLC (3% MeOH/MC), to obtain 20 mg of yellow solid (39%). MS (ESI): 450 [M+H]$^+$ The following examples were synthesized in the same method as the above example 91, by using an appropriate bromobenzene or bromopyridine start material.

| Examples | Structures | MS (ESI) |
|---|---|---|
| 92 | 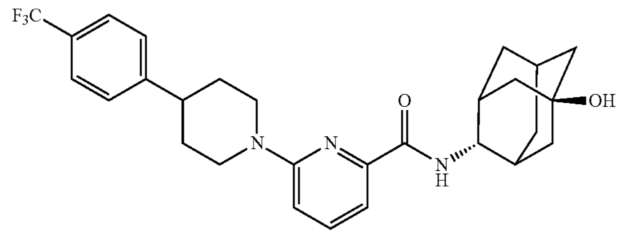 [SMILES: Cc1ccc(C2CCN(c3cccc(C(=O)N[C@H]4C5CC6CC4C[C@](O)(C6)C5)n3)CC2)cc1] | 500 [M + H]$^+$ |
| 93 | 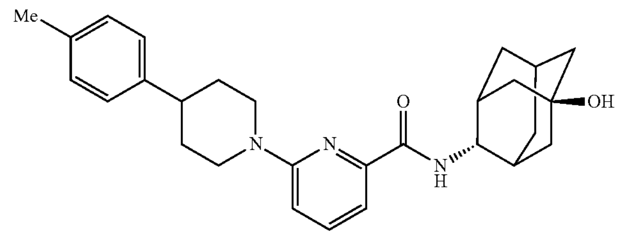 | 446 [M + H]$^+$ |
| 94 | 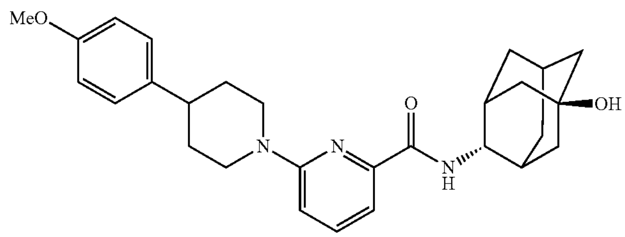 [SMILES: COc1ccc(C2CCN(c3cccc(C(=O)N[C@H]4C5CC6CC4C[C@](O)(C6)C5)n3)CC2)cc1] | 462 [M + H]$^+$ |
| 95 | 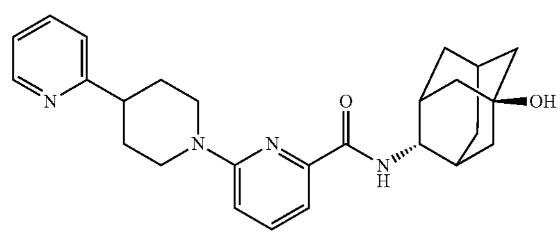 [SMILES: O=C(N[C@H]1C2CC3CC1C[C@](O)(C3)C2)c1cccc(N2CCC(c3ccccn3)CC2)n1] | 433 [M + H]$^+$ |
| 96 | 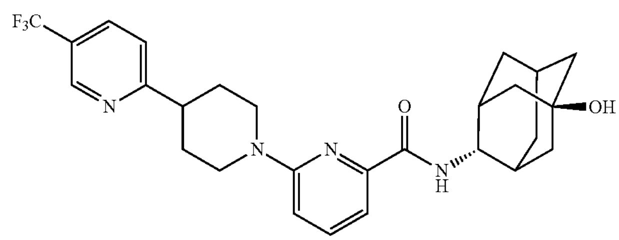 [SMILES: O=C(N[C@H]1C2CC3CC1C[C@](O)(C3)C2)c1cccc(N2CCC(c3ccc(C(F)(F)F)cn3)CC2)n1] | 501 [M + H]$^+$ |
| 97 | 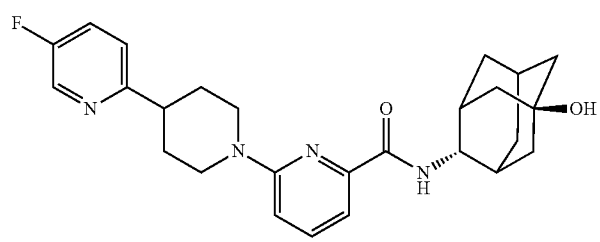 [SMILES: O=C(N[C@H]1C2CC3CC1C[C@](O)(C3)C2)c1cccc(N2CCC(c3ccc(F)cn3)CC2)n1] | 451 [M + H]$^+$ |

-continued

| Examples | Structures | MS (ESI) |
|---|---|---|
| 98 | (5-methylpyridin-2-yl at piperidine-4; piperidine-N linked to pyridine-2-carboxamide-N-(5-hydroxyadamantan-2-yl)) | 447 [M + H]+ |
| 99 | (5-cyanopyridin-2-yl at piperidine-4; same scaffold) | 458 [M + H]+ |
| 100 | (3-cyanopyridin-2-yl at piperidine-4; same scaffold) | 458 [M + H]+ |
| 101 | (pyridin-3-yl at piperidine-4; same scaffold) | 433 [M + H]+ |
| 102 | (6-methylpyridin-3-yl at piperidine-4; same scaffold) | 447 [M + H]+ |
| 103 | (6-aminopyridin-3-yl at piperidine-4; same scaffold) | 448 [M + H]+ |

Example 104

Synthesis of 6-(1-(4-cyanophenyl)piperidin-4-yl)-N-((E)-5-hydroxyadamantan-2-yl)picolinamide

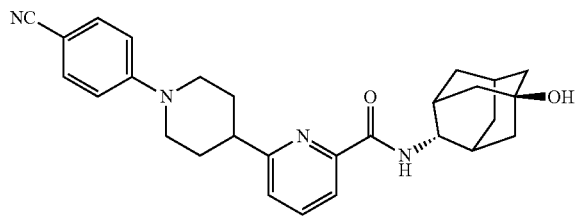 [SMILES: N#Cc1ccc(N2CCC(c3cccc(C(=O)N[C@H]4C5CC6CC4C[C@](O)(C6)C5)n3)CC2)cc1]

Step 1: Synthesis of tert-butyl 6-(((E)-5-hydroxyadamantan-2-yl)carbamoyl)-5',6'-dihydro-[2,4'-bipyridine]-1'(2'H)-carboxylate)

6-Bromo-N-((E)-5-hydroxyadamantan-2-yl)picolinamide (300 mg, 0.854 mmol), tert-butyl 4-(4,4,5,5-tetramethyl-1,3,2-dioxaborolan-2-yl)-5,6-dihydropyridine-1(2H)-carboxylate (317 mg, 1.025 mmol), and potassium carbonate (236 mg, 1.708 mmol) were suspended in toluene (10 ml), followed by addition of EtOH (0.5 ml) and Pd(PPh3)4 (49 mg, 0.043 mmol), and then the resulting liquid was stirred at 100° C. under nitrogen stream for 4 hours. A saturated aqueous ammonium chloride solution (20 ml) was added to the resulting reaction liquid, followed by extraction with MC (50 ml×2). The organic layer was dried over anhydrous sodium sulfate, followed by filtration and concentration, and then the residue thus obtained was subjected to MPLC (3% MeOH/MC), to obtain 320 mg of pale yellow solid (83%).

Step 2: Synthesis of tert-butyl 4-(6-(((E)-5-hydroxyadamantan-2-yl)carbamoyl)pyridin-2-yl)piperidine-1-carboxylate Tert-butyl 6-(((E)-5-hydroxyadamantan-2-yl)carbamoyl)-5',6'-dihydro-[2,4'-bipyridine]-1'(2'H)-carboxylate (320 mg, 0.706 mmol) was dissolved in EtOH (15 ml), followed by addition of Pd (10 wt % on activated carbon, 200 mg), and then the resulting liquid was stirred at room temperature under hydrogen stream for 5 hours. The resulting reaction liquid was filtered, and then concentrated under reduced pressure. The residue thus obtained was subjected to MPLC (5% MeOH/MC), to obtain 285 mg of white solid (89%).

Step 3: Synthesis of N-((E)-5-Hydroxyadamantan-2-yl)-6-(piperidin-4-yl)picolinamide Tert-butyl 4-(6-(((E)-5-hydroxyadamantan-2-yl)carbamoyl)pyridin-2-yl)piperidine-1-carboxylate (285 mg, 0.626 mmol) was dissolved in MC (4 ml), followed by addition of trifluoroacetic acid (4 ml), and then the resulting mixture was stirred at room temperature for 4 hours. The resulting reaction liquid was concentrated under reduced pressure, followed by addition of distilled water (10 ml), and then extracted with MC (15 ml). The aqueous layer was neutralized by addition of a saturated aqueous NaHCO3 solution, followed by extraction with 5% MeOH/MC (25 ml×4), and then the organic layer was dried over anhydrous sodium sulfate, followed by filtration, concentration, and vacuum drying, to obtain 186 mg of white solid (84%).

Step 4: Synthesis of 6-(1-(4-Cyanophenyl)piperidin-4-yl)-N-((E)-5-hydroxyadamantan-2-yl)picolinamide N-((E)-5-hydroxyadamantan-2-yl)-6-(piperidin-4-yl)picolinamide (33 mg, 0.093 mmol), 4-bromobenzonitrile (19 mg, 0.102 mmol), Pd2(dba)3 (2 mg, 0.002 mmol), BINAP (3.5 mg, 0.006 mmol), and sodium-tert-butoxide (13 mg, 0.140 mmol) were suspended in toluene (2 ml), and then the resulting liquid was stirred at 80° C. under nitrogen stream for 4 hours. Distilled water (10 ml) was added to the resulting reaction liquid, followed by extraction with MC (15 ml×2). The organic layer was dried over anhydrous sodium sulfate, followed by filtration and concentration, and then the residue thus obtained was subjected to MPLC (3% MeOH/MC), to obtain 31 mg of white solid (73%). MS (ESI): 457 [M+H]+

Example 105

Synthesis of 6-(1-(5-cyanopyridin-2-yl)piperidin-4-yl)-N-((E)-5-hydroxyadamantan-2-yl)picolinamide

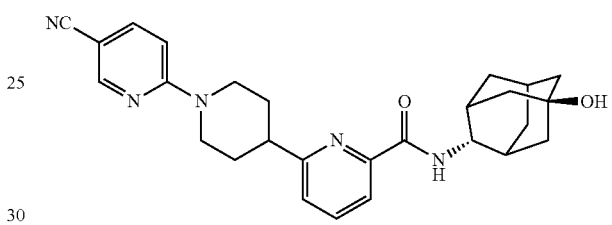

N-((E)-5-hydroxyadamantan-2-yl)-6-(piperidin-4-yl)picolinamide (40 mg, 0.113 mmol) and 6-chloronicotinonitril (19 mg, 0.135 mmol) were dissolved in acetonitrile (1 ml), followed by addition of triethylamine (0.03 ml, 0.226 mmol), and then the resulting liquid was stirred at 100° C. under nitrogen stream for 5 hours. A saturated aqueous ammonium chloride solution (10 ml) was added to the resulting reaction liquid, followed by extraction with MC (15 ml×2). The organic layer was dried over anhydrous sodium sulfate, followed by filtration and concentration, and then the residue thus obtained was subjected to MPLC (3% MeOH/MC), to obtain 42 mg of white solid (82%). MS (ESI): 458 [M+H]+

Example 106

Synthesis of 6-((R)-4-(4-Cyanophenyl)-2-methylpiperazin-1-yl)-N-((E)-5-hydroxyadamantan-2-yl)picolinamide

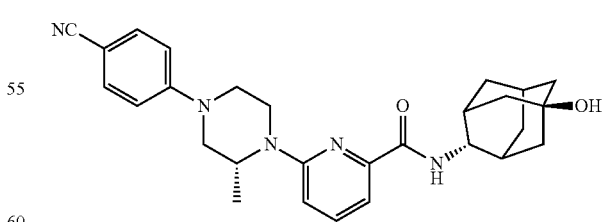

Step 1: Synthesis of (R)-4-(3-methylpiperazin-1-yl)benzonitrile

4-Bromobenzonitrile (200 mg, 1.099 mmol), (R)-2-methylpiperazine (121 mg, 1.209 mmol), Pd2(dba)3 (20 mg, 0.022 mmol), BINAP (41 mg, 0.066 mmol), and sodium-tert-butoxide (211 mg, 2.199 mmol) were suspended in toluene (5 ml), and then the resulting liquid was stirred at 100° C. under nitrogen stream for 5 hours. 1N aqueous HCl solution (20 ml) was added to the resulting reaction liquid, followed by extraction with MC (10 ml×2). The aqueous layer was neutralized by addition of 5N aqueous NaOH solution, followed by extraction with 5% MeOH/MC (20 ml×2). The organic layer was dried over anhydrous sodium sulfate, followed by filtration and concentration, and then the residue thus obtained was subjected to MPLC (10% MeOH/MC), to obtain 152 mg of pale yellow oil (69%).

Step 2: Synthesis of 6-((R)-4-(4-Cyanophenyl)-2-methylpiperazin-1-yl)-N-((E)-5-hydroxyadamantan-2-yl)picolinamide 6-Bromo-N-((E)-5-hydroxyadamantan-2-yl)picolinamide (80 mg, 0.228 mmol), (R)-4-(3-methylpiperazin-1-yl)benzonitrile (55 mg, 0.273 mmol), $Pd_2(dba)_3$ (4.2 mg, 0.005 mmol), xantphos (7.9 mg, 0.014 mmol) and sodium-tert-butoxide (33 mg, 0.342 mmol) were suspended in toluene (5 ml), and then the resulting liquid was stirred at 100° C. under nitrogen stream for 15 hours. A saturated aqueous ammonium chloride solution (10 ml) was added to the resulting reaction liquid, followed by extraction with MC (20 ml×2). The organic layer was dried over anhydrous sodium sulfate, followed by filtration and concentration, and then the residue thus obtained was subjected to MPLC (4% MeOH/MC), to obtain 20 mg of pale yellow solid (19%). MS (ESI): 472 [M+H]$^+$ The following examples were synthesized in the same method as the above example 106, by using an appropriate bromobenzene or bromopyridine start material and a piperazine start material.

| Examples | Structures | MS (ESI) |
|---|---|---|
| 107 | 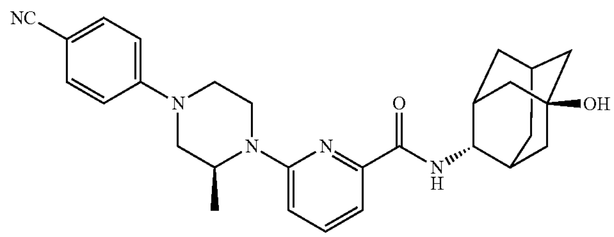 [SMILES: C[C@H]1CN(c2ccc(C#N)cc2)CCN1c1cccc(C(=O)N[C@H]2C3CC4CC2C[C@](O)(C4)C3)n1] | 472 [M + H]$^+$ |
| 108 | 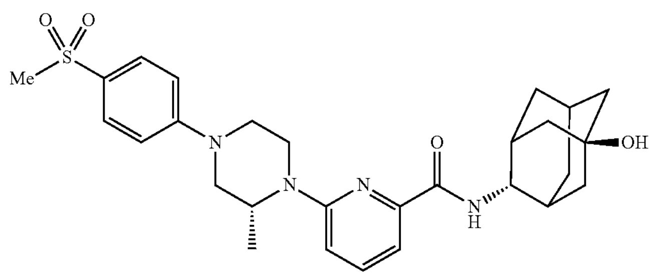 [SMILES: C[C@@H]1CN(c2ccc(S(C)(=O)=O)cc2)CCN1c1cccc(C(=O)N[C@H]2C3CC4CC2C[C@](O)(C4)C3)n1] | 525 [M + H]$^+$ |
| 109 | 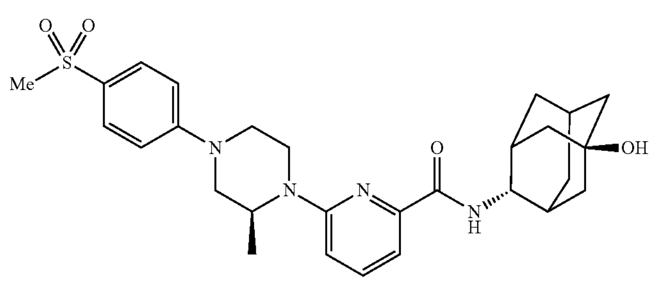 [SMILES: C[C@H]1CN(c2ccc(S(C)(=O)=O)cc2)CCN1c1cccc(C(=O)N[C@H]2C3CC4CC2C[C@](O)(C4)C3)n1] | 525 [M + H]$^+$ |
| 110 | 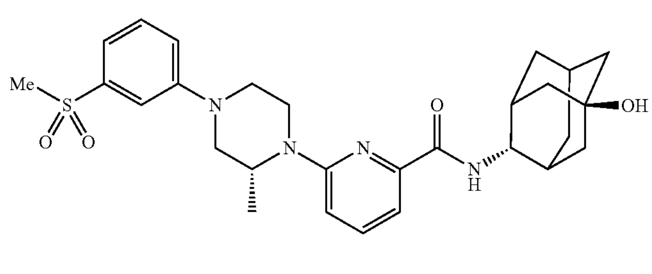 [SMILES: C[C@@H]1CN(c2cccc(S(C)(=O)=O)c2)CCN1c1cccc(C(=O)N[C@H]2C3CC4CC2C[C@](O)(C4)C3)n1] | 525 [M + H]$^+$ |

-continued

| Examples | Structures | MS (ESI) |
|---|---|---|
| 111 | MeO-phenyl-piperazine(Me)-pyridine-C(O)NH-adamantyl-OH | 477 [M + H]+ |
| 112 | MeO,F-phenyl-piperazine(Me)-pyridine-C(O)NH-adamantyl-OH | 495 [M + H]+ |
| 113 | MeO,F-phenyl-piperazine(Me)-pyridine-C(O)NH-adamantyl-OH | 495 [M + H]+ |
| 114 | MeO,MeO-phenyl-piperazine(Me)-pyridine-C(O)NH-adamantyl-OH | 507 [M + H]+ |
| 115 | Me$_2$N-phenyl-piperazine(Me)-pyridine-C(O)NH-adamantyl-OH | 490 [M + H]+ |
| 116 | F$_3$CO-phenyl-piperazine(Me)-pyridine-C(O)NH-adamantyl-OH | 531 [M + H]+ |

| Examples | Structures | MS (ESI) |
|---|---|---|
| 117 | 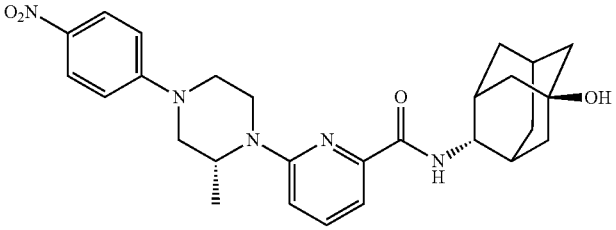 | 492 [M + H]+ |
| 118 | 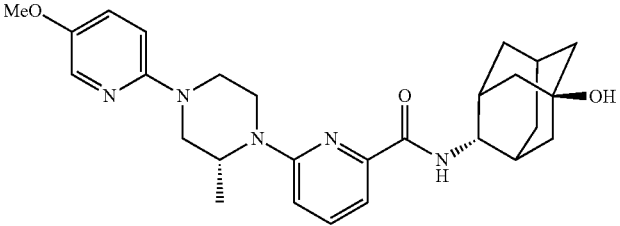 [SMILES: COc1ccc(N2CCN(c3cccc(C(=O)N[C@H]4C5CC6CC4C[C@](O)(C6)C5)n3)[C@H](C)C2)nc1] | 478 [M + H]+ |
| 119 | 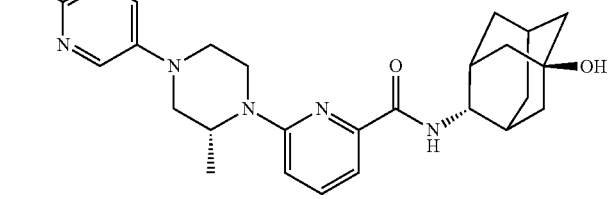 | 478 [M + H]+ |
| 120 | 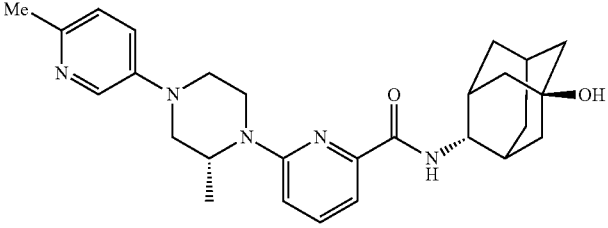 | 462 [M + H]+ |
| 121 | 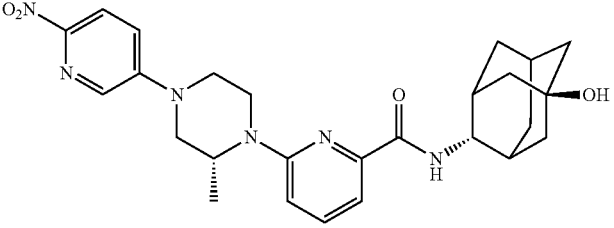 [SMILES: C[C@@H]1CN(c2ccc([N+](=O)[O-])nc2)CCN1c1cccc(C(=O)N[C@H]2C3CC4CC2C[C@](O)(C4)C3)n1] | 493 [M + H]+ |
| 122 | 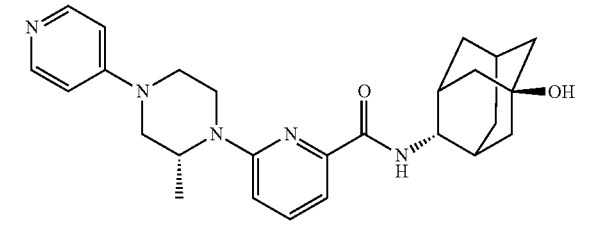 [SMILES: C[C@@H]1CN(c2ccncc2)CCN1c1cccc(C(=O)N[C@H]2C3CC4CC2C[C@](O)(C4)C3)n1] | 448 [M + H]+ |

| Examples | Structures | MS (ESI) |
|---|---|---|
| 123 | 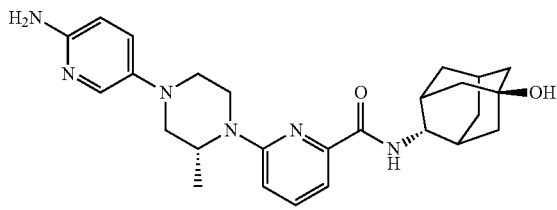 | 525 [M + H]+ |
| 124 | 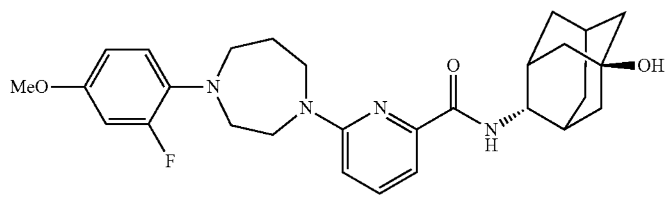 [SMILES: COc1ccc(N2CCCN(c3cccc(C(=O)N[C@H]4C5CC6CC4C[C@](O)(C6)C5)n3)CC2)c(F)c1] | 495 [M + H]+ |

Example 125

Synthesis of 6-((R)-4-(6-aminopyridin-3-yl)-2-methylpiperazin-1-yl)-N-((E)-5-hydroxyadamantan-2-yl)picolinamide

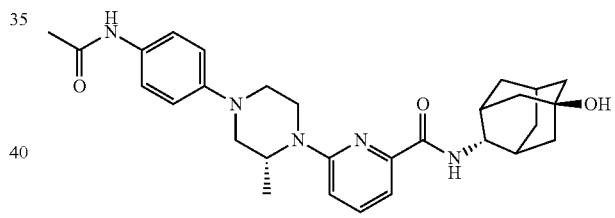

N-((E)-5-hydroxyadamantan-2-yl)-6-((R)-2-methyl-4-(6-nitropyridin-3-yl)piperazin-1-yl)picolinamide (85 mg, 0.173 mmol) was dissolved in 20% MeOH/EtOH (12 ml), followed by addition of Pd (10 wt % on activated carbon, 40 mg), and then the resulting liquid was stirred at room temperature under hydrogen stream for 3 hours. The resulting reaction liquid was filtered, and then concentrated under reduced pressure. The residue thus obtained was subjected to MPLC (7% MeOH/MC), to obtain 33 mg of yellow solid (41%). MS (ESI): 463 [M+H]+

Example 126

Synthesis of 6-((R)-4-(4-aminophenyl)-2-methylpiperazin-1-yl)-N-((E)-5-hydroxyadamantan-2-yl)picolinamide

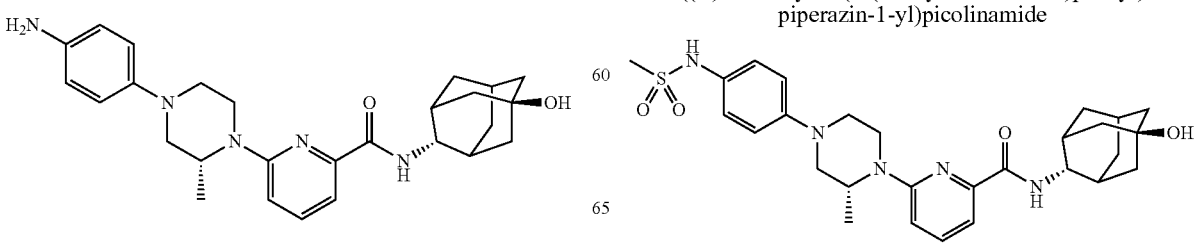

The same method as the example 125, except that N-((E)-5-hydroxyadamantan-2-yl)-6-((R)-2-methyl-4-(4-nitrophenyl)piperazin-1-yl)picolinamide (119 mg, 0.242 mmol) was used instead of N-((E)-5-hydroxyadamantan-2-yl)-6-((R)-2-methyl-4-(6-nitropyridin-3-yl)piperazin-1-yl)picolinamide, was performed to obtain 105 mg of yellow solid (94%). MS (ESI): 462 [M+H]+

Example 127

Synthesis of 6-((R)-4-(4-acetamidophenyl)-2-methylpiperazin-1-yl)-N-((E)-5-hydroxyadamantan-2-yl)picolinamide 6-((R)-4-(4-aminophenyl)-2-methylpiperazin-1-yl)-N-((E)-5-hydroxyadamantan-2-yl)picolinamide (109 mg, 0.236 mmol) was dissolved in MC (5 ml), followed by sequential addition of triethylamine (0.049 ml, 0.354 mmol) and acetic anhydride (0.022 ml, 0.236 mmol), and then the resulting liquid was stirred at room temperature under nitrogen stream for 2 hours. The resulting reaction liquid was concentrated under reduced pressure, and then the residue thus obtained was subjected to MPLC (5% MeOH/MC), to obtain 94 mg of white solid (79%). MS (ESI): 504 [M+H]+

Example 128

Synthesis of N-((E)-5-hydroxyadamantan-2-yl)-6-((R)-2-methyl-4-(4-(methylsulfonamido)phenyl)piperazin-1-yl)picolinamide 6-((R)-4-(4-aminophenyl)-2-methylpiperazin-1-yl)-N-((E)-5-hydroxyadamantan-2-yl)picolinamide (36 mg, 0.077 mmol) was dissolved in pyridine (1 ml), followed by addition of methanesulfonyl chloride (0.010 ml, 0.129 mmol), and then the resulting liquid was stirred at room temperature under nitrogen stream for 3 hours. The resulting reaction liquid was concentrated under reduced pressure, and then the residue thus obtained was subjected to MPLC (5% MeOH/MC), to obtain 14 mg of white solid (34%). MS (ESI): 540 [M+H]$^+$ Example 129

Synthesis of N-((E)-5-hydroxyadamantan-2-yl)-6-((R)-2-methylpiperazin-1-yl)picolinamide (Intermediate 10)

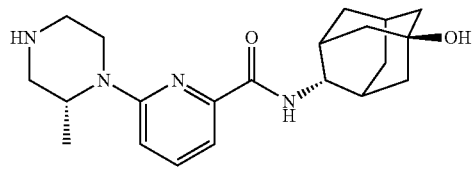 [SMILES: C[C@@H]1CNCCN1c1cccc(C(=O)N[C@H]2C3CC4CC2C[C@](O)(C4)C3)n1]

Step 1: Synthesis of (R)-tert-butyl 4-(6-(((E)-5-hydroxyadamantan-2-yl)carbamoyl)pyridin-2-yl)-3-methylpiperazine-1-carboxylate 6-Bromo-N-((E)-5-hydroxyadamantan-2-yl)picolinamide (1.0 g, 2.847 mmol), (R)-tert-butyl 3-methylpiperazine-1-carboxylate (855 mg, 4.271 mmol), Pd$_2$(dba)$_3$ (52 mg, 0.057 mmol), xantphos (99 mg, 0.171 mmol), and sodium-tert-butoxide (410 mg, 4.271 mmol) were suspended in toluene (20 ml), and then the resulting liquid was stirred at 100° C. under nitrogen stream for 3 hours. A saturated aqueous ammonium chloride solution (20 ml) was added to the resulting reaction liquid, followed by extraction with MC (40 ml×2). The organic layer was dried over anhydrous sodium sulfate, followed by filtration and concentration, and then the residue thus obtained was subjected to MPLC (90% EtOAc/Hexanes), to obtain 720 mg of pale yellow solid (54%).

Step 2: Synthesis of N-((E)-5-hydroxyadamantan-2-yl)-6-((R)-2-methylpiperazin-1-yl)picolinamide (Intermediate 10)

(R)-Tert-butyl 4-(6-(((E)-5-hydroxyadamantan-2-yl)carbamoyl)pyridin-2-yl)-3-methylpiperazine-1-carboxylate (715 mg, 1.519 mmol) was dissolved in MC (10 ml), followed by addition of trifluoroacetic acid (10 ml), and then the resulting mixture was stirred at room temperature for 3 hours. Distilled water (30 ml) was added to the resulting reaction liquid, followed by extraction with MC (15 ml×2). The aqueous layer was neutralized by addition of 5N aqueous NaOH solution, followed by extraction with 5% MeOH/MC (40 ml×3), and then the organic layer was dried over anhydrous sodium sulfate, followed by filtration, concentration, and vacuum drying, to obtain 516 mg of white solid (92%). MS (ESI): 371 [M+H]$^+$ Example 130

Synthesis of methyl 4-((R)-4-(6-(((E)-5-hydroxyadamantan-2-yl)carbamoyl)pyridin-2-yl)-3-methylpiperazin-1-yl)benzoate

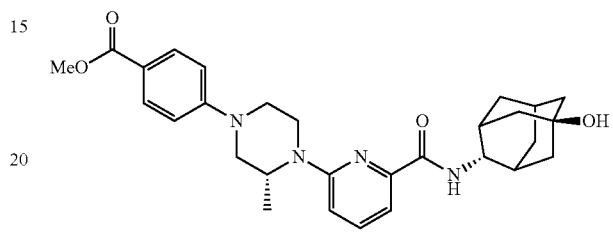

N-((E)-5-hydroxyadamantan-2-yl)-6-((R)-2-methylpiperazin-1-yl)picolinamide (200 mg, 0.540 mmol), methyl 4-bromobenzoate (174 mg, 0.810 mmol), Pd(OAc)$_2$ (5 mg, 0.022 mmol), xantphos (19 mg, 0.032 mmol), and cesium carbonate (264 mg, 0.810 mmol) were suspended in toluene (20 ml), and then the resulting liquid was stirred at 100° C. under nitrogen stream for 15 hours. The resulting reaction liquid was concentrated under reduced pressure, and then the residue thus obtained was subjected to MPLC (100% EtOAc), to obtain 224 mg of pale yellow solid (82%). MS (ESI): 505 [M+H]$^+$ Example 131

Synthesis of 4-((R)-4-(6-(((E)-5-hydroxyadamantan-2-yl)carbamoyl)pyridin-2-yl)-3-methylpiperazin-1-yl)benzoic acid

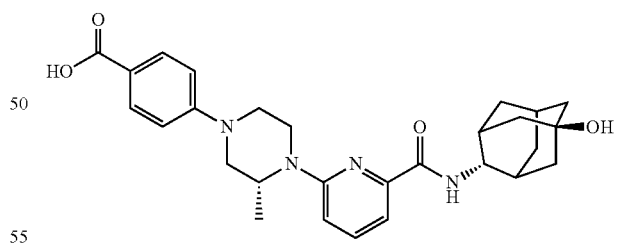

Methyl 4-((R)-4-(6-(((E)-5-hydroadamantan-2-yl)carbamoyl)pyridin-2-yl)-3-methylpiperazin-1-yl)benzoate (100 mg, 0.198 mmol) was dissolved in MeOH (5 ml), followed by addition of 2N aqueous NaOH solution (0.50 ml, 0.991 mmol), and then the resulting mixture was stirred at room temperature for 20 hours. The resulting reaction liquid was concentrated under reduced pressure, and dissolved by addition of distilled water (10 ml), and then the resulting liquid was neutralized by addition of 1N aqueous HCl solution, while stirring at 0° C. The precipitated solid was filtered, followed by vacuum drying, to obtain 72 mg of pale yellow solid (74%). MS (ESI): 491 [M+H]+

Example 132

Synthesis of 6-((R)-4-(4-carbamoylphenyl)-2-methylpiperazin-1-yl)-N-((E)-5-hydroxyadamantan-2-yl)picolinamide

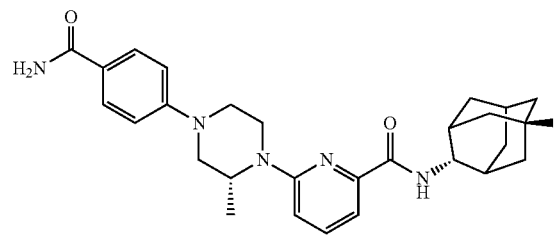

4-((R)-4-(6-(((E)-5-Hydroadamantan-2-yl)carbamoyl)pyridin-2-yl)-3-methylpiperazin-1-yl)benzoic acid (60 mg, 0.122 mmol) was dissolved in acetonitrile (2 ml), followed by sequential addition of ammonia (0.5M solution in dioxane, 0.49 ml, 0.244 mmol) N,N-diisopropylethylamine (0.043 ml, 0.244 mmol), and HBTU (56 mg, 0.146 mmol), and then the resulting mixture was stirred at room temperature under nitrogen stream for 3 hours. A saturated aqueous ammonium chloride solution (10 ml) was added to the resulting reaction liquid, followed by extraction with 10% MeOH/MC (15 ml×2). The organic layer was dried over anhydrous sodium sulfate, followed by filtration and concentration, and then the residue thus obtained was subjected to MPLC (5% MeOH/MC), to obtain 47 mg of pale yellow solid (78%). MS (ESI): 512 [M+Na]+

Example 133

Synthesis of N-((E)-5-hydroxyadamantan-2-yl)-6-((R)-2-methyl-4-(4-(methylcarbamoyl)phenyl)piperazin-1-yl)picolinamide

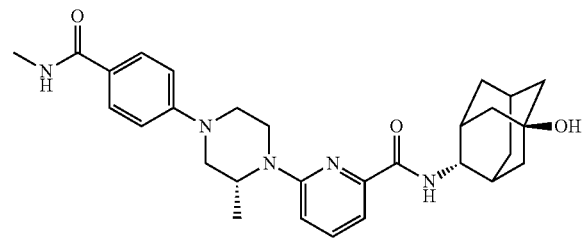 [SMILES: CNC(=O)c1ccc(N2CCN(c3cccc(C(=O)N[C@H]4C5CC6CC4C[C@](O)(C6)C5)n3)[C@H](C)C2)cc1]

The same method as the example 132, except that methylamine (2M solution in THF) was used instead of ammonia, was performed to obtain 17 mg of pale yellow solid (28%). MS (ESI): 504 [M+H]+

Example 134

Synthesis of 6-((R)-4-(4-(cyclopropylcarbamoyl)phenyl)-2-methylpiperazin-1-yl)-N-((E)-5-hydroxyadamantan-2-yl)picolinamide

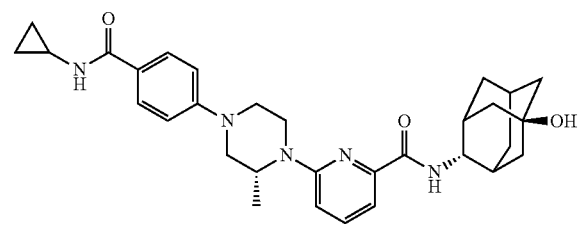 [SMILES: C[C@@H]1CN(c2ccc(C(=O)NC3CC3)cc2)CCN1c1cccc(C(=O)N[C@H]2C3CC4CC2C[C@](O)(C4)C3)n1]

The same method as the example 132, except that cyclopropylamine was used instead of ammonia, was performed to obtain 44 mg of pale yellow solid (70%). MS (ESI): 530 [M+H]+

Example 135

Synthesis of N-((E)-5-hydroxyadamantan-2-yl)-6-((R)-4-(4-((2-hydroxyethyl)carbamoyl)phenyl)-2-methylpiperazin-1-yl)picolinamide

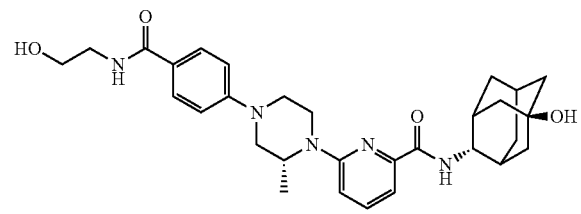 [SMILES: C[C@@H]1CN(c2ccc(C(=O)NCCO)cc2)CCN1c1cccc(C(=O)N[C@H]2C3CC4CC2C[C@](O)(C4)C3)n1]

The same method as the example 132, except that 2-aminoethanole was used instead of ammonia, was performed to obtain 50 mg of pale yellow solid (77%). MS (ESI): 534 [M+H]+

The following examples were synthesized in the same method as the above examples 130, 131, 132, and 133, by using the intermediate 10 and an appropriate bromobenzene or bromopyridine start material.

| Examples | Structures | MS (ESI) |
| --- | --- | --- |
| 136 | 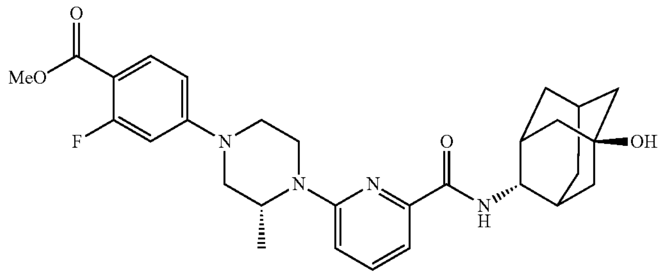 [SMILES: COC(=O)c1ccc(N2CCN(c3cccc(C(=O)N[C@H]4C5CC6CC4C[C@](O)(C6)C5)n3)[C@H](C)C2)cc1F] | 523 [M + H]+ |
| 137 | 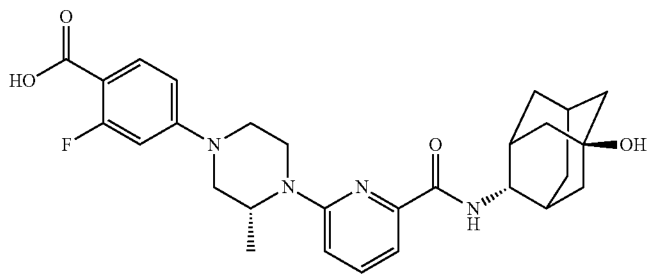 [SMILES: C[C@@H]1CN(c2ccc(C(=O)O)c(F)c2)CCN1c1cccc(C(=O)N[C@H]2C3CC4CC2C[C@](O)(C4)C3)n1] | 509 [M + H]+ |
| 138 | 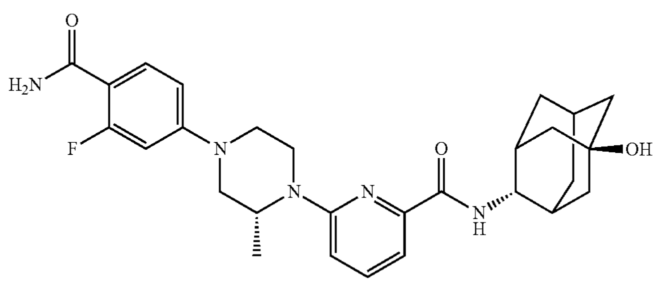 [SMILES: C[C@@H]1CN(c2ccc(C(N)=O)c(F)c2)CCN1c1cccc(C(=O)N[C@H]2C3CC4CC2C[C@](O)(C4)C3)n1] | 508 [M + H]+ |
| 139 | 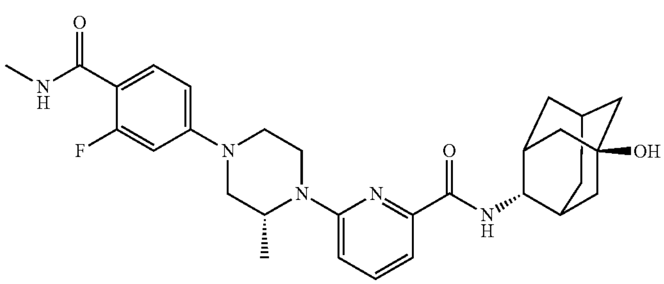 [SMILES: CNC(=O)c1ccc(N2CCN(c3cccc(C(=O)N[C@H]4C5CC6CC4C[C@](O)(C6)C5)n3)[C@H](C)C2)cc1F] | 522 [M + H]+ |
| 140 | 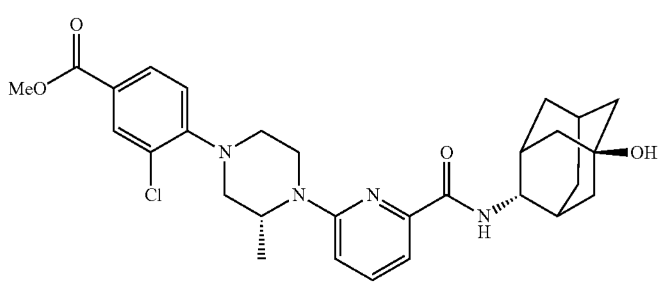 [SMILES: COC(=O)c1ccc(N2CCN(c3cccc(C(=O)N[C@H]4C5CC6CC4C[C@](O)(C6)C5)n3)[C@H](C)C2)c(Cl)c1] | 539 [M + H]+ |

| Examples | Structures | MS (ESI) |
|---|---|---|
| 141 | 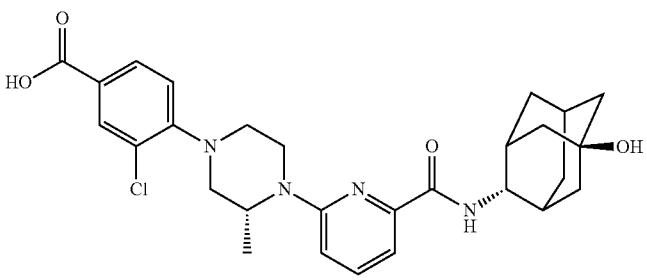 [SMILES: C[C@@H]1CN(c2ccc(C(=O)O)cc2Cl)CCN1c1cccc(C(=O)N[C@H]2C3CC4CC2C[C@](O)(C4)C3)n1] | 525 [M + H]+ |
| 142 | 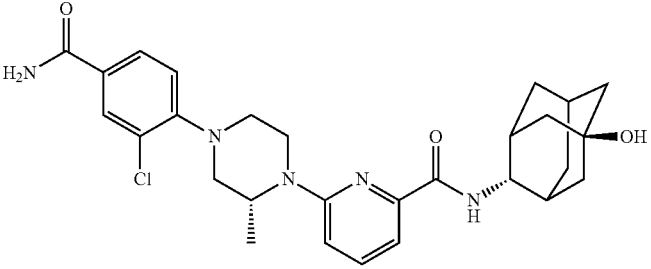 [SMILES: C[C@@H]1CN(c2ccc(C(N)=O)cc2Cl)CCN1c1cccc(C(=O)N[C@H]2C3CC4CC2C[C@](O)(C4)C3)n1] | 524 [M + H]+ |
| 143 | 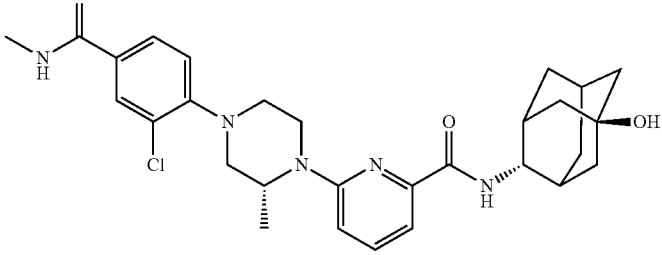 | 538 [M + H]+ |
| 144 | 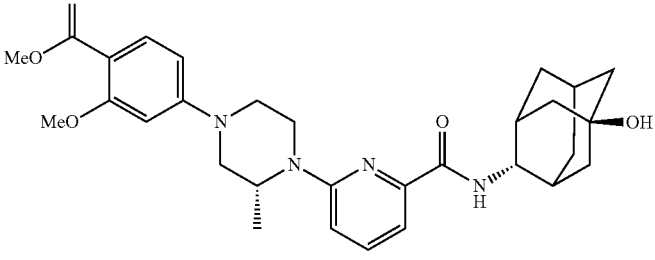 | 535 [M + H]+ |
| 145 | 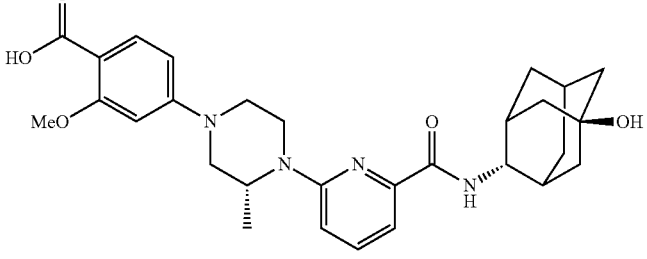 | 521 [M + H]+ |

-continued

| Examples | Structures | MS (ESI) |
| --- | --- | --- |
| 146 | 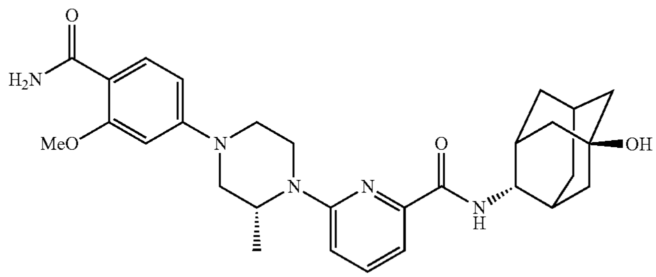 [SMILES: COc1cc(N2CCN(c3cccc(C(=O)N[C@H]4C5CC6CC4C[C@](O)(C6)C5)n3)[C@H](C)C2)ccc1C(N)=O] | 520 [M + H]+ |
| 147 | 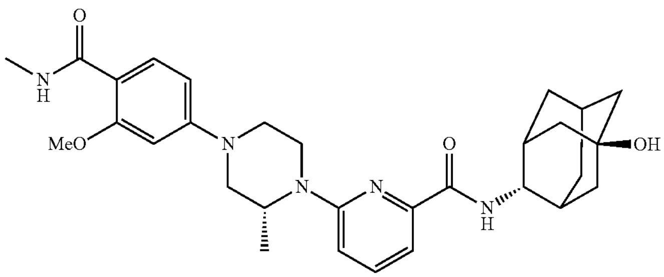 [SMILES: CNC(=O)c1ccc(N2CCN(c3cccc(C(=O)N[C@H]4C5CC6CC4C[C@](O)(C6)C5)n3)[C@H](C)C2)cc1OC] | 534 [M + H]+ |
| 148 | 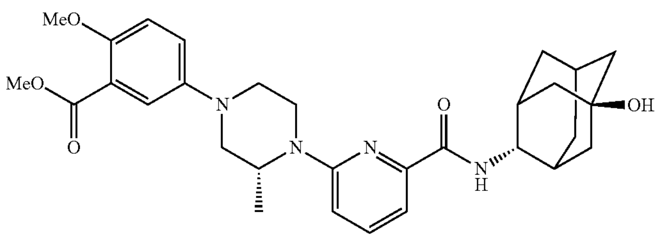 | 535 [M + H]+ |
| 149 | 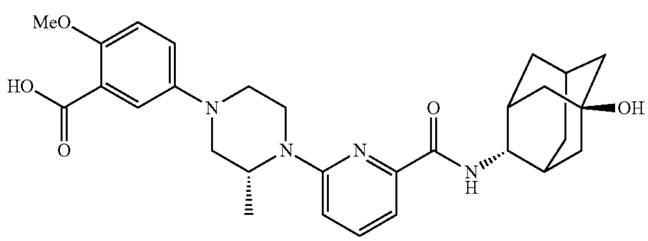 [SMILES: COc1ccc(N2CCN(c3cccc(C(=O)N[C@H]4C5CC6CC4C[C@](O)(C6)C5)n3)[C@H](C)C2)cc1C(=O)O] | 521 [M + H]+ |
| 150 | 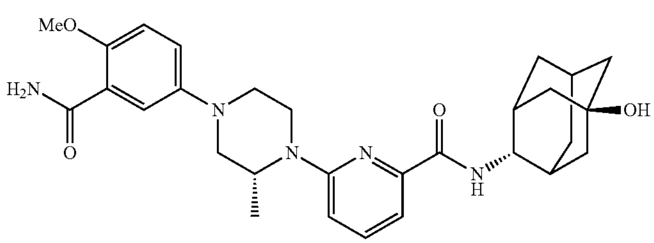 [SMILES: COc1ccc(N2CCN(c3cccc(C(=O)N[C@H]4C5CC6CC4C[C@](O)(C6)C5)n3)[C@H](C)C2)cc1C(N)=O] | 520 [M + H]+ |
| 151 | 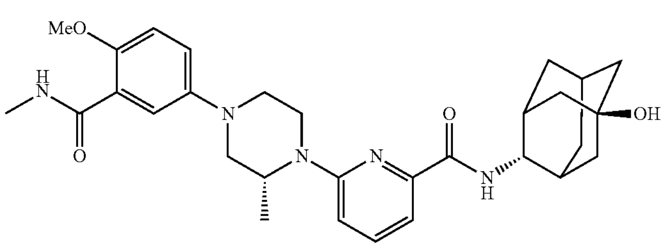 [SMILES: CNC(=O)c1cc(N2CCN(c3cccc(C(=O)N[C@H]4C5CC6CC4C[C@](O)(C6)C5)n3)[C@H](C)C2)ccc1OC] | 534 [M + H]+ |

-continued

| Examples | Structures | MS (ESI) |
|---|---|---|
| 152 | (structure) | 523 [M + H]+ |
| 153 | (structure) | 509 [M + H]+ |
| 154 | (structure) | 522 [M + H]+ |
| 155 | (structure) | 506 [M + H]+ |
| 156 | (structure) | 492 [M + H]+ |
| 157 | (structure) | 491 [M + H]+ |

| Examples | Structures | MS (ESI) |
|---|---|---|
| 158 | 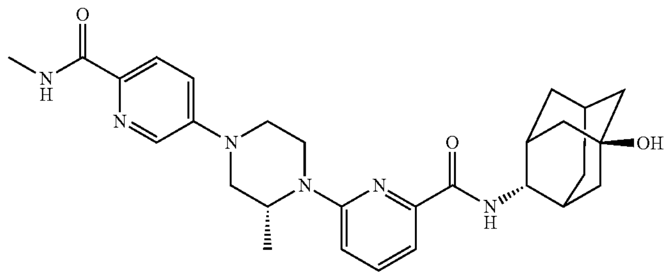 [SMILES: CNC(=O)c1ccc(N2CCN(c3cccc(C(=O)N[C@H]4C5CC6CC4C[C@](O)(C6)C5)n3)[C@H](C)C2)cn1] | 505 [M + H]+ |

Example 159

Synthesis of methyl 6-((R)-4-(6-(((E)-5-hydroxyadamantan-2-yl)carbamoyl)pyridin-2-yl)-3-methylpiperazin-1-yl)nicotinate

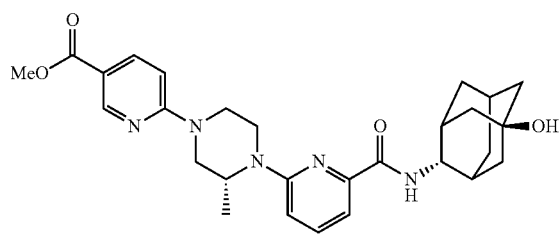 [SMILES: COC(=O)c1ccc(N2CCN(c3cccc(C(=O)N[C@H]4C5CC6CC4C[C@](O)(C6)C5)n3)[C@H](C)C2)nc1]

N-((E)-5-hydroxyadamantan-2-yl)-6-((R)-2-methylpiperazin-1-yl)picolinamide (120 mg, 0.324 mmol) and methyl 6-bromonicotinate (84 mg, 0.389 mmol) were suspended in acetonitrile (4 ml), followed by addition of triethylamine (0.09 ml, 0.648 mmol), and then the resulting liquid was stirred at 95° C. under nitrogen stream for 24 hours. A saturated aqueous ammonium chloride solution (10 ml) was added to the resulting reaction liquid, followed by extraction with MC (30 ml×2). The organic layer was dried over anhydrous sodium sulfate, followed by filtration and concentration, and then the residue thus obtained was subjected to MPLC (4% MeOH/MC), to obtain 160 mg of pale yellow oil (98%). MS (ESI): 506 [M+H]+

Example 160

Synthesis of 6-((R)-4-(6-(((E)-5-hydroxyadamantan-2-yl)carbamoyl)pyridin-2-yl)-3-methylpiperazin-1-yl)nicotinic acid

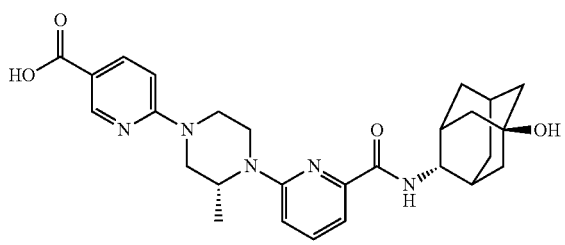 [SMILES: C[C@@H]1CN(c2ccc(C(=O)O)cn2)CCN1c1cccc(C(=O)N[C@H]2C3CC4CC2C[C@](O)(C4)C3)n1]

The same method as the example 131, except that methyl 6-((R)-4-(6-(((E)-5-hydroxyadamantan-2-yl)carbamoyl)pyridin-2-yl)-3-methylpiperazin-1-yl)nicotinate (155 mg, 0.307 mmol) was used instead of methyl 4-((R)-4-(6-(((E)-5-hydroxyadamantan-2-yl)carbamoyl)pyridin-2-yl)-3-methylpiperazin-1-yl)benzoate, was performed to obtain 135 mg of pale yellow solid (90%). MS (ESI): 492 [M+H]+

Example 161

Synthesis of 6-((R)-4-(5-carbamoylpyridin-2-yl)-2-methylpiperazin-1-yl)-N-((E)-5-hydroxyadamantan-2-yl)picolinamide

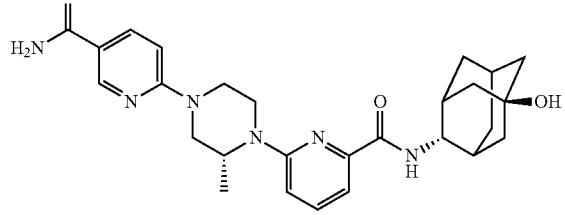

The same method as the example 132, except that 6-((R)-4-(6-(((E)-5-hydroxyadamantan-2-yl)carbamoyl)pyridin-2-yl)-3-methylpiperazin-1-yl)nicotinic acid (40 mg, 0.081 mmol) was used instead of 4-((R)-4-(6-(((E)-5-hydroxyadamantan-2-yl)carbamoyl)pyridin-2-yl)-3-methylpiperazin-1-yl)benzoic acid, was performed to obtain 28 mg of white solid (70%). MS (ESI): 491 [M+H]+

Example 162

Synthesis of N-((E)-5-hydroxyadamantan-2-yl)-6-((R)-2-methyl-4-(5-(methylcarbamoyl)pyridin-2-yl)piperazin-1-yl)picolinamide

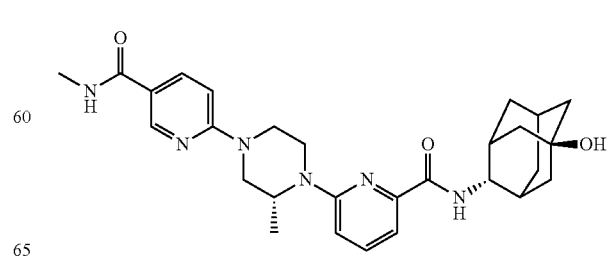

The same method as the example 133, except that 6-((R)-4-(6-(((E)-5-hydroxyadamantan-2-yl)carbamoyl)pyridin-2-yl)-3-methylpiperazin-1-yl)nicotinic acid (40 mg, 0.081 mmol) was used instead of 4-((R)-4-(6-(((E)-5-hydroxyadamantan-2-yl)carbamoyl)pyridin-2-yl)-3-methylpiperazin-1-yl)benzoic acid, was performed to obtain 25 mg of white solid (61%). MS (ESI): 505 [M+H]+

The following examples were synthesized in the same method as the above examples 159, 160, 161, and 162, by using the intermediate 10 and ethyl 5,6-dichloronicotinate.

| Examples | Structures | MS (ESI) |
| --- | --- | --- |
| 163 | 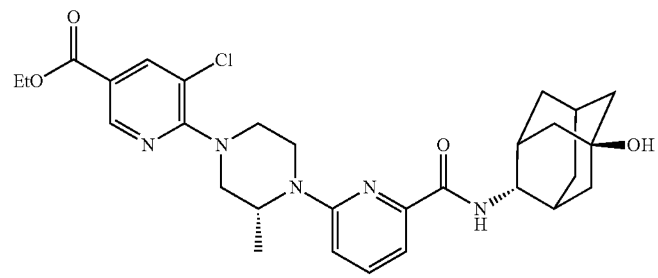 | 554 [M + H]+ |
| 164 | 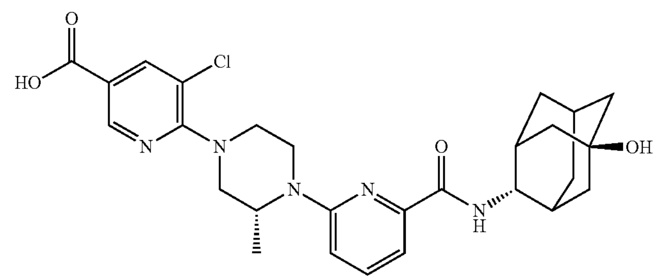 | 526 [M + H]+ |
| 165 | 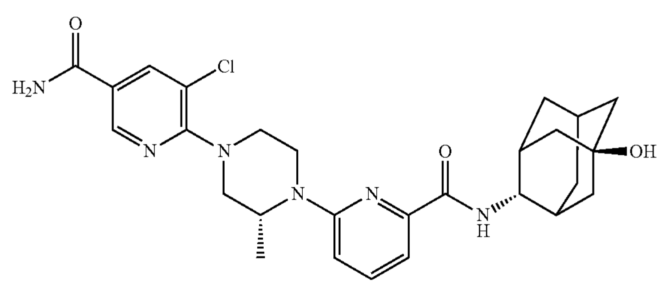 | 525 [M + H]+ |
| 166 | 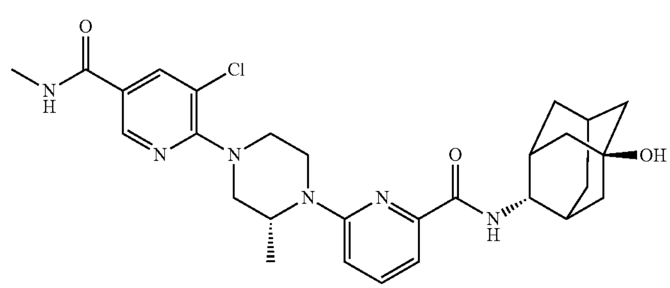 [SMILES: CNC(=O)c1cnc(N2CCN(c3cccc(C(=O)N[C@H]4C5CC6CC4C[C@](O)(C6)C5)n3)[C@H](C)C2)c(Cl)c1] | 539 [M + H]+ |

Example 167

Synthesis of N-((E)-5-hydroxyadamantan-2-yl)-6-((R)-2-methyl-4-(4-sulfamoylphenyl)piperazin-1-yl)picolinamide

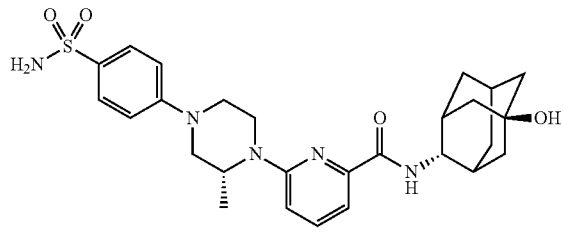 [SMILES: C[C@@H]1CN(c2ccc(S(N)(=O)=O)cc2)CCN1c1cccc(C(=O)N[C@H]2C3CC4CC2C[C@](O)(C4)C3)n1]

Step 1: Synthesis of 4-bromo-N-(tert-butyl)benzene sulfonamide 4-bromobenzenesulfonyl chloride (200 mg, 0.783 mmol) was dissolved in MC (10 ml), followed by dropwise addition of tert-butylamine (0.41 ml, 3.91 mmol) at 0° C., and then the resulting mixture was stirred at room temperature under nitrogen stream for 1 hour. Distilled water (15 ml) was added to the resulting reaction liquid, followed by extraction with MC (30 ml×2). The organic layer was dried over anhydrous sodium sulfate, followed by filtration and concentration, and then the residue thus obtained was dried under vacuum, to obtain 228 mg of white solid (100%).

Step 2: Synthesis of 6-((R)-4-(4-(N-(tert-butyl)sulfamoyl)phenyl)-2-methylpiperazin-1-yl)-N-((E)-5-hydroxyadamantan-2-yl)picolinamide N-((E)-5-hydroxyadamantan-2-yl)-6-((R)-2-methylpiperazin-1-yl)picolinamide (30 mg, 0.0810 mmol), 4-bromo-N-(tert-butyl)benzenesulfonyl amide (28 mg, 0.0972 mmol), Pd[P(o-tolyl)$_3$]$_2$Cl$_2$ (1 mg, 0.000810 mmol), BINAP (3 mg, 0.00486 mmol), and cesium carbonate (26 mg, 0.0810 mmol) were suspended in toluene (5 ml), and then the resulting liquid was stirred at 90° C. under nitrogen stream for 15 hours. The resulting reaction liquid was concentrated under reduced pressure, and then the residue thus obtained was subjected to MPLC (5% MeOH/MC), to obtain 45 mg of pale yellow solid (96%).

Step 3: Synthesis of N-((E)-5-hydroxyadamantan-2-yl)-6-((R)-2-methyl-4-(4-sulfamoylphenyl)piperazin-1-yl)picolinamide 6-((R)-4-(4-(N-(tert-butyl)sulfamoyl)phenyl)-2-methylpiperazin-1-yl)-N-((E)-5-hydroxyadamantan-2-yl)picolinamide (69 mg, 0.119 mmol) was dissolved in MC (3 ml), followed by addition of trifluoroacetic acid (3 ml), and then the resulting mixture was stirred at room temperature for 15 hours. The resulting reaction liquid was concentrated under reduced pressure, followed by addition of distilled water (10 ml), and then extracted with MC (5 ml). The aqueous layer was neutralized by addition of a saturated aqueous NaHCO$_3$ solution, followed by extraction with 10% MeOH/MC (25 ml×2). The organic layer was dried over anhydrous sodium sulfate, followed by filtration and concentration, and then the residue thus obtained was subjected to MPLC (5% MeOH/MC), to obtain 40 mg of pale yellow solid (64%). MS (ESI): 526 [M+H]$^+$

Example 168

Synthesis of N-((E)-5-hydroxyadamantan-2-yl)-6-((R)-2-methyl-4-(4-(N-methylsulfamoyl)phenyl)piperazin-1-yl)picolinamide

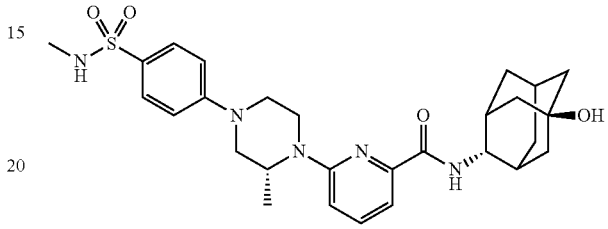

Step 1: Synthesis of 4-bromo-N-(tert-butyl)-N-methylbenzene sulfonamide

4-Bromo-N-(tert-butyl)benzenesulfonyl amide (100 mg, 0.342 mmol) and potassium carbonate (95 mg, 0.684 mmol) were dissolved in DMF (2 ml), followed by addition of iodomethane (0.043 ml, 0.684 mmol), and then the resulting liquid was stirred at room temperature for 18 hours. Distilled water (10 ml) was added to the resulting reaction liquid, followed by extraction with EtOAc (10 ml×3). The organic layer was dried over anhydrous sodium sulfate, followed by filtration and concentration, and then the residue thus obtained was subjected to MPLC (20% EtOAc/Hexanes), to obtain 77 mg of yellow oil (73%).

Step 2: Synthesis of 6-((R)-4-(4-(N-(tert-butyl)-N-methylsulfamoyl)phenyl)-2-methylpiperazin-1-yl)-N-((E)-5-hydroxyadamantan-2-yl)picolinamide N-((E)-5-hydroxyadamantan-2-yl)-6-((R)-2-methylpiperazin-1-yl)picolinamide (70 mg, 0.189 mmol), 4-bromo-N-(tert-butyl)-N-methylbenzenesulfonamide (69 mg, 0.227 mmol), Pd[P(o-tolyl)$_3$]$_2$Cl$_2$ (1.5 mg, 0.00189 mmol), BINAP (7 mg, 0.0113 mmol), and cesium carbonate (62 mg, 0.189 mmol) were suspended in toluene (5 ml), and then the resulting liquid was stirred at 90° C. under nitrogen stream for 18 hours. The resulting reaction liquid was concentrated under reduced pressure, and then the residue thus obtained was subjected to MPLC (3% MeOH/MC), to obtain 43 mg of yellow solid (38%).

Step 3: Synthesis of N-((E)-5-hydroxyadamantan-2-yl)-6-((R)-2-methyl-4-(4-(N-methylsulfamoyl)phenyl)piperazin-1-yl)picolinamide Trifluoroacetic acid (3 ml) was added to 6-((R)-4-(4-(N-(tert-butyl)-N-methylsulfamoyl)phenyl)-2-methylpiperazin-1-yl)-N-((E)-5-hydroxyadamantan-2-yl)picolinamide (43 mg, 0.0722 mmol), and then the resulting mixture was stirred at 90° C. for 2 hours. The resulting reaction liquid was neutralized by slow addition of a saturated aqueous NaHCO₃ solution, followed by extraction with MC (30 ml×3). The organic layer was dried over anhydrous sodium sulfate, followed by filtration and concentration, and then the residue thus obtained was subjected to MPLC (10% MeOH/MC), to obtain 14 mg of pale yellow solid (36%). MS (ESI): 562 [M+Na]⁺

The following examples were synthesized in the same method as the above examples 167 and 168, by using appropriate 4-bromobenzenesulfonyl chloride.

| Examples | Structures | MS (ESI) |
|---|---|---|
| 169 | 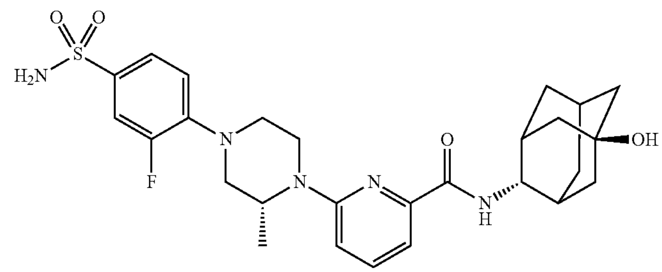 [SMILES: C[C@@H]1CN(c2ccc(S(N)(=O)=O)cc2F)CCN1c1cccc(C(=O)N[C@H]2C3CC4CC2C[C@](O)(C4)C3)n1] | 544 [M + H]⁺ |
| 170 | 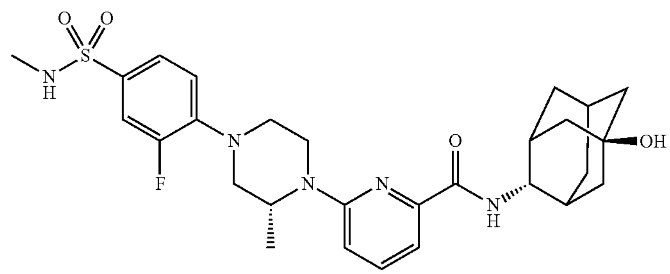 [SMILES: CNS(=O)(=O)c1ccc(N2CCN(c3cccc(C(=O)N[C@H]4C5CC6CC4C[C@](O)(C6)C5)n3)[C@H](C)C2)c(F)c1] | 558 [M + H]⁺ |
| 171 | 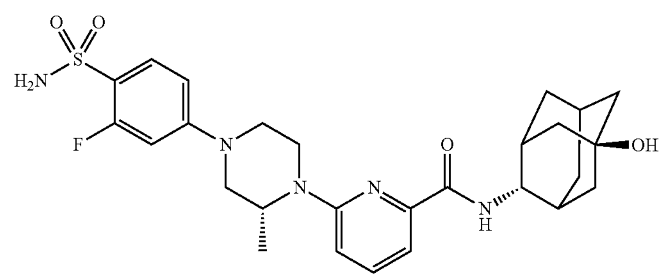 [SMILES: C[C@@H]1CN(c2ccc(S(N)(=O)=O)c(F)c2)CCN1c1cccc(C(=O)N[C@H]2C3CC4CC2C[C@](O)(C4)C3)n1] | 544 [M + H]⁺ |
| 172 | 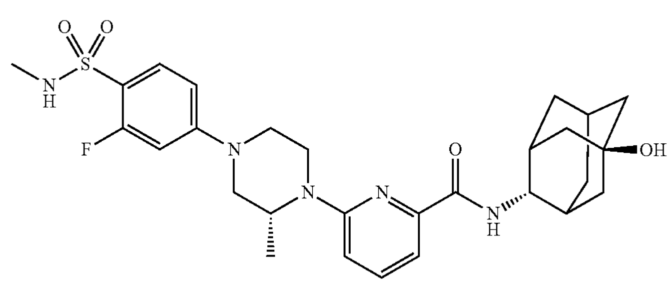 [SMILES: CNS(=O)(=O)c1ccc(N2CCN(c3cccc(C(=O)N[C@H]4C5CC6CC4C[C@](O)(C6)C5)n3)[C@H](C)C2)cc1F] | 558 [M + H]⁺ |

Example 173

Synthesis of N-((E)-5-hydroxyadamantan-2-yl)-6-((R)-4-(4-(2-hydroxypropan-2-yl)phenyl)-2-methylpiperazin-1-yl)picolinamide

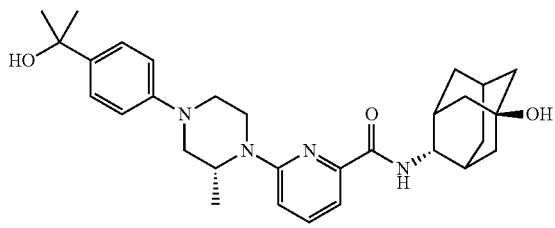 [SMILES: C[C@@H]1CN(c2ccc(C(C)(C)O)cc2)CCN1c1cccc(C(=O)N[C@H]2C3CC4CC2C[C@](O)(C4)C3)n1]

N-((E)-5-hydroxyadamantan-2-yl)-6-((R)-2-methylpiperazin-1-yl)picolinamide (30 mg, 0.081 mmol), 2-(4-bromophenyl)propan-2-ol (21 mg, 0.097 mmol), Pd$_2$(dba)$_3$ (1.5 mg, 0.0016 mmol), BINAP (3 mg, 0.0049 mmol), and sodium-tert-butoxide (12 mg, 0.122 mmol) were suspended in toluene (1 ml), and then the resulting liquid was stirred at 100° C. under nitrogen stream for 15 hours. Distilled water (10 ml) was added to the resulting reaction liquid, followed by extraction with MC (15 ml×2). The organic layer was dried over anhydrous sodium sulfate, followed by filtration and concentration, and then the residue thus obtained was subjected to MPLC (4% MeOH/MC), to obtain 23 mg of pale yellow solid (56%). MS (ESI): 487 [M−OH]$^+$

Example 174

Synthesis of N-((E)-5-hydroxyadamantan-2-yl)-6-((R)-4-(6-(2-hydroxypropan-2-yl)pyridin-3-yl)-2-methylpiperazin-1-yl)picolinamide

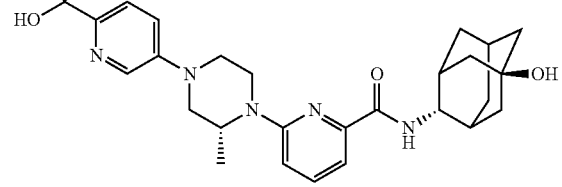

The same method as the example 173, except that 2-(5-bromopyridin-2-yl)propan-2-ol was used instead of 2-(4-bromophenyl)propan-2-ol, was performed to obtain 51 mg of pale yellow solid (29%). MS (ESI): 488 [M−OH]$^+$ The following examples were synthesized in the same method as the above example 173, by using appropriate bromobenzene.

| Examples | Structures | MS (ESI) |
|---|---|---|
| 175 | 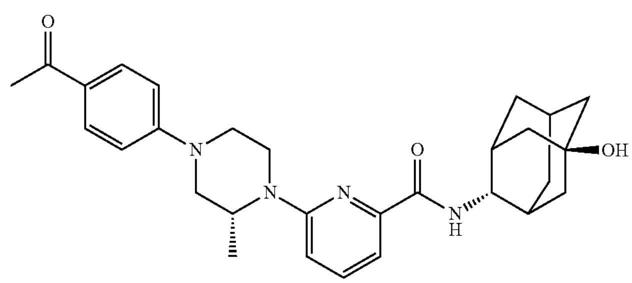 [SMILES: CC(=O)c1ccc(N2CCN(c3cccc(C(=O)N[C@H]4C5CC6CC4C[C@](O)(C6)C5)n3)[C@H](C)C2)cc1] | 489 [M + H]$^+$ |
| 176 | 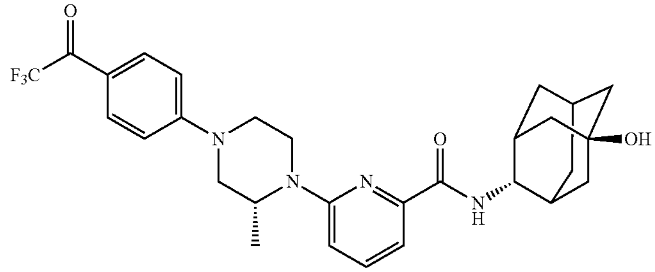 [SMILES: C[C@@H]1CN(c2ccc(C(=O)C(F)(F)F)cc2)CCN1c1cccc(C(=O)N[C@H]2C3CC4CC2C[C@](O)(C4)C3)n1] | 543 [M + H]$^+$ |
| 177 | 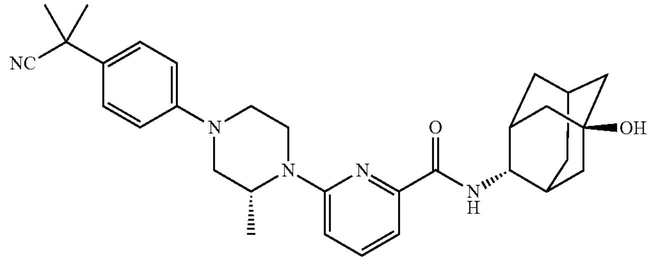 [SMILES: C[C@@H]1CN(c2ccc(C(C)(C)C#N)cc2)CCN1c1cccc(C(=O)N[C@H]2C3CC4CC2C[C@](O)(C4)C3)n1] | 514 [M + H]$^+$ |

-continued

| Examples | Structures | MS (ESI) |
|---|---|---|
| 178 | 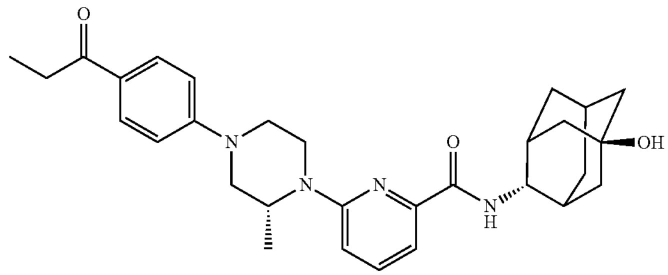 [SMILES: CCC(=O)c1ccc(N2CCN(c3cccc(C(=O)N[C@H]4C5CC6CC4C[C@](O)(C6)C5)n3)[C@H](C)C2)cc1] | 503 [M + H]⁺ |
| 179 | 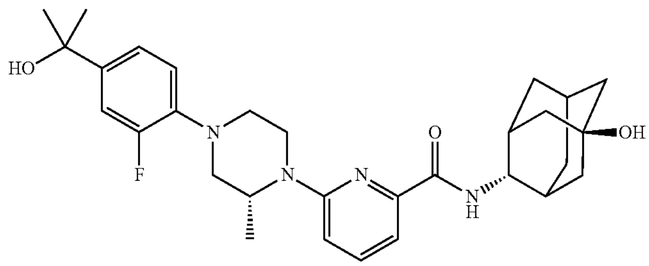 [SMILES: C[C@@H]1CN(c2ccc(C(C)(C)O)cc2F)CCN1c1cccc(C(=O)N[C@H]2C3CC4CC2C[C@](O)(C4)C3)n1] | 505 [M + H]⁺ |
| 180 | 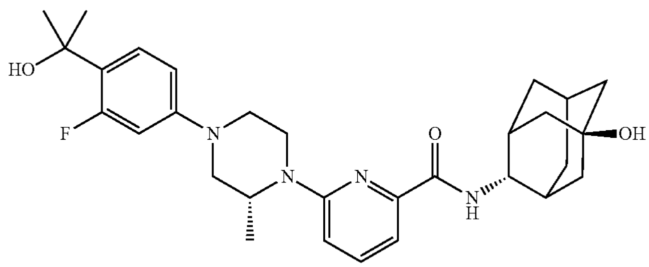 [SMILES: C[C@@H]1CN(c2ccc(C(C)(C)O)c(F)c2)CCN1c1cccc(C(=O)N[C@H]2C3CC4CC2C[C@](O)(C4)C3)n1] | 505 [M + H]⁺ |
| 181 | 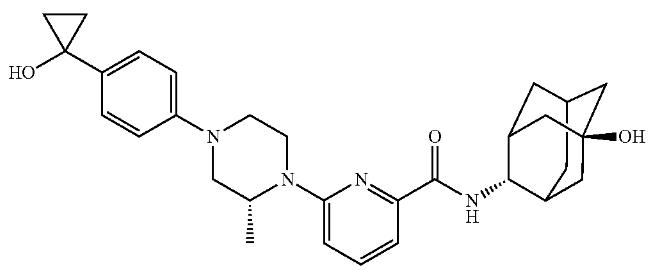 [SMILES: C[C@@H]1CN(c2ccc(C3(O)CC3)cc2)CCN1c1cccc(C(=O)N[C@H]2C3CC4CC2C[C@](O)(C4)C3)n1] | 503 [M + H]⁺ |
| 182 | 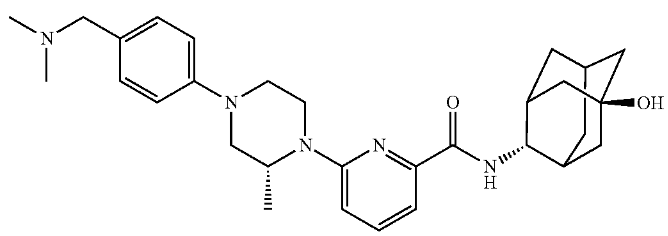 [SMILES: C[C@@H]1CN(c2ccc(CN(C)C)cc2)CCN1c1cccc(C(=O)N[C@H]2C3CC4CC2C[C@](O)(C4)C3)n1] | 504 [M + H]⁺ |
| 183 | 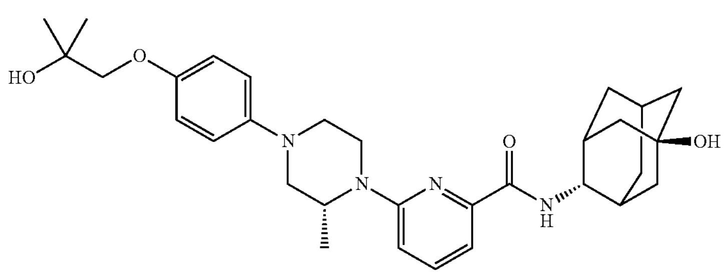 [SMILES: C[C@@H]1CN(c2ccc(OCC(C)(C)O)cc2)CCN1c1cccc(C(=O)N[C@H]2C3CC4CC2C[C@](O)(C4)C3)n1] | 535 [M + H]⁺ |

Example 184

Synthesis of N-((E)-5-hydroxyadamantan-2-yl)-6-((2R)-4-(4-(1-hydroxyethyl)phenyl)-2-methylpiperazin-1-yl)picolinamide

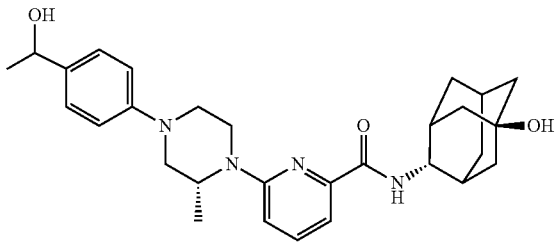 [SMILES: CC(O)c1ccc(N2CCN(c3cccc(C(=O)N[C@H]4C5CC6CC4C[C@](O)(C6)C5)n3)[C@H](C)C2)cc1]

6-((R)-4-(4-acetylphenyl)-2-methylpiperazin-1-yl)-N-((E)-5-hydroxyadamantan-2-yl)picolinamide (41 mg, 0.084 mmol) was dissolved in MeOH (2 ml), and then NaBH₄ (4.8 mg, 0.126 mmol) was added thereto at room temperature under nitrogen stream. Stirring for 30 minutes was repeatedly performed on the resulting liquid a total of four times. Distilled water (10 ml) was added to the resulting reaction liquid, followed by extraction with EtOAc (15 ml×3). The organic layer was dried over anhydrous sodium sulfate, followed by filtration and concentration, and then the residue thus obtained was subjected to MPLC (3% MeOH/MC), to obtain 26 mg of white solid (63%). MS (ESI): 473 [M−OH]$^+$

Example 185

Synthesis of N-((E)-5-hydroxyadamantan-2-yl)-6-((2R)-2-methyl-4-(4-(2,2,2-trifluoro-1-hydroxyethyl)phenyl)piperazin-1-yl)picolinamide

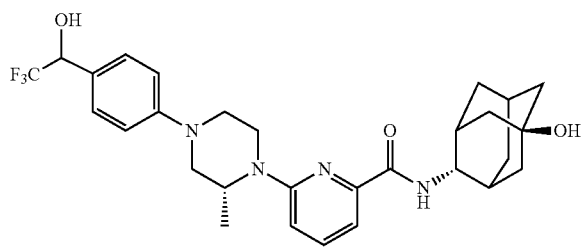 [SMILES: C[C@@H]1CN(c2ccc(C(O)C(F)(F)F)cc2)CCN1c1cccc(C(=O)N[C@H]2C3CC4CC2C[C@](O)(C4)C3)n1]

The same method as the example 184, except that N-((E)-5-hydroxyadamantan-2-yl)-6-((R)-2-methyl-4-(4-(2,2,2-trifluoroacetyl)phenyl)piperazin-1-yl)picolinamide was used instead of 6-((R)-4-(4-acetylphenyl)-2-methylpiperazin-1-yl)-N-((E)-5-hydroxyadamantan-2-yl)picolinamide, was performed to obtain 27 mg of pale yellow solid (20%). MS (ESI): 545 [M+H]$^+$

Example 186

Synthesis of 6-((R)-4-(4-(1-amino-2-methyl-1-oxopropan-2-yl)phenyl)-2-methylpiperazin-1-yl)-N-((E)-5-hydroxyadamantan-2-yl)picolinamide

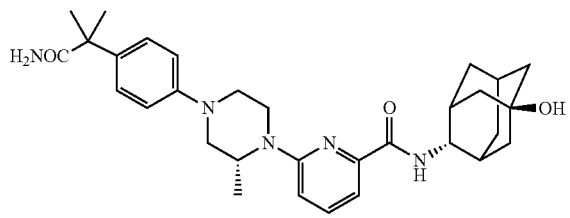 [SMILES: C[C@@H]1CN(c2ccc(C(C)(C)C(N)=O)cc2)CCN1c1cccc(C(=O)N[C@H]2C3CC4CC2C[C@](O)(C4)C3)n1]

6-((R)-4-(4-(2-cyanopropan-2-yl)phenyl)-2-methylpiperazin-1-yl)-N-((E)-5-hydroxyadamantan-2-yl)picolinamide (100 mg, 0.195 mmol) was dissolved in 2-methylpropan-2-ol (5 ml), followed by addition of KOH (257 mg, 3.894 mmol), and then the resulting liquid was heated at reflux for 4 hours. Distilled water (20 ml) was added to the resulting reaction liquid, followed by extraction with 5% MeOH/MC (30 ml×2). The organic layer was dried over anhydrous sodium sulfate, followed by filtration and concentration, and then the residue thus obtained was subjected to MPLC (3% MeOH/MC), to obtain 93 mg of pale yellow solid (90%). MS (ESI): 532 [M+H]$^+$

Example 187

Synthesis of 6-((R)-4-(3-chloro-4-hydroxyphenyl)-2-methylpiperazin-1-yl)-N-((E)-5-hydroxyadamantan-2-yl)picolinamide

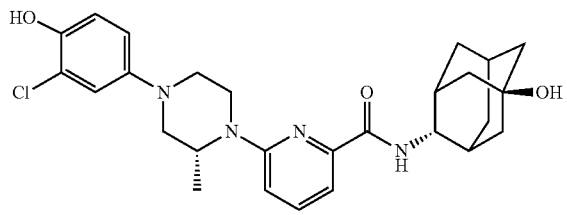 [SMILES: C[C@@H]1CN(c2ccc(O)c(Cl)c2)CCN1c1cccc(C(=O)N[C@H]2C3CC4CC2C[C@](O)(C4)C3)n1]

Step 1: synthesis of (4-bromo-2-chlorophenoxy)(tert-butyl)dimethylsilane 4-bromo-2-chlorophenol (1.0 g, 4.82 mmol) was dissolved in MC (30 ml), followed by addition of tert-butyldimethylsilyl chloride (1.09 g, 7.23 mmol) and imidazole (492 mg, 7.23 mmol), and then the resulting mixture was stirred at room temperature under nitrogen stream for 24 hours. The resulting reaction liquid was sequentially washed with distilled water (15 ml) and a saturated aqueous NaHCO₃ solution (15 ml), and then dried over anhydrous magnesium sulfate, followed by filtration and concentration. The residue thus obtained was subjected to MPLC (5% EtOAc/Hexanes), to obtain 1.69 g of colorless oil (99%).

Step 2: Synthesis of 6-((R)-4-(4-((tert-butyldimethylsilyl)oxy)-3-chlorophenyl)-2-methylpiperazin-1-yl)-N-((E)-5-hydroxyadamantan-2-yl)picolinamide N-((E)-5-hydroxyadamantan-2-yl)-6-((R)-2-methylpiperazin-1-yl)picolinamide (100 mg, 0.27 mmol) and (4-bromo-2-chlorophenoxy)(tert-butyl)dimethylsilane (130 mg, 0.405 mmol) were dissolved in toluene (2 ml), followed by addition of Pd₂(dba)₃ (5 mg, 2 mol %), BINAP (10 mg, 6 mol %), and sodium-tert-butoxide (39 mg, 0.405 mmol), and then the resulting liquid was stirred at 100° C. under nitrogen stream for 15 hours. Distilled water (5 ml) was added to the resulting reaction liquid, followed by extraction with MC (20 ml×2). The organic layer was dried over anhydrous magnesium sulfate, followed by filtration and concentration, and then the residue thus obtained was subjected to MPLC (3% MeOH/MC), to obtain 42 mg of yellow oil (25%).

Step 3: Synthesis of 6-((R)-4-(3-chloro-4-hydroxyphenyl)-2-methylpiperazin-1-yl)-N-((E)-5-hydroxyadamantan-2-yl)picolinamide 6-((R)-4-(4-((tert-butyldimethylsilyl)oxy)-3-chlorophenyl)-2-methylpiperazin-1-yl)-N-((E)-5-hydroxyadamantan-2-yl)picolinamide (42 mg, 0.069 mmol) was dissolved in THF (1 ml), followed by addition of tetrabutyl ammonium fluoride (1M solution in THF, 0.137 ml, 0.137 mmol), and then the resulting mixture was stirred at room temperature under nitrogen stream for 15 hours. Distilled water (5 ml) was added to the resulting reaction liquid, followed by extraction with MC (20 ml×2). The organic layer was dried over anhydrous magnesium sulfate, followed by filtration and concentration, and then the residue thus obtained was subjected to MPLC (3% MeOH/MC), to obtain 16 mg of yellow oil (47%). MS (ESI): 498 [M+H]$^+$ Example 188

Synthesis of ethyl 2-(2-chloro-4-((R)-4-(6-(((E)-5-hydroxyadamantan-2-yl)carbamoyl)pyridin-2-yl)-3-methylpiperazin-1-yl)phenoxy)acetate

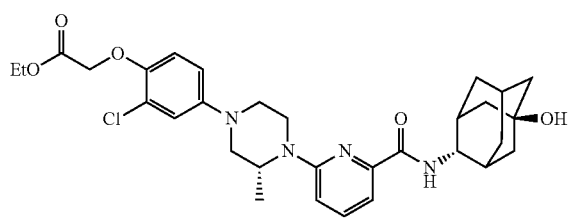 [SMILES: C[C@@H]1CN(c2ccc(OCC(=O)O)c(Cl)c2)CCN1c1cccc(C(=O)N[C@H]2C3CC4CC2C[C@](O)(C4)C3)n1]

6-((R)-4-(3-chloro-4-hydroxyphenyl)-2-methylpiperazin-1-yl)-N-((E)-5-hydroxyadamantan-2-yl)picolinamide (52 mg, 0.105 mmol) and potassium carbonate (20 mg, 0.126 mmol) were suspended in DMF (1 ml), followed by addition of ethyl bromoacetate (0.014 ml, 0.126 mmol), and then the resulting liquid was stirred at 100° C. under nitrogen stream for 2 hours. EtOAc (10 ml) was added to the resulting reaction liquid, and then the resulting liquid was sequentially washing with distilled water (5 ml×2) and a saturated aqueous sodium chloride solution (5 ml). The organic layer was dried over anhydrous magnesium sulfate, followed by filtration and concentration, and then the residue thus obtained was subjected to MPLC (3% MeOH/MC), to obtain 61 mg of pale yellow oil (99%). MS (ESI): 583 [M+H]$^+$ Example 189

Synthesis of 2-(2-chloro-4-((R)-4-(6-(((E)-5-hydroxyadamantan-2-yl)carbamoyl)pyridin-2-yl)-3-methylpiperazin-1-yl)phenoxy)acetic acid

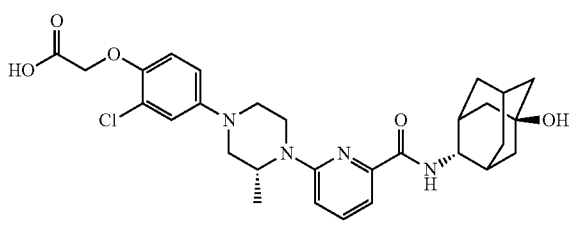

The same method as the example 84, except that ethyl 2-(2-chloro-4-((R)-4-(6-(((E)-5-hydroxyadamantan-2-yl)carbamoyl)pyridin-2-yl)-3-methylpiperazin-1-yl)phenoxy)acetate (88 mg, 0.150 mmol) was used instead of ethyl 2-(4-(4-(6-(((E)-5-hydroxyadamantan-2-yl)carbamoyl)pyridin-2-yl)piperazin-1-yl)phenoxy)acetate, was performed to obtain 79 mg of pale yellow solid (94%). MS (ESI): 555 [M+H]$^+$ Example 190

Synthesis of 6-((R)-4-(4-(2-amino-2-oxoethoxy)-3-chlorophenyl)-2-methylpiperazin-1-yl)-N-((E)-5-hydroxyadamantan-2-yl)picolinamide

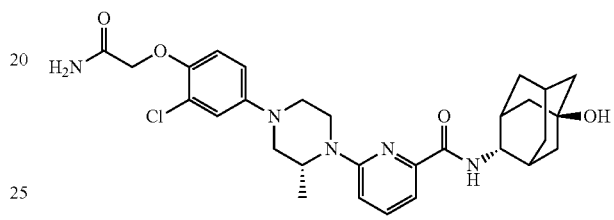

The same method as the example 132, except that 2-(2-chloro-4-((R)-4-(6-(((E)-5-hydroxyadamantan-2-yl)carbamoyl)pyridin-2-yl)-3-methylpiperazin-1-yl)phenoxy)acetic acid (62 mg, 0.112 mmol) was used instead of 4-((R)-4-(6-(((E)-5-hydroxyadamantan-2-yl)carbamoyl)pyridin-2-yl)-3-methylpiperazin-1-yl)benzoic acid, was performed to obtain 37 mg of pale yellow solid (60%). MS (ESI): 554 [M+H]$^+$ Example 191

Synthesis of N-((E)-5-hydroxyadamantan-2-yl)-6-((R)-4-(2-hydroxyethyl)-2-methylpiperazin-1-yl)picolinamide

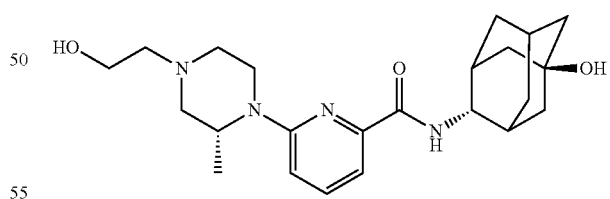

N-((E)-5-hydroxyadamantan-2-yl)-6-((R)-2-methylpiperazin-1-yl)picolinamide (50 mg, 0.135 mmol) and potassium carbonate (37 mg, 0.270 mmol) were suspended in acetonitrile (2 ml), followed by addition of 2-bromoethanol (0.014 ml, 0.202 mmol), and then the resulting liquid was stirred at 90° C. under nitrogen stream for 10 hours. The resulting reaction liquid was concentrated under reduced pressure, and then the residue thus obtained was subjected to MPLC (5% MeOH/MC), to obtain 44 mg of white solid (79%). MS (ESI): 415 [M+H]$^+$

Example 192

Synthesis of 6-((R)-4-(2-hydroxy-2-methylpropyl)-2-methylpiperazin-1-yl)-N-((E)-5-hydroxyadamantan-2-yl)picolinamide

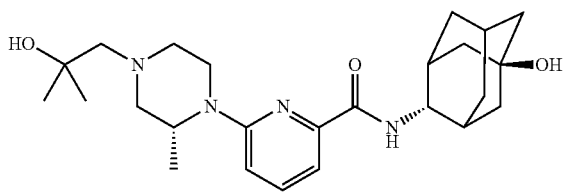 [SMILES: C[C@@H]1CN(CC(C)(C)O)CCN1c1cccc(C(=O)N[C@H]2C3CC4CC2C[C@](O)(C4)C3)n1]

N-((E)-5-hydroxyadamantan-2-yl)-6-((R)-2-methylpiperazin-1-yl)picolinamide (60 mg, 0.162 mmol), potassium carbonate (45 mg, 0.324 mmol), and potassium iodide (27 mg, 0.162 mmol) were suspended in acetonitrile (2 ml), followed by addition of 1-chloro-2-methylpropan-2-ol (0.10 ml, 0.972 mmol), and then the resulting liquid was stirred at 100° C. under nitrogen stream for 72 hours. The resulting reaction liquid was concentrated under reduced pressure, and then the residue thus obtained was subjected to MPLC (3% MeOH/MC), to obtain 10 mg of white solid (14%). MS (ESI): 443 [M+H]$^+$

Example 193

Synthesis of N-((E)-5-hydroxyadamantan-2-yl)-6-((R)-2-methyl-4-(2-(methylsulfonyl)ethyl)piperazin-1-yl)picolinamide

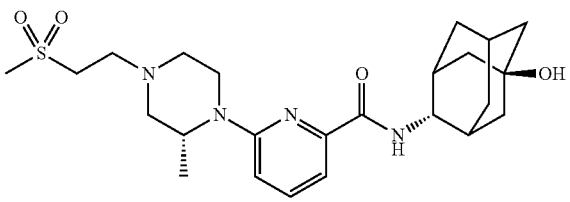 [SMILES: C[C@@H]1CN(CCS(C)(=O)=O)CCN1c1cccc(C(=O)N[C@H]2C3CC4CC2C[C@](O)(C4)C3)n1]

N-((E)-5-hydroxyadamantan-2-yl)-6-((R)-2-methylpiperazin-1-yl)picolinamide (60 mg, 0.162 mmol) was dissolved in THF (1 ml), followed by addition of (methylsulfonyl)ethene (69 mg, 0.648 mmol), and then the resulting liquid was stirred at 60° C. under nitrogen stream for 20 hours. The resulting reaction liquid was concentrated under reduced pressure, and then the residue thus obtained was subjected to MPLC (3% MeOH/MC), to obtain 37 mg of white solid (48%). MS (ESI): 477 [M+H]$^+$

Example 194

Synthesis of 6-((R)-4-((1-cyanocyclopropyl)methyl)-2-methylpiperazin-1-yl)-N-((E)-5-hydroxyadamantan-2-yl)picolinamide

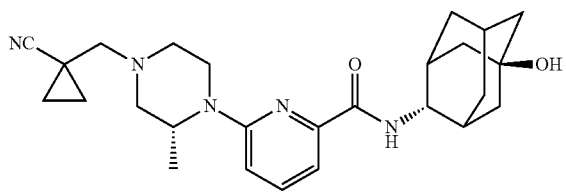 [SMILES: C[C@@H]1CN(CC2(C#N)CC2)CCN1c1cccc(C(=O)N[C@H]2C3CC4CC2C[C@](O)(C4)C3)n1]

N-((E)-5-hydroxyadamantan-2-yl)-6-((R)-2-methylpiperazin-1-yl)picolinamide (150 mg, 0.405 mmol) and (1-cyanocyclopropyl)methyl-4-methylbenzenesulfonate (122 mg, 0.486 mmol) were dissolved in acetonitrile (3 ml), followed by addition of N,N-diisopropylethylamine (0.14 ml, 0.810 mmol), and then the resulting liquid was stirred at 90° C. under nitrogen stream for 17 hours. A saturated aqueous ammonium chloride solution (10 ml) was added to the resulting reaction liquid, followed by extraction with MC (20 ml×2). The organic layer was dried over anhydrous sodium sulfate, followed by filtration and concentration, and then the residue thus obtained was subjected to MPLC (4% MeOH/MC), to obtain 157 mg of pale yellow solid (86%). MS (ESI): 450 [M+H]$^+$

Example 195

Synthesis of 6-((R)-4-((1-carbamoylcyclopropyl)methyl)-2-methylpiperazin-1-yl)-N-((E)-5-hydroxyadamantan-2-yl)picolinamide

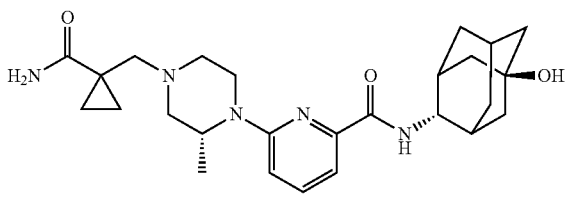 [SMILES: C[C@@H]1CN(CC2(C(N)=O)CC2)CCN1c1cccc(C(=O)N[C@H]2C3CC4CC2C[C@](O)(C4)C3)n1]

6-((R)-4-((1-cyanocyclopropyl)methyl)-2-methylpiperazin-1-yl)-N-((E)-5-hydroxyadamantan-2-yl)picolinamide (100 mg, 0.222 mmol) and KOH (294 mg, 4.448 mmol) were suspended in 2-methylpropan-2-ol (5 ml), and then the resulting liquid was stirred at 95° C. for 4 hours. Distilled water (15 ml) was added to the resulting reaction liquid, followed by extraction with 5% MeOH/MC (20 ml×3). The organic layer was dried over anhydrous sodium sulfate, followed by filtration and concentration, and then the residue thus obtained was subjected to MPLC (6% MeOH/MC), to obtain 81 mg of white solid (78%). MS (ESI): 468 [M+H]$^+$

Example 196

Synthesis of 6-((R)-4-cyclopropyl-2-methylpiperazin-1-yl)-N-((E)-5-hydroxyadamantan-2-yl)picolinamide

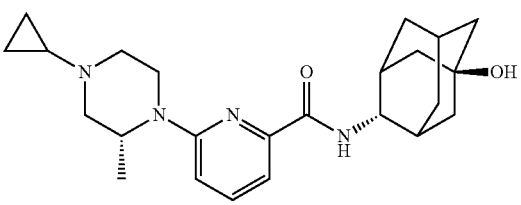 [SMILES: C[C@@H]1CN(C2CC2)CCN1c1cccc(C(=O)N[C@H]2C3CC4CC2C[C@](O)(C4)C3)n1]

N-((E)-5-hydroxyadamantan-2-yl)-6-((R)-2-methylpiperazin-1-yl)picolinamide (100 mg, 0.270 mmol) was dissolved in MeOH (2 ml), followed by sequential addition of 1-ethoxy-1-trimethylsilyoxycyclopropane (0.324 ml, 1.62 mmol), acetic acid (0.155 ml, 2.70 mmol), and sodium cyanoborohydride (76 mg, 1.21 mmol), and then the resulting liquid was stirred at 80° C. under nitrogen stream for 8 hours. EtOAc (30 ml) was added to the resulting reaction liquid, and then the resulting liquid was sequentially washed with 1N aqueous NaOH solution, a saturated aqueous sodium chloride solution. The organic layer was dried over anhydrous sodium sulfate, followed by filtration and concentration, and then the residue thus obtained was subjected to MPLC (3% MeOH/MC), to obtain 87 mg of white solid (79%). MS (ESI): 411 [M+H]$^+$

Example 197

Synthesis of N-((E)-5-hydroxyadamantan-2-yl)-6-((R)-2-methyl-4-(tetrahydro-2H-pyran-4-yl)piperazin-1-yl)picolinamide

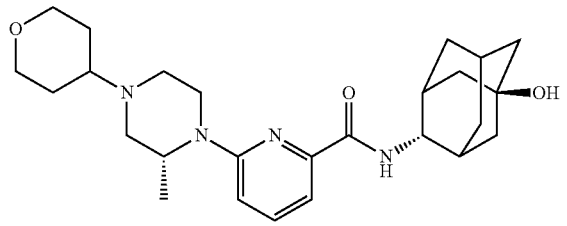 [SMILES: C[C@@H]1CN(C2CCOCC2)CCN1c1cccc(C(=O)N[C@H]2C3CC4CC2C[C@](O)(C4)C3)n1]

N-((E)-5-hydroxyadamantan-2-yl)-6-((R)-2-methylpiperazin-1-yl)picolinamide (100 mg, 0.270 mmol) was dissolved in 2:1 DCE/THF (1.5 ml), followed by sequential addition of 2,3,5,6-tetrahydropyran-4-one (0.087 ml, 0.945 mmol), acetic acid (0.031 ml, 0.540 mmol), and sodium triacetoxyborohydride (286 mg, 1.35 mmol), and then the resulting liquid was stirred at 75° C. under nitrogen stream for 18 hours. EtOAc (30 ml) was added to the resulting reaction liquid, and then the resulting liquid was sequentially washed with 1N aqueous NaOH solution, a saturated aqueous sodium chloride solution. The organic layer was dried over anhydrous sodium sulfate, followed by filtration and concentration, and then the residue thus obtained was subjected to MPLC (5% MeOH/MC), to obtain 76 mg of pale yellow solid (62%). MS (ESI): 455 [M+H]$^+$

Example 198

Synthesis of 6-((R)-4-(4-hydroxy-4-methylcyclohexyl)-2-methylpiperazin-1-yl)-N-((E)-5-hydroxyadamantan-2-yl)picolinamide

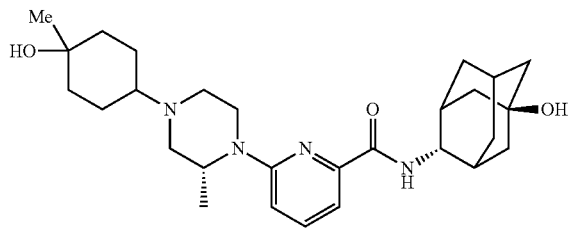 [SMILES: C[C@@H]1CN(C2CCC(C)(O)CC2)CCN1c1cccc(C(=O)N[C@H]2C3CC4CC2C[C@](O)(C4)C3)n1]

The same method as the example 197, except that 4-hydroxy-4-methylcyclohexanone was used instead of 2,3,5,6-tetrahydropyran-4-one, was performed to obtain 117 mg of white solid (90%). MS (ESI): 483 [M+H]$^+$

Example 199

Synthesis of N-((E)-5-hydroxyadamantan-2-yl)-6-((R)-2-methyl-4-(piperidin-4-yl)piperazin-1-yl)picolinamide

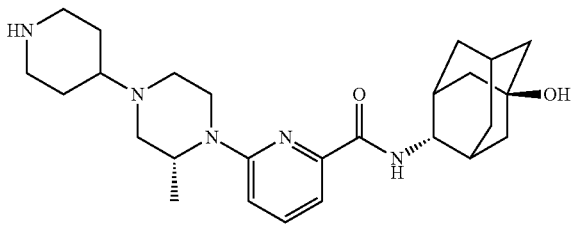 [SMILES: C[C@@H]1CN(C2CCNCC2)CCN1c1cccc(C(=O)N[C@H]2C3CC4CC2C[C@](O)(C4)C3)n1]

Step 1: Synthesis of tert-butyl 4-((R)-4-(6-(((E)-5-hydroxyadamantan-2-yl)carbamoyl)pyridin-2-yl)-3-methylpiperazin-1-yl)piperidine-1-carboxylate The same method as the example 197, except that 4-tert-butoxycarbonylcyclohexanone was used instead of 2,3,5,6-tetrahydropyran-4-one, was performed to obtain 120 mg of colorless oil (54%).

Step 2: Synthesis of N-((E)-5-hydroxyadamantan-2-yl)-6-((R)-2-methyl-4-(piperidin-4-yl)piperazin-1-yl)picolinamide Tert-butyl 4-((R)-4-(6-(((E)-5-hydroxyadamantan-2-yl)carbamoyl)pyridin-2-yl)-3-methylpiperazin-1-yl)piperidine-1-carboxylate (120 mg, 0.217 mmol) was dissolved in MC (3 ml), followed by addition of trifluoroacetic acid (3 ml), and then the resulting liquid was stirred at room temperature for 2 hours. The resulting reaction liquid was concentrated under reduced pressure, followed by addition of distilled water (10 ml), and then extracted with MC (5 ml). The aqueous layer was neutralized by addition of 1N aqueous NaOH solution, followed by extraction with 10% MeOH/MC (20 ml×2). The organic layer was dried over anhydrous sodium sulfate, followed by filtration and concentration, and then the residue thus obtained was subjected to MPLC (10% MeOH/MC), to obtain 75 mg of white solid (76%). MS (ESI): 454 [M+H]$^+$

Example 200

Synthesis of 6-((R)-4-(1-acetylpiperidin-4-yl)-2-methylpiperazin-1-yl)-N-((E)-5-hydroxyadamantan-2-yl)picolinamide

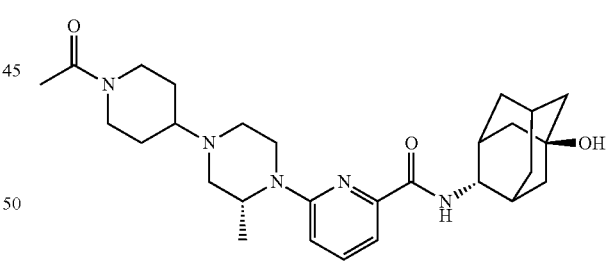

N-((E)-5-Hydroxyadamantan-2-yl)-6-((R)-2-methyl-4-(piperidin-4-yl)piperazin-1-yl)picolinamide (28 mg, 0.0617 mmol) was dissolved in MC (3 ml), followed by sequential addition of triethylamine (0.013 ml, 0.0926 mmol) and acetic anhydride (0.006 ml, 0.0617 mmol), and then the resulting liquid was stirred at room temperature under nitrogen stream for 2 hours. The resulting reaction liquid was concentrated under reduced pressure, and then the residue thus obtained was subjected to MPLC (10% MeOH/MC), to obtain 15 mg of white solid (49%). MS (ESI): 496 [M+H]$^+$

Example 201

Synthesis of N-((E)-5-hydroxyadamantan-2-yl)-6-((R)-2-methyl-4-(1-(methylsulfonyl)piperidin-4-yl)piperazin-1-yl)picolinamide

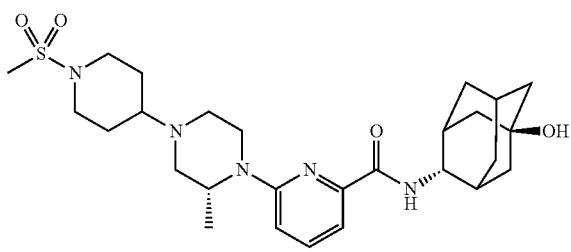 [SMILES: C[C@@H]1CN(C2CCN(S(C)(=O)=O)CC2)CCN1c1cccc(C(=O)N[C@H]2C3CC4CC2C[C@](O)(C4)C3)n1]

N-((E)-5-Hydroxyadamantan-2-yl)-6-((R)-2-methyl-4-(piperidin-4-yl)piperazin-1-yl)picolinamide (29 mg, 0.0639 mmol) was dissolved in MC (3 ml), followed by sequential addition of triethylamine (0.009 ml, 0.0671 mmol) and methanesulfonyl chloride (0.005 ml, 0.0671 mmol), and then the resulting liquid was stirred at room temperature under nitrogen stream for 2 hours. The resulting reaction liquid was concentrated under reduced pressure, and then the residue thus obtained was subjected to MPLC (5% MeOH/MC), to obtain 14 mg of white solid (41%). MS (ESI): 532 [M+H]$^+$ The following examples were synthesized in the same method as the above example 200 or 201, by using the intermediate 10 and appropriate acid chloride or sulfonyl chloride.

| Examples | Structures | MS (ESI) |
|---|---|---|
| 202 | 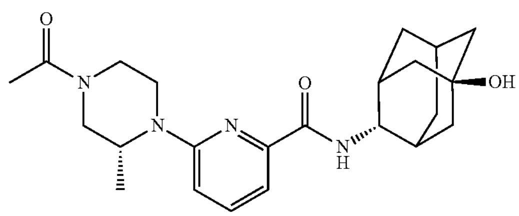 [SMILES: CC(=O)N1CCN(c2cccc(C(=O)N[C@H]3C4CC5CC3C[C@](O)(C5)C4)n2)[C@H](C)C1] | 413 [M + H]$^+$ |
| 203 | 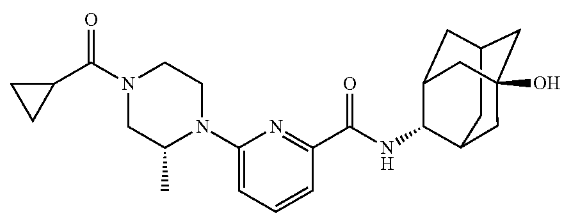 [SMILES: C[C@@H]1CN(C(=O)C2CC2)CCN1c1cccc(C(=O)N[C@H]2C3CC4CC2C[C@](O)(C4)C3)n1] | 439 [M + H]$^+$ |
| 204 | 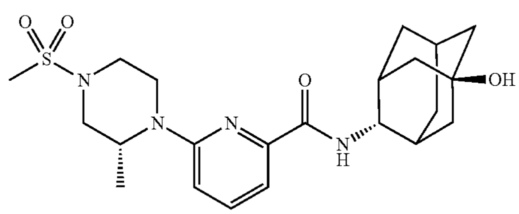 [SMILES: C[C@@H]1CN(S(C)(=O)=O)CCN1c1cccc(C(=O)N[C@H]2C3CC4CC2C[C@](O)(C4)C3)n1] | 449 [M + H]$^+$ |
| 205 | 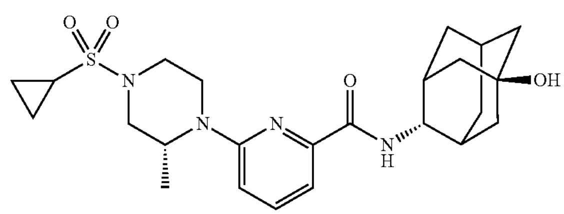 [SMILES: C[C@@H]1CN(S(=O)(=O)C2CC2)CCN1c1cccc(C(=O)N[C@H]2C3CC4CC2C[C@](O)(C4)C3)n1] | 475 [M + H]$^+$ |
| 206 | 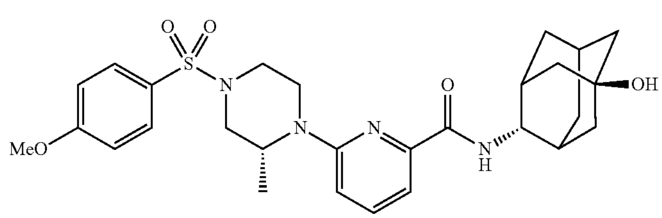 [SMILES: COc1ccc(S(=O)(=O)N2CCN(c3cccc(C(=O)N[C@H]4C5CC6CC4C[C@](O)(C6)C5)n3)[C@H](C)C2)cc1] | 541 [M + H]$^+$ |

| Examples | Structures | MS (ESI) |
|---|---|---|
| 207 | 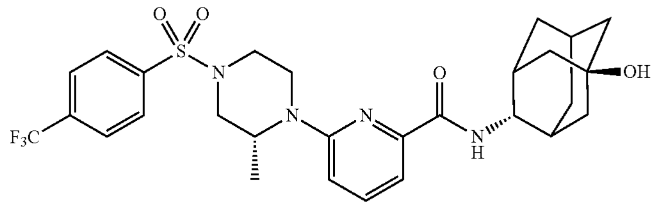 [SMILES: C[C@@H]1CN(S(=O)(=O)c2ccc(C(F)(F)F)cc2)CCN1c1cccc(C(=O)N[C@H]2C3CC4CC2C[C@](O)(C4)C3)n1] | 579 [M + H]⁺ |
| 208 | 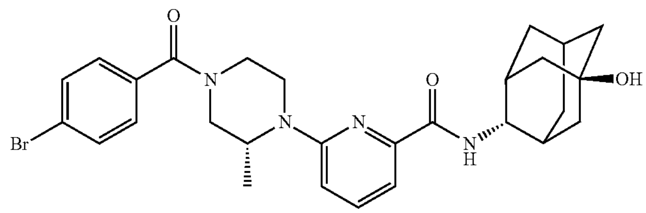 [SMILES: C[C@@H]1CN(C(=O)c2ccc(Br)cc2)CCN1c1cccc(C(=O)N[C@H]2C3CC4CC2C[C@](O)(C4)C3)n1] | 553 [M + H]⁺ |

Example 209

Synthesis of 6-((R)-4-(2-hydroxyacetyl)-2-methylpiperazin-1-yl)-N-((E)-5-hydroxyadamantan-2-yl)picolinamide

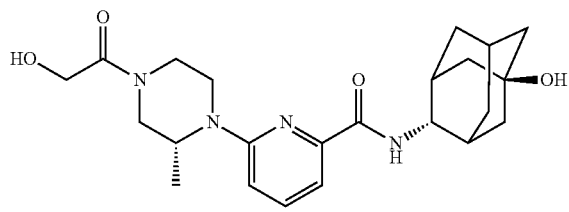 [SMILES: C[C@@H]1CN(C(=O)CO)CCN1c1cccc(C(=O)N[C@H]2C3CC4CC2C[C@](O)(C4)C3)n1]

N-((E)-5-hydroxyadamantan-2-yl)-6-((R)-2-methylpiperazin-1-yl)picolinamide (50 mg, 0.135 mmol), 2-hydroxyacetic acid (12 mg, 0.162 mmol), and HBTU (61 mg, 0.162 mmol) were suspended in acetonitrile (5 ml), followed by addition of N,N-diisopropylethylamine (0.028 ml, 0.162 mmol), and then the resulting liquid was stirred at room temperature under nitrogen stream for 4 hours. The resulting reaction liquid was concentrated under reduced pressure, and then the residue thus obtained was subjected to MPLC (10% MeOH/MC), to obtain 50 mg of white solid (86%). MS (ESI): 429 [M+H]⁺

The following examples were synthesized in the same method as the above example 209, by using the intermediate 10 and an appropriate acid start material.

| Examples | Structures | MS (ESI) |
|---|---|---|
| 210 | 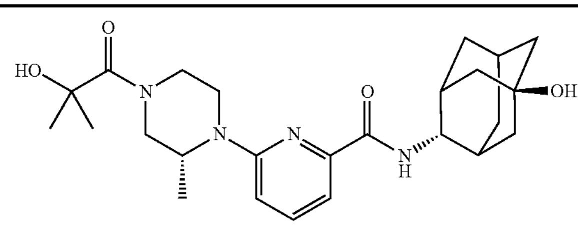 | 457 [M + H]⁺ |
| 211 | 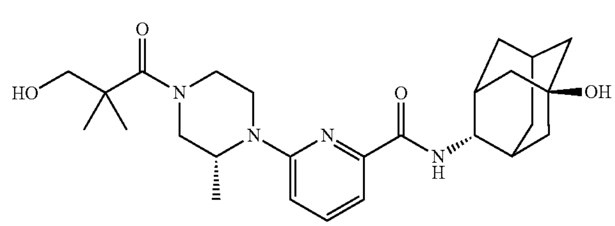 [SMILES: C[C@@H]1CN(C(=O)C(C)(C)CO)CCN1c1cccc(C(=O)N[C@H]2C3CC4CC2C[C@](O)(C4)C3)n1] | 471 [M + H]⁺ |

| Examples | Structures | MS (ESI) |
|---|---|---|
| 212 | 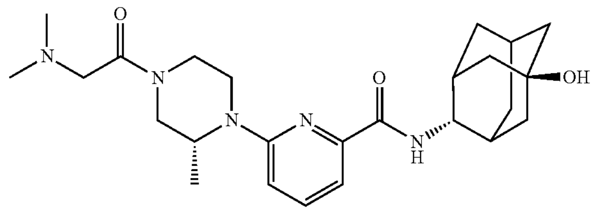 [SMILES: C[C@@H]1CN(C(=O)CN(C)C)CCN1c1cccc(C(=O)N[C@H]2C3CC4CC2C[C@](O)(C4)C3)n1] | 456 [M + H]⁺ |
| 213 | 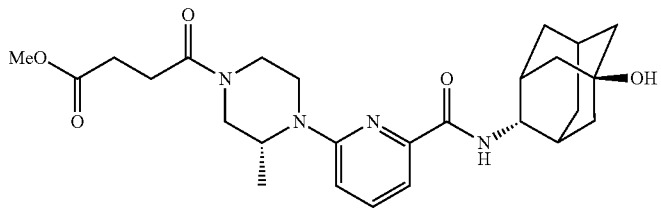 [SMILES: COC(=O)CCC(=O)N1CCN(c2cccc(C(=O)N[C@H]3C4CC5CC3C[C@](O)(C5)C4)n2)[C@H](C)C1] | 485 [M + H]⁺ |

Example 214

Synthesis of 6-((R)-4-(4-amino-4-oxobutanoyl)-2-methylpiperazin-1-yl)-N-((E)-5-hydroxyadamantan-2-yl)picolinamide

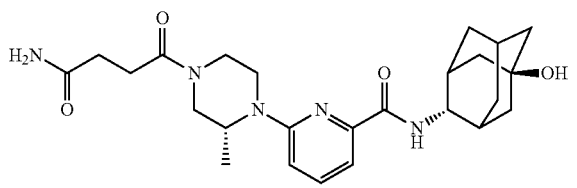 [SMILES: C[C@@H]1CN(C(=O)CCC(N)=O)CCN1c1cccc(C(=O)N[C@H]2C3CC4CC2C[C@](O)(C4)C3)n1]

The same method as the example 70, except that methyl 4-((R)-4-(6-(((E)-5-hydroxyadamantan-2-yl)carbamoyl)pyridin-2-yl)-3-methylpiperazin-1-yl)-4-oxobutanoate (40 mg, 0.083 mmol) was used instead of methyl 2-(1-(6-(((E)-5-hydroxyadamantan-2-yl)carbamoyl)pyridin-2-yl)piperidin-4-yl)acetate, was performed to obtain 11 mg of white solid (28%). MS (ESI): 470 [M+H]

Example 215

Synthesis of 4-((R)-4-(6-(((E)-5-hydroxyadamantan-2-yl)carbamoyl)pyridin-2-yl)-3-methylpiperazin-1-yl)-4-oxobutanoic acid

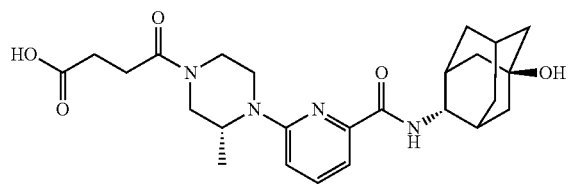 [SMILES: C[C@@H]1CN(C(=O)CCC(=O)O)CCN1c1cccc(C(=O)N[C@H]2C3CC4CC2C[C@](O)(C4)C3)n1]

The same method as the example 71, except that methyl 4-((R)-4-(6-(((E)-5-hydroxyadamantan-2-yl)carbamoyl)pyridin-2-yl)-3-methylpiperazin-1-yl)-4-oxobutanoate (40 mg, 0.083 mmol) was used instead of methyl 2-(1-(6-(((E)-5-hydroxyadamantan-2-yl)carbamoyl)pyridin-2-yl)piperidin-4-yl)acetate, was performed to obtain 29 mg of white solid (75%). MS (ESI): 471 [M+H]⁺

Example 216

Synthesis of 5-fluoro-N-((E)-5-hydroxyadamantan-2-yl)-6-((R)-2-methylpiperazin-1-yl)picolinamide

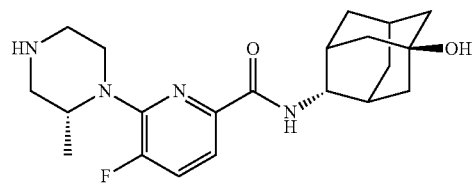 [SMILES: C[C@@H]1CNCCN1c1nc(C(=O)N[C@H]2C3CC4CC2C[C@](O)(C4)C3)ccc1F]

Step 1: Synthesis of 5-fluoro-2-(methoxycarbonyl)pyridine 1-oxide

Methyl 5-fluoropicolinate (440 mg, 2.836 mmol) was dissolved in CHCl₃ (10 ml), followed by addition of mCPBA (954 mg, 4.254 mmol), and then the resulting mixture was stirred at room temperature for 15 hours. A saturated aqueous Na₂S₂O₃ solution (15 ml) was added to the resulting reaction liquid, followed by extraction with 5% MeOH/MC (30 ml×2). The organic layer was dried over anhydrous sodium sulfate, followed by filtration and concentration, and then the residue thus obtained was subjected to MPLC (2% MeOH/MC), to obtain 318 mg of colorless oil (66%).

Step 2: Synthesis of methyl 6-chloro-5-fluoropicolinate 5-fluoro-2-(methoxycarbonyl)pyridine 1-oxide (100 mg, 0.584 mmol) was dissolved in POCl₃ (2 ml), and then heated at reflux under nitrogen stream for 4 hours. The resulting reaction liquid was slowly added to ice (15 g), and then extracted with MC (30 ml×2). The organic layer was dried over anhydrous sodium sulfate, followed by filtration and concentration, and then the residue thus obtained was subjected to MPLC (20% EtOAc/Hexanes), to obtain 88 mg of white solid (79%).

Step 3: Synthesis of 6-chloro-5-fluoropicolinic acid

Methyl 6-chloro-5-fluoropicolinate (1.35 g, 7.095 mmol) was dissolved in THF:H$_2$O=6:1 (42 ml), followed by addition of lithium hydroxide monohydrate (596 mg, 14.19 mmol), and then the resulting mixture was stirred at room temperature for 3 hours. The resulting reaction liquid was concentrated under reduced pressure, dissolved by addition of distilled water (20 ml), acidified by slow addition of 1N aqueous HCl solution, and then extracted with 5% MeOH/MC (30 ml×2). The organic layer was dried over anhydrous sodium sulfate, followed by filtration, concentration, and vacuum drying, to obtain 1.04 g of white solid (80%).

Step 4: Synthesis of 6-chloro-5-fluoro-N-((E)-5-hydroxyadamantan-2-yl)picolinamide The same method as the step 1 of the example 36, except that 6-chloro-5-fluoropicolinic acid (1.04 g, 5.92 mmol) was used instead of 6-bromopicolinic acid, was performed to obtain 1.20 g of white solid (62%).

Step 5: Synthesis of 5-fluoro-N-((E)-5-hydroxyadamantan-2-yl)-6-((R)-2-methylpiperazin-1-yl)picolinamide The same method as the example 129, except that 6-chloro-5-fluoro-N-((E)-5-hydroxyadamantan-2-yl)picolinamide (715 mg, 2.20 mmol) was used instead of 6-bromo-N-((E)-5-hydroxyadamantan-2-yl)picolinamide, was performed to obtain 337 mg of pale yellow solid (39%). MS (ESI): 389 [M+H]$^+$ The following examples were synthesized in the same method as the above example 173, by using 5-fluoro-N-((E)-5-hydroxyadamantan-2-yl)-6-((R)-2-methylpiperazin-1-yl) picolinamide and appropriate bromobenzene or bromopyridine.

| Examples | Structures | MS (ESI) |
|---|---|---|
| 217 | 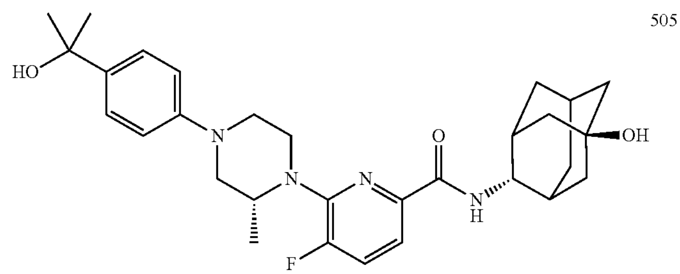 | 505 [M − OH]$^+$ |
| 218 | 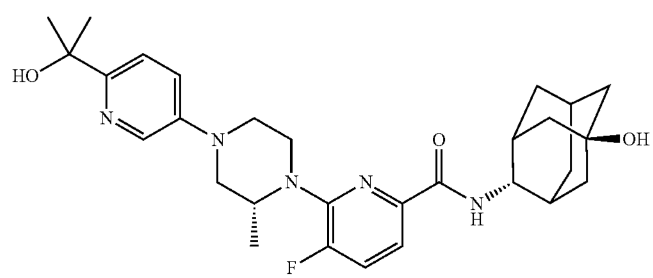 [SMILES: C[C@@H]1CN(c2ccc(C(C)(C)O)nc2)CCN1c1nc(C(=O)N[C@H]2C3CC4CC2C[C@](O)(C4)C3)ccc1F] | 524 [M + H]$^+$ |
| 219 | 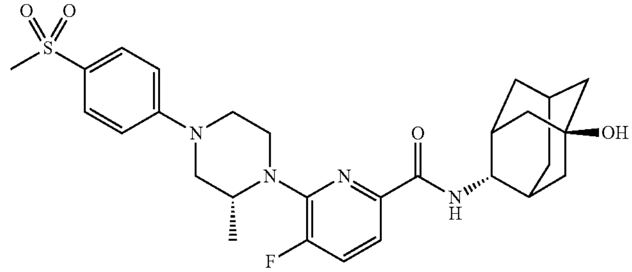 [SMILES: C[C@@H]1CN(c2ccc(S(C)(=O)=O)cc2)CCN1c1nc(C(=O)N[C@H]2C3CC4CC2C[C@](O)(C4)C3)ccc1F] | 543 [M + H]$^+$ |

Example 220

Synthesis of N-((E)-5-hydroxyadamantan-2-yl)-5-methyl-6-(piperidin-1-yl)picolinamide

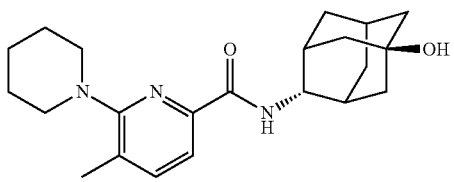 [SMILES: Cc1ccc(C(=O)N[C@H]2C3CC4CC2C[C@](O)(C4)C3)nc1N1CCCCC1]

Step 1: Synthesis of 2-(methoxycarbonyl)-5-methylpyridine 1-oxide

The same method as the step 1 of the example 216, except that methyl 5-methylpicolinate (761 mg, 5.03 mmol) was used instead of methyl 5-fluoropicolinate, was performed to obtain 484 mg of white solid (58%).

Step 2: Synthesis of methyl 6-chloro-5-methylpicolinate

The same method as the step 2 of the example 216, except that 2-(methoxycarbonyl)-5-methylpyridine 1-oxide (648 mg, 3.88 mmol) was used instead of 5-fluoro-2-(methoxycarbonyl)pyridine 1-oxide, was performed to obtain 435 mg of pale yellow solid (60%).

Step 3: Synthesis of 6-chloro-5-methylpicolinic acid

The same method as the step 3 of the example 216, except that methyl 6-chloro-5-methylpicolinate (385 mg, 2.07 mmol) was used instead of methyl 6-chloro-5-fluoropicolinate, was performed to obtain 277 mg of white solid (78%).

Step 4: Synthesis of 6-chloro-N-((E)-5-hydroxyadamantan-2-yl)-5-methylpicolinamide The same method as the step 1 of the example 36, except that 6-chloro-5-methylpicolinic acid (277 mg, 1.61 mmol) was used instead of 6-bromopicolinic acid, was performed to obtain 385 mg of yellow solid (75%).

Step 5: Synthesis of N-((E)-5-hydroxyadamantan-2-yl)-5-methyl-6-(piperidin-1-yl)picolinamide 6-chloro-N-((E)-5-hydroxyadamantan-2-yl)-5-methylpicolinamide (79 mg, 0.25 mmol), piperidine (0.049 ml, 0.5 mmol), Pd$_2$(dba)$_3$ (23 mg, 0.025 mmol), triisobutylphosphatrane (0.009 ml, 0.025 mmol), and sodium tert-butoxide (36 mg, 0.375 mmol) were suspended in toluene (1.25 ml), and then the resulting liquid was stirred at 100° C. under nitrogen stream for 24 hours. A saturated aqueous NH$_4$Cl solution (10 ml) was added to the resulting reaction liquid, followed by extraction with MC (30 ml×2). The organic layer was dried over anhydrous sodium sulfate, followed by filtration and concentration, and then the residue thus obtained was subjected to MPLC (10% EtOAc/Hexanes), to obtain 22 mg (24%). MS (ESI): 370 [M+H]

Example 221

Synthesis of N-((E)-5-hydroxyadamantan-2-yl)-5-methyl-6-(piperazin-1-yl)picolinamide

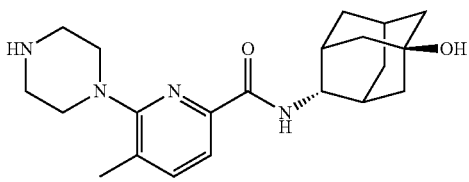 [SMILES: Cc1ccc(C(=O)N[C@H]2C3CC4CC2C[C@](O)(C4)C3)nc1N1CCNCC1]

Step 1: Synthesis of tert-butyl 4-(6-(((E)-5-hydroxyadamantan-2-yl)carbamoyl)-3-methylpyridin-2-yl)piperazine-1-carboxylate 6-chloro-N-((E)-5-hydroxyadamantan-2-yl)-5-methylpicolinamide (385 mg, 1.20 mmol), 1-BOC-piperazine (358 mg, 1.92 mmol), Pd$_2$(dba)$_3$ (22 mg, 0.024 mmol), triisobutylphosphatrane (0.026 ml, 0.072 mmol), and sodium tert-butoxide (173 mg, 1.80 mmol) were suspended in toluene (6 ml), and then the resulting liquid was stirred at 100° C. under nitrogen stream for 24 hours. A saturated aqueous NH$_4$Cl solution (15 ml) was added to the resulting reaction liquid, followed by extraction with MC (50 ml×2). The organic layer was dried over anhydrous sodium sulfate, followed by filtration and concentration, and then the residue thus obtained was subjected to MPLC (50% EtOAc/Hexanes), to obtain 410 mg of pale yellow solid (72%).

Step 2: Synthesis of N-((E)-5-hydroxyadamantan-2-yl)-5-methyl-6-(piperazin-1-yl)picolinamide Tert-butyl 4-(6-(((E)-5-hydroxyadamantan-2-yl)carbamoyl)-3-methylpyridin-2-yl)piperazine-1-carboxylate (410 mg, 0.87 mmol) was dissolved in MC (1.5 ml), followed by addition of trifluoroacetic acid (1.5 ml), and then the resulting mixture was stirred at room temperature for 2 hours. The resulting reaction liquid was concentrated under reduced pressure, followed by addition of distilled water (20 ml), and then extracted with MC (10 ml). The aqueous layer was neutralized by addition of 15% aqueous NaOH solution, followed by extraction with MC (50 ml×2), and then the organic layer was dried over anhydrous sodium sulfate, followed by filtration, concentration, and vacuum drying, to obtain 277 mg (86%). MS (ESI): 371 [M+H]$^+$ The following examples were synthesized in the same method as the above example 173, by using N-((E)-5-hydroxyadamantan-2-yl)-5-methyl-6-(piperazin-1-yl)picolinamide and appropriate bromobenzene or bromopyridine.

| Examples | Structures | MS (ESI) |
|---|---|---|
| 222 | 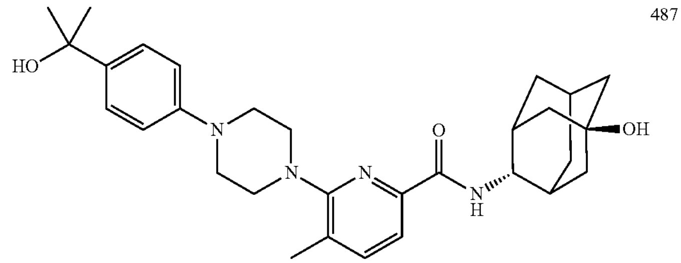 | 487 [M − OH]⁺ |
| 223 | 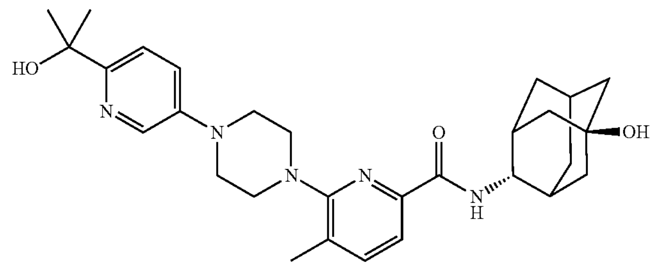 [SMILES: Cc1ccc(C(=O)N[C@H]2C3CC4CC2C[C@](O)(C4)C3)nc1N1CCN(c2ccc(C(C)(C)O)nc2)CC1] | 506 [M + H]⁺ |
| 224 | 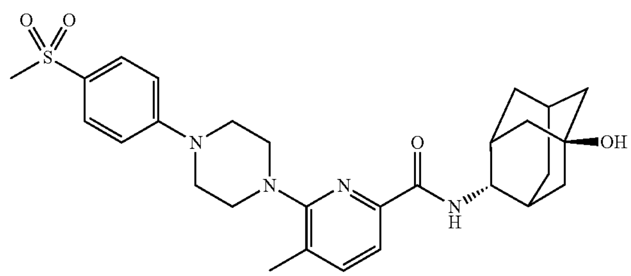 [SMILES: Cc1ccc(C(=O)N[C@H]2C3CC4CC2C[C@](O)(C4)C3)nc1N1CCN(c2ccc(S(C)(=O)=O)cc2)CC1] | 525 [M + H]⁺ |

Example 225

Synthesis of N-((E)-4-Hydroxycyclohexyl)-6-(piperidin-1-yl)picolinamide

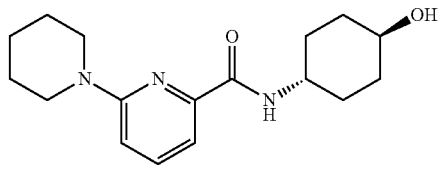 [SMILES: O=C(N[C@H]1CC[C@H](O)CC1)c1cccc(N2CCCCC2)n1]

Step 1: Synthesis of 6-bromo-N-((E)-4-hydroxycyclohexyl)picolinamide

6-Bromopicolinic acid (600 mg, 2.97 mmol) was suspended in acetonitrile (20 ml), followed by sequential addition of trans-4-aminocyclohexanol hydrochloride (500 mg, 2.48 mmol), N,N-diisopropylethylamine (1.0 ml, 6.19 mmol), and HBTU (1.1 g, 2.97 mmol), and then the resulting mixture was stirred at room temperature under nitrogen stream for 13 hours. Distilled water (20 ml) was added to the resulting reaction liquid, followed by extraction with MC (40 ml×2). The organic layer was dried over anhydrous sodium sulfate, followed by filtration and concentration, and then the residue thus obtained was subjected to MPLC (5% MeOH/MC), to obtain 538 mg of white solid (73%).

Step 2: Synthesis of N-((E)-4-hydroxycyclohexyl)-6-(piperidin-1-yl)picolinamide 6-Bromo-N-((E)-4-hydroxycyclohexyl)picolinamide (50 mg, 0.167 mmol) was dissolved in acetonitrile (1 ml), followed by addition of piperidine (0.13 ml, 1.336 mmol), and then the resulting liquid was subjected to microwave irradiation at 150° C. for 2 hours. The resulting reaction liquid was concentrated under reduced pressure, and then the residue thus obtained was subjected to MPLC (5% MeOH/MC), to obtain 45 mg of pale yellow solid (89%). MS (ESI): 304 [M+H]⁺

Example 226

Synthesis of N-cyclopropyl-N—((Z)-4-hydroxycyclohexyl)-6-(piperidin-1-yl)picolinamide and N-cyclopropyl-N-((E)-4-hydroxycyclohexyl)-6-(piperidin-1-yl)picolinamide

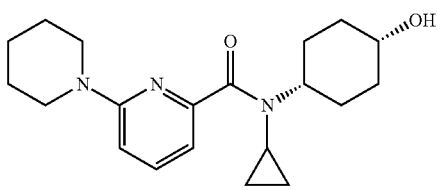

-continued

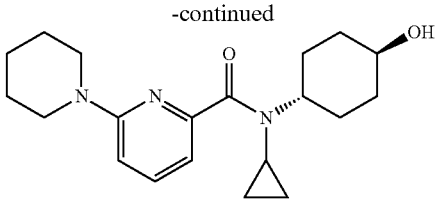

Step 1: Synthesis of 4-hydroxycyclohexanone 1,4-cyclohexandione mono-ethylene ketal (1.0 g, 6.4 mmol) was dissolved in MeOH (30 ml), followed by addition of sodium borohydride (750 mg, 19.2 mmol) at 0° C., and then the resulting mixture was stirred at room temperature under nitrogen stream for 2 hours. The resulting reaction liquid was concentrated under reduced pressure, followed by addition of a saturated aqueous sodium chloride solution (30 ml), and extracted with EtOAc (50 ml×2). The organic layer was dried over anhydrous sodium sulfate, and then filtered, concentrated, and vacuum-dried. The residue thus obtained was dissolved in THF (30 ml), followed by addition of 1N aqueous HCl solution (15 ml), and then the resulting mixture was stirred at room temperature for 18 hours. The resulting reaction liquid was neutralized by addition of 10% aqueous NaOH solution, followed by extraction with MC (30 ml×3). The organic layer was dried over anhydrous sodium sulfate, followed by filtration and concentration, and then the residue thus obtained was subjected to MPLC (60% EtOAc/Hexanes), to obtain 450 mg of colorless oil (62%).

Step 2: Synthesis of 4-(cyclopropylamino)cyclohexanol 4-hydroxycyclohexanone (443 mg, 3.88 mmol) was dissolved in 1,2-dichloroethane (20 ml), followed by sequential addition of cyclopropylamine (0.295 ml, 4.27 mmol), NaBH(OAc)$_3$ (1.3 g, 6.21 mmol), and acetic acid (0.2 ml, 3.88 mmol), and then the resulting mixture was stirred at room temperature under nitrogen stream for 13 hours. The resulting reaction liquid was neutralized by addition of 10% aqueous NaOH solution, and extracted with 10% MeOH/MC (15 ml×4). The organic layer was dried over anhydrous sodium sulfate, followed by filtration, concentration, and vacuum drying, to obtain 580 mg of yellow solid (96%).

Step 3: Synthesis of N-cyclopropyl-N—((Z)-4-hydroxycyclohexyl)-6-(piperidin-1-yl)picolinamide and N-cyclopropyl-N-((E)-4-hydroxycyclohexyl)-6-(piperidin-1-yl)picolinamide The same method as the example 225, except that 4-(cyclopropylamino)cyclohexanol was used instead of trans-4-aminocyclohexanol hydrochloride, was performed to obtain N-cyclopropyl-N—((Z)-4-hydroxycyclohexyl)-6-(piperidin-1-yl)picolinamide and N-cyclopropyl-N-((E)-4-hydroxycyclohexyl)-6-(piperidin-1-yl)picolinamide, respectively. MS (ESI): 344 [M+H]$^+$, 344 [M+H]$^+$ Example 227

Synthesis of N-cyclopropyl-N-((1s,4s)-4-hydroxy-4-methylcyclohexyl)-6-(piperidin-1-yl)picolinamide and N-cyclopropyl-N-((1r,4r)-4-hydroxy-4-methylcyclohexyl)-6-(piperidin-1-yl)picolinamide

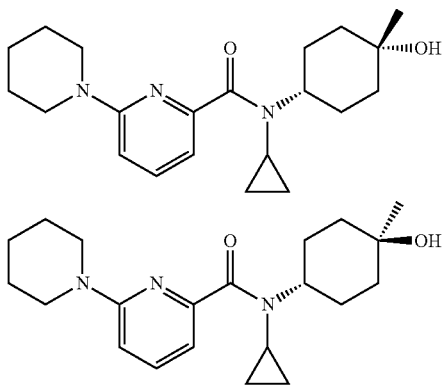

Step 1: Synthesis of 8-methyl-1,4-dioxaspiro[4.5]decan-8-ol 1,4-cyclohexandione mono-ethylene ketal (1.0 g, 6.4 mmol) was dissolved in THF (30 ml), followed by addition of MeMgCl (3.0M solution in THF, 2.6 ml, 7.7 mmol) at 0° C., and then the resulting mixture was stirred at room temperature under nitrogen stream for 3 hours. A saturated aqueous ammonium chloride solution was added to the resulting reaction liquid, followed by extraction with MC (50 ml×2). The organic layer was dried over anhydrous sodium sulfate, followed by filtration and concentration, and then the residue thus obtained was subjected to MPLC (50% EtOAc/Hexanes), to obtain 654 mg of white solid (59%).

Step 2: Synthesis of 4-hydroxy-4-methylcyclohexanone

8-Methyl-1,4-dioxaspiro[4.5]decane-8-ol (650 mg, 3.77 mmol) was dissolved in THF (10 ml), followed by addition of 1N aqueous HCl solution (5 ml), and then the resulting mixture was stirred at room temperature for 6 hours. The resulting reaction liquid was concentrated under reduced pressure, and then extracted with 10% MeOH/MC (20 ml×5). The organic layer was dried over anhydrous sodium sulfate, followed by filtration and concentration, and then the residue thus obtained was subjected to MPLC (50% EtOAc/Hexanes), to obtain 443 mg of yellow oil (92%).

Step 3: Synthesis of 4-(cyclopropylamino)-1-methylcyclohexanol

4-Hydroxy-4-methylcyclohexanone (440 mg, 3.43 mmol) was dissolved in 1,2-dichloroethane (15 ml), followed by sequential addition of cyclopropylamine (0.26 ml, 3.78 mmol), NaBH(OAc)$_3$ (1.16 g, 5.49 mmol), and acetic acid (0.20 ml, 3.43 mmol), and then the resulting mixture was stirred at room temperature under nitrogen stream for 20 hours. The resulting reaction liquid was neutralized by addition of 10% aqueous NaOH solution, and extracted with 5% MeOH/MC (15 ml×4). The organic layer was dried over anhydrous sodium sulfate, followed by filtration, concentration, and vacuum drying, to obtain 417 mg of yellow solid (72%).

Step 4: Synthesis of N-cyclopropyl-N-((1s,4s)-4-hydroxy-4-methylcyclohexyl)-6-(piperidin-1-yl)picolinamide) and N-cyclopropyl-N-((1r,4r)-4-hydroxy-4-methylcyclohexyl)-6-(piperidin-1-yl)picolinamide The same method as the example 225, except that 4-(cyclopropylamino)-1-methylcyclohexanol was used instead of trans-4-aminocyclohexanol hydrochloride, was performed to obtain N-cyclopropyl-N-((1s,4s)-4-hydroxy-4-methylcyclohexyl)-6-(piperidin-1-yl)picolinamide) and N-cyclopropyl-N-((1r,4r)-4-hydroxy-4-methylcyclohexyl)-6-(piperidin-1-yl)picolinamide, respectively. MS (ESI): 358 [M+H]$^+$, 358 [M+H]$^+$ Example 228

Synthesis of N-cyclopropyl-N-((1s,4s)-4-hydroxy-4-(trifluoromethyl)cyclohexyl)-6-(piperidin-1-yl)picolinamide) and N-cyclopropyl-N-((1r,4r)-4-hydroxy-4-(trifluoromethyl)cyclohexyl)-6-(piperidin-1-yl)picolinamide

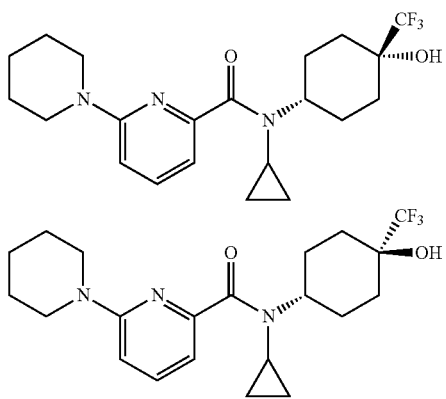

Step 1: Synthesis of 8-(trifluoromethyl)-1,4-dioxaspiro[4.5]decan-8-ol 1,4-cyclohexandione mono-ethylene ketal (1.5 g, 9.6 mmol) was dissolved in THF (35 ml), followed by sequential addition of trimethyl(trifluoromethyl)silane (2.8 ml, 19.2 mmol) and tetrabutylammonium fluoride (1.0M solution in THF, 20 ml, 20.0 mmol) at 0° C., and then the resulting mixture was stirred at room temperature for 2 hours. A saturated aqueous ammonium chloride solution (10 ml) was added to the resulting reaction liquid, and then, the resulting mixture was stirred for 10 minutes, followed by concentration under reduced pressure. Distilled water (10 ml) was added to the residue thus obtained, followed by extraction with MC (50 ml×2). The organic layer was dried over anhydrous sodium sulfate, followed by filtration and concentration, and then the residue thus obtained was subjected to MPLC (40% EtOAc/Hexanes), to obtain 2.1 g of yellow oil (97%).

Step 2: Synthesis of 4-hydroxy-4-(trifluoromethyl)cyclohexanone 8-(trifluoromethyl)-1,4-dioxaspiro[4.5]decane-8-ol (2.0 g, 8.84 mmol) was dissolved in THF (30 ml), followed by addition of 1N aqueous HCl solution (15 ml), and then the resulting mixture was stirred at room temperature for 24 hours. The resulting reaction liquid was concentrated under reduced pressure, and then extracted with 10% MeOH/MC (15 ml×6). The organic layer was dried over anhydrous sodium sulfate, followed by filtration and concentration, and then the residue thus obtained was subjected to MPLC (40% EtOAc/Hexanes), to obtain 1.24 g of white solid (77%).

Step 3: Synthesis of 4-(cyclopropylamino)-1-(trifluoromethyl)cyclohexanol 4-hydroxy-4-(trifluoromethyl)cyclohexanone (570 mg, 3.13 mmol) was dissolved in 1,2-dichloroethane (20 ml), followed by sequential addition of cyclopropylamine (0.24 ml, 3.44 mmol), NaBH(OAc)$_3$ (1.06 g, 5.01 mmol), and acetic acid (0.18 ml, 3.13 mmol), and then the resulting mixture was stirred at room temperature under nitrogen stream for 13 hours. The resulting reaction liquid was neutralized by addition of 10% aqueous NaOH solution, and extracted with 5% MeOH/MC (20 ml×3). The organic layer was dried over anhydrous sodium sulfate, followed by filtration, concentration, and vacuum drying, to obtain 650 mg of yellow solid (93%).

Step 4: Synthesis of N-cyclopropyl-N-((1s,4s)-4-hydroxy-4-(trifluoromethyl)cyclohexyl)-6-(piperidin-1-yl)picolinamide) and N-cyclopropyl-N-((1r,4r)-4-hydroxy-4-(trifluoromethyl)cyclohexyl)-6-(piperidin-1-yl)picolinamide The same method as the example 225, except that 4-(cyclopropylamino)-1-(trifluoromethyl)cyclohexanol was used instead of trans-4-aminocyclohexanol hydrochloride, was performed to obtain N-cyclopropyl-N-((1s,4s)-4-hydroxy-4-(trifluoromethyl)cyclohexyl)-6-(piperidin-1-yl)picolinamide) and N-cyclopropyl-N-((1r,4r)-4-hydroxy-4-(trifluoromethyl)cyclohexyl)-6-(piperidin-1-yl)picolinamide, respectively. MS (ESI): 412 [M+H]$^+$, 412 [M+H]$^+$ Example 229

Synthesis of N-((1s,4s)-4-hydroxy-4-(trifluoromethyl)cyclohexyl)-6-(piperidin-1-yl)picolinamide and N-((1r,4r)-4-hydroxy-4-(trifluoromethyl)cyclohexyl)-6-(piperidin-1-yl)picolinamide

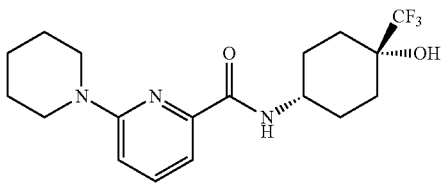

113

-continued

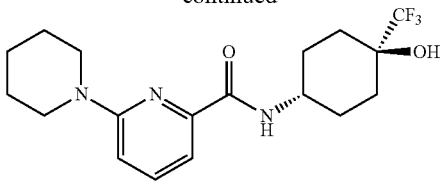

Step 1: Synthesis of
4-amino-1-(trifluoromethyl)cyclohexanol 4-hydroxy-4-(trifluoromethyl)cyclohexanone (570 mg, 3.13 mmol) was dissolved in 1,2-dichloroethane (20 ml), followed by sequential addition of benzylamine (0.38 ml, 3.44 mmol), NaBH(OAc)$_3$ (1.06 g, 5.01 mmol), and acetic acid (0.18 ml, 3.13 mmol), and then the resulting mixture was stirred at room temperature under nitrogen stream for 13 hours. The resulting reaction liquid was neutralized by addition of 10% aqueous NaOH solution, and extracted with 5% MeOH/MC (20 ml×3). The organic layer was dried over anhydrous sodium sulfate, and then filtered, concentrated under reduced pressure, and dried under vacuum. The residue thus obtained was dissolved in EtOH (20 ml), followed by addition of Pd (10 wt % on activated carbon, 80 mg), and then the resulting mixture was stirred at room temperature under hydrogen stream for 15 hours. The resulting reaction liquid was filtered, concentrated under reduced pressure, and dried under vacuum, to obtain 471 mg of yellow solid (82%).

Step 2: Synthesis of N-((1s,4s)-4-hydroxy-4-(trifluoromethyl)cyclohexyl)-6-(piperidin-1-yl)picolinamide) and N-((1r,4r)-4-hydroxy-4-(trifluoromethyl)cyclohexyl)-6-(piperidin-1-yl)picolinamide The same method as the example 225, except that 4-amino-1-(trifluoromethyl)cyclohexanol was used instead of trans-4-aminocyclohexanol hydrochloride, was performed to obtain N-((1s,4s)-4-hydroxy-4-(trifluoromethyl)cyclohexyl)-6-(piperidin-1-yl)picolinamide) and N-((1r,4r)-4-hydroxy-4-(trifluoromethyl)cyclohexyl)-6-(piperidin-1-yl)picolinamide, respectively. MS (ESI): 372 [M+H]$^+$, 372 [M+H]$^+$ Example 230

Synthesis of N-((E)-5-hydroxyadamantan-2-yl)-2-((R)-2-methyl-4-(4-(methylsulfonyl)phenyl)piperazin-1-yl)pyrimidine-4-carboxamide

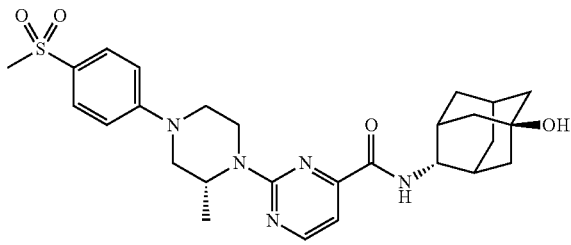 [SMILES: C[C@@H]1CN(c2ccc(S(C)(=O)=O)cc2)CCN1c1nccc(C(=O)N[C@H]2C3CC4CC2C[C@](O)(C4)C3)n1]

114

Step 1: Synthesis of tert-butyl
2-chloropyrimidine-4-carboxylate (Intermediate 11)

2-Chloropyrimidine-4-carboxylic acid (500 mg, 3.154 mmol) was suspended in 2-methylpropan-2-ol (20 ml), followed by addition of pyridine (3 ml) and p-toluenesulfonyl chloride (1.2 g, 6.308 mmol), and then resulting mixture was stirred at room temperature under nitrogen stream for 4 hours. The resulting reaction liquid was neutralized by slow addition of a saturated aqueous NaHCO$_3$ solution, and then concentrated under reduced pressure, followed by addition of distilled water (5 ml). The precipitated solid was filtered, followed by vacuum drying, to obtain 420 mg of pale yellow solid (62%).

Step 2: Synthesis of (R)-tert-butyl 2-(2-methyl-4-(4-(methylsulfonyl)phenyl)piperazin-1-yl)pyrimidine-4-carboxylate Tert-butyl 2-chloropyrimidine-4-carboxylate (70 mg, 0.326 mmol) and (R)-3-methyl-1-(4-(methylsulfonyl)phenyl)piperazine (166 mg, 0.652 mmol) were dissolved in acetonitrile (2 ml), followed by addition of N,N-diisopropylethylamine (0.11 ml, 0.652 mmol), and then the resulting liquid was stirred at 100° C. under nitrogen stream for 24 hours. The resulting reaction liquid was concentrated under reduced pressure, and then the residue thus obtained was subjected to MPLC (50% EtOAc/Hexanes), to obtain 120 mg of pale yellow solid (85%).

Step 3: Synthesis of N-((E)-5-hydroxyadamantan-2-yl)-2-((R)-2-methyl-4-(4-(methylsulfonyl)phenyl)piperazin-1-yl)pyrimidine-4-carboxamide (R)-tert-butyl 2-(2-methyl-4-(4-(methylsulfonyl)phenyl)piperazin-1-yl)pyrimidine-4-carboxylate (120 mg, 0.277 mmol) was dissolved in MC (2 ml), followed by addition of trifluoroacetic acid (2 ml), and then the resulting mixture was stirred at room temperature for 15 hours. The resulting reaction liquid was concentrated under reduced pressure, and dried under vacuum. The residue thus obtained was suspended in acetonitrile (5 ml), followed by sequential addition of 5-hydroxy-2-adamantanemine (2:1 E/Z mixture, 56 mg, 0.332 mmol), N,N-diisopropylethylamine (0.15 ml, 0.831 mmol), and HBTU (126 mg, 0.332 mmol), and then the resulting mixture was stirred at room temperature under nitrogen stream for 6 hours. A saturated aqueous ammonium chloride solution (15 ml) was added to the resulting reaction liquid, followed by extraction with MC (20 ml×2). The organic layer was dried over anhydrous sodium sulfate, followed by filtration and concentration, and then the residue thus obtained was subjected to MPLC (4% MeOH/MC), to obtain 90 mg of pale yellow solid (62%). MS (ESI): 526 [M+H]$^+$ The following examples were synthesized in the same method as the above example 230, by using the intermediate 11 and an appropriate piperazine start material.

| Examples | Structures | MS (ESI) |
|---|---|---|
| 231 | 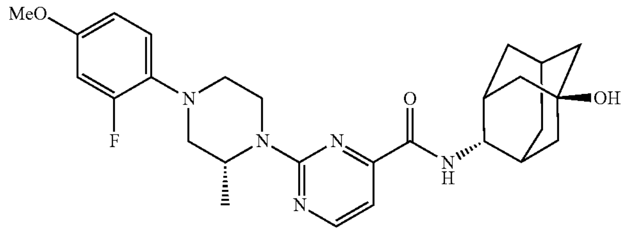 [SMILES: COc1ccc(N2CCN(c3nccc(C(=O)N[C@H]4C5CC6CC4C[C@](O)(C6)C5)n3)[C@H](C)C2)c(F)c1] | 496 [M + H]⁺ |
| 232 | 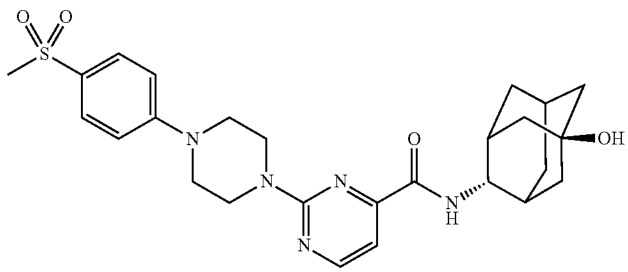 [SMILES: CS(=O)(=O)c1ccc(N2CCN(c3nccc(C(=O)N[C@H]4C5CC6CC4C[C@](O)(C6)C5)n3)CC2)cc1] | 512 [M + H]⁺ |
| 233 | 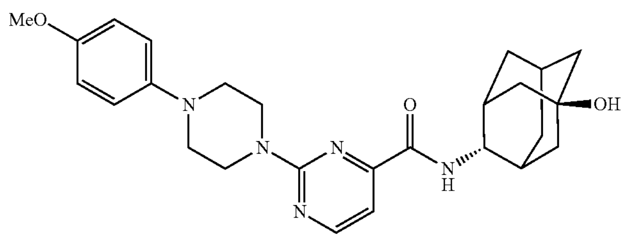 [SMILES: COc1ccc(N2CCN(c3nccc(C(=O)N[C@H]4C5CC6CC4C[C@](O)(C6)C5)n3)CC2)cc1] | 464 [M + H]⁺ |

Example 234

Synthesis of 2-((R)-4-benzyl-2-methylpiperazin-1-yl)-N-((E)-5-hydroxyadamantan-2-yl)pyrimidine-4-carboxamide

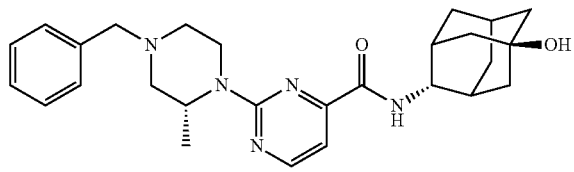 [SMILES: C[C@@H]1CN(Cc2ccccc2)CCN1c1nccc(C(=O)N[C@H]2C3CC4CC2C[C@](O)(C4)C3)n1]

Step 1: Synthesis of (R)-tert-butyl 2-(4-benzyl-2-methylpiperazin-1-yl)pyrimidine-4-carboxylate Tert-butyl 2-chloropyrimidine-4-carboxylate (4.12 g, 19.2 mmol) and (R)-1-benzyl-3-methylpiperazine (1.83 g, 9.6 mmol) were suspended in acetonitrile (50 ml), followed by addition of N,N-diisopropylethylamine (3.34 ml, 19.2 mmol), and then the resulting liquid was heated at reflux under nitrogen stream for 15 hours. The resulting reaction liquid was concentrated, followed by addition of distilled water (50 ml), and then extracted with MC (100 ml×2). The organic layer was dried over anhydrous sodium sulfate, followed by filtration and concentration, and then the residue thus obtained was subjected to MPLC (1% MeOH/MC), to obtain 3.34 g of yellow solid (94%).

Step 2: Synthesis of 2-((R)-4-benzyl-2-methylpiperazin-1-yl)-N-((E)-5-hydroxyadamantan-2-yl)pyrimidine-4-carboxamide The same method as the step 3 of the example 230, except that (R)-tert-butyl 2-(4-benzyl-2-methylpiperazin-1-yl)pyrimidine-4-carboxylate (3.34 g, 9.06 mmol) was used instead of (R)-tert-butyl 2-(2-methyl-4-(4-(methylsulfonyl)phenyl)piperazin-1-yl)pyrimidine-4-carboxylate, was performed to obtain 2.83 g of white solid (68%). MS (ESI): 462 [M+H]⁺

Example 235

Synthesis of N-((E)-5-hydroxyadamantan-2-yl)-2-((R)-4-(4-(2-hydroxypropan-2-yl)phenyl)-2-methylpiperazin-1-yl)pyrimidine-4-carboxamide

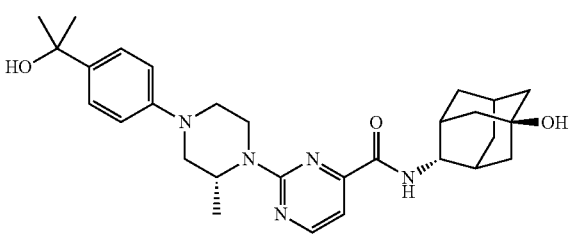 [SMILES: C[C@@H]1CN(c2ccc(C(C)(C)O)cc2)CCN1c1nccc(C(=O)N[C@H]2C3CC4CC2C[C@](O)(C4)C3)n1]

Step 1: Synthesis of N-((E)-5-hydroxyadamantan-2-yl)-2-((R)-2-methylpiperazin-1-yl)pyrimidine-4-carboxamide (Intermediate 12)

The same method as the example 63, except that 2-((R)-4-benzyl-2-methylpiperazin-1-yl)-N-((E)-5-hydroxyadamantan-2-yl)pyrimidine-4-carboxamide (2.83 g, 6.13 mmol) was used instead of 6-(4-benzylpiperazin-1-yl)-N-((E)-5-hydroxyadamantan-2-yl)picolinamide, was performed to obtain 1.86 g of white solid (81%).

Step 2: Synthesis of N-((E)-5-hydroxyadamantan-2-yl)-2-((R)-4-(4-(2-hydroxypropan-2-yl)phenyl)-2-methylpiperazin-1-yl)pyrimidine-4-carboxamide The same method as the example 173, except that N-((E)-5-hydroxyadamantan-2-yl)-2-((R)-2-methylpiperazin-1-yl)pyrimidine-4-carboxamide (150 mg, 0.404 mmol) was used instead of N-((E)-5-hydroxyadamantan-2-yl)-6-((R)-2-methylpiperazin-1-yl)picolinamide, was performed to obtain 97 mg of pale yellow solid (47%). MS (ESI): 488 [M−OH]⁺

The following examples were synthesized in the same method as the above example 173, by using the intermediate 12 and appropriate bromobenzene or bromopyridine.

| Examples | Structures | MS (ESI) |
|---|---|---|
| 236 | 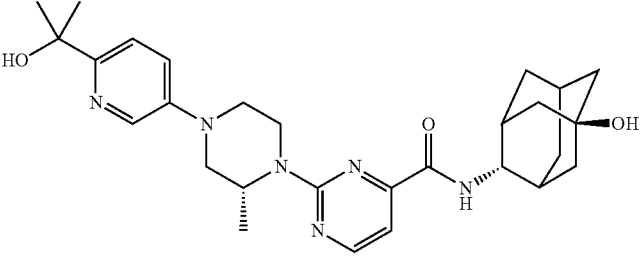 [SMILES: C[C@@H]1CN(c2ccc(C(C)(C)O)nc2)CCN1c1nccc(C(=O)N[C@H]2C3CC4CC2C[C@](O)(C4)C3)n1] | 507 [M + H]⁺ |
| 237 | 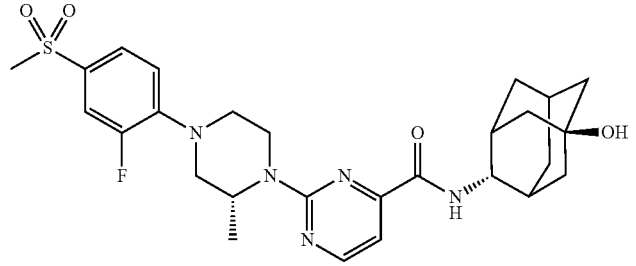 [SMILES: C[C@@H]1CN(c2ccc(S(C)(=O)=O)cc2F)CCN1c1nccc(C(=O)N[C@H]2C3CC4CC2C[C@](O)(C4)C3)n1] | 544 [M + H]⁺ |
| 238 | 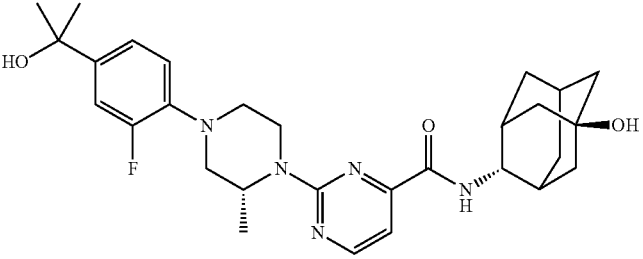 [SMILES: C[C@@H]1CN(c2ccc(C(C)(C)O)cc2F)CCN1c1nccc(C(=O)N[C@H]2C3CC4CC2C[C@](O)(C4)C3)n1] | 524 [M + H]⁺ |
| 239 | 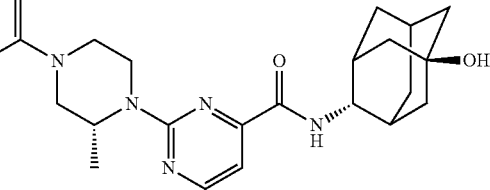 | 473 [M + H]⁺ |
| 240 | 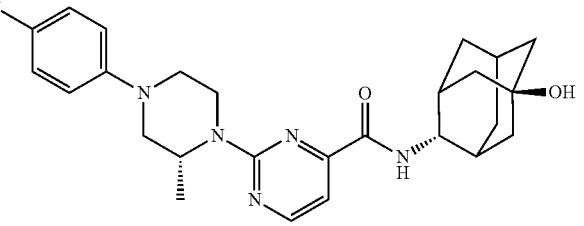 | 466 [M + H]⁺ |

-continued

| Examples | Structures | MS (ESI) |
|---|---|---|
| 241 | 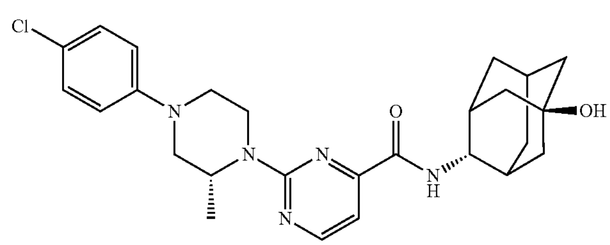 [SMILES: C[C@@H]1CN(c2ccc(Cl)cc2)CCN1c1nccc(C(=O)N[C@H]2C3CC4CC2C[C@](O)(C4)C3)n1] | 482 [M + H]+ |
| 242 | 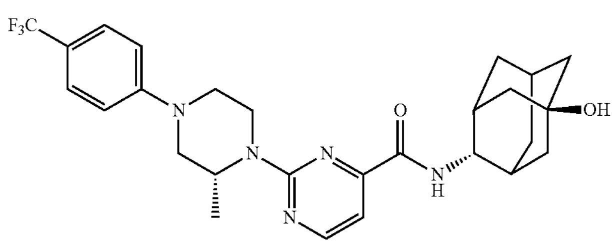 [SMILES: C[C@@H]1CN(c2ccc(C(F)(F)F)cc2)CCN1c1nccc(C(=O)N[C@H]2C3CC4CC2C[C@](O)(C4)C3)n1] | 516 [M + H]+ |
| 243 | 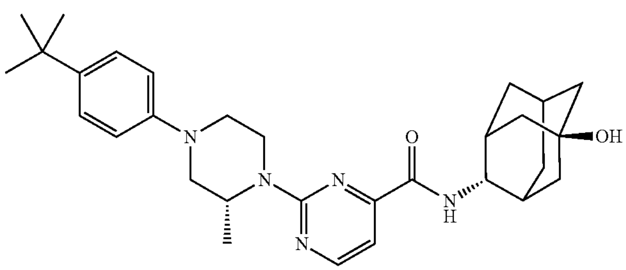 [SMILES: C[C@@H]1CN(c2ccc(C(C)(C)C)cc2)CCN1c1nccc(C(=O)N[C@H]2C3CC4CC2C[C@](O)(C4)C3)n1] | 504 [M + H]+ |
| 244 | 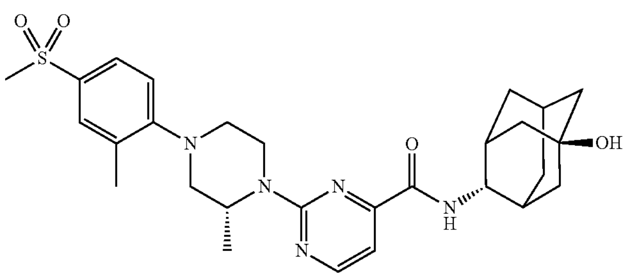 | 540 [M + H]+ |
| 245 | 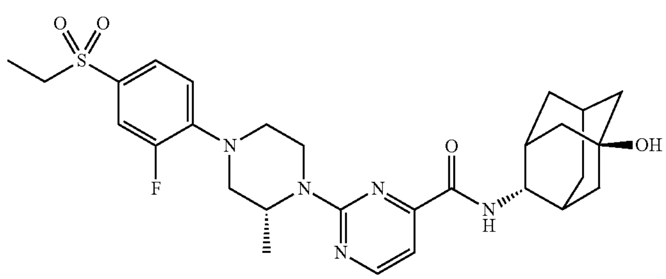 [SMILES: CCS(=O)(=O)c1ccc(N2CCN(c3nccc(C(=O)N[C@H]4C5CC6CC4C[C@](O)(C6)C5)n3)[C@H](C)C2)c(F)c1] | 558 [M + H]+ |
| 246 | 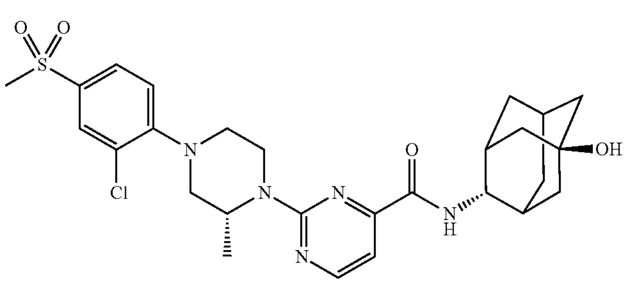 [SMILES: C[C@@H]1CN(c2ccc(S(C)(=O)=O)cc2Cl)CCN1c1nccc(C(=O)N[C@H]2C3CC4CC2C[C@](O)(C4)C3)n1] | 560 [M + H]+ |

-continued
| Examples | Structures | MS (ESI) |
|---|---|---|
| 247 | 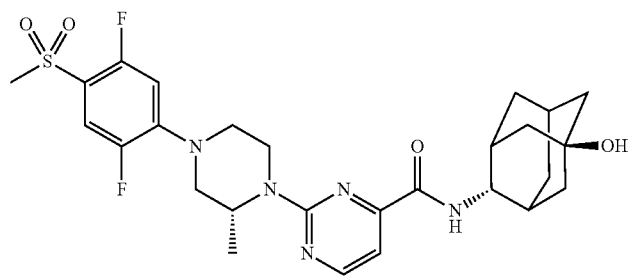 [SMILES: C[C@@H]1CN(c2cc(F)c(S(C)(=O)=O)cc2F)CCN1c1nccc(C(=O)N[C@H]2C3CC4CC2C[C@](O)(C4)C3)n1] | 562 [M + H]⁺ |
| 248 | 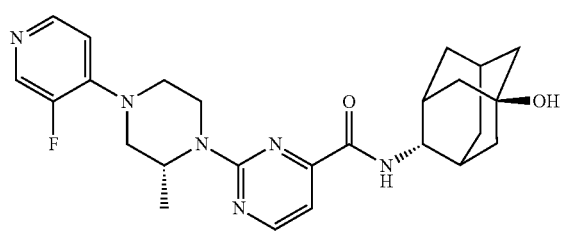 [SMILES: C[C@@H]1CN(c2ccncc2F)CCN1c1nccc(C(=O)N[C@H]2C3CC4CC2C[C@](O)(C4)C3)n1] | 467 [M + H]⁺ |
| 249 | 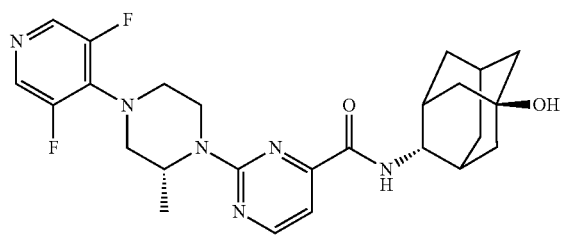 [SMILES: C[C@@H]1CN(c2c(F)cncc2F)CCN1c1nccc(C(=O)N[C@H]2C3CC4CC2C[C@](O)(C4)C3)n1] | 485 [M + H]⁺ |
| 250 | 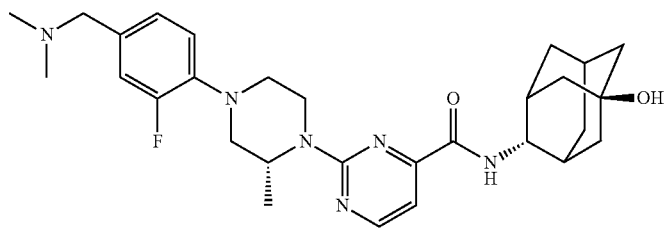 [SMILES: C[C@@H]1CN(c2ccc(CN(C)C)cc2F)CCN1c1nccc(C(=O)N[C@H]2C3CC4CC2C[C@](O)(C4)C3)n1] | 523 [M + H]⁺ |
| 251 | 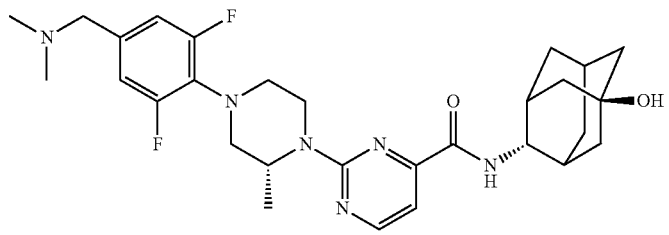 [SMILES: C[C@@H]1CN(c2c(F)cc(CN(C)C)cc2F)CCN1c1nccc(C(=O)N[C@H]2C3CC4CC2C[C@](O)(C4)C3)n1] | 541 [M + H]⁺ |
| 252 | 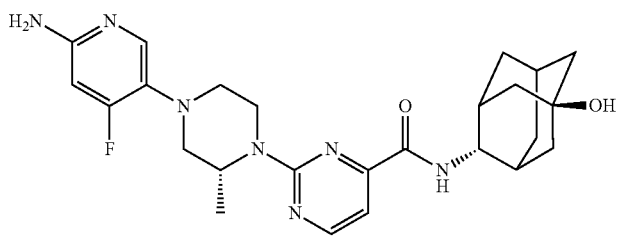 [SMILES: C[C@@H]1CN(c2cnc(N)cc2F)CCN1c1nccc(C(=O)N[C@H]2C3CC4CC2C[C@](O)(C4)C3)n1] | 482 [M + H]⁺ |

-continued

| Examples | Structures | MS (ESI) |
|---|---|---|
| 253 | 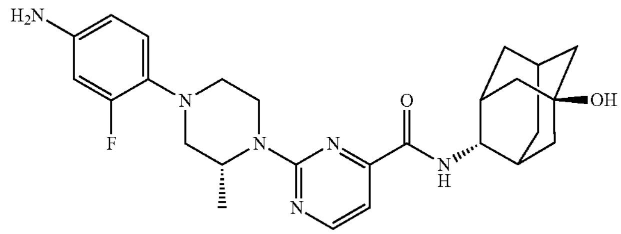 | 481 [M + H]⁺ |
| 254 | 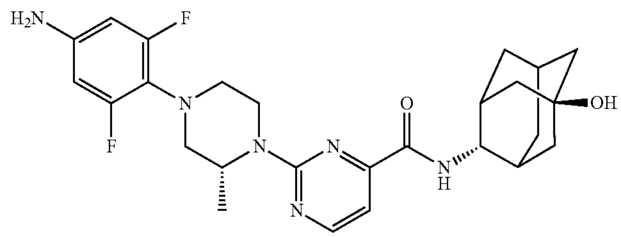 [SMILES: C[C@@H]1CN(c2c(F)cc(N)cc2F)CCN1c1nccc(C(=O)N[C@H]2C3CC4CC2C[C@](O)(C4)C3)n1] | 499 [M + H]⁺ |
| 255 | 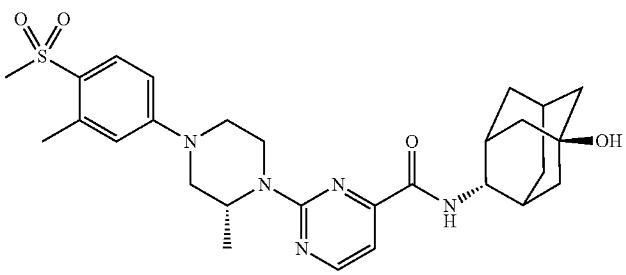 [SMILES: Cc1cc(N2CCN(c3nccc(C(=O)N[C@H]4C5CC6CC4C[C@](O)(C6)C5)n3)[C@H](C)C2)ccc1S(C)(=O)=O] | 540 [M + H]⁺ |
| 256 | 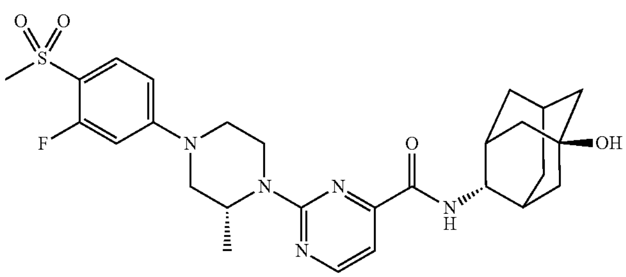 [SMILES: C[C@@H]1CN(c2ccc(S(C)(=O)=O)c(F)c2)CCN1c1nccc(C(=O)N[C@H]2C3CC4CC2C[C@](O)(C4)C3)n1] | 544 [M + H]⁺ |
| 257 | 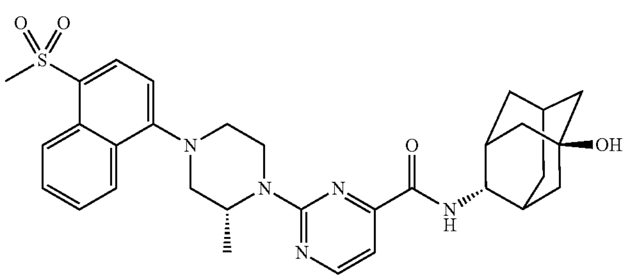 [SMILES: C[C@@H]1CN(c2ccc(S(C)(=O)=O)c3ccccc23)CCN1c1nccc(C(=O)N[C@H]2C3CC4CC2C[C@](O)(C4)C3)n1] | 576 [M + H]⁺ |
| 258 | 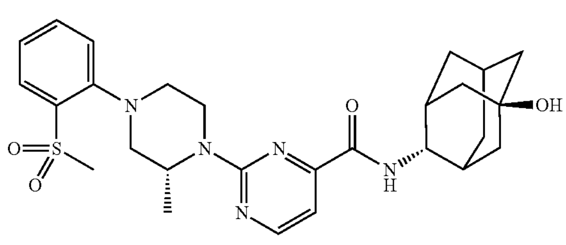 [SMILES: C[C@@H]1CN(c2ccccc2S(C)(=O)=O)CCN1c1nccc(C(=O)N[C@H]2C3CC4CC2C[C@](O)(C4)C3)n1] | 526 [M + H]⁺ |

| Examples | Structures | MS (ESI) |
|---|---|---|
| 259 | (structure) | 604 [M + H]$^+$ |
| 260 | (structure) | 524 [M + H]$^+$ |
| 261 | (structure) | 491 [M + H]$^+$ |
| 262 | (structure) | 491 [M + H]$^+$ |
| 263 | (structure) | 508 [M + H]$^+$ |

The following examples were synthesized in the same method as the above example 230, by using the intermediate 11 and an appropriate amine start material.

| Examples | Structures | MS (ESI) |
|---|---|---|
| 264 | 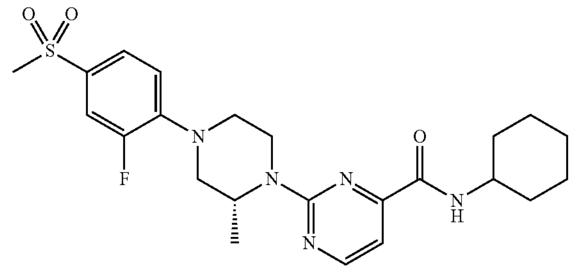 [SMILES: C[C@@H]1CN(c2ccc(S(C)(=O)=O)cc2F)CCN1c1nccc(C(=O)NC2CCCCC2)n1] | 476 [M + H]⁺ |
| 265 | 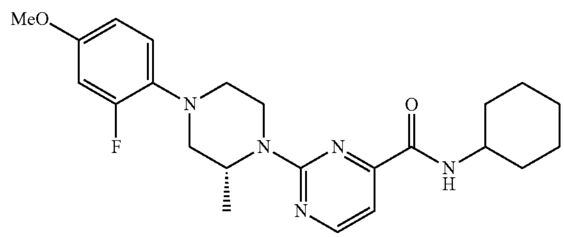 [SMILES: COc1ccc(N2CCN(c3nccc(C(=O)NC4CCCCC4)n3)[C@H](C)C2)c(F)c1] | 428 [M + H]⁺ |
| 266 | 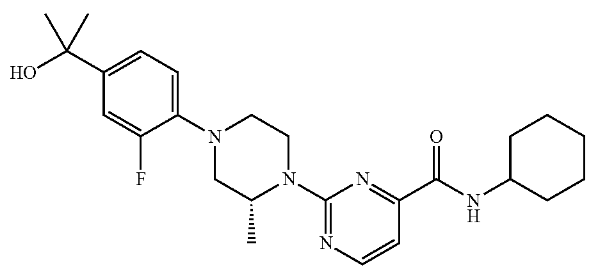 [SMILES: C[C@@H]1CN(c2ccc(C(C)(C)O)cc2F)CCN1c1nccc(C(=O)NC2CCCCC2)n1] | 456 [M + H]⁺ |
| 267 | 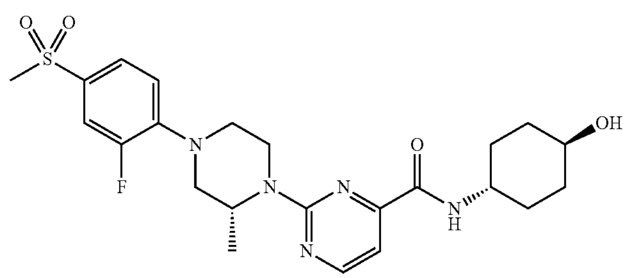 [SMILES: C[C@@H]1CN(c2ccc(S(C)(=O)=O)cc2F)CCN1c1nccc(C(=O)N[C@H]2CC[C@H](O)CC2)n1] | 492 [M + H]⁺ |
| 268 | 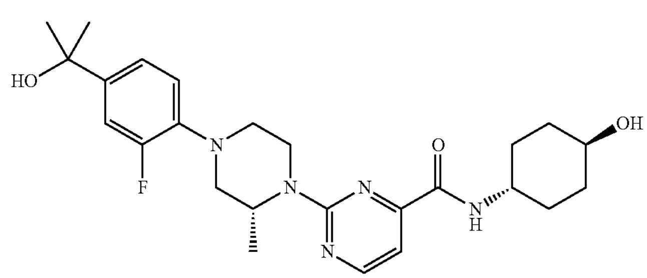 [SMILES: C[C@@H]1CN(c2ccc(C(C)(C)O)cc2F)CCN1c1nccc(C(=O)N[C@H]2CC[C@H](O)CC2)n1] | 472 [M + H]⁺ |

-continued

| Examples | Structures | MS (ESI) |
|---|---|---|
| 269 | 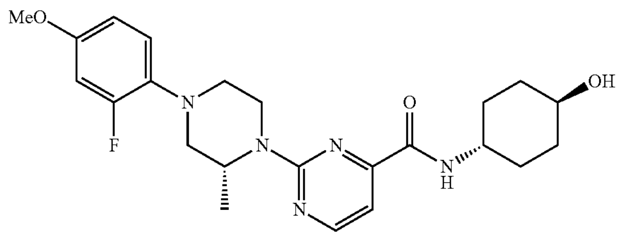 [SMILES: COc1ccc(N2CCN(c3nccc(C(=O)N[C@H]4CC[C@H](O)CC4)n3)[C@H](C)C2)c(F)c1] | 444 [M + H]⁺ |
| 270 | 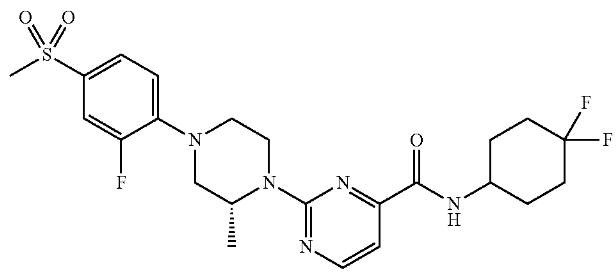 [SMILES: C[C@@H]1CN(c2ccc(S(C)(=O)=O)cc2F)CCN1c1nccc(C(=O)NC2CCC(F)(F)CC2)n1] | 512 [M + H]⁺ |
| 271 | 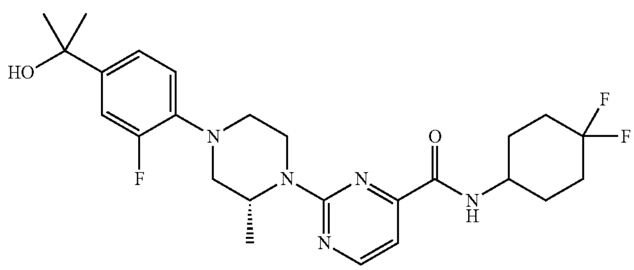 [SMILES: C[C@@H]1CN(c2ccc(C(C)(C)O)cc2F)CCN1c1nccc(C(=O)NC2CCC(F)(F)CC2)n1] | 492 [M + H]⁺ |
| 272 | 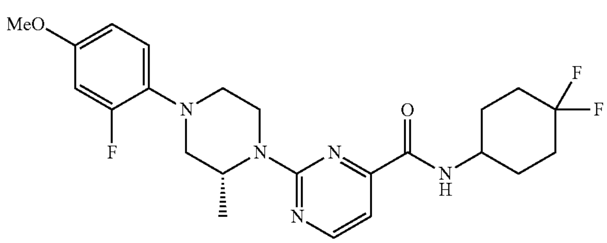 [SMILES: COc1ccc(N2CCN(c3nccc(C(=O)NC4CCC(F)(F)CC4)n3)[C@H](C)C2)c(F)c1] | 464 [M + H]⁺ |
| 273 | 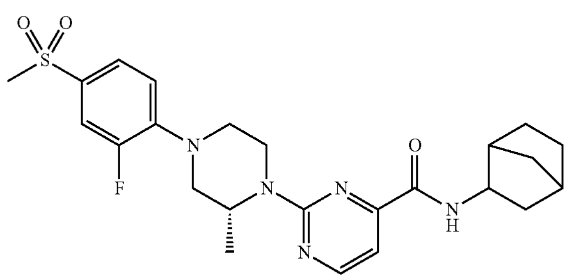 [SMILES: C[C@@H]1CN(c2ccc(S(C)(=O)=O)cc2F)CCN1c1nccc(C(=O)NC2CC3CCC2C3)n1] | 488 [M + H]⁺ |
| 274 | 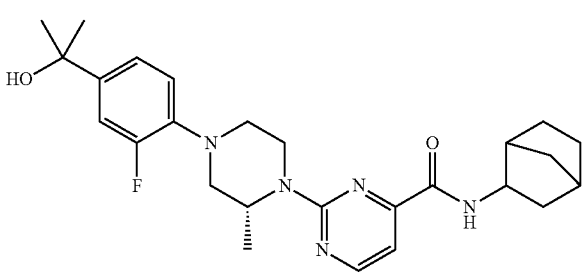 [SMILES: C[C@@H]1CN(c2ccc(C(C)(C)O)cc2F)CCN1c1nccc(C(=O)NC2CC3CCC2C3)n1] | 468 [M + H]⁺ |

-continued

| Examples | Structures | MS (ESI) |
|---|---|---|
| 275 | 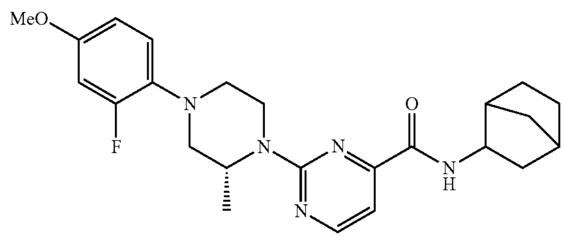 [SMILES: COc1ccc(N2CCN(c3nccc(C(=O)NC4CC5CCC4C5)n3)[C@H](C)C2)c(F)c1] | 440 [M + H]⁺ |
| 276 | 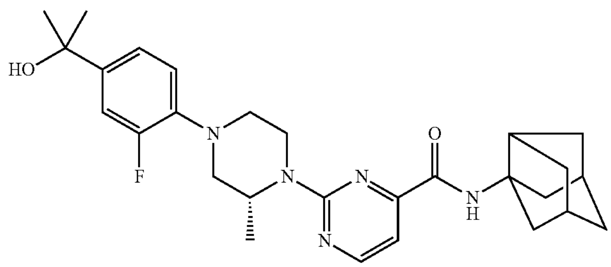 [SMILES: C[C@@H]1CN(c2ccc(C(C)(C)O)cc2F)CCN1c1nccc(C(=O)NC23CC4CC(CC2C4)C3)n1] | 494 [M + H]⁺ |
| 277 | 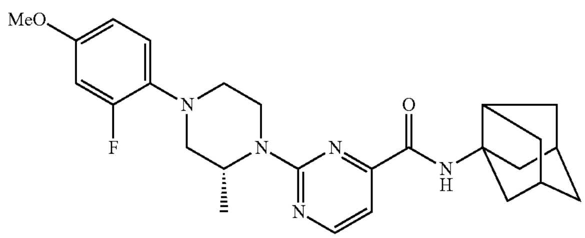 [SMILES: COc1ccc(N2CCN(c3nccc(C(=O)NC45CC6CC(CC4C6)C5)n3)[C@H](C)C2)c(F)c1] | 466 [M + H]⁺ |
| 278 | 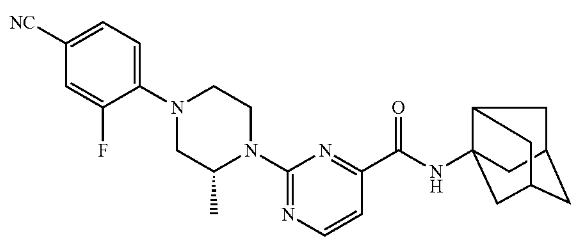 [SMILES: C[C@@H]1CN(c2ccc(C#N)cc2F)CCN1c1nccc(C(=O)NC23CC4CC(CC2C4)C3)n1] | 461 [M + H]⁺ |
| 279 | 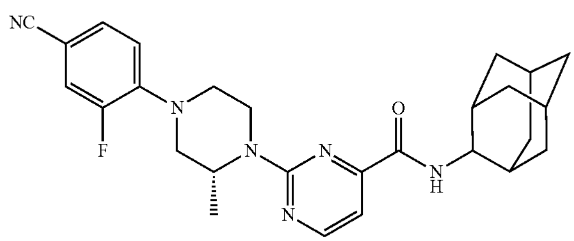 [SMILES: C[C@@H]1CN(c2ccc(C#N)cc2F)CCN1c1nccc(C(=O)NC2C3CC4CC(C3)CC2C4)n1] | 475 [M + H]⁺ |
| 280 | 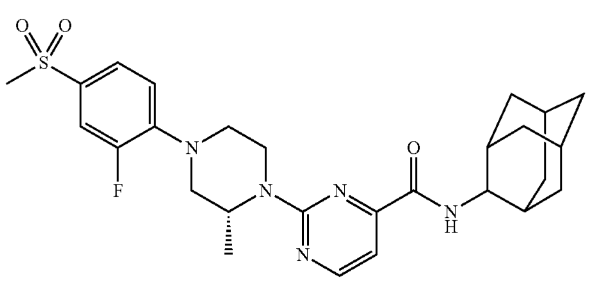 [SMILES: C[C@@H]1CN(c2ccc(S(C)(=O)=O)cc2F)CCN1c1nccc(C(=O)NC2C3CC4CC(C3)CC2C4)n1] | 528 [M + H]⁺ |

-continued

| Examples | Structures | MS (ESI) |
|---|---|---|
| 281 | 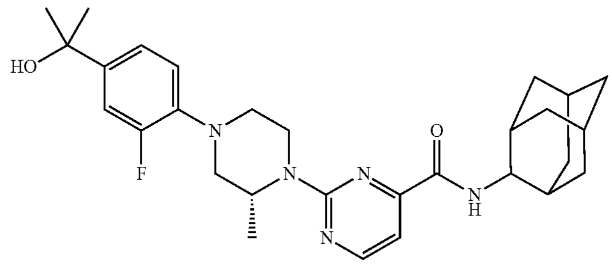 [SMILES: C[C@@H]1CN(c2ccc(C(C)(C)O)cc2F)CCN1c1nccc(C(=O)NC2C3CC4CC(C3)CC2C4)n1] | 508 [M + H]+ |
| 282 | 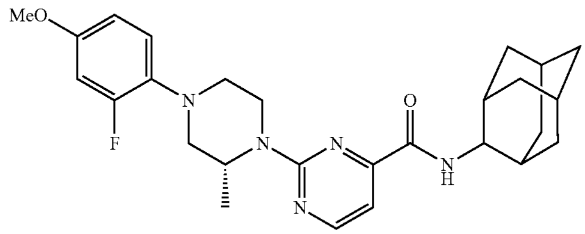 [SMILES: COc1ccc(N2CCN(c3nccc(C(=O)NC4C5CC6CC(C5)CC4C6)n3)[C@H](C)C2)c(F)c1] | 480 [M + H]+ |
| 283 | 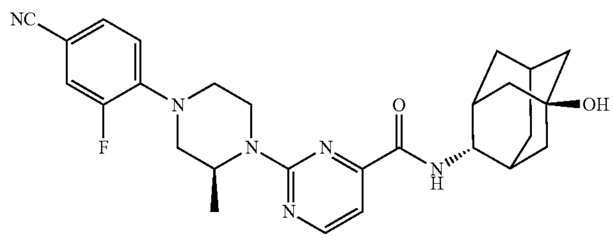 [SMILES: C[C@H]1CN(c2ccc(C#N)cc2F)CCN1c1nccc(C(=O)N[C@H]2C3CC4CC2C[C@](O)(C4)C3)n1] | 491 [M + H]+ |
| 284 | 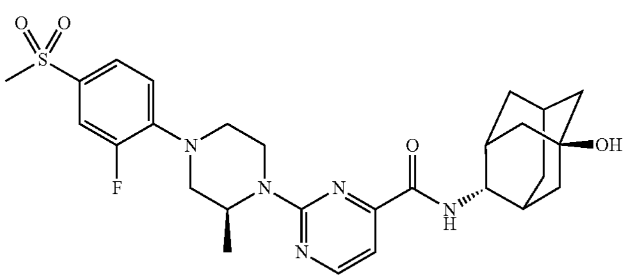 [SMILES: C[C@H]1CN(c2ccc(S(C)(=O)=O)cc2F)CCN1c1nccc(C(=O)N[C@H]2C3CC4CC2C[C@](O)(C4)C3)n1] | 544 [M + H]+ |
| 285 | 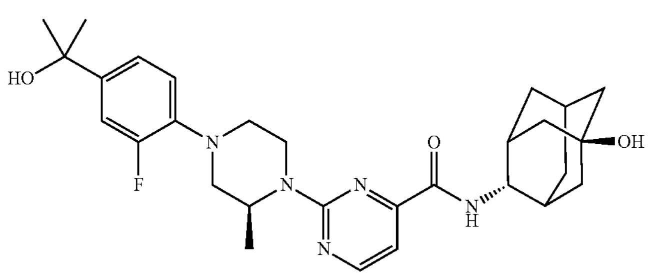 [SMILES: C[C@H]1CN(c2ccc(C(C)(C)O)cc2F)CCN1c1nccc(C(=O)N[C@H]2C3CC4CC2C[C@](O)(C4)C3)n1] | 524 [M + H]+ |
| 286 | 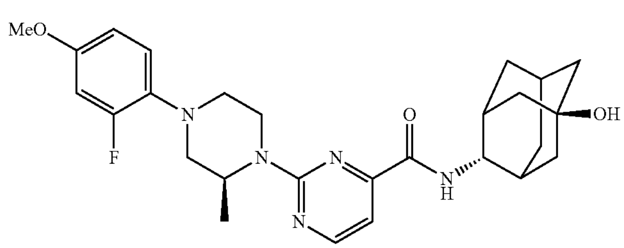 [SMILES: COc1ccc(N2CCN(c3nccc(C(=O)N[C@H]4C5CC6CC4C[C@](O)(C6)C5)n3)[C@@H](C)C2)c(F)c1] | 496 [M + H]+ |

| Examples | Structures | MS (ESI) |
|---|---|---|
| 287 | 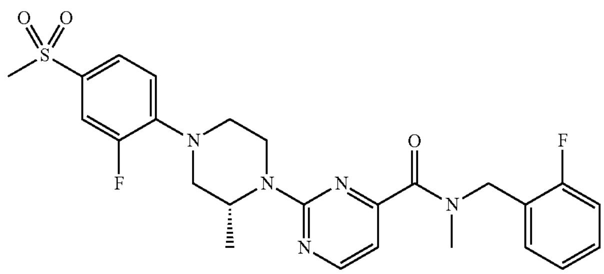 [SMILES: C[C@@H]1CN(c2ccc(S(C)(=O)=O)cc2F)CCN1c1nccc(C(=O)N(C)Cc2ccccc2F)n1] | 516 [M + H]+ |
| 288 | 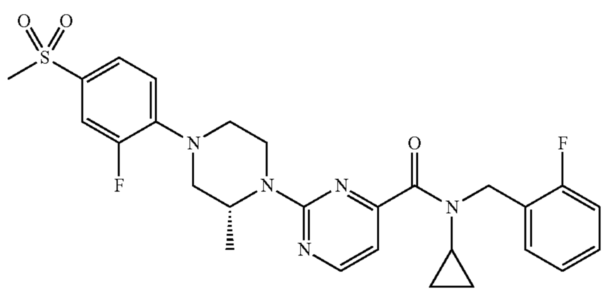 [SMILES: C[C@@H]1CN(c2ccc(S(C)(=O)=O)cc2F)CCN1c1nccc(C(=O)N(Cc2ccccc2F)C2CC2)n1] | 542 [M + H]+ |
| 289 | 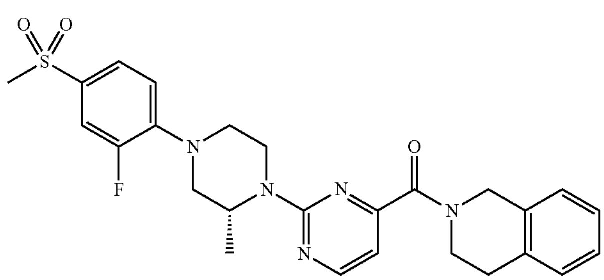 [SMILES: C[C@@H]1CN(c2ccc(S(C)(=O)=O)cc2F)CCN1c1nccc(C(=O)N2CCc3ccccc3C2)n1] | 510 [M + H]+ |
| 290 | | 532 [M + H]+ |

-continued
| Examples | Structures | MS (ESI) |
|---|---|---|
| 291 | 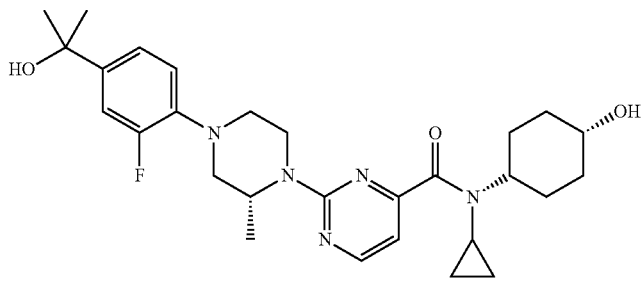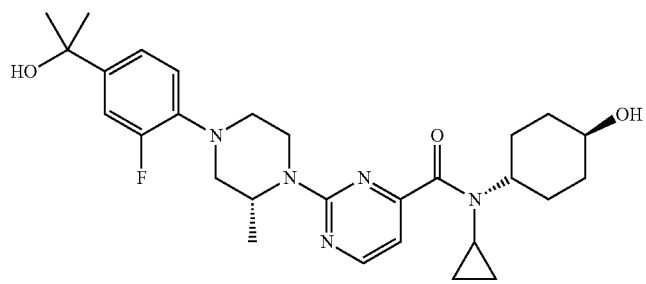 | 512 [M + H]⁺ |
| 292 | 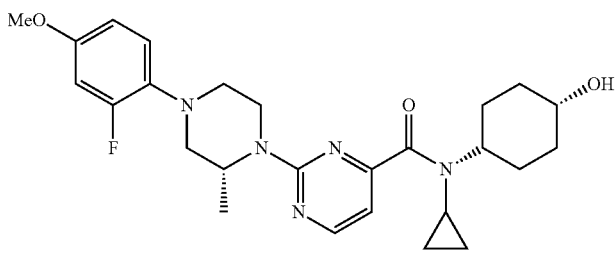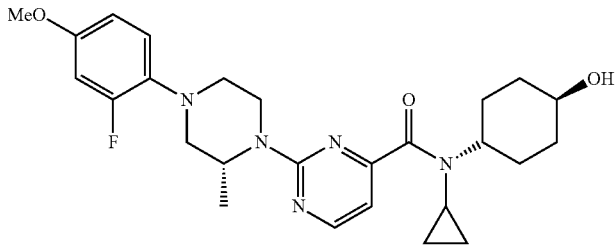 | 484 [M + H]⁺ |

| Examples | Structures | MS (ESI) |
|---|---|---|
| 293 | 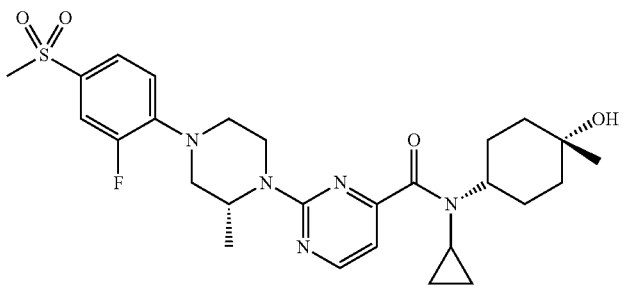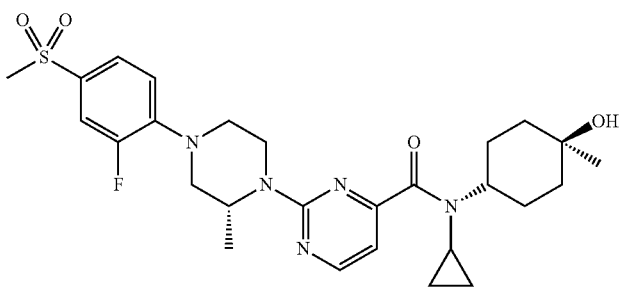 | 546 [M + H]+ |
| 294 | 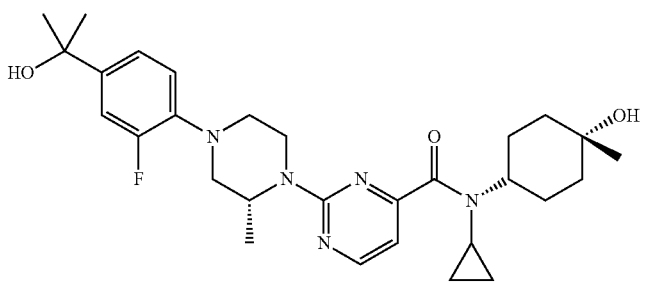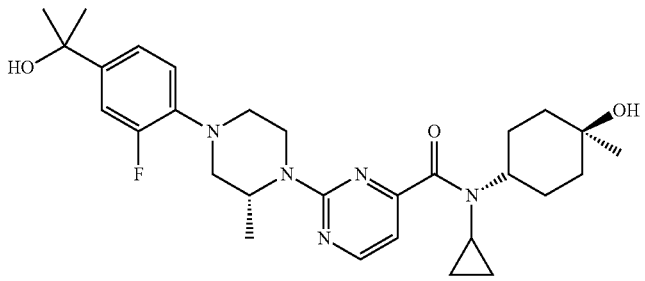 | 526 [M + H]+ |

| Examples | Structures | MS (ESI) |
|---|---|---|
| 295 | 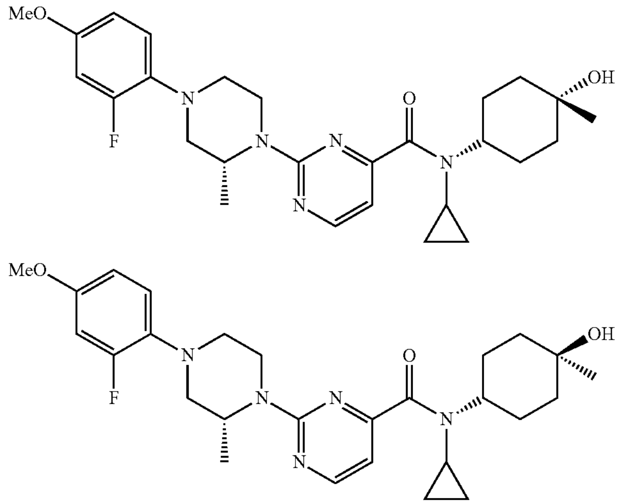 | 498 [M + H]⁺ |

Example 296

Synthesis of 2-((R)-4-(2-fluoro-4-(methylsulfonyl)phenyl)-2-methylpiperazin-1-yl)-N-((1s,4S)-4-hydroxy-4-methylcyclohexyl)pyrimidine-4-carboxamide and 2-((R)-4-(2-fluoro-4-(methylsulfonyl)phenyl)-2-methylpiperazin-1-yl)-N-((1r,4R)-4-hydroxy-4-methylcyclohexyl)pyrimidine-4-carboxamide

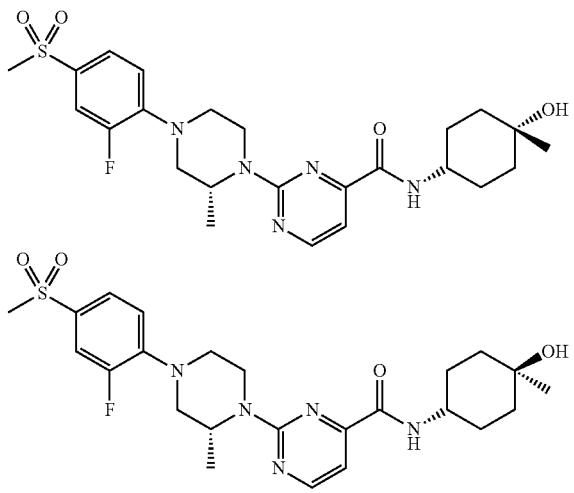

Step 1: Synthesis of 4-(benzylamino)-1-methylcyclohexanol 4-hydroxy-4-methylcyclohexanone (270 mg, 1.48 mmol) was dissolved in 1,2-dichloroethane (8.3 ml), followed by sequential addition of benzylamine (0.2 ml, 1.83 mmol), NaBH(OAc)₃ (560 mg, 2.66 mmol), and acetic acid (0.1 ml, 1.66 mmol), and then the resulting mixture was stirred at room temperature under nitrogen stream for 72 hours. The resulting reaction liquid was neutralized by addition of 10% aqueous NaOH solution, and extracted with 5% MeOH/MC (50 ml×3). The organic layer was dried over anhydrous sodium sulfate, followed by filtration and concentration, and then the residue thus obtained was subjected to MPLC (10% MeOH/MC), to obtain 350 mg of yellow solid (96%).

Step 2: Synthesis of 4-amino-1-methylcyclohexanol 4-(Benzylamino)-1-methylcyclohexanol (335 mg, 1.53 mmol) was dissolved in EtOH (7.95 ml), followed by addition of Pd (10 wt % on activated carbon, 35 mg), and then the resulting liquid was stirred at room temperature under hydrogen stream for 31 hours. The resulting reaction liquid was filtered, concentrated under reduced pressure, and dried under vacuum, to obtain 164 mg of white solid (83%).

Step 3: Synthesis of 2-((R)-4-(2-fluoro-4-(methylsulfonyl)phenyl)-2-methylpiperazin-1-yl)-N-((1s,4S)-4-hydroxy-4-methylcyclohexyl)pyrimidine-4-carboxamide and 2-((R)-4-(2-fluoro-4-(methylsulfonyl)phenyl)-2-methylpiperazin-1-yl)-N-((1r,4R)-4-hydroxy-4-methylcyclohexyl)pyrimidine-4-carboxamide The same method as the example 230 was performed by using the intermediate 11, and (R)-1-(2-fluoro-4-(methylsulfonyl)phenyl)-3-methylpiperazine and 4-amino-1-methylcyclohexanol, to obtain 2-((R)-4-(2-fluoro-4-(methylsulfonyl)phenyl)-2-methylpiperazin-1-yl)-N-((1s,4S)-4-hydroxy-4-methylcyclohexyl)pyrimidine-4-carboxamide and 2-((R)-4-(2-fluoro-4-(methylsulfonyl)phenyl)-2-methylpiperazin-1-yl)-N-((1r,4R)-4-hydroxy-4-methylcyclohexyl)pyrimidine-4-carboxamide, respectively. MS (ESI): 506 [M+H]⁺, 506 [M+H]⁺

The following examples were synthesized in the same method as the above example 296, by using the intermediate 11 and an appropriate piperazine start material.

| Examples | Structures | MS (ESI) |
|---|---|---|
| 297 | 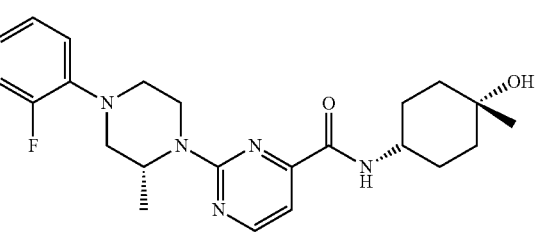 | 458 [M + H]+ |
| | 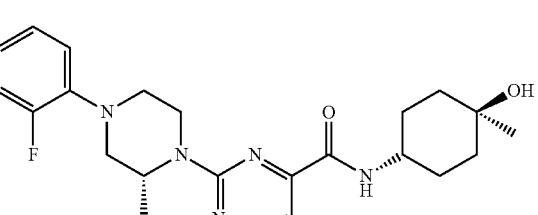 | |
| 298 | 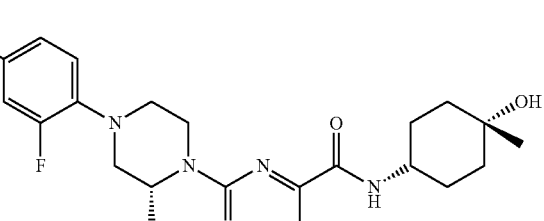 | 486 [M + H]+ |
| | 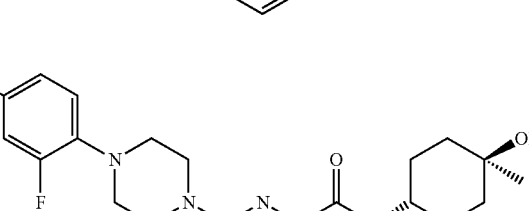 | |
| 299 | 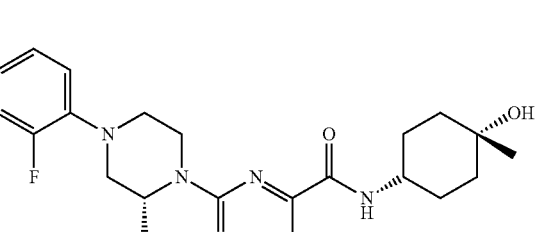 | 453 [M + H]+ |
| | 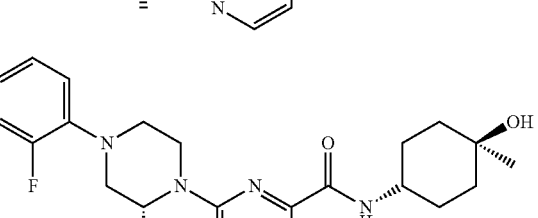 | |

The following examples were synthesized in the same method as the above example 173, by using the intermediate 12 and appropriate bromobenzene, bromopyridine, or bromopyrazole.

| Examples | Structures | MS (ESI) |
|---|---|---|
| 300 | 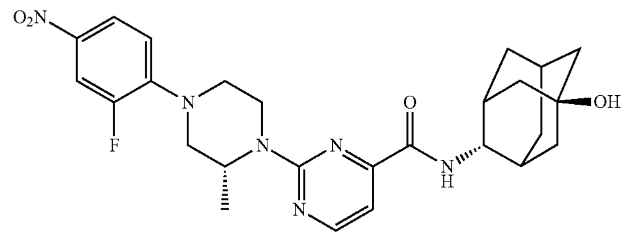 [SMILES: C[C@@H]1CN(c2ccc([N+](=O)[O-])cc2F)CCN1c1nccc(C(=O)N[C@H]2C3CC4CC2C[C@](O)(C4)C3)n1] | 511 [M + H]⁺ |
| 301 | 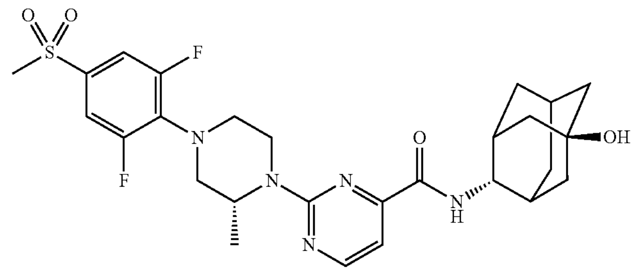 [SMILES: C[C@@H]1CN(c2c(F)cc(S(C)(=O)=O)cc2F)CCN1c1nccc(C(=O)N[C@H]2C3CC4CC2C[C@](O)(C4)C3)n1] | 562 [M + H]⁺ |
| 302 | 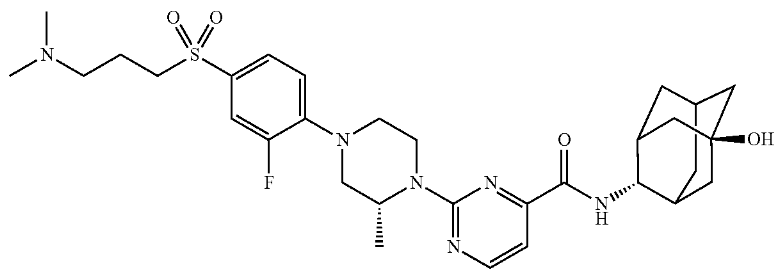 [SMILES: C[C@@H]1CN(c2ccc(S(=O)(=O)CCCN(C)C)cc2F)CCN1c1nccc(C(=O)N[C@H]2C3CC4CC2C[C@](O)(C4)C3)n1] | 615 [M + H]⁺ |
| 303 | 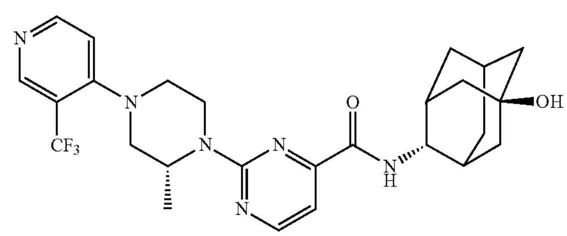 [SMILES: C[C@@H]1CN(c2ccncc2C(F)(F)F)CCN1c1nccc(C(=O)N[C@H]2C3CC4CC2C[C@](O)(C4)C3)n1] | 517 [M + H]⁺ |
| 304 | 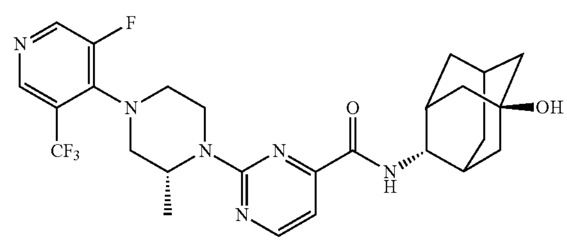 [SMILES: C[C@@H]1CN(c2c(F)cncc2C(F)(F)F)CCN1c1nccc(C(=O)N[C@H]2C3CC4CC2C[C@](O)(C4)C3)n1] | 535 [M + H]⁺ |
| 305 | 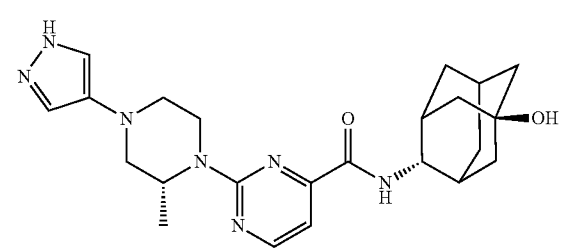 [SMILES: C[C@@H]1CN(c2cn[nH]c2)CCN1c1nccc(C(=O)N[C@H]2C3CC4CC2C[C@](O)(C4)C3)n1] | 438 [M + H]⁺ |

| Examples | Structures | MS (ESI) |
|---|---|---|
| 306 | 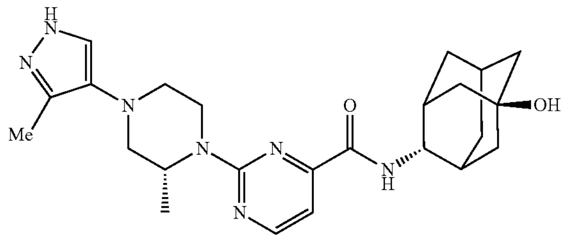 [SMILES: Cc1n[nH]cc1N1CCN(c2nccc(C(=O)N[C@H]3C4CC5CC3C[C@](O)(C5)C4)n2)[C@H](C)C1] | 452 [M + H] + |
| 307 | 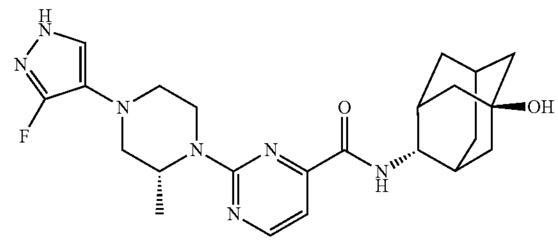 [SMILES: C[C@@H]1CN(c2c[nH]nc2F)CCN1c1nccc(C(=O)N[C@H]2C3CC4CC2C[C@](O)(C4)C3)n1] | 456 [M + H] + |
| 308 | 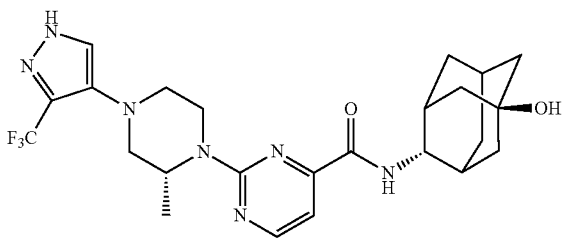 [SMILES: C[C@@H]1CN(c2c[nH]nc2C(F)(F)F)CCN1c1nccc(C(=O)N[C@H]2C3CC4CC2C[C@](O)(C4)C3)n1] | 506 [M + H] + |

Experimental Examples

Experimental Example 1

Cell Assay on 11β-HSD1

In order to investigate inhibitory effects of the compounds according to the present invention on activity of human-derived 11β-HSD1 (h11β-HSD1) enzyme, the following experiment was performed.

To assay the activity of the 11β-HSD1 enzyme, a recombinant DNA having h11β-HSD1 gene was introduced into an animal cell to induce overexpression of the enzyme [Arampatzis, S. *J Mol. Endocrinol.* 2005, 35, 89-101]. First, HEK-293 cells were incubated using a cell incubator until they reached 70-80% confluency on a surface of the container. The recombinant DNA having h11β-HSD1 gene was mixed with Fugene 6, followed by reaction at room temperature for 1 hour. The resulting material was used to treat the cells, and thus DNA was injected into the cells. The next day, the cell supernatant was removed, followed by supplement of fresh medium, and then the cells were further incubated for 24 hours in the cell incubator.

When the cells were incubated at 70-80% confluency, the cells were detached with trypsin, and the number of cells was measured by using a Hemacytometer. The incubated liquid was diluted to contain 20,000 cells/ml, and 100 μl of the diluted liquid was plated onto each well of the 96-well plate. Following incubation for 24 hours, the compound dissolved in DMSO was diluted to 1/100 by the incubated liquid. 100 μl of the resulting compound-diluted liquid was dispensed into each well, and then incubated for 30 minutes. 10 mM of cortisone was diluted to 21 μM by the incubated liquid, and then 5 μl of the resulting liquid was input to each well, followed by reaction for 2 hours in the cell incubator [Jeffrey J. et al. *J Med. Chem.* 2007, 50, 149-164].

The quantitative assay of cortisol generated in this reaction was performed by using a system provided from Assay Designs Inc. The resultant enzyme reactant was added to the plate coated with anti-mouse IgG, and then a specific antibody binding to the cortisol and alkaline phosphatase-bound cortisol are together input thereto, followed by reaction at room temperature for 2 hours. The contents in the wells after reaction were thrown away, and then washing was performed with a buffer solution consisting of surfactant and tris-buffered saline three times. After that, a p-nitrophenyl phosphate solution, which is a substrate for the alkaline phosphatase, was input thereto for coloring reaction, followed by reaction for 1 hour, and then the light absorbance at 405 nm was measured by using a plate reader. The measurement results were tabulated in Table 1.

TABLE 1

| | hHSD1 inhibiting activity | |
|---|---|---|
| Example | % inhibition at 100 μM | % inhibition at 10 μM |
| 36 | 99 | 62 |
| 37 | 97 | 51 |
| 40 | 98 | 40 |
| 41 | 96 | 26 |
| 42 | 97 | 35 |
| 47 | 96 | 36 |
| 49 | 96 | 24 |
| 50 | 97 | 23 |
| 51 | 99 | 67 |

TABLE 1-continued

| | hHSD1 inhibiting activity | |
|---|---|---|
| Example | % inhibition at 100 μM | % inhibition at 10 μM |
| 57 | 82 | 53 |
| 58 | 85 | 72 |
| 60 | 82 | 68 |
| 61 | 83 | 68 |
| 72 | 83 | 12 |
| 74 | 80 | 34 |
| 77 | 87 | 73 |
| 78 | 84 | 32 |
| 79 | 87 | 42 |
| 87 | 79 | 40 |
| 88 | 84 | 40 |
| 91 | 76 | 34 |
| 97 | 77 | 58 |
| 98 | 78 | 38 |
| 104 | 87 | 49 |
| 105 | 91 | 38 |
| 106 | 90 | 86 |
| 118 | 84 | 64 |
| 119 | 81 | 65 |
| 124 | 85 | 54 |
| 125 | 79 | 48 |
| 132 | 87 | 71 |
| 133 | 85 | 70 |
| 150 | 87 | 76 |
| 151 | 85 | 75 |
| 167 | 85 | 42 |
| 168 | 88 | 77 |
| 173 | 87 | 81 |
| 174 | 82 | 79 |
| 190 | 89 | 76 |
| 192 | 85 | 41 |
| 196 | 86 | 64 |
| 201 | 78 | 40 |
| 204 | 76 | 41 |
| 230 | 82 | 69 |
| 231 | 78 | 42 |
| 235 | 85 | 62 |
| 239 | 76 | 52 |
| 242 | 77 | 39 |
| 284 | 86 | 56 |
| 290 | 83 | 67 |

Formulation Examples

Formulation Example 1

Preparation of Tablets (Pressurization Type)

As an active ingredient, 5.0 mg of a compound represented by the formula 1, of the present invention, was sieved, and then mixed with 14.1 mg of lactose, 0.8 mg of crospovidone USNF and 0.1 mg of magnesium stearate, followed by pressurization, to formulate tablets.

Formulation Example 2

Preparation of Tablets (Wet Granulation)

As an active ingredient, 5.0 mg of a compound represented by the formula 1, of the present invention, was sieved, and then mixed with 16.0 mg of lactose and 4.0 mg of starch. 0.3 mg of polysolvate 80 was dissolved in pure water, and then an appropriate amount of this solution was added to the resulting mixture, followed by micronization. The micronized particles thus obtained were sieved, and then mixed with 2.7 mg of colloidal silicon dioxide and 2.0 mg of magnesium stearate, followed by pressurization, to formulate tablets.

Formulation Example 3

Preparation of Powder and Capsule Agents

As an active ingredient, 5.0 mg of a compound represented by the formula 1, of the present invention, was sieved, and then mixed with 14.8 mg of lactose, 10.0 mg of polyvinyl pyrrolidone and 0.2 mg of magnesium stearate. The resulting mixture filled a hard gelatin capsule No. 5 by using an appropriate apparatus.

Formulation Example 4

Preparation of Injectables

As an active ingredient, 100 mg of a compound represented by the formula 1, of the present invention was contained, and beside this, 180 mg of mannitol, 26 mg of $Na_2HPO_4$ $12H_2O$, and 2,974 mg of distilled water were also contained to prepare an injectable.

Although the present invention has been described in detail with reference to the examples, it is obvious to those skilled in the art that various changes and modifications can be made in the technical spirit of the present invention, and thus, it is apparent that these changes and modifications are included within the scope of the appended claims and their equivalents.

The invention claimed is:

1. An amide compound represented by the formula 1 below, or a pharmaceutically acceptable salt, solvate, hydrate, prodrug, racemate, or stereoisomer thereof,

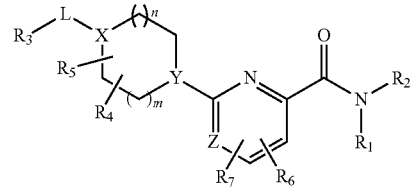

[Formula 1]

[In the formula 1,

X represents N or CR, and Y represents N or CH, provided that X and Y are not carbon at the same time;

Z represents N or CH;

$R_1$ and $R_2$ independently represent hydrogen, (C3-C10) cycloalkyl, norbornyl, adamantyl, or noradamantyl, provided that both $R_1$ and $R_2$ are not hydrogen at the same time;

L represents a single bond, —O—, —$NR_{11}$—, —CO—, —$SO_2$—, —$(CR_{21}R_{22})$—$(CH_2)_c$— (c represents an integer of 0 to 5), —$CO(CR_{21}R_{22})_d$— (d represents an integer of 1 to 6), (C3-C10)cycloalkylene, (C6-C20) arylene or (C3-C20)heteroarylene;

$R_{21}$ and $R_{22}$ independently represent hydrogen or (C1-C10)alkyl, or $R_{21}$ and $R_{22}$ may be linked via alkylene or alkenylene to form a cycloaliphatic ring or an aromatic ring;

R and $R_3$ independently represent hydrogen, (C1-C10) alkyl, (C3-C10)cyclo alkyl, (C1-C10)alkoxy, halogen, hydroxy, cyano, —$NR_{31}R_{32}$, nitro, —$CONH_2$, —$CO_2R_{33}$, —$SO_3H$, —$SO_2NR_{34}R_{35}$, —$SO_2R_{36}$, —$O(CH_2)_aCO_2H$ (a represents an integer of 1 to 3), —$O(CH_2)_bCONH_2$ (b represents an integer of 1 to 3), —$NH(CO)R_{37}$, —$NH(SO_2)R_{38}$, 5- to 7-membered heterocycle, (C6-C20)aryl or (C3-C20)heteroaryl;

R₄ and R₅ independently represent hydrogen, (C1-C10)alkyl, (C3-C10)cycloalkyl, (C1-C10)alkoxy, halogen, hydroxy, cyano, amino, nitro, —CONH₂ or —CO₂R₁₂, and include all of isomers and racemic compounds thereof all, or R₄ and R₅ may be substituted with adjacent carbon atoms to form (C1-C10) saturated or unsaturated carbocycle, heterocycle, bicarbocycle, biheterocycle, fused carbocycle, or fused heterocycle, or may be linked to R₃ to form saturated or unsaturated carbocycle;

R₆ and R₇ independently represent hydrogen, (C1-C10)alkyl, (C3-C10)cycloalkyl, (C1-C10)alkoxy, halogen, hydroxy, cyano, amino, nitro, —CONH₂ or —CO₂R₁₂;

the cycloalkylene, arylene or heteroarylene of L; the alkyl, cycloalkyl, norbornyl, adamantyl, or noradamantyl of R₁ and R₂; the alkyl, cycloalkyl, alkoxy, heterocycle, aryl or heteroaryl of R and R₃; the alkyl, cycloalkyl or alkoxy of R₄ and R₅; the saturated or unsaturated carbocycle, heterocycle, bicarbocycle, biheterocycle, fused carbocycle or fused heterocycle formed by the substitution of R₄ and R₅ with adjacent carbon atoms; and the alkyl, cycloalkyl or alkoxy of R₆ and R₇ may be further substituted with one or more substituent(s) selected from the group consisting of (C1-C10)alkyl, (C3-C10)cycloalkyl, (C1-C10)alkoxy, halo(C1-C10)alkyl, halo(C1-C10)alkoxy, halogen, hydroxy, cyano, —NR₄₁R₄₂, nitro, —CO₂R₄₃, —CONH₂, —SO₃H, —SO₂NR₄₄R₄₅, —SO₂(CH₂)$_c$R₄₄R₄₅ (c represents an integer of 1 to 3), —SO₂R₄₆, —O(CH₂)$_c$CO₂H (c represents an integer of 1 to 3), —O(CH₂)$_d$CONH₂ (d represents an integer of 1 to 3), —NH(CO)R₄₇, —NH(SO₂)R₄₈, (C6-C20)aryl and (C3-C20)heteroaryl;

R₁₁, R₁₂, R₃₁, R₃₂, R₃₃, R₃₄, R₃₅, R₃₆, R₃₇, R₃₈, R₄₁, R₄₂, R₄₃, R₄₄, R₄₅, R₄₆, R₄₇ and R₄₈ independently represent hydrogen, (C1-C10)alkyl, (C3-C10)cycloalkyl or (C6-C20)aryl; and m and n independently represent an integer of 0 to 3, provided that m+n represents an integer of 2 or more.

2. The amide compound, or the pharmaceutically acceptable salt, solvate, hydrate, prodrug, racemate, or stereoisomer thereof, of claim 1,
wherein R₁ and R₂ independently represent hydrogen, (C3-C10)cycloalkyl, norbornyl, adamantyl, or noradamantyl;
L represents a single bond, —CO—, —SO₂—, —(CR₂₁R₂₂)—(CH₂)$_c$— (c represents an integer of 0 to 5),

—CO(CR₂₁R₂₂)$_d$— (d represents an integer of 1 to 6), (C3-C10)cycloalkylene, (C6-C20)arylene or (C3-C20)heteroarylene;

R₂₁ and R₂₂ independently represent hydrogen or (C1-C10)alkyl;

R₃ represents hydrogen, (C1-C10)alkyl, (C3-C10)cycloalkyl, (C1-C10)alkoxy, halogen, hydroxy, cyano, —NR₃₁R₃₂, nitro, —CONH₂, —CO₂R₃₃, —SO₂NR₃₄R₃₅, —SO₂R₃₆, —O(CH₂)$_a$CO₂H (a represents an integer of 1 to 3), —O(CH₂)$_b$CONH₂ (b represents an integer of 1 to 3), —NH(CO)R₃₇, —NH(SO₂)R₃₈, 5- to 7-membered heterocycle, (C6-C20)aryl or (C3-C20)heteroaryl;

R₆ and R₇ independently represent hydrogen, (C1-C10)alkyl or halogen;

the cycloalkylene, arylene or heteroarylene of the L; the cycloalkyl, norbornyl, adamantyl, or noradamantyl of R₁ and R₂; the alkyl, cycloalkyl, alkoxy, heterocycle, aryl or heteroaryl of R₃; and the alkyl of R₆ and R₇ may be further substituted with one or more substituent(s) selected from the group consisting of (C1-C10)alkyl, (C3-C10)cycloalkyl, (C1-C10)alkoxy, halo(C1-C10)alkyl, halo(C1-C10)alkoxy, halogen, hydroxy, cyano, —NR₄₁R₄₂, nitro, —CO₂R₄₃, —CONH₂, —SO₃H, —SO₂NR₄₄R₄₅, —SO₂(CH₂)$_c$NR₄₄R₄₅ (c represents an integer of 1 to 3), —SO₂R₄₆, —O(CH₂)$_c$CO₂H (c represents an integer of 1 to 3), —O(CH₂)$_d$CONH₂ (d represents an integer of 1 to 3), —NH(CO)R₄₇, —NH(SO₂)R₄₈, (C6-C20)aryl and (C3-C20) heteroaryl; and R₁₁, R₁₂, R₃₁, R₃₂, R₃₃, R₃₄, R₃₅, R₃₆, R₃₇, R₃₈, R₄₁, R₄₂, R₄₃, R₄₄, R₄₅, R₄₆, R₄₇ and R₄₈ independently represent hydrogen, (C1-C10)alkyl, (C3-C10)cycloalkyl or (C6-C20)aryl.

3. The amide compound, or the pharmaceutically acceptable salt, solvate, hydrate, prodrug, racemate, or stereoisomer thereof, of claim 1, selected from the group consisting of:
N-cyclohexyl-6-(piperidin-1-yl)picolinamide;
N-cyclohexyl-6-(4-methylpiperidin-1-yl)picolinamide;
N-cyclohexyl-6-(4-(4-methoxyphenyl)piperidin-1-yl)picolinamide;
N-cyclohexyl-6-(4-(4-chlorophenyl)piperidin-1-yl)picolinamide;
N-cyclohexyl-6-(4-(4-fluorophenyl)piperidin-1-yl)picolinamide;
(N-(Adamantan-2-yl)-6-(4-(4-methoxyphenyl)piperazin-1-yl)picolinamide)(N-(adamantan-2-yl)-6-(piperidin-1-yl)picolinamide;
N-(adamantan-2-yl)-6-(4-methylpiperidin-1-yl)picolinamide;
(N-(adamantan-2-yl)-6-(4-(4-chlorophenyl)piperazin-1-yl)picolinamide;
N-(adamantan-2-yl)-6-(4-(4-fluorophenyl)piperazin-1-yl)picolinamide;
N-(adamantan-2-yl)-6-(4-methylpiperazin-1-yl)picolinamide;
N-(adamantan-2-yl)-6-(4-acetylpiperidin-1-yl)picolinamide;
(N-(adamantan-2-yl)-6-(piperazin-1-yl)picolinamide;
(N-(adamantan-2-yl)-6-(4-(2-hydroxyethyl)piperazin-1-yl)picolinamide;
methyl 3-(4-(6-(adamantan-2-ylcarbamoyl)pyridin-2-yl)piperazin-1-yl)propanoate;
3-(4-(6-(adamantan-2-ylcarbamoyl)pyridin-2-yl)piperazin-1-yl)propanoic acid;
N-(adamantan-2-yl)-6-(4-(3-amino3-oxopropyl)piperazin-1-yl)picolinamide;
N-((E)-5-hydroxyadamantan-2-yl)-6-(piperidin-1-yl)picolinamide;
N-((E)-5-hydroxyadamantan-2-yl)-6-(4-(trifluoromethyl)-4-hydroxypiperidin-1-yl)picolinamide;
N-((E)-5-hydroxyadamantan-2-yl)-6-(3-(trifluoromethyl)-3-hydroxypiperidin-1-yl)picolinamide;
N-((E)-5-hydroxyadamantan-2-yl)-6-(4-hydroxy-4-methylpiperidin-1-yl)picolinamide;
N-((E)-5-hydroxyadamantan-2-yl)-6-(4-cyclopropyl-4-hydroxypiperidin-1-yl)picolinamide;
N-((E)-5-hydroxyadamantan-2-yl)-6-(4-hydroxy-4-phenylpiperidin-1-yl)picolinamide;
N-((E)-5-hydroxyadamantan-2-yl)-6-(4-(hydroxymethyl)piperidin-1-yl)picolinamide;

N-((E)-5-hydroxyadamantan-2-yl)-6-(4-(methoxycarbonylmethyl)piperidin-1-yl)picolinamide;
N-((E)-5-hydroxyadamantan-2-yl)-6-(4-(methoxycarbonylethyl)piperidin-1-yl)picolinamide;
N-((E)-5-hydroxyadamantan-2-yl)-6-(4-(piperidin-1-yl)piperidin-1-yl)picolinamide;
N-((E)-5-hydroxyadamantan-2-yl)-6-(4-morpholinopiperidin-1-yl)picolinamide;
N-((E)-5-hydroxyadamantan-2-yl)-6-(4-phenylpiperidin-1-yl)picolinamide;
N-((E)-5-hydroxyadamantan-2-yl)-6-(4-(4-cyanophenyl)piperidin-1-yl)picolinamide;
N-((E)-5-hydroxyadamantan-2-yl)-6-(4-(pyridin-2-yl)piperazin-1-yl)picolinamide;
N-((E)-5-hydroxyadamantan-2-yl)-6-(4-phenylpiperazin-1-yl)picolinamide;
N-((E)-5-hydroxyadamantan-2-yl)-6-(4-(4-cyanophenyl)piperazin-1-yl)picolinamide;
N-((E)-5-hydroxyadamantan-2-yl)-6-(4-(4-hydroxyphenyl)piperazin-1-yl)picolinamide;
N-((E)-5-hydroxyadamantan-2-yl)-6-(4-(4-chlorophenyl)piperazin-1-yl)picolinamide;
N-((E)-5-hydroxyadamantan-2-yl)-6-(4-(4-trifluoromethyl)phenyl)piperazin-1-yl)picolinamide;
N-((E)-5-hydroxyadamantan-2-yl)-6-(4-(4-fluorophenyl)piperazin-1-yl)picolinamide;
N-((E)-5-hydroxyadamantan-2-yl)-6-(4-(4-p-tolylpiperazin-1-yl)picolinamide;
N-((E)-5-hydroxyadamantan-2-yl)-6-(4-(4-methoxyphenyl)piperazin-1-yl)picolinamide;
N-((E)-5-hydroxyadamantan-2-yl)-6-(4-(4-nitrophenyl)piperazin-1-yl)picolinamide;
N-((E)-5-hydroxyadamantan-2-yl)-6-(3,4-dihydroquinoline-1(2H)-yl)picolinamide;
N-((E)-5-hydroxyadamantan-2-yl)-6-(3,4-dihydroisoquinoline-2(1H)-yl)picolinamide;
N-((E)-5-hydroxyadamantan-2-yl)-6-(2-methylpiperidin-1-yl)picolinamide;
N-((E)-5-hydroxyadamantan-2-yl)-6-(4-benzylpiperazin-1-yl)picolinamide;
N-((E)-5-hydroxyadamantan-2-yl)-6-(piperazin-1-yl)picolinamide;
N-((E)-5-hydroxyadamantan-2-yl)-6-(4-(pyridin-3-ylmethyl)piperazin-1-yl)picolinamide;
N-((E)-5-hydroxyadamantan-2-yl)-6-(4-(pyridin-2-ylmethyl)piperazin-1-yl)picolinamide;
N-((E)-5-hydroxyadamantan-2-yl)-6-(4-(2-hydroxyethyl)piperazin-1-yl)picolinamide;
methyl 3-(4-(6-(((E)-5-hydroxyadamantan-2-yl)carbamoyl)pyridin-2-yl)piperazin-1-yl)propanoate;
3-(4-(6-(((E)-5-hydroxyadamantan-2-yl)carbamoyl)pyridin-2-yl)piperazin-1-yl)propanic acid;
6-(4-(3-amino-3-oxopropyl)piperazin-1-yl)-N-((E)-5-hydroxyadamantan-2-yl)picolinamide;
6-(4-(2-amino-2-oxoethyl)piperazin-1-yl)-N-((E)-5-hydroxyadamantan-2-yl)picolinamide;
2-(1-(6-(((E)-5-hydroxyadamantan-2-yl)carbamoyl)pyridin-2-yl)piperidin-4-yl)acetic acid;
6-(4-(3-amino-3-oxopropyl)piperidin-1-yl)-N-((E)-5-hydroxyadamantan-2-yl)picolinamide;
3-(1-(6-(((E)-5-hydroxyadamantan-2-yl)carbamoyl)pyridin-2-yl)piperidin-4-yl)propanic acid;
6-(4-(4-carbamoylphenyl)piperazin-1-yl)-N-((E)-5-hydroxyadamantan-2-yl)picolinamide;
6-(4-(4-carbamoylphenyl)piperidin-1-yl)-N-((E)-5-hydroxyadamantan-2-yl)picolinamide;
6-(4-(4-aminophenyl)piperazin-1-yl)-N-((E)-5-hydroxyadamantan-2-yl)picolinamide;
N-((E)-5-hydroxyadamantan-2-yl)-6-(4-(4-(methylsulfonyl)phenyl)piperazin-1-yl)picolinamide;
N-((E)-5-hydroxyadamantan-2-yl)-6-(4-(4-cyano-3-fluorophenyl)piperazin-1-yl)picolinamide;
N-((E)-5-hydroxyadamantan-2-yl)-6-(4-(2-chloro-4-cyanophenyl)piperazin-1-yl)picolinamide;
N-((E)-5-hydroxyadamantan-2-yl)-6-(4-(3,4-dimethoxyphenyl)piperazin-1-yl)picolinamide;
N-((E)-5-hydroxyadamantan-2-yl)-6-(4-(4-ethoxycarbonylmethoxyphenyl)piperazin-1-yl)picolinamide;
6-(4-(4-carbamoyl-3-fluorophenyl)piperazin-1-yl)-N-((E)-5-hydroxyadamantan-2-yl)picolinamide;
6-(4-(4-carbamoyl-2-chlorophenyl)piperazin-1-yl)-N-((E)-5-hydroxyadamantan-2-yl)picolinamide;
2-(4-(4-(6-(((E)-5-hydroxyadamantan-2-yl)carbamoyl)pyridin-2-yl)piperazin-1-yl)phenoxy)acetic acid;
6-(4-(5-chloropyridin-2-yl)piperazin-1-yl)-N-((E)-5-hydroxyadamantan-2-yl)picolinamide;
6-(4-(5-(trifluoromethyl)pyridin-2-yl)piperazin-1-yl)-N-((E)-5-hydroxyadamantan-2-yl)picolinamide;
6-(4-(5-fluoropyridin-2-yl)piperazin-1-yl)-N-((E)-5-hydroxyadamantan-2-yl)picolinamide;
6-(4-(5-methylpyridin-2-yl)piperazin-1-yl)-N-((E)-5-hydroxyadamantan-2-yl)picolinamide;
6-(4-(5-cyanopyridin-2-yl)piperazin-1-yl)-N-((E)-5-hydroxyadamantan-2-yl)picolinamide;
6-(4-(5-carbamoylpyridin-2-yl)piperazin-1-yl)-N-((E)-5-hydroxyadamantan-2-yl)picolinamide;
6-(4-(4-fluorophenyl)piperidin-1-yl)-N-((E)-5-hydroxyadamantan-2-yl)picolinamide;
6-(4-(4-(trifluoromethyl)phenyl)piperidin-1-yl)-N-((E)-5-hydroxyadamantan-2-yl)picolinamide;
6-(4-p-tolylpiperidin-1-yl)-N-((E)-5-hydroxyadamantan-2-yl)picolinamide;
6-(4-(4-methoxyphenyl)piperidin-1-yl)-N-((E)-5-hydroxyadamantan-2-yl)picolinamide;
6-(4-(pyridin-2-yl)piperidin-1-yl)-N-((E)-5-hydroxyadamantan-2-yl)picolinamide;
6-(4-(5-(trifluoromethyl)pyridin-2-yl)piperidin-1-yl)-N-((E)-5-hydroxyadamantan-2-yl)picolinamide;
6-(4-(5-fluoropyridin-2-yl)piperidin-1-yl)-N-((E)-5-hydroxyadamantan-2-yl)picolinamide;
6-(4-(5-methylpyridin-2-yl)piperidin-1-yl)-N-((E)-5-hydroxyadamantan-2-yl)picolinamide;
6-(4-(5-cyanopyridin-2-yl)piperidin-1-yl)-N-((E)-5-hydroxyadamantan-2-yl)picolinamide;
6-(4-(3-cyanopyridin-2-yl)piperidin-1-yl)-N-((E)-5-hydroxyadamantan-2-yl)picolinamide;
6-(4-(pyridin-3-yl)piperidin-1-yl)-N-((E)-5-hydroxyadamantan-2-yl)picolinamide;
6-(4-(6-methylpyridin-3-yl)piperidin-1-yl)-N-((E)-5-hydroxyadamantan-2-yl)picolinamide;
6-(4-(6-aminopyridin-3-yl)piperidin-1-yl)-N-((E)-5-hydroxyadamantan-2-yl)picolinamide;
6-(1-(4-cyanophenyl)piperidin-4-yl)-N-((E)-5-hydroxyadamantan-2-yl)picolinamide;
6-(1-(5-cyanopyridin-2-yl)piperidin-4-yl)-N-((E)-5-hydroxyadamantan-2-yl)picolinamide;
6-((R)-4-(4-cyanophenyl)-2-methylpiperazin-1-yl)-N-((E)-5-hydroxyadamantan-2-yl)picolinamide;
6-((S)-4-(4-cyanophenyl)-2-methylpiperazin-1-yl)-N-((E)-5-hydroxyadamantan-2-yl)picolinamide;
6-((R)-2-methyl-4-(4-(methylsulfonyl)phenyl)piperazin-1-yl)-N-((E)-5-hydroxyadamantan-2-yl)picolinamide;

6-((S)-2-methyl-4-(4-(methylsulfonyl)phenyl)piperazin-1-yl)-N-((E)-5-hydroxyadamantan-2-yl)picolinamide;
6-((R)-2-methyl-4-(3-(methylsulfonyl)phenyl)piperazin-1-yl)-N-((E)-5-hydroxyadamantan-2-yl)picolinamide
6-((R)-4-(4-methoxyphenyl)-2-methylpiperazin-1-yl)-N-((E)-5-hydroxyadamantan-2-yl)picolinamide;
6-((R)-4-(3-fluoro-4-methoxyphenyl)-2-methylpiperazin-1-yl)-N-((E)-5-hydroxyadamantan-2-yl)picolinamide;
6-((R)-4-(2-fluoro-4-methoxyphenyl)-2-methylpiperazin-1-yl)-N-((E)-5-hydroxyadamantan-2-yl)picolinamide;
6-((R)-4-(3,4-dimethoxyphenyl)-2-methylpiperazin-1-yl)-N-((E)-5-hydroxyadamantan-2-yl)picolinamide;
6-((R)-4-(4-(dimethylamino)phenyl)-2-methylpiperazin-1-yl)-N-((E)-5-hydroxyadamantan-2-yl)picolinamide;
6-((R)-2-methyl-4-(4-(trifluoromethoxy)phenyl)piperazin-1-yl)-N-((E)-5-hydroxyadamantan-2-yl)picolinamide;
6-((R)-2-methyl-4-(4-nitrophenyl)piperazin-1-yl)-N-((E)-5-hydroxyadamantan-2-yl)picolinamide;
6-((R)-4-(5-methoxypyridin-2-yl)-2-methylpiperazin-1-yl)-N-((E)-5-hydroxyadamantan-2-yl)picolinamide;
6-((R)-4-(6-methoxypyridin-3-yl)-2-methylpiperazin-1-yl)-N-((E)-5-hydroxyadamantan-2-yl)picolinamide;
6-((R)-2-methyl-4-(6-methylpyridin-3-yl)piperazin-1-yl)-N-((E)-5-hydroxyadamantan-2-yl)picolinamide;
6-((R)-2-methyl-4-(6-nitropyridin-3-yl)piperazin-1-yl)-N-((E)-5-hydroxyadamantan-2-yl)picolinamide;
6-((R)-2-methyl-4-(pyridin-4-yl)piperazin-1-yl)-N-((E)-5-hydroxyadamantan-2-yl)picolinamide;
6-(4-(4-(methylsulfonyl)phenyl)-1,4-diazepan-1-yl)-N-((E)-5-hydroxyadamantan-2-yl)picolinamide;
6-(4-(2-fluoro-4-methoxyphenyl)-1,4-diazepan-1-yl)-N-((E)-5-hydroxyadamantan-2-yl)picolinamide;
6-((R)-4-(6-aminopyridin-3-yl)-2-methylpiperazin-1-yl)-N-((E)-5-hydroxyadamantan-2-yl)picolinamide;
6-((R)-4-(4-aminophenyl)-2-methylpiperazin-1-yl)-N-((E)-5-hydroxyadamantan-2-yl)picolinamide;
6-((R)-4-(4-acetamidophenyl)-2-methylpiperazin-1-yl)-N-((E)-5-hydroxyadamantan-2-yl)picolinamide;
N-((E)-5-hydroxyadamantan-2-yl)-6-((R)-2-methyl-4-(4-(methylsulfoneamido)phenyl)piperazin-1-yl)picolinamide;
N-((E)-5-hydroxyadamantan-2-yl)-6-((R)-2-methylpiperazin-1-yl)picolinamide;
methyl 4-((R)-4-(6-(((E)-5-hydroxyadamantan-2-yl)carbamoyl)pyridin-2-yl)-3-methylpiperazin-1-yl)benzoate;
4-((R)-4-(6-(((E)-5-hydroxyadamantan-2-yl)carbamoyl)pyridin-2-yl)-3-methylpiperazin-1-yl)benzoic acid;
6-((R)-4-(4-carbamoylphenyl)-2-methylpiperazin-1-yl)-N-((E)-5-hydroxyadamantan-2-yl)picolinamide;
N-((E)-5-hydroxyadamantan-2-yl)-6-((R)-2-methyl-4-(4-(methylcarbamoyl)phenyl)piperazin-1-yl)picolinamide;
6-((R)-4-(4-(cyclopropylcarbamoyl)phenyl)-2-methylpiperazin-1-yl)-N-((E)-5-hydroxyadamantan-2-yl)picolinamide;
N-((E)-5-hydroxyadamantan-2-yl)-6-((R)-4-(4-((2-hydroxyethyl)carbamoyl)phenyl)-2-methylpiperazin-1-yl)picolinamide;
methyl 4-((R)-4-(6-(((E)-5-hydroxyadamantan-2-yl)carbamoyl)pyridin-2-yl)-3-methylpiperazin-1-yl)-2-fluorobenzoate;
4-((R)-4-(6-(((E)-5-hydroxyadamantan-2-yl)carbamoyl)pyridin-2-yl)-3-methylpiperazin-1-yl)-2-fluorobenzoic acid;
6-((R)-4-(4-carbamoyl-3-fluorophenyl)-2-methylpiperazin-1-yl)-N-((E)-5-hydroxyadamantan-2-yl)picolinamide;
N-((E)-5-hydroxyadamantan-2-yl)-6-((R)-2-methyl-4-(4-(methylcarbamoyl)-3-fluorophenyl)piperazin-1-yl)picolinamide;
methyl 4-((R)-4-(6-(((E)-5-hydroxyadamantan-2-yl)carbamoyl)pyridin-2-yl)-3-methylpiperazin-1-yl)3-chlorobenzoate;
4-((R)-4-(6-(((E)-5-hydroxyadamantan-2-yl)carbamoyl)pyridin-2-yl)-3-methylpiperazin-1-yl)3-chlorobenzoic acid;
6-((R)-4-(4-carbamoyl-2-chlorophenyl)-2-methylpiperazin-1-yl)-N-((E)-5-hydroxyadamantan-2-yl)picolinamide;
6-((R)-4-(4-(methylcarbamoyl)-2-chlorophenyl)-2-methylpiperazin-1-yl)-N-((E)-5-hydroxyadamantan-2-yl)picolinamide;
methyl 4-((R)-4-(6-(((E)-5-hydroxyadamantan-2-yl)carbamoyl)pyridin-2-yl)-3-methylpiperazin-1-yl)-2-methoxybenzoate;
4-((S)-4-(6-(((E)-5-hydroxyadamantan-2-yl)carbamoyl)pyridin-2-yl)-3-methylpiperazin-1-yl)-2-methoxybenzoic acid;
6-((R)-4-(4-carbamoyl-3-methoxyphenyl)-2-methylpiperazin-1-yl)-N-((E)-5-hydroxyadamantan-2-yl)picolinamide;
6-((R)-4-(4-(methylcarbamoyl)-3-methoxyphenyl)-2-methylpiperazin-1-yl)-N-((E)-5-hydroxyadamantan-2-yl)picolinamide;
methyl 5-((R)-4-(6-(((E)-5-hydroxyadamantan-2-yl)carbamoyl)pyridin-2-yl)-3-methylpiperazin-1-yl)-2-methoxybenzoate;
5-((R)-4-(6-(((E)-5-hydroxyadamantan-2-yl)carbamoyl)pyridin-2-yl)-3-methylpiperazin-1-yl)-2-methoxybenzoic acid;
6-((R)-4-(3-carbamoyl-4-methoxyphenyl)-2-methylpiperazin-1-yl)-N-((E)-5-hydroxyadamantan-2-yl)picolinamide;
6-((R)-4-(3-(methylcarbamoyl)-4-methoxyphenyl)-2-methylpiperazin-1-yl)-N-((E)-5-hydroxyadamantan-2-yl)picolinamide;
methyl 5-((R)-4-(6-(((E)-5-hydroxyadamantan-2-yl)carbamoyl)pyridin-2-yl)-3-methylpiperazin-1-yl)-2-fluorobenzoate;
5-((R)-4-(6-(((E)-5-hydroxyadamantan-2-yl)carbamoyl)pyridin-2-yl)-3-methylpiperazin-1-yl)-2-fluorobenzoic acid;
6-((R)-4-(3-(methylcarbamoyl)-4-fluorophenyl)-2-methylpiperazin-1-yl)-N-((E)-5-hydroxyadamantan-2-yl)picolinamide;
6-((R)-2-methyl-4-(6-methoxycarbonylpyridin-3-yl)piperazin-1-yl)-N-((E)-5-hydroxyadamantan-2-yl)picolinamide;
6-((R)-2-methyl-4-(6-hydroxycarbonylpyridin-3-yl)piperazin-1-yl)-N-((E)-5-hydroxyadamantan-2-yl)picolinamide;
6-((R)-4-(6-carbamoylpyridin-3-yl)-2-methylpiperazin-1-yl)-N-((E)-5-hydroxyadamantan-2-yl)picolinamide;
6-((R)-4-(6-(methylcarbamoyl)pyridin-3-yl)-2-methylpiperazin-1-yl)-N-((E)-5-hydroxyadamantan-2-yl)picolinamide;
methyl 6-((R)-4-(6-(((E)-5-hydroxyadamantan-2-yl)carbamoyl)pyridin-2-yl)-3-methylpiperazin-1-yl)nicotinate;
6-((R)-4-(6-(((E)-5-hydroxyadamantan-2-yl)carbamoyl)pyridin-2-yl)-3-methylpiperazin-1-yl)nicotinic acid;

6-((R)-4-(5-carbamoylpyridin-2-yl)-2-methylpiperazin-1-yl)-N-((E)-5-hydroxyadamantan-2-yl)picolinamide;
N-((E)-5-hydroxyadamantan-2-yl)-6-((R)-2-methyl-4-(5-(methylcarbamoyl)pyridin-2-yl)piperazin-1-yl)picolinamide;
ethyl 6-((R)-4-(6-(((E)-5-hydroxyadamantan-2-yl)carbamoyl)pyridin-2-yl)-3-methylpiperazin-1-yl)-5-chloronicotinate;
6-((R)-4-(6-(((E)-5-hydroxyadamantan-2-yl)carbamoyl)pyridin-2-yl)-3-methylpiperazin-1-yl)-5-chloronicotinic acid;
6-((R)-4-(5-carbamoyl-3-chloropyridin-2-yl)-2-methylpiperazin-1-yl)-N-((E)-5-hydroxyadamantan-2-yl)picolinamide;
N-((E)-5-hydroxyadamantan-2-yl)-6-((R)-2-methyl-4-(5-(methylcarbamoyl)-3-chloropyridin-2-yl)piperazin-1-yl)picolinamide;
N-((E)-5-hydroxyadamantan-2-yl)-6-((R)-2-methyl-4-(4-sulfamoylphenyl)piperazin-1-yl)picolinamide;
N-((E)-5-hydroxyadamantan-2-yl)-6-((R)-2-methyl-4-(4-(N-methylsulfamoyl)phenyl)piperazin-1-yl)picolinamide;
N-((E)-5-hydroxyadamantan-2-yl)-6-((R)-2-methyl-4-(4-sulfamoyl-2-fluorophenyl)piperazin-1-yl)picolinamide;
N-((E)-5-hydroxyadamantan-2-yl)-6-((R)-2-methyl-4-(4-(N-methylsulfamoyl)-2-fluorophenyl)piperazin-1-yl)picolinamide;
N-((E)-5-hydroxyadamantan-2-yl)-6-((R)-2-methyl-4-(4-sulfamoyl-3-fluorophenyl)piperazin-1-yl)picolinamide;
N-((E)-5-hydroxyadamantan-2-yl)-6-((R)-2-methyl-4-(4-(N-methylsulfamoyl)-3-fluorophenyl)piperazin-1-yl)picolinamide;
N-((E)-5-hydroxyadamantan-2-yl)-6-((R)-4-(4-(2-hydroxypropan-2-yl)phenyl)-2-methylpiperazin-1-yl)picolinamide;
N-((E)-5-hydroxyadamantan-2-yl)-6-((R)-4-(6-(2-hydroxypropan-2-yl)pyridin-3-yl)-2-methylpiperazin-1-yl)picolinamide;
6-((R)-4-(4-acetylphenyl)-2-methylpiperazin-1-yl)-N-((E)-5-hydroxyadamantan-2-yl)picolinamide;
6-((R)-4-(4-trifluoroacetylphenyl)-2-methylpiperazin-1-yl)-N-((E)-5-hydroxyadamantan-2-yl)picolinamide;
6-((R)-4-(4-(2-cyanopropan-2-yl)phenyl)-2-methylpiperazin-1-yl)-N-((E)-5-hydroxyadamantan-2-yl)picolinamide;
6-((R)-4-(4-(ethylcarbonyl)phenyl)-2-methylpiperazin-1-yl)-N-((E)-5-hydroxyadamantan-2-yl)picolinamide;
6-((R)-4-(2-fluoro-4-(2-hydroxypropan-2-yl)phenyl)-2-methylpiperazin-1-yl)-N-((E)-5-hydroxyadamantan-2-yl)picolinamide;
6-((R)-4-(3-fluoro-4-(2-hydroxypropan-2-yl)phenyl)-2-methylpiperazin-1-yl)-N-((E)-5-hydroxyadamantan-2-yl)picolinamide;
6-((R)-4-(4-(1-hydroxycyclopropyl)phenyl)-2-methylpiperazin-1-yl)-N-((E)-5-hydroxyadamantan-2-yl)picolinamide;
6-((R)-4-(4-(dimethylaminomethyl)phenyl)-2-methylpiperazin-1-yl)-N-((E)-5-hydroxyadamantan-2-yl)picolinamide;
6-((R)-4-(4-(2-methyl-2-hydroxypropoxy)phenyl)-2-methylpiperazin-1-yl)-N-((E)-5-hydroxyadamantan-2-yl)picolinamide;
N-((E)-5-hydroxyadamantan-2-yl)-6-((2R)-4-(4-(1-hydroxyethyl)phenyl)-2-methylpiperazin-1-yl)picolinamide;
N-((E)-5-hydroxyadamantan-2-yl)-6-((2R)-2-methyl-4-(4-(2,2,2-trifluoro-1-hydroxyethyl)phenyl)piperazin-1-yl)picolinamide;
6-((R)-4-(4-(1-amino-2-methyl-1-oxopropan-2-yl)phenyl)-2-methylpiperazin-1-yl)-N-((E)-5-hydroxyadamantan-2-yl)picolinamide
6-((R)-4-(3-chloro-4-hydroxyphenyl)-2-methylpiperazin-1-yl)-N-((E)-5-hydroxyadamantan-2-yl)picolinamide;
ethyl 2-(2-chloro-4-((R)-4-(6-(((E)-5-hydroxyadamantan-2-yl)carbamoyl)pyridin-2-yl)-3-methylpiperazin-1-yl)phenoxy)acetate;
2-(2-chloro-4-((R)-4-(6-(((E)-5-hydroxyadamantan-2-yl)carbamoyl)pyridin-2-yl)-3-methylpiperazin-1-yl)phenoxy)acetic acid;
6-((R)-4-(4-(2-amino-2-oxoethoxy)-3-chlorophenyl)-2-methylpiperazin-1-yl)-N-((E)-5-hydroxyadamantan-2-yl)picolinamide;
N-((E)-5-hydroxyadamantan-2-yl)-6-((R)-4-(2-hydroxyethyl)-2-methylpiperazin-1-yl)picolinamide;
6-((R)-4-(2-hydroxy-2-methylpropyl)-2-methylpiperazin-1-yl)-N-((E)-5-hydroxyadamantan-2-yl)picolinamide;
N-((E)-5-hydroxyadamantan-2-yl)-6-((R)-2-methyl-4-(2-(methylsulfonyl)ethyl)piperazin-1-yl)picolinamide;
6-((R)-4-((1-cyanocyclopropyl)methyl)-2-methylpiperazin-1-yl)-N-((E)-5-hydroxyadamantan-2-yl)picolinamide;
6-((R)-4-((1-carbamoylcyclopropyl)methyl)-2-methylpiperazin-1-yl)-N-((E)-5-hydroxyadamantan-2-yl)picolinamide;
6-((R)-4-cyclopropyl-2-methylpiperazin-1-yl)-N-((E)-5-hydroxyadamantan-2-yl)picolinamide;
N-((E)-5-hydroxyadamantan-2-yl)-6-((R)-2-methyl-4-(tetrahydro-2H-pyran-4-yl)piperazin-1-yl)picolinamide;
6-((R)-4-(4-hydroxy-4-methylcyclohexyl)-2-methylpiperazin-1-yl)-N-((E)-5-hydroxyadamantan-2-yl)picolinamide;
N-((E)-5-hydroxyadamantan-2-yl)-6-((R)-2-methyl-4-(piperidin-4-yl)piperazin-1-yl)picolinamide;
6-((R)-4-(1-acetylpiperidin-4-yl)-2-methylpiperazin-1-yl)-N-((E)-5-hydroxyadamantan-2-yl)picolinamide;
N-((E)-5-hydroxyadamantan-2-yl)-6-((R)-2-methyl-4-(1-(methylsulfonyl)piperidin-4-yl)piperazin-1-yl)picolinamide;
6-((R)-4-acetyl-2-methylpiperazin-1-yl)-N-((E)-5-hydroxyadamantan-2-yl)picolinamide;
6-((R)-4-cyclopropylcarbonyl-2-methylpiperazin-1-yl)-N-((E)-5-hydroxyadamantan-2-yl)picolinamide;
6-((R)-4-methylsulfonyl-2-methylpiperazin-1-yl)-N-((E)-5-hydroxyadamantan-2-yl)picolinamide;
6-((R)-4-cyclopropylsulfonyl-2-methylpiperazin-1-yl)-N-((E)-5-hydroxyadamantan-2-yl)picolinamide;
6-((R)-4-(4-methoxyphenylsulfonyl)-2-methylpiperazin-1-yl)-N-((E)-5-hydroxyadamantan-2-yl)picolinamide;
6-((R)-4-(4-trifluoromethylphenylsulfonyl)-2-methylpiperazin-1-yl)-N-((E)-5-hydroxyadamantan-2-yl)picolinamide;
6-((R)-4-(4-bromophenylcarbonyl)-2-methylpiperazin-1-yl)-N-((E)-5-hydroxyadamantan-2-yl)picolinamide;
6-((R)-4-(2-hydroxyacetyl)-2-methylpiperazin-1-yl)-N-((E)-5-hydroxyadamantan-2-yl)picolinamide;
6-((R)-4-(2-hydroxy-2,2-dimethylacetyl)-2-methylpiperazin-1-yl)-N-((E)-5-hydroxyadamantan-2-yl)picolinamide;

6-((R)-4-(2-hydroxymethyl-2,2-dimethylacetyl)-2-methylpiperazin-1-yl)-N-((E)-5-hydroxyadamantan-2-yl)picolinamide;
6-((R)-4-(2-dimethylaminoacetyl)-2-methylpiperazin-1-yl)-N-((E)-5-hydroxyadamantan-2-yl)picolinamide;
6-((R)-4-(2-methoxycarbonylmethylacetyl)-2-methylpiperazin-1-yl)-N-((E)-5-hydroxyadamantan-2-yl)picolinamide;
6-((R)-4-(4-amino-4-oxobutanoyl)-2-methylpiperazin-1-yl)-N-((E)-5-hydroxyadamantan-2-yl)picolinamide;
4-((R)-4-(6-(((E)-5-hydroxyadamantan-2-yl)carbamoyl)pyridin-2-yl)-3-methylpiperazin-1-yl)-4-oxobutanoic acid;
5-fluoro-N-((E)-5-hydroxyadamantan-2-yl)-6-((R)-2-methylpiperazin-1-yl)picolinamide;
5-fluoro-6-((R)-4-(4-(2-hydroxypropan-2-yl)phenyl)-2-methylpiperazin-1-yl)-N-((E)-5-hydroxyadamantan-2-yl)picolinamide;
5-fluoro-6-((R)-4-(2-(2-hydroxypropan-2-yl)pyridin-5-yl)-2-methylpiperazin-1-yl)-N-((E)-5-hydroxyadamantan-2-yl)picolinamide;
5-fluoro-6-((R)-4-(4-(methylsulfonyl)phenyl)-2-methylpiperazin-1-yl)-N-((E)-5-hydroxyadamantan-2-yl)picolinamide;
N-((E)-5-hydroxyadamantan-2-yl)-5-methyl-6-(piperidin-1-yl)picolinamide;
N-((E)-5-hydroxyadamantan-2-yl)-5-methyl-6-(piperazin-1-yl)picolinamide;
5-methyl-6-(4-(4-(2-hydroxypropan-2-yl)phenyl)piperazin-1-yl)-N-((E)-5-hydroxyadamantan-2-yl)picolinamide;
5-methyl-6-(4-(2-(2-hydroxypropan-2-yl)pyridin-5-yl)piperazin-1-yl)-N-((E)-5-hydroxyadamantan-2-yl)picolinamide;
5-methyl-6-(4-(4-(methylsulfonyl)phenyl)piperazin-1-yl)-N-((E)-5-hydroxyadamantan-2-yl)picolinamide;
N-((E)-4-hydroxycyclohexyl)-6-(piperidin-1-yl)picolinamide;
N-cyclopropyl-N—((Z)-4-hydroxycyclohexyl)-6-(piperidin-1-yl)picolinamide;
N-cyclopropyl-N-((E)-4-hydroxycyclohexyl)-6-(piperidin-1-yl)picolinamide;
N-cyclopropyl-N-((1s,4s)-4-hydroxy-4-methylcyclohexyl)-6-(piperidin-1-yl)picolinamide;
N-cyclopropyl-N-((1r,4r)-4-hydroxy-4-methylcyclohexyl)-6-(piperidin-1-yl)picolinamide;
N-cyclopropyl-N-((1s,4s)-4-hydroxy-4-(trifluoromethyl)cyclohexyl)-6-(piperidin-1-yl)picolinamide;
N-cyclopropyl-N-((1r,4r)-4-hydroxy-4-(trifluoromethyl)cyclohexyl)-6-(piperidin-1-yl)picolinamide;
N-((1s,4s)-4-hydroxy-4-(trifluoromethyl)cyclohexyl)-6-(piperidin-1-yl)picolinamide;
N-((1r,4r)-4-hydroxy-4-(trifluoromethyl)cyclohexyl)-6-(piperidin-1-yl picolinamide;
N-((E)-5-hydroxyadamantan-2-yl)-2-((R)-2-methyl-4-(4-(methylsulfonyl)phenyl)piperazin-1-yl)pyrimidine-4-carboxamide;
N-((E)-5-hydroxyadamantan-2-yl)-2-(((R)-4-(2-fluoro-4-methoxyphenyl)-2-methylpiperazin-1-yl)pyrimidine-4-carboxamide;
N-((E)-5-hydroxyadamantan-2-yl)-2-(4-(4-(methylsulfonyl)phenyl)piperazin-1-yl)pyrimidine-4-carboxamide;
N-((E)-5-hydroxyadamantan-2-yl)-2-(4-(4-methoxyphenyl)piperazin-1-yl)pyrimidine-4-carboxamide;
2-((R)-4-benzyl-2-methylpiperazin-1-yl)-N-((E)-5-hydroxyadamantan-2-yl)pyrimidine-4-carboxamide;
N-((E)-5-hydroxyadamantan-2-yl)-2-((R)-4-(2-hydroxypropan-2-yl)phenyl)-2-methylpiperazin-1-yl)pyrimidine-4-carboxamide;
N-((E)-5-hydroxyadamantan-2-yl)-2-((R)-4-(2-(2-hydroxypropan-2-yl)pyridin-5-yl)-2-methylpiperazin-1-yl)pyrimidine-4-carboxamide;
N-((E)-5-hydroxyadamantan-2-yl)-2-((R)-4-(2-fluoro-4-(methylsulfonyl)phenyl)-2-methylpiperazin-1-yl)pyrimidine-4-carboxamide;
N-((E)-5-hydroxyadamantan-2-yl)-2-((R)-4-(2-fluoro-4-(2-hydroxypropan-2-yl)phenyl)-2-methylpiperazin-1-yl)pyrimidine-4-carboxamide;
N-((E)-5-hydroxyadamantan-2-yl)-2-((R)-4-(4-cyanophenyl)-2-methylpiperazin-1-yl)pyrimidine-4-carboxamide;
N-((E)-5-hydroxyadamantan-2-yl)-2-((R)-4-(4-fluorophenyl)-2-methylpiperazin-1-yl)pyrimidine-4-carboxamide;
N-((E)-5-hydroxyadamantan-2-yl)-2-((R)-4-(4-chlorophenyl)-2-methylpiperazin-1-yl)pyrimidine-4-carboxamide;
N-((E)-5-hydroxyadamantan-2-yl)-2-((R)-4-(4-trifluoromethylphenyl)-2-methylpiperazin-1-yl)pyrimidine-4-carboxamide;
N-((E)-5-hydroxyadamantan-2-yl)-2-((R)-4-(4-t-butylphenyl)-2-methylpiperazin-1-yl)pyrimidine-4-carboxamide;
N-((E)-5-hydroxyadamantan-2-yl)-2-((R)-4-(2-methyl-4-(methylsulfonyl)phenyl)-2-methylpiperazin-1-yl)pyrimidine-4-carboxamide;
N-((E)-5-hydroxyadamantan-2-yl)-2-((R)-4-(2-fluoro-4-(ethylsulfonyl)phenyl)-2-methylpiperazin-1-yl)pyrimidine-4-carboxamide;
N-((E)-5-hydroxyadamantan-2-yl)-2-((R)-4-(2-chloro-4-(methylsulfonyl)phenyl)-2-methylpiperazin-1-yl)pyrimidine-4-carboxamide;
N-((E)-5-hydroxyadamantan-2-yl)-2-((R)-4-(2,5-difluoro-4-(methylsulfonyl)phenyl)-2-methylpiperazin-1-yl)pyrimidine-4-carboxamide;
N-((E)-5-hydroxyadamantan-2-yl)-2-((R)-4-(3-fluoropyridin-4-yl)-2-methylpiperazin-1-yl)pyrimidine-4-carboxamide;
N-((E)-5-hydroxyadamantan-2-yl)-2-((R)-4-(3,5-difluoro-pyridin-4-yl)-2-methylpiperazin-1-yl)pyrimidine-4-carboxamide;
N-((E)-5-hydroxyadamantan-2-yl)-2-((R)-4-(2-fluoro-4-(dimethylaminomethyl)phenyl)-2-methylpiperazin-1-yl)pyrimidine-4-carboxamide;
N-((E)-5-hydroxyadamantan-2-yl)-2-((R)-4-(2,6-difluoro-4-(dimethylaminomethyl)phenyl)-2-methylpiperazin-1-yl)pyrimidine-4-carboxamide;
N-((E)-5-hydroxyadamantan-2-yl)-2-((R)-4-(2-amino-4-fluoro-pyridin-5-yl)-2-methylpiperazin-1-yl)pyrimidine-4-carboxamide;
N-((E)-5-hydroxyadamantan-2-yl)-2-((R)-4-(4-amino-2-fluorophenyl)-2-methylpiperazin-1-yl)pyrimidine-4-carboxamide;
N-((E)-5-hydroxyadamantan-2-yl)-2-((R)-4-(4-amino-2,6-difluorophenyl)-2-methylpiperazin-1-yl)pyrimidine-4-carboxamide;
N-((E)-5-hydroxyadamantan-2-yl)-2-((R)-4-(3-methyl-4-(methylsulfonyl)phenyl)-2-methylpiperazin-1-yl)pyrimidine-4-carboxamide;
N-((E)-5-hydroxyadamantan-2-yl)-2-((R)-4-(3-fluoro-4-(methylsulfonyl)phenyl)-2-methylpiperazin-1-yl)pyrimidine-4-carboxamide;

N-((E)-5-hydroxyadamantan-2-yl)-2-((R)-4-(4-(methylsulfonyl)naphthyl)-2-methylpiperazin-1-yl)pyrimidine-4-carboxamide;
N-((E)-5-hydroxyadamantan-2-yl)-2-((R)-4-(2-(methylsulfonyl)phenyl)-2-methylpiperazin-1-yl)pyrimidine-4-carboxamide;
N-((E)-5-hydroxyadamantan-2-yl)-2-((R)-4-(2-(methylsulfonyl)-5-bromophenyl)-2-methylpiperazin-1-yl)pyrimidine-4-carboxamide;
N-((E)-5-hydroxyadamantan-2-yl)-2-((R)-4-(4-(2-hydroxypropan-2-yl)-3-fluorophenyl)-2-methylpiperazin-1-yl)pyrimidine-4-carboxamide;
N-((E)-5-hydroxyadamantan-2-yl)-2-((R)-4-(4-cyano-3-fluorophenyl)-2-methylpiperazin-1-yl)pyrimidine-4-carboxamide;
N-((E)-5-hydroxyadamantan-2-yl)-2-((R)-4-(4-cyano-2-fluorophenyl)-2-methylpiperazin-1-yl)pyrimidine-4-carboxamide;
N-((E)-5-hydroxyadamantan-2-yl)-2-((R)-4-(4-cyano-2-chlorophenyl)-2-methylpiperazin-1-yl)pyrimidine-4-carboxamide;
N-cyclohexyl-2-((R)-4-(2-fluoro-4-(methylsulfonyl)phenyl)-2-methylpiperazin-1-yl)pyrimidine-4-carboxamide;
N-cyclohexyl-2-((R)-4-(2-fluoro-4-methoxyphenyl)-2-methylpiperazin-1-yl)pyrimidine-4-carboxamide;
N-cyclohexyl-2-((R)-4-(2-fluoro-4-(2-hydroxypropan-2-yl)phenyl)-2-methylpiperazin-1-yl)pyrimidine-4-carboxamide;
2-((R)-4-(2-fluoro-4-(methylsulfonyl)phenyl)-2-methylpiperazin-1-yl)-N-((1r,4r)-4-hydroxycyclohexyl)pyrimidine-4-carboxamide;
2-((R)-4-(2-fluoro-4-(2-hydroxypropan-2-yl)phenyl)-2-methylpiperazin-1-yl)-N-((1r,4r)-4-hydroxycyclohexyl)pyrimidine-4-carboxamide;
2-((R)-4-(2-fluoro-4-methoxyphenyl)-2-methylpiperazin-1-yl)-N-((1r,4r)-4-hydroxycyclohexyl)pyrimidine-4-carboxamide;
2-((R)-4-(2-fluoro-4-(methylsulfonyl)phenyl)-2-methylpiperazin-1-yl)-N-(4,4-difluorocyclohexyl)pyrimidine-4-carboxamide;
2-((R)-4-(2-fluoro-4-(2-hydroxypropan-2-yl)phenyl)-2-methylpiperazin-1-yl)-N-(4,4-difluorocyclohexyl)pyrimidine-4-carboxamide;
2-((R)-4-(2-fluoro-4-methoxyphenyl)-2-methylpiperazin-1-yl)-N-(4,4-difluorocyclohexyl)pyrimidine-4-carboxamide;
N-(bicyclo[2.2.1]heptan-2-yl)-2-((R)-4-(2-fluoro-4-(methylsulfonyl)phenyl)-2-methylpiperazin-1-yl)pyrimidine-4-carboxamide;
N-(bicyclo[2.2.1]heptan-2-yl)-2-((R)-4-(2-fluoro-4-(2-hydroxypropan-2-yl)phenyl)-2-methylpiperazin-1-yl)pyrimidine-4-carboxamide;
N-(bicyclo[2.2.1]heptan-2-yl)-2-((R)-4-(2-fluoro-4-methoxyphenyl)-2-methylpiperazin-1-yl)pyrimidine-4-carboxamide;
2-((R)-4-(2-fluoro-4-(2-hydroxypropan-2-yl)phenyl)-2-methylpiperazin-1-yl)-N-((2R,3as,5S,6aS)-octahydro-2,5-methanopentalen-3a-yl)pyrimidine-4-carboxamide;
2-((R)-4-(2-fluoro-4-methoxyphenyl)-2-methylpiperazin-1-yl)-N-((2R,3as,5S,6aS)-octahydro-2,5-methanopentalen-3a-yl)pyrimidine-4-carboxamide;
2-((R)-4-(4-cyano-2-fluorophenyl)-2-methylpiperazin-1-yl)-N-((2R,3as,5S,6aS)-octahydro-2,5-methanopentalen-3a-yl)pyrimidine-4-carboxamide;
N-(adamantan-2-yl)-2-((R)-4-(4-cyano-2-fluorophenyl)-2-methylpiperazin-1-yl)pyrimidine-4-carboxamide;
N-(adamantan-2-yl)-2-((R)-4-(4-methylsulfonyl-2-fluorophenyl)-2-methylpiperazin-1-yl)pyrimidine-4-carboxamide;
N-(adamantan-2-yl)-2-((R)-4-(4-(2-hydroxypropan-2-yl)-2-fluorophenyl)-2-methylpiperazin-1-yl)pyrimidine-4-carboxamide;
N-(adamantan-2-yl)-2-((R)-4-(4-methoxy-2-fluorophenyl)-2-methylpiperazin-1-yl)pyrimidine-4-carboxamide;
N-((E)-5-hydroxyadamantan-2-yl)-2-((S)-4-(4-cyano-2-fluorophenyl)-2-methylpiperazin-1-yl)pyrimidine-4-carboxamide;
N-((E)-5-hydroxyadamantan-2-yl)-2-((S)-4-(4-methylsulfonyl-2-fluorophenyl)-2-methylpiperazin-1-yl)pyrimidine-4-carboxamide;
N-((E)-5-hydroxyadamantan-2-yl)-2-((S)-4-(4-(2-hydroxypropan-2-yl)-2-fluorophenyl)-2-methylpiperazin-1-yl)pyrimidine-4-carboxamide;
N-((E)-5-hydroxyadamantan-2-yl)-2-((S)-4-(4-methoxy-2-fluorophenyl)-2-methylpiperazin-1-yl)pyrimidine-4-carboxamide;
N-cyclopropyl-2-((R)-4-(2-fluoro-4-(methylsulfonyl)phenyl)-2-methylpiperazin-1-yl)-N-((1s,4s)-4-hydroxycyclohexyl)pyrimidine-4-carboxamide;
N-cyclopropyl-2-((R)-4-(2-fluoro-4-(methylsulfonyl)phenyl)-2-methylpiperazin-1-yl)-N-((1r,4r)-4-hydroxycyclohexyl)pyrimidine-4-carboxamide;
N-cyclopropyl-2-((R)-4-(2-fluoro-4-(2-hydroxypropan-2-yl)phenyl)-2-methylpiperazin-1-yl)-N-((1s,4s)-4-hydroxycyclohexyl)pyrimidine-4-carboxamide;
N-cyclopropyl-2-((R)-4-(2-fluoro-4-(2-hydroxypropan-2-yl)phenyl)-2-methylpiperazin-1-yl)-N-((1r,4r)-4-hydroxycyclohexyl)pyrimidine-4-carboxamide;
N-cyclopropyl-2-((R)-4-(2-fluoro-4-methoxyphenyl)-2-methylpiperazin-1-yl)-N-((1s,4s)-4-hydroxycyclohexyl)pyrimidine-4-carboxamide;
N-cyclopropyl-2-((R)-4-(2-fluoro-4-methoxyphenyl)-2-methylpiperazin-1-yl)-N-((1r,4r)-4-hydroxycyclohexyl)pyrimidine-4-carboxamide;
N-cyclopropyl-2-((R)-4-(2-fluoro-4-(methylsulfonyl)phenyl)-2-methylpiperazin-1-yl)-N-((1s,4s)-4-hydroxy-4-methylcyclohexyl)pyrimidine-4-carboxamide;
N-cyclopropyl-2-((R)-4-(2-fluoro-4-(methylsulfonyl)phenyl)-2-methylpiperazin-1-yl)-N-((1r,4r)-4-hydroxy-4-methylcyclohexyl)pyrimidine-4-carboxamide;
N-cyclopropyl-2-((R)-4-(2-fluoro-4-(2-hydroxypropan-2-yl)phenyl)-2-methylpiperazin-1-yl)-N-((1s,4s)-4-hydroxy-4-methylcyclohexyl)pyrimidine-4-carboxamide;
N-cyclopropyl-2-((R)-4-(2-fluoro-4-(2-hydroxypropan-2-yl)phenyl)-2-methylpiperazin-1-yl)-N-((1r,4r)-4-hydroxy-4-methylcyclohexyl)pyrimidine-4-carboxamide;
N-cyclopropyl-2-((R)-4-(2-fluoro-4-methoxyphenyl)-2-methylpiperazin-1-yl)-N-((1s,4s)-4-hydroxy-4-methylcyclohexyl)pyrimidine-4-carboxamide;
N-cyclopropyl-2-((R)-4-(2-fluoro-4-methoxyphenyl)-2-methylpiperazin-1-yl)-N-((1r,4r)-4-hydroxy-4-methylcyclohexyl)pyrimidine-4-carboxamide;
2-((R)-4-(2-fluoro-4-(methylsulfonyl)phenyl)-2-methylpiperazin-1-yl)-N-((1s,4S)-4-hydroxy-4-methylcyclohexyl)pyrimidine-4-carboxamide;
2-((R)-4-(2-fluoro-4-(methylsulfonyl)phenyl)-2-methylpiperazin-1-yl)-N-((1 r,4R)-4-hydroxy-4-methylcyclohexyl)pyrimidine-4-carboxamide;

2-((R)-4-(2-fluoro-4-methoxyphenyl)-2-methylpiperazin-1-yl)-N-((1s,4s)-4-hydroxy-4-methylcyclohexyl)pyrimidine-4-carboxamide;
2-((R)-4-(2-fluoro-4-methoxyphenyl)-2-methylpiperazin-1-yl)-N-((1r,4r)-4-hydroxy-4-methylcyclohexyl)pyrimidine-4-carboxamide;
2-((R)-4-(2-fluoro-4-(2-hydroxypropan-2-yl)phenyl)-2-methylpiperazin-1-yl)-N-((1s,4s)-4-hydroxy-4-methylcyclohexyl)pyrimidine-4-carboxamide;
2-((R)-4-(2-fluoro-4-(2-hydroxypropan-2-yl)phenyl)-2-methylpiperazin-1-yl)-N-((1r,4r)-4-hydroxy-4-methylcyclohexyl)pyrimidine-4-carboxamide;
2-((R)-4-(4-cyano-2-fluorophenyl)-2-methylpiperazin-1-yl)-N-((1s,4s)-4-hydroxy-4-methylcyclohexyl)pyrimidine-4-carboxamide;
2-((R)-4-(4-cyano-2-fluorophenyl)-2-methylpiperazin-1-yl)-N-((1r,4r)-4-hydroxy-4-methylcyclohexyl)pyrimidine-4-carboxamide;
N-((E)-5-hydroxyadamantan-2-yl)-2-((R)-2-methyl-4-(4-nitro-2-fluorophenyl)piperazin-1-yl)pyrimidine-4-carboxamide;
N-((E)-5-hydroxyadamantan-2-yl)-2-((R)-2-methyl-4-(2,6-difluoro-4-(methylsulfonyl)phenyl)piperazin-1-yl)pyrimidine-4-carboxamide;
N-((E)-5-hydroxyadamantan-2-yl)-2-((R)-2-methyl-4-(2-fluoro-4-(3-dimethylaminopropylsulfonyl)phenyl)piperazin-1-yl)pyrimidine-4-carboxamide;
N-((E)-5-hydroxyadamantan-2-yl)-2-((R)-2-methyl-4-(3-trifluoromethylpyridin-4-yl) piperazin-1-yl)pyrimidine-4-carboxamide;
N-((E)-5-hydroxyadamantan-2-yl)-2-((R)-2-methyl-4-(3-trifluoromethyl-5-fluoropyridin-4-yl)piperazin-1-yl)pyrimidine-4-carboxamide;
N-((E)-5-hydroxyadamantan-2-yl)-2-((R)-2-methyl-4-(1H-pyrazol-4-yl)piperazin-1-yl)pyrimidine-4-carboxamide;
N-((E)-5-hydroxyadamantan-2-yl)-2-((R)-2-methyl-4-(3-methyl-1H-pyrazol-4-yl)piperazin-1-yl)pyrimidine-4-carboxamide;
N-((E)-5-hydroxyadamantan-2-yl)-2-((R)-2-methyl-4-(3-fluoro-1H-pyrazol-4-yl)piperazin-1-yl)pyrimidine-4-carboxamide;
N-((E)-5-hydroxyadamantan-2-yl)-2-((R)-2-methyl-4-(3-trifluoromethyl-1H-pyrazol-4-yl)piperazin-1-yl)pyrimidine-4-carboxamide.

4. A pharmaceutical composition comprising the amide compound or the pharmaceutically acceptable salt, solvate, hydrate, prodrug, racemate, or stereoisomer thereof according to claim 1, and a pharmaceutically acceptable carrier.

5. A pharmaceutical composition for treating diseases caused, mediated, and/or spread by the high cortisol level, the pharmaceutical composition comprising the amide compound or the pharmaceutically acceptable salt, solvate, hydrate, prodrug, racemate, or stereoisomer thereof according to claim 1, and a pharmaceutically acceptable carrier.

6. A pharmaceutical composition for treating diabetes, pre-diabetes, insulin tolerance, low glucose tolerance, hyperglycemia, dyslipidemia, hyperlipidemia, hypertriglyceridemia, hypercholesterolemia, or lipid disorders, the pharmaceutical composition comprising the amide compound or the pharmaceutically acceptable salt, solvate, hydrate, prodrug, racemate, or stereoisomer thereof according to claim 1, and a pharmaceutically acceptable carrier.

7. The pharmaceutical composition as claimed in claim 6, wherein the diabetes is non-insulin dependent diabetes.

8. The pharmaceutical composition as claimed in claim 6, wherein the lipid disorders are low HDL levels or high LDL levels.

\* \* \* \* \*